(12) United States Patent
Gray et al.

(10) Patent No.: US 12,318,452 B2
(45) Date of Patent: Jun. 3, 2025

(54) DEGRADERS OF WEE1 KINASE

(71) Applicant: DANA-FARBER CANCER INSTITUTE, INC., Boston, MA (US)

(72) Inventors: Nathanael S. Gray, Boston, MA (US); David Scott, Newton, MA (US); Zhengnian Li, Brookline, MA (US); Benika J. Pinch, Brookline, MA (US); Calla Olson, Brookline, MA (US); Eric S. Fischer, Chestnut Hill, MA (US); Radoslaw P. Nowak, Boston, MA (US); Katherine A. Donovan, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1056 days.

(21) Appl. No.: 17/278,890

(22) PCT Filed: Sep. 26, 2019

(86) PCT No.: PCT/US2019/053124
§ 371 (c)(1),
(2) Date: Mar. 23, 2021

(87) PCT Pub. No.: WO2020/069105
PCT Pub. Date: Apr. 2, 2020

(65) Prior Publication Data
US 2022/0047709 A1 Feb. 17, 2022

Related U.S. Application Data

(60) Provisional application No. 62/737,523, filed on Sep. 27, 2018.

(51) Int. Cl.
*A61K 47/55* (2017.01)
*A61K 31/502* (2006.01)
*A61K 31/519* (2006.01)
*A61K 45/06* (2006.01)
*A61K 47/54* (2017.01)

(52) U.S. Cl.
CPC ............ *A61K 47/55* (2017.08); *A61K 31/502* (2013.01); *A61K 31/519* (2013.01); *A61K 47/545* (2017.08); *A61K 47/555* (2017.08)

(58) Field of Classification Search
CPC .... A61K 47/55; A61K 31/502; A61K 31/519; A61K 47/545; A61K 47/555; A61K 45/06
See application file for complete search history.

(56) References Cited

U.S. PATENT DOCUMENTS

2010/0124544 A1 5/2010 Kawasaki et al.

FOREIGN PATENT DOCUMENTS

| WO | 2017/075629 A2 | 5/2017 |
| WO | 2018/011569 A1 | 1/2018 |
| WO | 2018/064589 A1 | 4/2018 |
| WO | 2018/183891 A1 | 10/2018 |
| WO | 2019/173516 A1 | 9/2019 |
| WO | WO-2019201123 A1 * | 10/2019 |

OTHER PUBLICATIONS

English translation of the foreign patent document: WO-2019201123-A1, https://patents.google.com/patent/WO2019201123A1/en?oq=2019201123, Assessed on Jul. 6, 2024. (Year: 2024).*
Kim, et al., "Targeting the WEE1 Kinase as a Molecular Targeted Therapy for Gastric Cancer," Oncotarget, 2016, 7(31):49902-49916.

* cited by examiner

*Primary Examiner* — Samantha L Shterengarts
*Assistant Examiner* — Sagar Patel
(74) *Attorney, Agent, or Firm* — ArentFox Schiff LLP; Daniel W. Clarke; Shawn P. Foley

(57) ABSTRACT

Disclosed are bifunctional compounds (degraders) that target Wee1 tyrosine kinase for degradation. Also disclosed are pharmaceutical compositions containing the degraders and methods of using the compounds to treat disease.

19 Claims, 22 Drawing Sheets

AZD1775

AZD1775

Lenalidomide

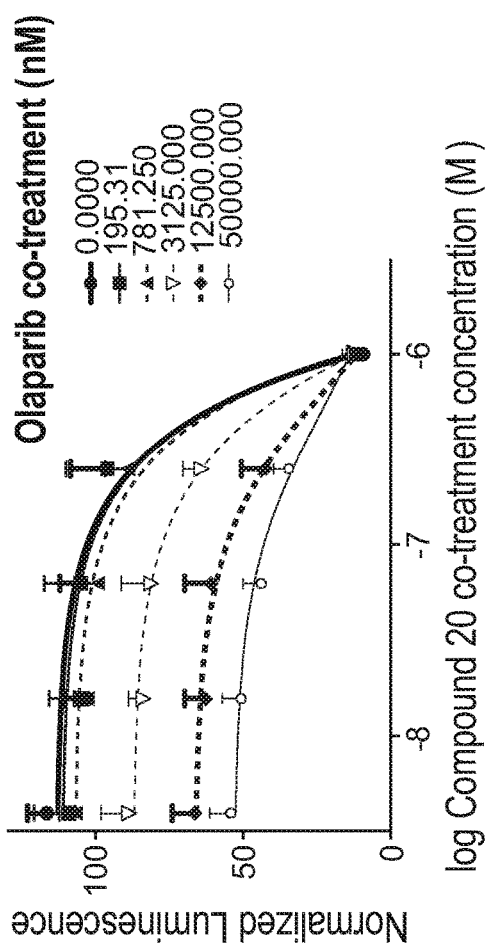
FIG. 11A
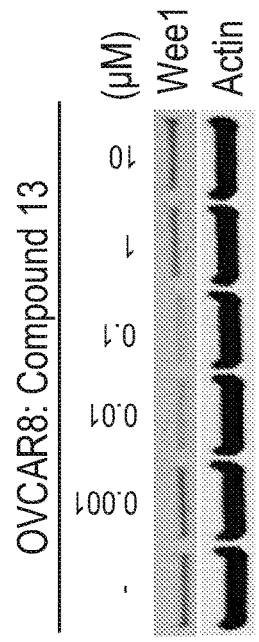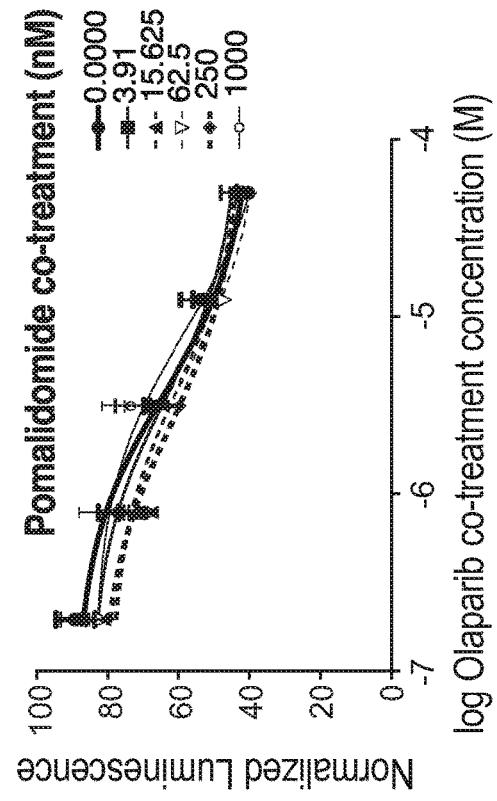
FIG. 11B
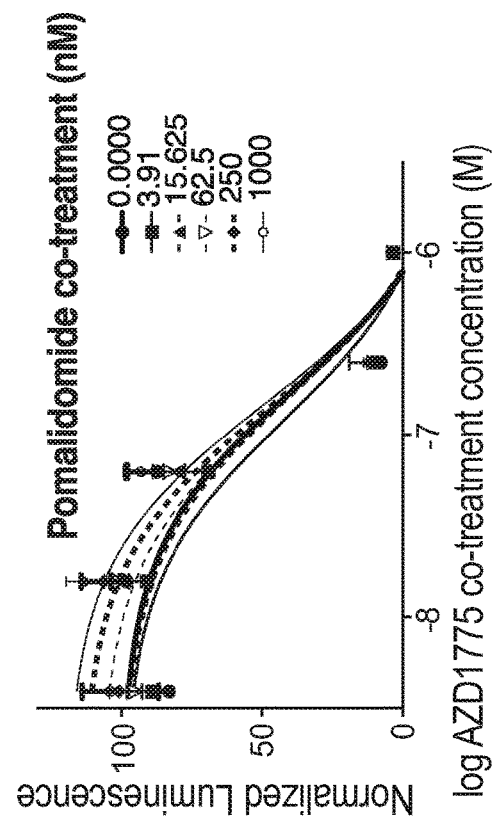
FIG. 11C
FIG. 11D

DEGRADERS OF WEE1 KINASE

RELATED APPLICATIONS

This application is a national stage application, filed under 35 U.S.C. § 371, of International Application No. PCT/US2019/053124, filed Sep. 26, 2019, which claims the benefit of priority under 35 U.S.C. § 119(e) to U.S. Provisional Application No. 62/737,523, filed on Sep. 27, 2018, each of which is incorporated herein by reference in its entirety.

GOVERNMENT LICENSE RIGHTS

This invention was made with government support under grant number F31 CA225066-01, 5 T32 GM007306-41 and 5 T32 GM095450-04 awarded by the National Institutes of Health. The government has certain rights in the invention.

BACKGROUND OF THE INVENTION

Cells depend on cell cycle checkpoint enzymes to allow time for DNA repair and maintenance of genomic integrity before they begin cell division, a process known as mitosis. Damage to cellular DNA activates the intracellular DNA damage response mechanisms. Essential to this process is the activation of Wee1 tyrosine kinase. Wee1, a nuclear tyrosine kinase, regulates the G2-M cell-cycle checkpoint via phosphorylation and inactivation of Cyclin Dependent Kinase 1 (CDK1) at Tyr15 in response to extrinsic DNA damage and errors in DNA synthesis, thereby preventing entry into mitosis (Schmidt et al., Molecules 22:2045 (2017). More specifically, the phosphorylation of Wee1 tyrosine kinase in turn phosphorylates and inactivates cyclin dependent kinases 1 and 2. This causes cells to arrest in the G2 phase that precedes mitosis, thus allowing the cell the time to repair damaged DNA before beginning mitosis. Thus, Wee1 is thus regarded as essential to the DNA repair process, and is viewed as a mitotic gatekeeper. Once the damaged DNA is repaired, cells transition into mitosis and Wee1 activity is reduced, allowing CDK1/cyclin B1 to initiate mitosis. Wee1 is therefore critical for properly timing cell division in normal unperturbed cells (Wantanabe et al., EMBO J. 14:1878-91 (1995); Dominguez-Kelly et al., J. Cell Biol. 194:567-79 (2011); Do et al., J. Clin. Oncol. 33:3409-15 (2015); Tominaga et al., Intl. J. Biol. Sci., 2(4):161-170 (2006); Raleigh et al., J. Cell Sci. 113(10): 1727-36 (2000)).

Many conventional anticancer treatments, including antimetabolites, ionizing radiation, alkylating agents, platinum compounds and DNA topoisomerase inhibitors exert their antitumor effects by damaging DNA in tumor cells (Dominguez-Kelly et al., J. Cell Biol. 194:567-79 (2011)). However, these treatments also cause activation of cell cycle checkpoints, including Wee1 and CDK1 and 2, which gives the tumor cell time to repair the damaged DNA before it begins mitosis. Thus, tumor cells can exploit the DNA repair process, rendering them somewhat refractory or even immune to the anticancer therapy (Beck et al., Mol. Cell Biol. 32:4226-36 (2012)).

The majority of human cancer cells have a deficient G1-S checkpoint, often via mutation of p53, which enables the build-up of damaged and under-replicated DNA, and oncogenic mutations. This leaves cancer cells particularly reliant on a functional G2-M checkpoint to avoid mitotic catastrophe and apoptosis. Abrogation of the G2-M checkpoint by inhibiting Wee1 therefore sensitizes tumors to the effects of DNA-damaging therapies, such as ionizing radiation, antimetabolites, DNA topoisomerase inhibitors, poly ADP ribose polymerase (PARP) inhibitors, and platinum-based chemotherapy (Matheson et al., Trends Pharmacol. Sci. 37:872-881 (2016); Carrassa et al., Cancer Treat. Rev. 60:139-151 (2017)).

AZD1775 is an adenosine triphosphate (ATP)-competitive Wee1 inhibitor that potently inhibits downstream phosphorylation of CDK1 on Tyr15 (Hirai et al., Mol. Cancer Ther. 8:2992-3000 (2009)). AZD1775 has also been shown to induce premature mitotic entry, sensitize p53-mutant tumor cells to DNA-damaging agents, and to cause tumor regression in preclinical cancer models (Hirai et al., Mol. Cancer Ther. 8:2992-3000 (2009); Fu et al., Expert Opin. Investig. Drugs 27:741-751 (2018); Guertin et al., Mol. Cancer Ther. 12:1442-1452 (2013)). Since then, numerous clinical trials have been initiated to evaluate AZD1775 in combination with a variety of DNA-damaging agents in advanced solid tumors and leukemia. Several trials are also testing AZD1775 monotherapy, for example in ovarian cancer patients with germline BRCA1/2 mutation (ClinicalTrials.gov Identifier: NCT02482311).

While AZD1775 shows promising efficacy in the clinic, it has been associated with a number of dose-limiting toxicities, including neutropenia, thrombocytopenia, anemia, and nausea (Guertin et al., Mol. Cancer Ther. 12:1442-1452 (2013); Do et al., J. Clin. Oncol. 33:3409-3415 (2015)). AZD1775 is also known to have off-target activity against other kinases; for example, it is equipotent against recombinant Wee1 and the Ser/Thr kinase, PLK1 (Wright et al., ACS Chem. Biol. 12:1883-1892 (2017). Furthermore, analogs of AZD1775 have been reported to maintain potency against Wee1, but have reduced cellular cytotoxicity (Matheson et al., ACS Chem. Biol. 11:2066-2067 (2016)).

These limitations of AZD1775 highlight the need for an agent that more selectively eliminates Wee1 activity, and that offers the potential for reducing off-target toxicities.

SUMMARY OF THE INVENTION

A first aspect of the present invention is directed to a bifunctional compound (also referred to herein as a "degrader" or "PROTAC"), which has a structure represented by formula (I):

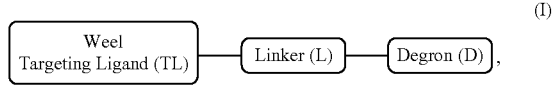

(I)

wherein the targeting ligand represents a moiety that binds Wee1 kinase, the degron represents a ligand that binds an E3 ubiquitin ligase, and the linker represents a moiety that connects covalently the degron and the targeting ligand, or a pharmaceutically acceptable salt or stereoisomer thereof.

A second aspect of the present invention is directed to a pharmaceutical composition containing a therapeutically effective amount of a compound of formula (I), or a pharmaceutically acceptable salt or stereoisomer thereof, and pharmaceutically acceptable carrier.

A further aspect of the invention is directed to a method of treating a disease or disorder mediated by aberrant Wee1 kinase activity, that includes administrating a therapeutically effective amount of an inventive bifunctional compound or a pharmaceutically acceptable salt or stereoisomer thereof, to a subject in need thereof.

In some embodiments, the disease is a cancer (e.g., ovarian cancer).

In some embodiments, the method further comprises administering the therapeutically effective amount of the compound of formula I or a pharmaceutically acceptable salt or stereoisomer thereof in combination with a therapeutically effective amount effective amount of an additional chemotherapeutic agent (e.g., poly ADP ribose polymerase (PARP) inhibitor).

In some embodiment the PARP inhibitor is Olaparib.

Further aspects of the present invention are directed to methods of making the bifunctional compounds.

Without intending to be bound by any particular theory of operation, the bifunctional compounds of formula (I) of the present invention are believed to degrade Wee1 kinase via the cell's ubiquitin/proteasome system, whose function is to routinely identify and remove damaged proteins. The degron functional moiety recruits the E3 ubiquitin ligase to tag Wee1 kinase (which is bound by the targeting ligand functionality) for ubiquitination and degradation through the proteasome, which is a large endogenous complex that degrades ubiquitinated proteins into small peptide fragments. After destruction of a Wee1 kinase molecule, the degrader is released and continues to be active. Thus, by engaging and exploiting the body's own natural protein disposal system, the bifunctional compounds of the present invention may represent a potential improvement over traditional small molecule inhibitors of Wee1 kinase such as AZD1775 in the treatment of cancers and other diseases or disorders that have proven or may prove to be difficult to treat. Thus, effective intracellular concentrations of the degraders may be lower than for small molecule Wee1 inhibitors. The present bifunctional compounds may offer additional advantages including improved pharmacodynamic effects, decreased tyrosine kinase inhibitor resistance imparted by intrinsic scaffolding functions of kinases, and decreased likelihood of de novo resistance mutations to the degraders (since efficient degradation of Wee1 may be achieved with targeting ligands that have relatively less affinity to Wee1 compared to known Wee1 inhibitors). Collectively, the present bifunctional compounds may represent an advancement over known Wee1 inhibitors and may overcome one or more limitations regarding their use.

BRIEF DESCRIPTION OF THE DRAWINGS

FIG. 2D is an image showing an immunoblot analysis MOLT4 cells treated for 5 hours with the indicated concentrations of compound 24, a negative control of compound 21.

FIG. 4A is an image showing an immunoblot analysis of MOLT4 parental or CRBN$^{-/-}$ cells treated with inventive compound 13 at the indicated concentrations for 5 hours.

FIG. 4B is an image showing an immunoblot analysis of MOLT4 cells pre-treated with DMSO, carfilzomib (Carf. 400 nM), MLN4924 (MLN 1 µM), pomalidomide (Pom. 10 µM), or AZD1775 (1 µM) for 2 hours, and then co-treated with inventive compound 13 (100 nM) for 5 hours.

FIG. 4C is an image showing an immunoblot analysis of MOLT4 cells treated with inventive compound 13 (100 nM) for the indicated time points.

FIG. 4D is an image showing immunoblot analysis of MOLT4 cells treated with inventive compound 13 (100 nM) or negative control, compound 20 (100 nM), for the indicated time points.

FIG. 4E is a scatter plot showing log fold-change in abundance of proteins as measured using multiplexed quantitative-mass spectrometry-based proteomics of MOLT4 cells treated with inventive compound 13 (100 nM) for 2 hours versus p-value. n=3 biological replicates.

FIG. 5A is an image showing an immunoblot analysis of MOLT4 cells treated with inventive compound 13 (100 nM), compound 20 (100 nM), AZD1775 (100 nM, 1 µM), or pomalidomide (1 µM) for 24 hours.

FIG. 5B is a bar graph showing the percentage of MOLT4 cell population in each cell cycle phase after treatment with inventive compound 13 (100 nM) or compound 20 (100 nM) for the indicated time points and stained with propidium iodide. Error bars represent standard deviation from the mean for technical triplicates from one biological replicate.

FIG. 5C is bar graph showing the percentage of wild-type MOLT4 cell population in each cell cycle phase after treatment with the indicated concentrations of inventive compound 13, compound 20, AZD1775, or lenalidomide for 24 hours and stained with propidium iodide. Error bars represent standard deviation from the mean for technical triplicates from one biological replicate.

FIG. 5D is bar graph showing the percentage of CRBN$^{-/-}$ MOLT4 cell population in each cell cycle phase after treatment with the indicated concentrations of inventive compound 13, compound 20, AZD1775, or lenalidomide for 24 hours and stained with propidium iodide. Error bars represent standard deviation from the mean for technical triplicates from one biological replicate.

FIG. 6A is a graph showing cell viability of parental (wildtype) or CRBN$^{-/-}$ MOLT4 cells treated with compound 13 for 72 hours, as approximated by CellTiter-Glo®. Data points are plotted as the average of three replicates ±SEM.

FIG. 6B is a graph showing cell viability of parental (wildtype) or CRBN$^{-/-}$ MOLT4 cells treated with compound 20 for 72 hours, as approximated by CellTiter-Glo®. Data points are plotted as the average of three replicates ±SEM.

FIG. 6C is a graph showing cell viability of parental (wildtype) or CRBN$^{-/-}$ MOLT4 cells treated with AZD1775 for 72 hours, as approximated by CellTiter-Glo®. Data points are plotted as the average of three replicates ±SEM.

FIG. 6D is a graph showing cell viability of OVCAR8 cells treated with AZD1775, inventive compound 13 or compound 20 for 72 hours, as approximated by CellTiter-Glo®. Data points are plotted as the average of three replicates ±SEM.

FIG. 6E is a graph showing cell viability of OVCAR8 cells co-treated with compound 13 and Olaparib at the indicated concentrations for 72 hours, as approximated by CellTiter-Glo®. Data points are plotted as the average of three replicates ±SEM.

FIG. 6F is a graph showing cell viability of OVCAR8 cells co-treated with AZD1775 and Olaparib at the indicated concentrations for 72 hours, as approximated by CellTiter-Glo®. Data points are plotted as the average of three replicates ±SEM.

FIG. 7A-FIG. 7G are a set of immunoblots of MOLT4 cells treated for 5 hours with the indicated concentrations of inventive compounds 7, 12, 11, and 13, compound 20, AZD1775, and pomalidomide.

FIG. 7A is an image showing an immunoblot analysis MOLT4 cells treated for 5 hours with the indicated concentrations of inventive compound 7.

FIG. 7B is an image showing an immunoblot analysis MOLT4 cells treated for 5 hours with the indicated concentrations of inventive compound 12.

FIG. 7C is an image showing an immunoblot analysis MOLT4 cells treated for 5 hours with the indicated concentrations of inventive compound 11.

FIG. 7D is an image showing an immunoblot analysis MOLT4 cells treated for 5 hours with the indicated concentrations of inventive compound 13.

FIG. 7E is an image showing an immunoblot analysis MOLT4 cells treated for 5 hours with the indicated concentrations of compound 20.

FIG. 7F is an image showing an immunoblot analysis MOLT4 cells treated for 5 hours with the indicated concentrations of AZD1775.

FIG. 7G is an image showing an immunoblot analysis MOLT4 cells treated for 5 hours with the indicated concentrations of pomalidomide.

FIG. 10A is graph showing

FIG. 11A is an image of an immunoblot analysis of OVCAR8 cells treated for 5 hours with the indicated concentrations of compound 13.

FIG. 11B is a graph showing cell viability of OVCAR8 cells co-treated with compound 20 and Olaparib at the indicated concentrations for 72 hours, as approximated by CellTiter-Glo®. Data points are plotted as the average of three replicates ±SEM.

FIG. 11C is a graph showing cell viability of OVCAR8 cells co-treated with Pomalidomide and Olaparib at the indicated concentrations for 72 hours, as approximated by CellTiter-Glo®. Data points are plotted as the average of three replicates ±SEM.

FIG. 11D is a graph showing cell viability of OVCAR8 cells co-treated with Pomalidomide and AZD1775 at the indicated concentrations for 72 hours, as approximated by CellTiter-Glo®. Data points are plotted as the average of three replicates ±SEM.

DETAILED DESCRIPTION OF THE INVENTION

Figure 1A:
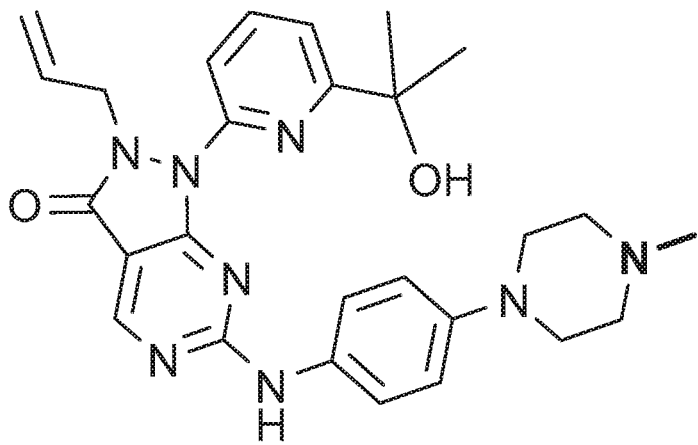
FIG. 1A is an image showing the chemical structure of Wee1 inhibitor, AZD1775, with linker attachment point highlighted in blue.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a" "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "aliphatic" refers to a non-cyclic hydrocarbon group and includes branched and unbranched, alkyl, alkenyl, or alkynyl groups.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group. In some embodiments, an alkyl group is a $C_1$-$C_2$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "haloalkyl" refers to an alkyl group as defined herein that is substituted with one or more (e.g., 1, 2, 3, or 4) halo groups.

As used herein, the term "alkenyl" refers to a linear or branched-chain monovalent hydrocarbon radical with at least one carbon-carbon double bond. An alkenyl includes radicals having "cis" and "trans" orientations, or alternatively, "E" and "Z" orientations. In one example, the alkenyl radical is a $C_2$-$C_{18}$ group. In other embodiments, the alkenyl radical is a $C_2$-$C_{12}$, $C_2$-$C_{10}$, $C_2$-$C_8$, $C_2$-$C_6$ or $C_2$-$C_3$ group. Examples include ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

As used herein, the term "alkynyl" refers to a linear or branched monovalent hydrocarbon radical with at least one carbon-carbon triple bond. In one example, the alkynyl radical is a $C_2$-$C_{18}$ group. In other examples, the alkynyl radical is $C_2$-$C_{12}$, $C_2$-$C_{10}$, $C_2$-$C_8$, $C_2$-$C_6$ or $C_2$-$C_3$. Examples include ethynyl prop-1-ynyl, prop-2-ynyl, but-1-ynyl, but-2-ynyl and but-3-ynyl.

As used herein, the term "aldehyde" is represented by the formula —C(O)H. The terms "C(O)" and C=O are used interchangeably herein.

The terms "alkoxyl" or "alkoxy" as used herein refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl.

As used herein, the term "halogen" (or "halo" or "halide") refers to fluorine, chlorine, bromine, or iodine.

As used herein, the term "carboxylic acid" is represented by the formula —C(O)OH, and a "carboxylate" is represented by the formula —C(O)O—.

As used herein, the term "ester" is represented by the formula —OC(O)$Z^1$ or —C(O)O$Z$, where $Z^1$ may be an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ether" is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "ketone" is represented by the formula $Z^1C(O)Z^2$, where $A^1$ and $A^2$ independently represent alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonyl" refers to the sulfo-oxo group represented by the formula —S(O)$_2Z^1$, where $Z^1$ may be hydrogen, an alkyl, halogenated alkyl, alkenyl, alkynyl, aryl, heteroaryl, cycloalkyl, cycloalkenyl, heterocycloalkyl, or heterocycloalkenyl group, all as described herein.

As used herein, the term "sulfonylamino" (or "sulfonamide") is represented by the formula —S(O)$_2NH_2$.

As used herein, the term "thiol" is represented by the formula —SH.

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6]ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —$R^c$-carbocyclyl where $R^c$ is an alkylene chain. The term carbocyclic also embraces carbocyclylalkoxy groups which as used herein refer to a group bonded through an oxygen atom of the formula —O—$R^c$-carbocyclyl where $R^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes $C_3$-$C_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and Spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]+OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl groups include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —$R^c$-heterocyclyl where $R^c$ is an alkylene chain. The term heterocyclic also embraces heterocyclylalkoxy groups which as used herein refer to a radical bonded through an oxygen atom of the formula —O—$R^c$-heterocyclyl where $R^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, where $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1 2 3, or 4) heteroatoms such as oxygen, sulfur, and nitrogen grouped in a linear, branched, or cyclic structural format.

Representative examples of substituents may thus include alkyl, substituted alkyl (e.g., C1-C6, C1-5, C1-4, C1-3, C1-2, C1), alkoxy (e.g., C1-C6, C1-5, C1-4, C1-3, C1-2, C1), substituted alkoxy (e.g., C1-C6, C1-5, C1-4, C1-3, C1-2, C1), alkenyl (e.g., C2-C6, C2-5, C2-4, C2-3, C2), substituted alkenyl (e.g., C2-C6, C2-5, C2-4, C2-3, C2), alkynyl (e.g., C2-C6, C2-5, C2-4, C2-3, C2), substituted alkynyl (e.g., C2-C6, C2-5, C2-4, C2-3, C2), cyclic (e.g., C3-C12, C5-C6), substituted cyclic (e.g., C3-C12, C5-C6), carbocyclic (e.g., C3-C12, C5-C6), substituted carbocyclic (e.g., C3-C12, C5-C6), heterocyclic (e.g., C3-C12, C5-C6), substituted heterocyclic (e.g., C3-C12, C5-C6), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., C6-C12, C6), substituted aryloxy (e.g., C6-C12, C6), alkylthio (e.g., C1-C6), substituted alkylthio (e.g., C1-C6), arylthio (e.g., C6-C12, C6), substituted arylthio (e.g., C6-C12, C6), cyano, carbonyl, substituted carbonyl, carboxyl, substituted carboxyl, amino, substituted amino, amido, substituted amido, sulfonyl, substituted sulfonyl, amino acid, and peptide groups.

The term "binding" as it relates to interaction between the targeting ligand and the targeted protein, which includes Wee1, typically refers to an inter-molecular interaction that enables recruitment of Wee1 into close proximity with the E3 ubiquitin ligase and subsequent degradation of Wee1. The targeting ligands that may be used in the inventive compounds such as AZD1775 may also bind polo-like kinase 1 (PLK1), the inhibition of which may enhance the therapeutic effect of the inventive compounds. The binding may also be substantially selective in that binding with any other non-target proteins present in the cell is functionally insignificant.

The term "binding" as it relates to interaction between the degron and the E3 ubiquitin ligase, typically refers to an inter-molecular interaction that may or may not exhibit an affinity level that equals or exceeds that affinity between the targeting ligand and the target protein, but nonetheless wherein the affinity is sufficient to achieve recruitment of the ligase to the targeted degradation and the selective degradation of the targeted protein.

Wee1 Targeting Ligands

Broadly, the bifunctional compounds (degraders) of the present invention target Wee1 kinase for degradation.

In some embodiments, the Wee1 targeting ligand is derived from AZD-1775, the structure of which is as shown below.

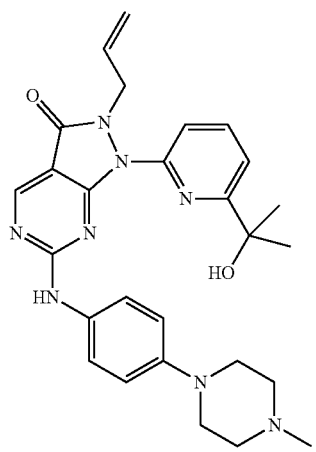 [SMILES: C=CCn1c(=O)c2cnc(Nc3ccc(N4CCN(C)CC4)cc3)nc2n1-c1cccc(C(C)(C)O)n1]

AZD-1775 (MK-1775) is also known as 2-allyl-1-[6-(1-hydroxy-1-methylethyl)pyridin-2-yl]-6-{[4-(4-methylpip-era-zin-1-yl)phenyl]amino}-1,2-dihydro-3H-pyrazolo[3,4-d]pyrimidin-3-one. AZD-1775 is been described in U.S. Pat. No. 7,834,019 and in PCT International Publication Nos. WO 2007/126122, WO 2007/126128 and WO 2008/153207.

In some embodiments, the Wee1 targeting ligand is derived from MK-3652, the structure of which is as shown below.

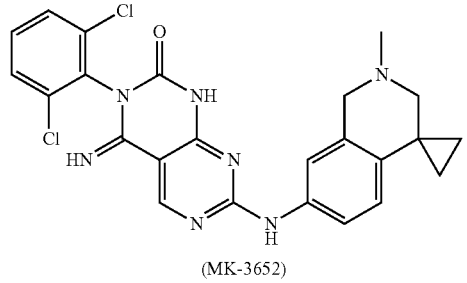 [SMILES: CN1Cc2cc(Nc3ncc4c(=N)n(-c5c(Cl)cccc5Cl)c(=O)[nH]c4n3)ccc2C2(CC2)C1]

(MK-3652)

MK-3652 is also known as 3-(2,6-dichlorophenyl)-4-imino-7-[(2'-methyl-2',3'-dihydro-1'H-spiro[cycl-opropane-1,4'-isoquinolin]-7'-yl)amino]-3,4-dihydropyrimido[4,5-d]pyrimidin-2(1H)-one. MK-3652 has been described in PCT International Publication WO 2008/153207 and U.S. Patent Application Publication 2011/0135601 A1.

Further representative compounds that may be useful as Wee1 targeting ligands are described in U.S. Patent Application Publication Nos. 20100105674, 20100113445, 20100221211, and 20110135601.

In some embodiments, the bifunctional compounds of the present invention include a Wee1 targeting ligand (Wee1 TL or TL) that is represented by any one of the following structures (TL1-5):

(TL1)

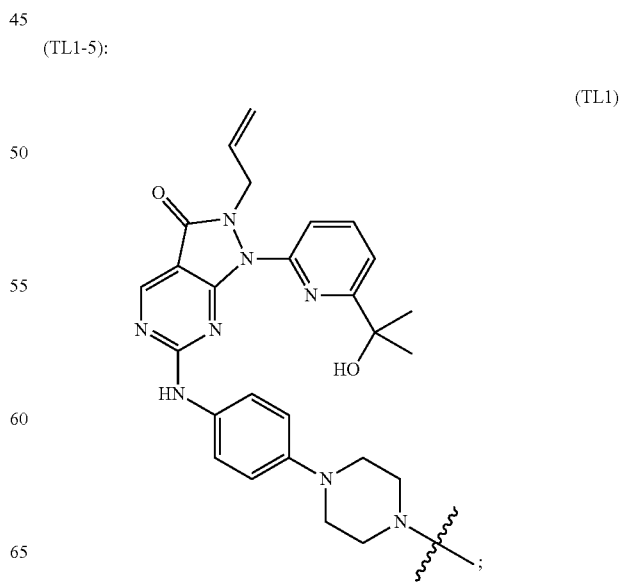

(TL2)
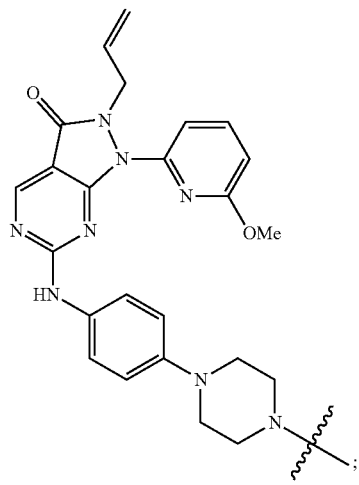
(TL3)
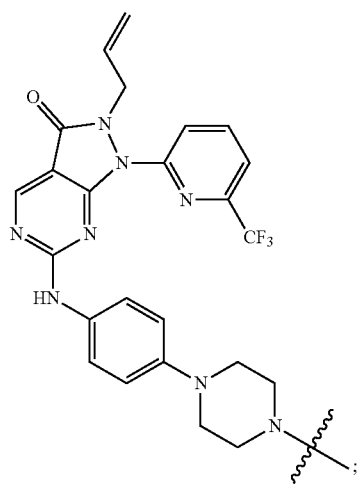
(TL4)
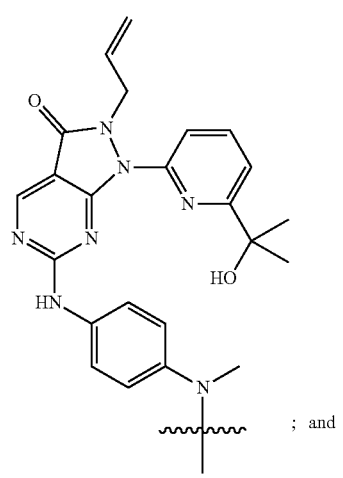
; and
(TL5)
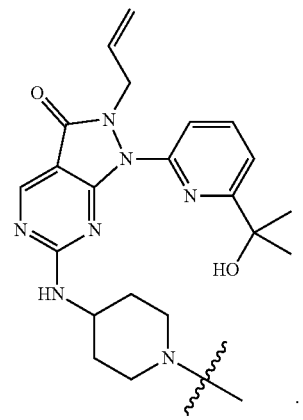
Thus, in some embodiments, the bifunctional compounds of the present invention are represented by any one of the following structures:
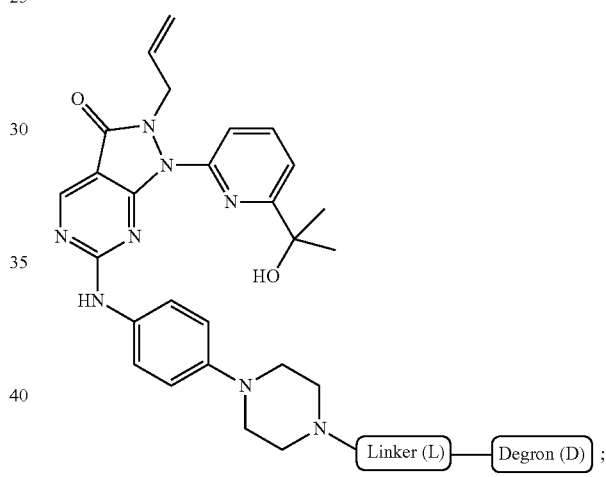
;
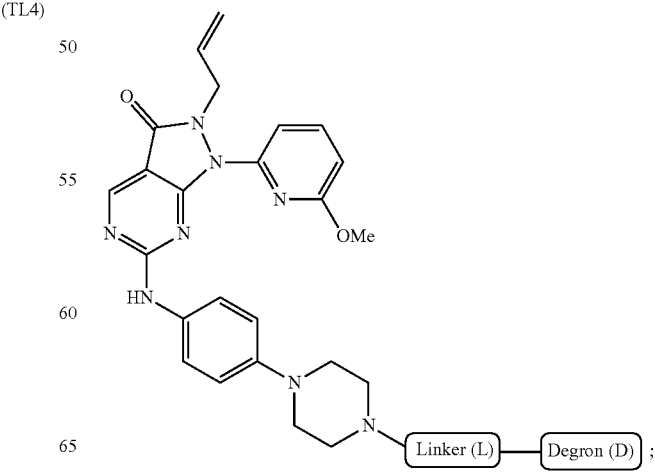
;

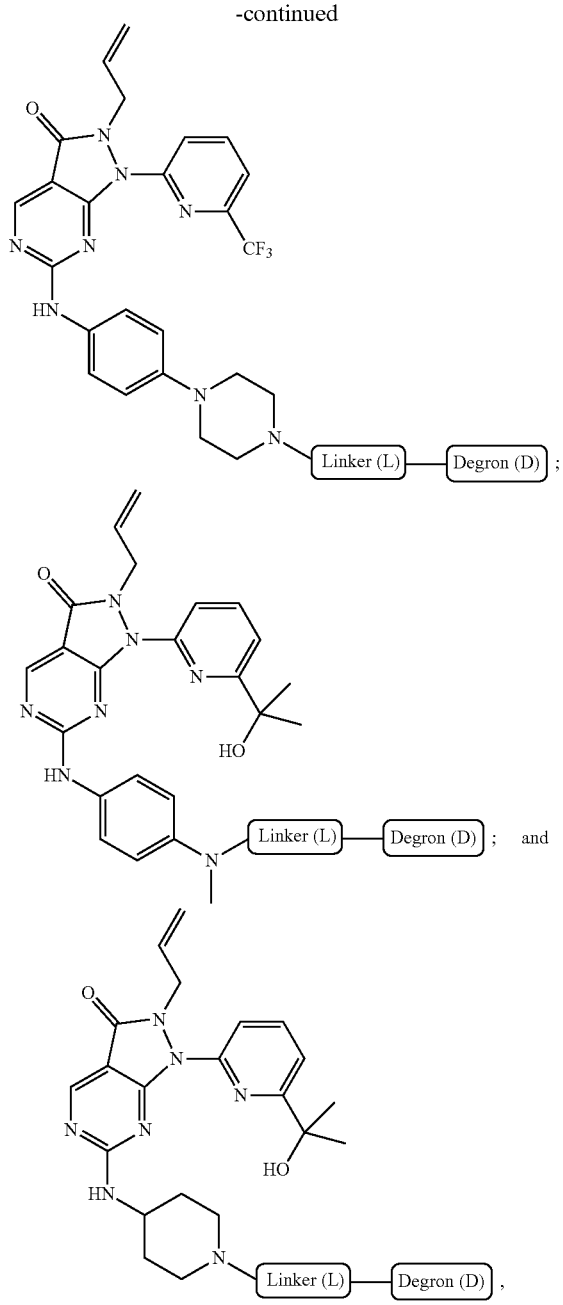

or a pharmaceutically acceptable salt or stereoisomer thereof.

Linkers

The linker ("L") provides a covalent attachment the targeting ligand and the degron. The structure of linker may not be critical, provided it does not substantially interfere with the activity of the targeting ligand or the degron. In some embodiments, the linker may be an alkylene chain or a bivalent alkylene chain, either of which may be interrupted by and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)₂—, —OS(O)—, —S(O)O—, —S(O)—, —OS(O)₂—, —S(O)₂O—, —N(R')S(O)₂—, —S(O)₂N(R')—, —N(R')S(O)—, —S(O)N(R')—, —N(R')S(O)₂N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different.

In some embodiments, the linker may be a polyethylene glycol chain which may terminate (at either or both termini) in at least one of —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)₂—, —OS(O)—, —S(O)O—, —S(O)—, —OS(O)₂—, —S(O)₂O—, —N(R')S(O)₂—, —S(O)₂N(R')—, —N(R')S(O)—, —S(O)N(R')—, —N(R')S(O)₂N(R')—, —N(R')S(O)N(R')—, $C_3$-12 carbocyclene, 3- to 12-membered heterocyclene, 5- to 12-membered heteroarylene or any combination thereof, wherein R' is H or $C_1$-$C_6$ alkyl, wherein the one or both terminating groups may be the same or different.

"Carbocyclene" refers to a bivalent carbocycle radical, which is optionally substituted.

"Heterocyclene" refers to a bivalent heterocyclyl radical which may be optionally substituted.

"Heteroarylene" refers to a bivalent heteroaryl radical which may be optionally substituted.

Representative examples of linkers that may be suitable for use in the present invention include alkylene chains:

(L1)

wherein n is an integer of 1-10 ("of" meaning inclusive), e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, 9-10 and 1, 2, 3, 4, 5, 6, 7, 8, 9 and 10, examples of which include:

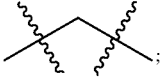
(L1-a)

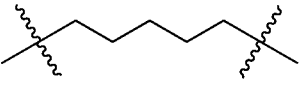
(L1-b)

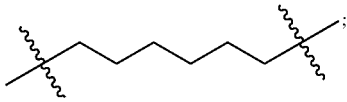
(L1-c)

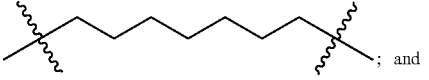
(L1-d)

; and (L1-e)

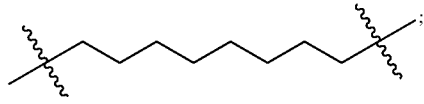

alkylene chains terminating in various functional groups (as described above), examples of which are as follows:

(L2-a)

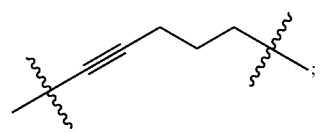

(L2-b)

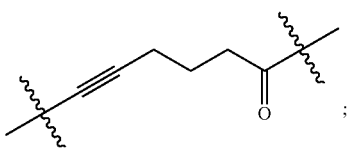

(L2-c)

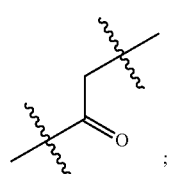

(L2-d)

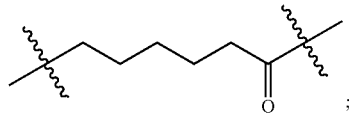

(L2-e)

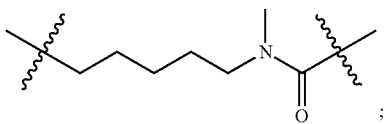

(L2-f)

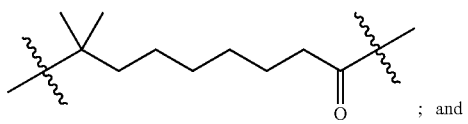
; and (L2-g)

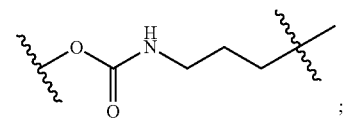

alkylene chains interrupted with various functional groups (as described above), examples of which are as follows:

(L3-a)

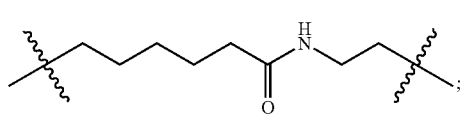

(L3-b)

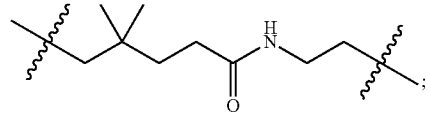

(L3-c)

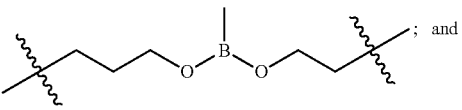
; and (L3-d)

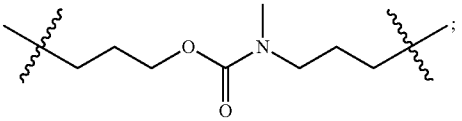

alkylene chains interrupted or terminating with heterocyclene groups, e.g., (L4)

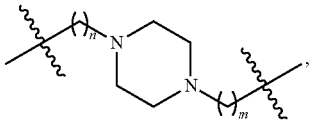

wherein m and n are independently integers of 0-10, examples of which include:

(L4-a)

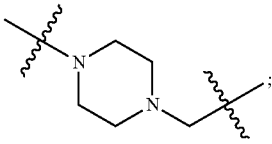

(L4-b)

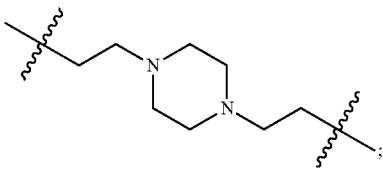

(L4-c)

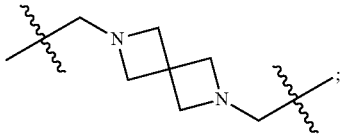

(L4-d)

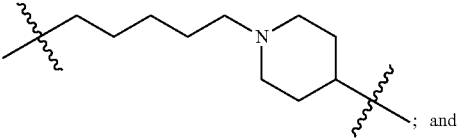
; and (L4-e)

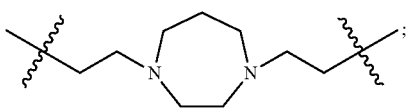

alkylene chains interrupted by amide, heterocyclene and/or aryl groups, examples of which include:

(L5-a)

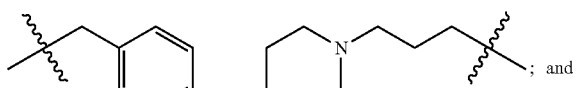
; and (L5-b)

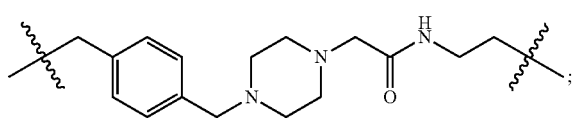
;

alkylene chains interrupted by heterocyclene and aryl groups, and a heteroatom, examples of which include:

(L6-a)

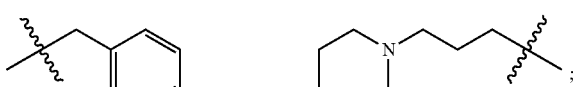
;

(L6-b)

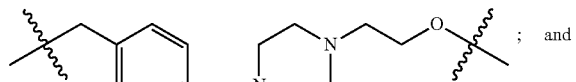
; and (L6-c)

;

and
alkylene chains interrupted by a heteroatom such as N, O or B, e.g., (L7)

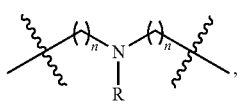

wherein n is an integer of 1-10, e.g., 1-9, 1-8, 1-7, 1-6, 1-5, 1-4, 1-3, 1-2, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4- 6, 4-5, 5-10, 5-9, 5-8, 5-7, 5-6, 6-10, 6-9, 6-8, 6-7, 7-10, 7-9, 7-8, 8-10, 8-9, 9-10, and 1, 2, 3, 4, 5, 6, 7, 8, 9 and 10, and R is H, or C1 to C4 alkyl, an example of which is (L7-a)

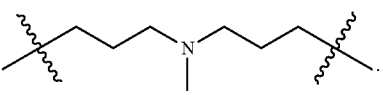

In some embodiments, the linker is a polyethylene glycol chain, examples of which include:

(L8)

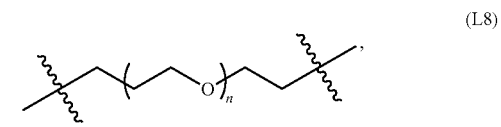

wherein n is an integer of 2-10, examples of which include:

(L8-a)

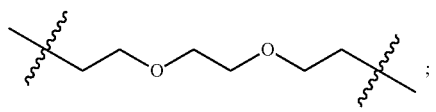
;

(L8-b)

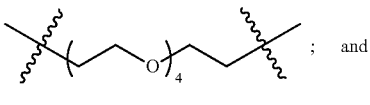
;

(L8-c)

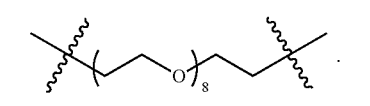
; and (L8-d)

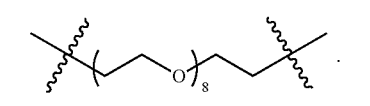
.

In some embodiments, the polyethylene glycol chain may terminate in a functional group, examples of which are as follows:

(L9-a)

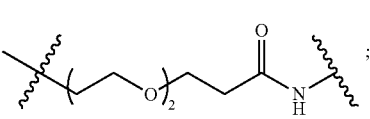
;

(L9-b)

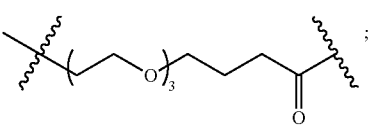
;

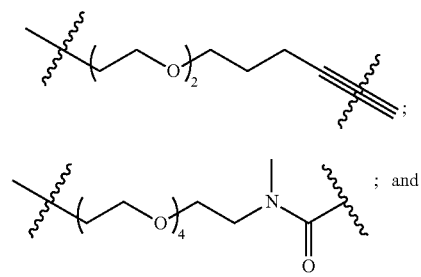
(L9-c)
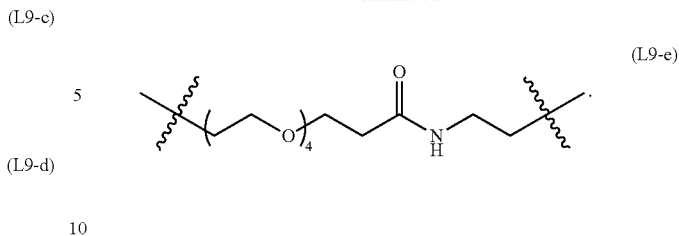
(L9-e)
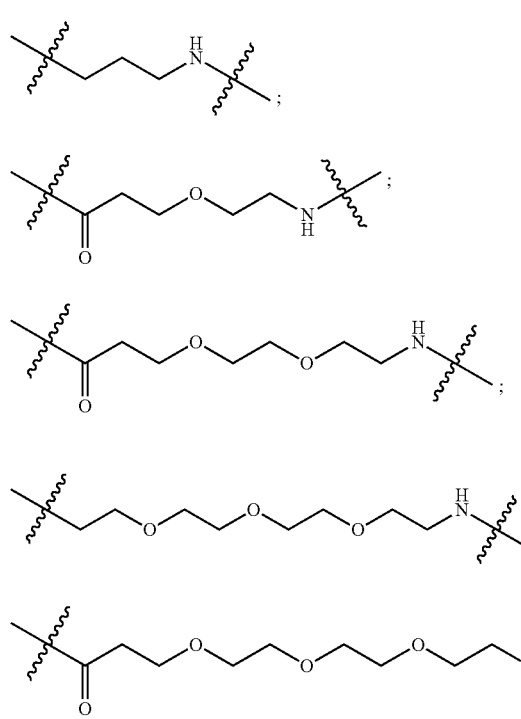
(L9-d) ; and
In some embodiments, the bifunctional compound of formula (I) includes a linker that is represented by any one of the following structures:
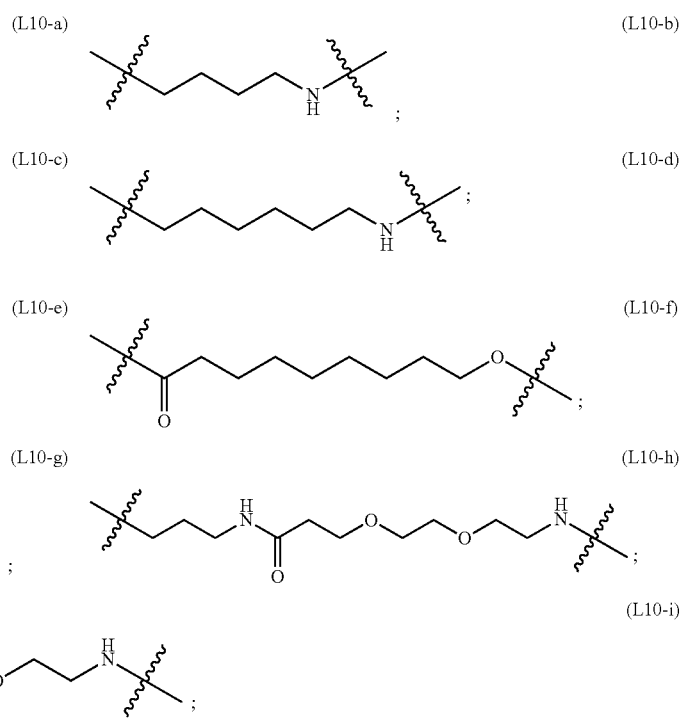
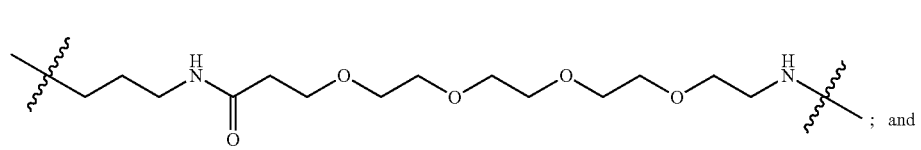
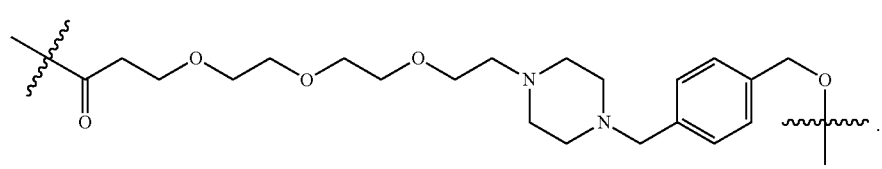

Thus, in some embodiments, the bifunctional compounds of the present invention are represented by any one of the following structures:
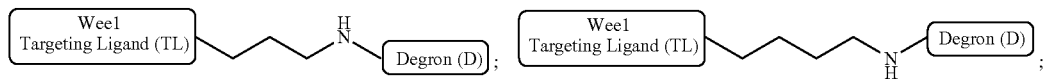
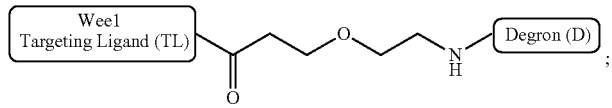
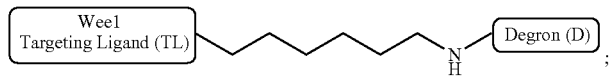
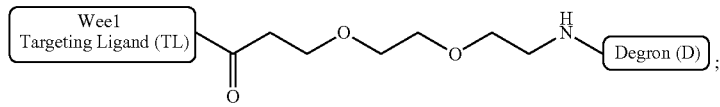
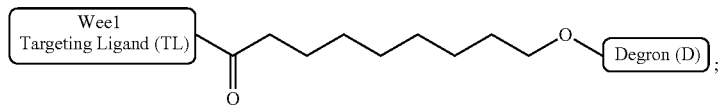
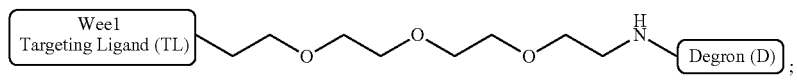
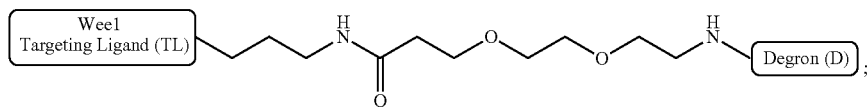
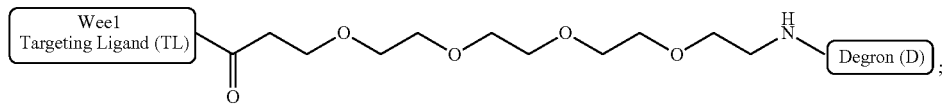
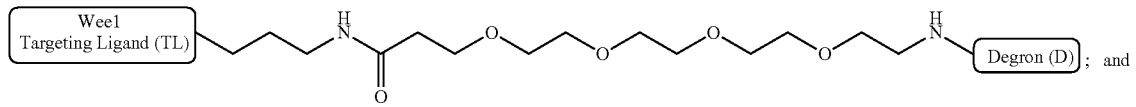
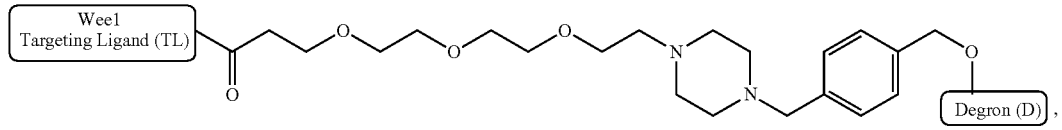
or a pharmaceutically acceptable salt or stereoisomer thereof.

In some embodiments, the bifunctional compounds of the present invention are represented by any one of the following structures
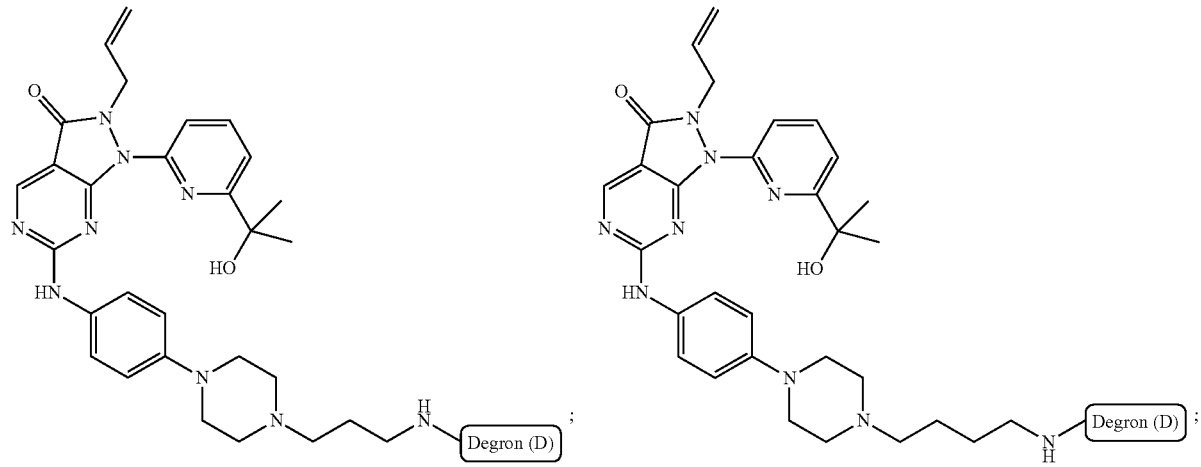
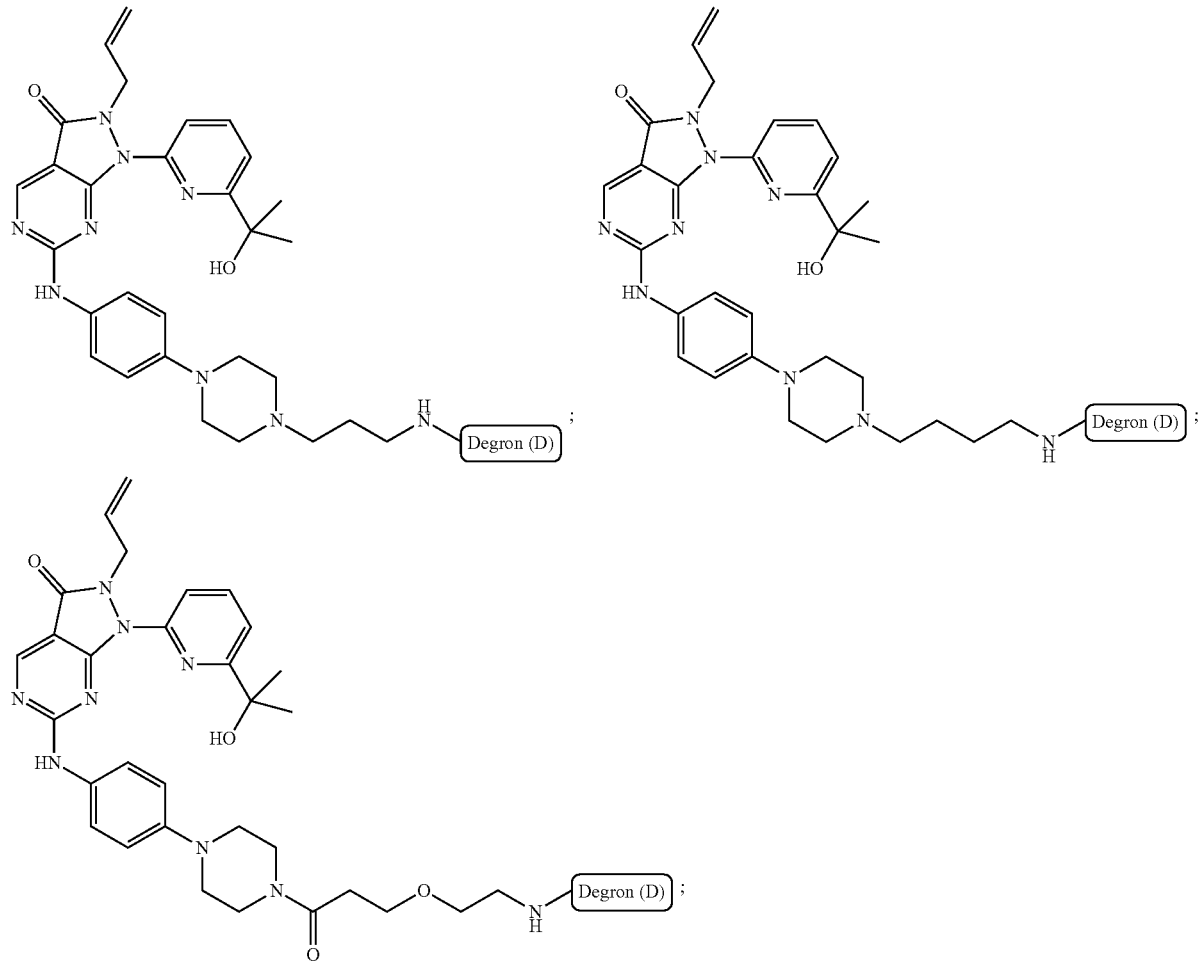
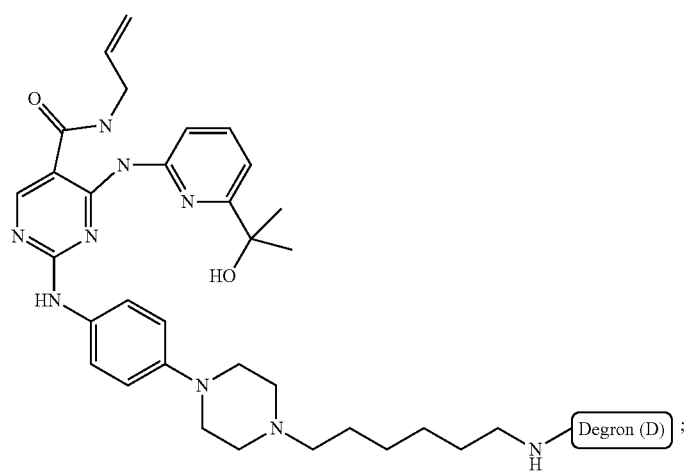

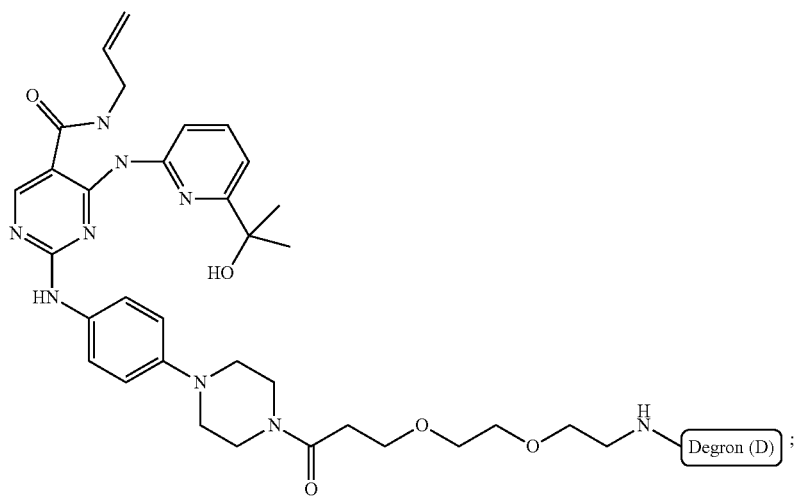
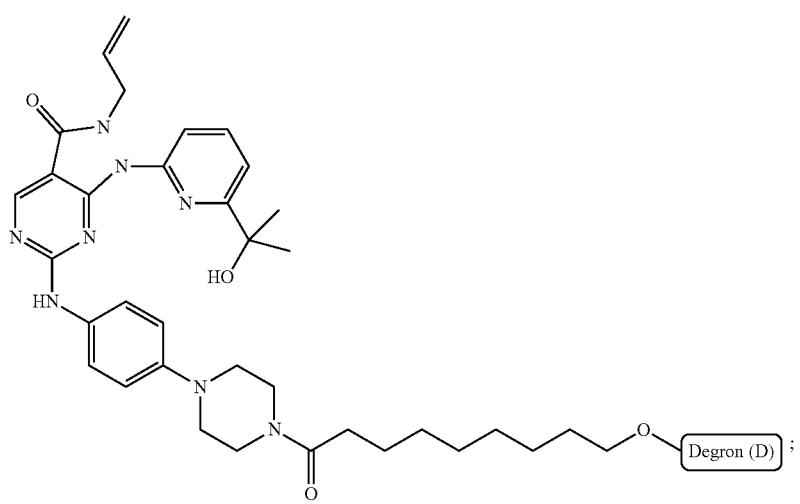
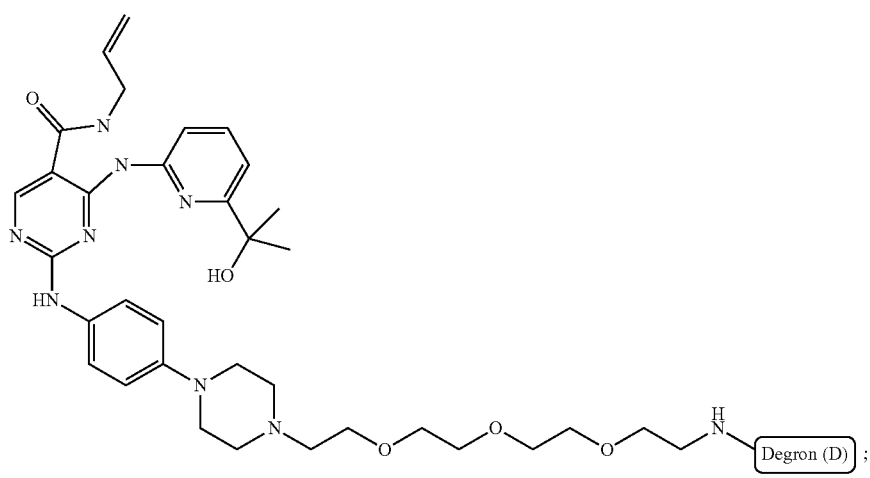

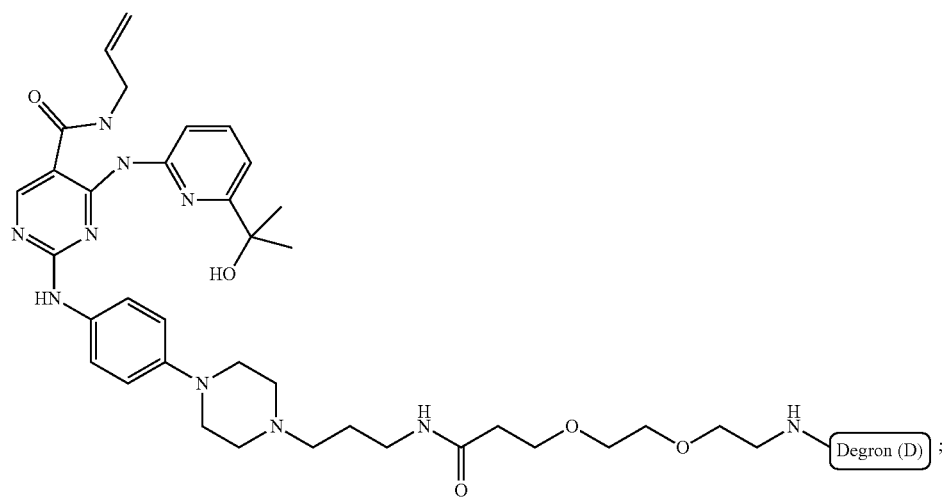
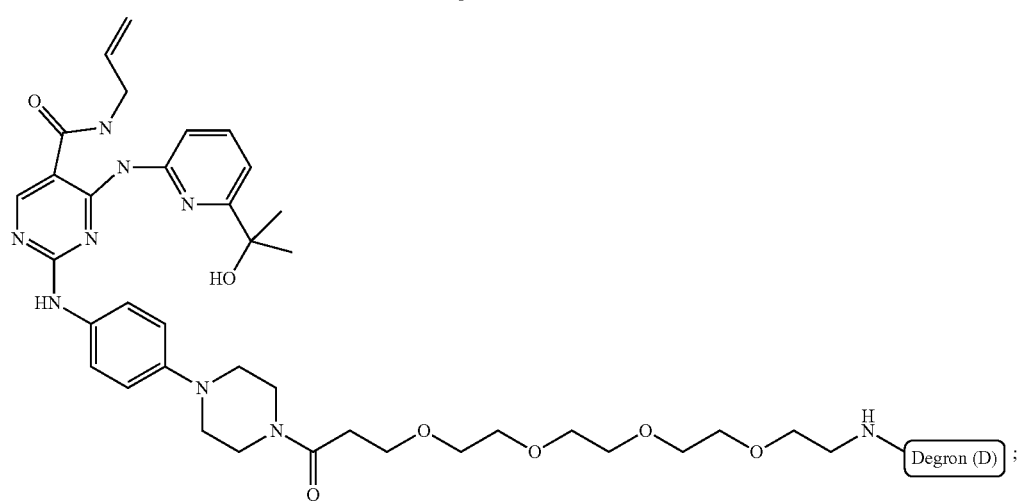
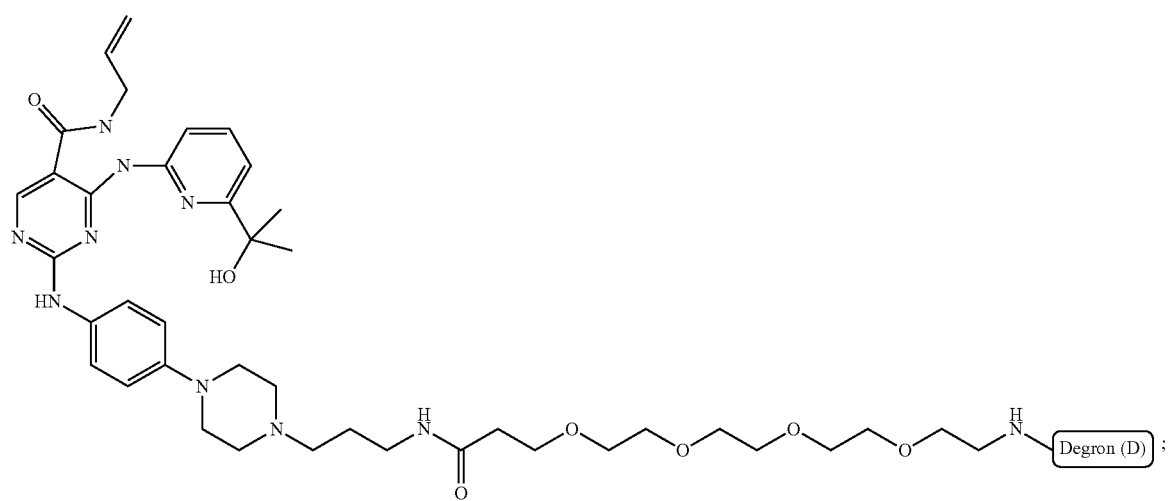

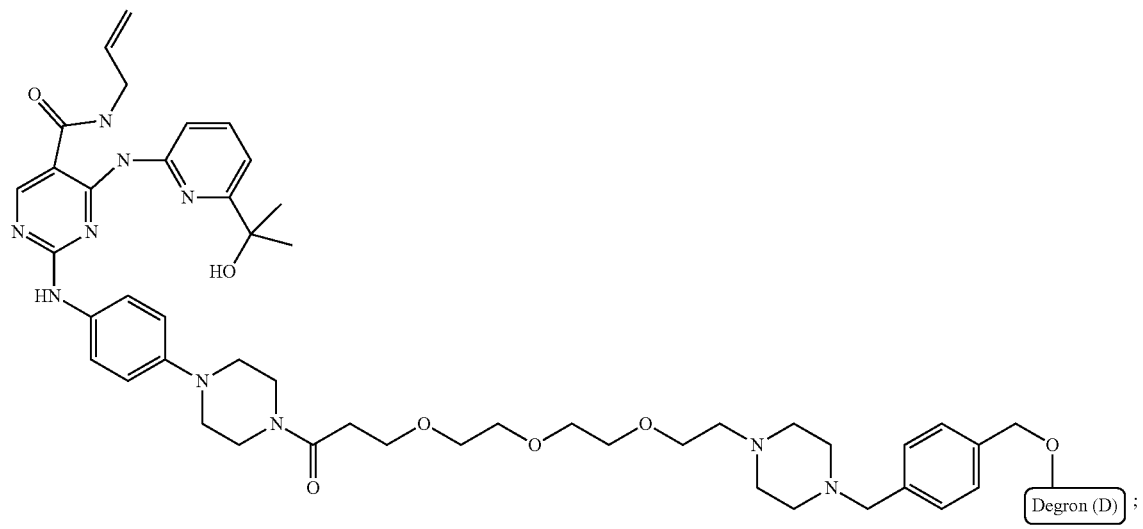
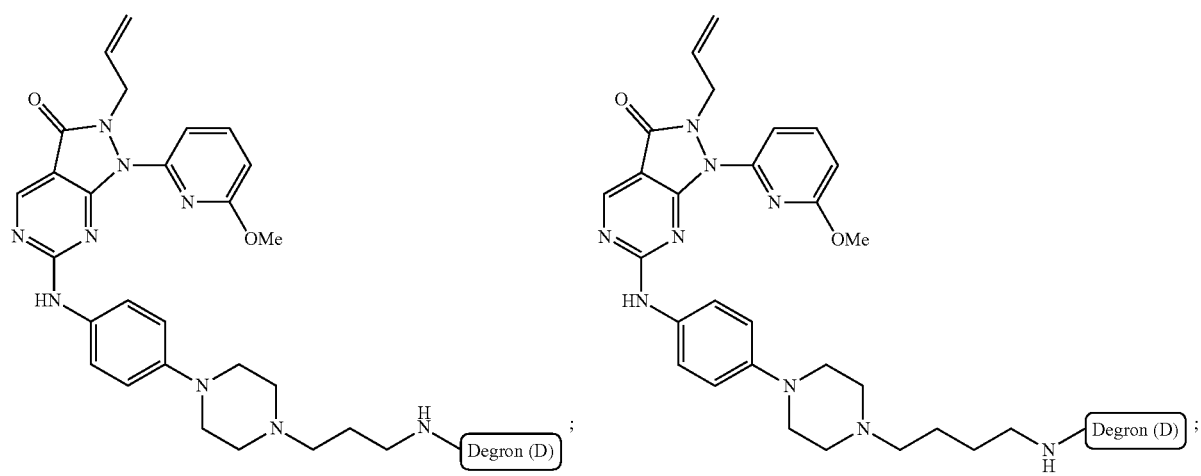
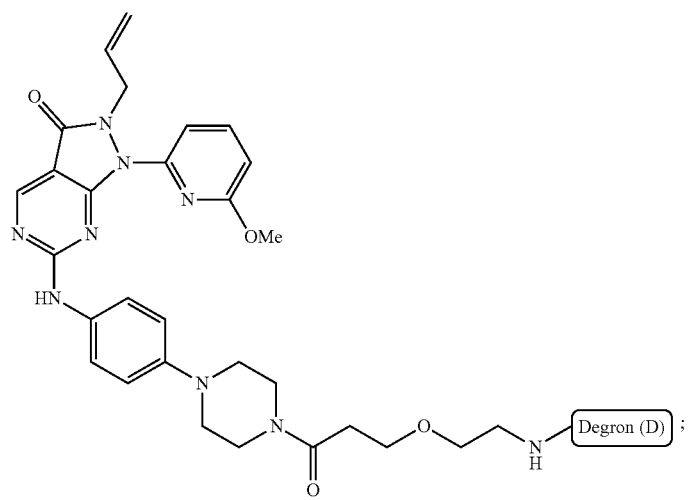

-continued
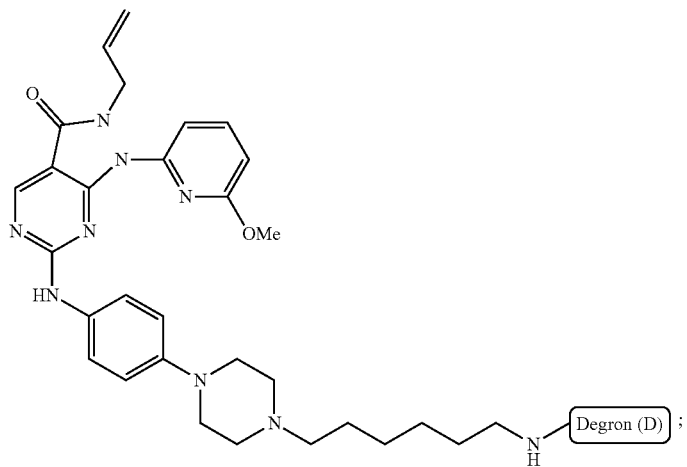
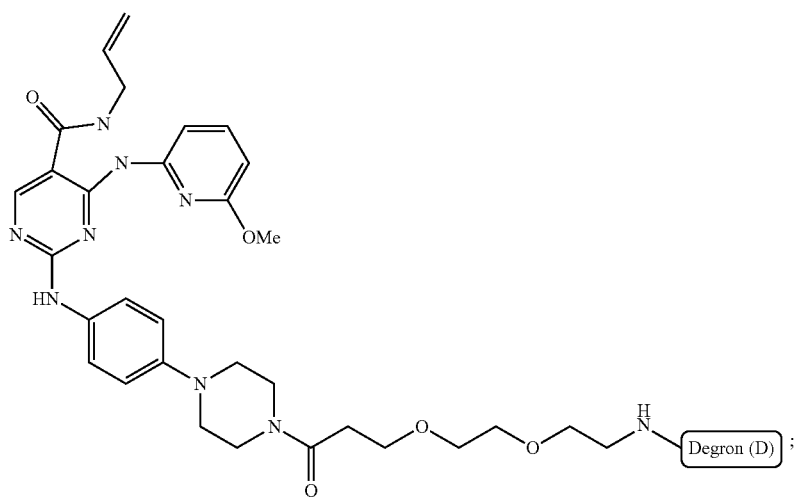
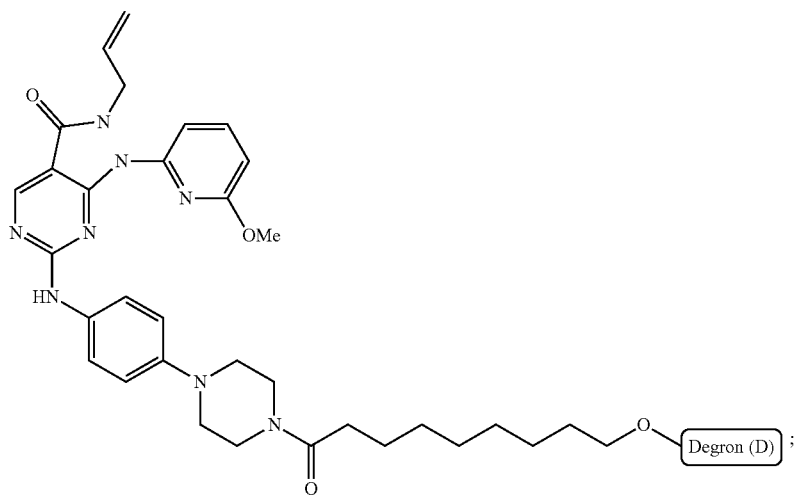

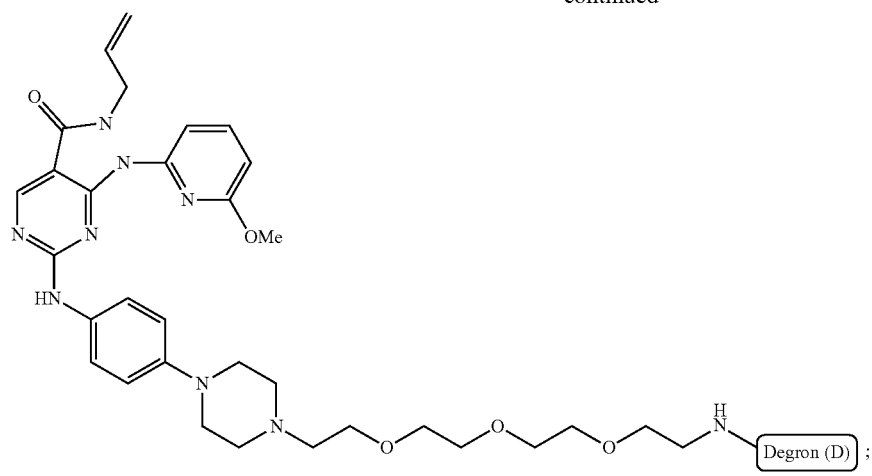
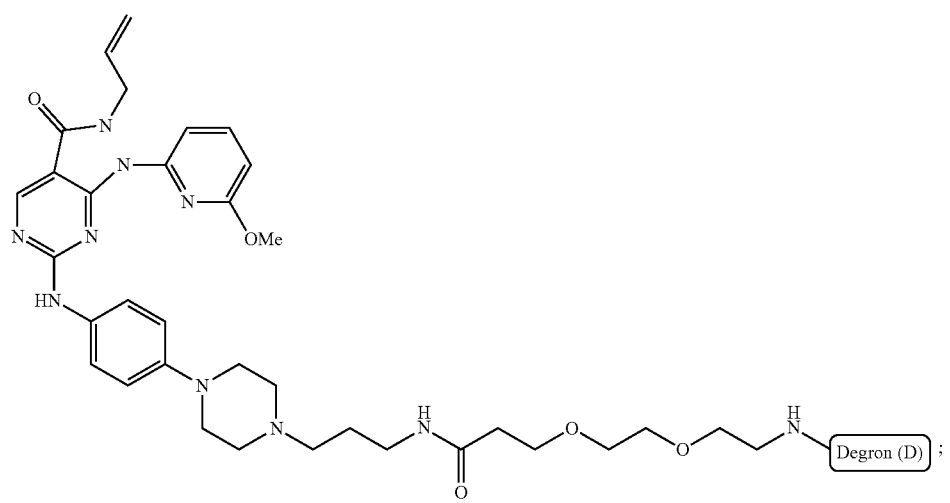
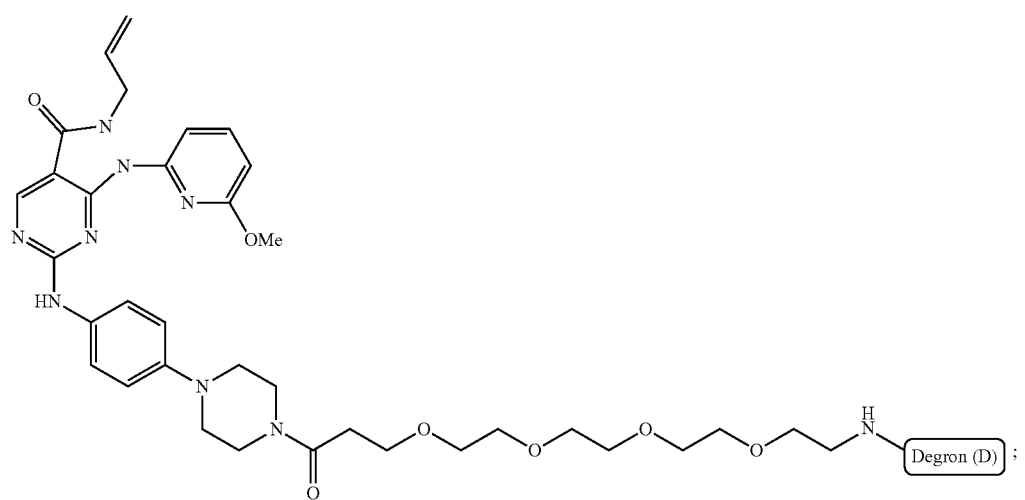

-continued
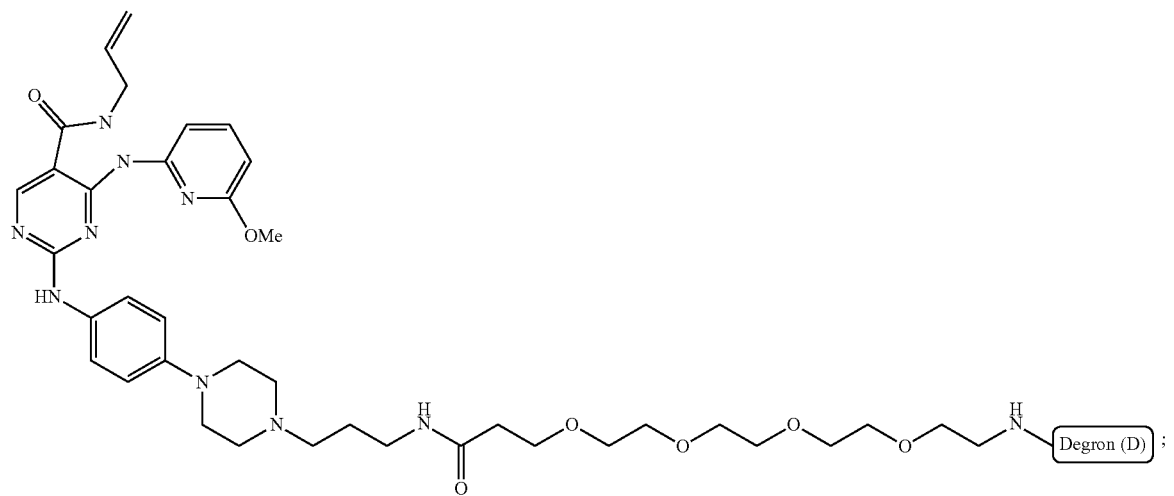
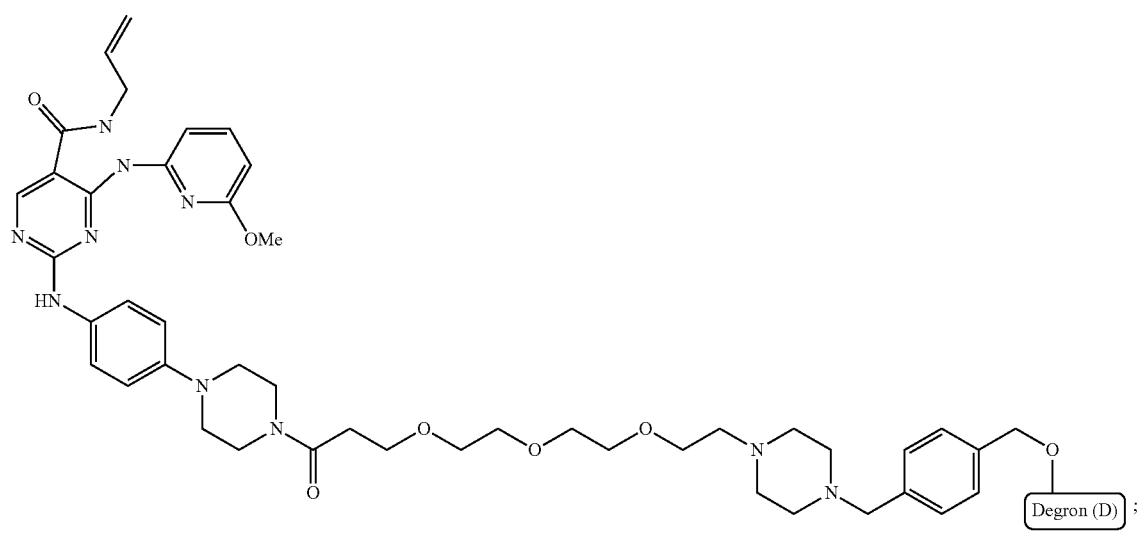
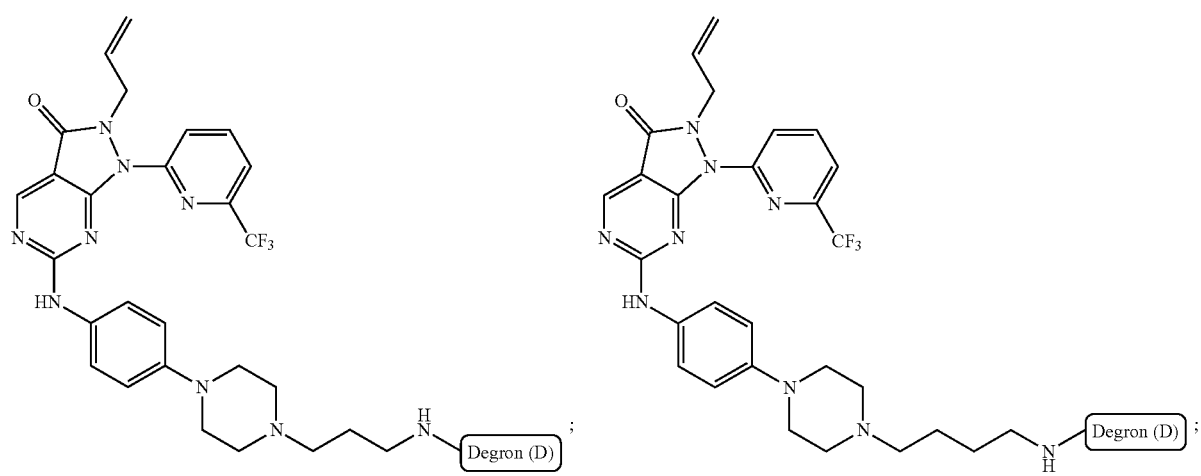

-continued
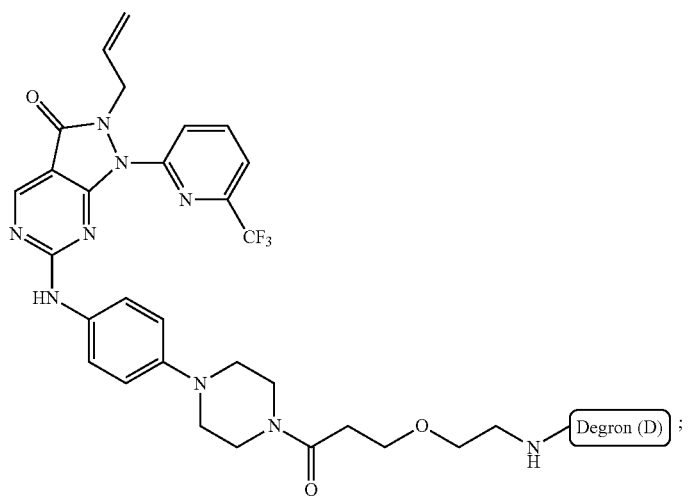
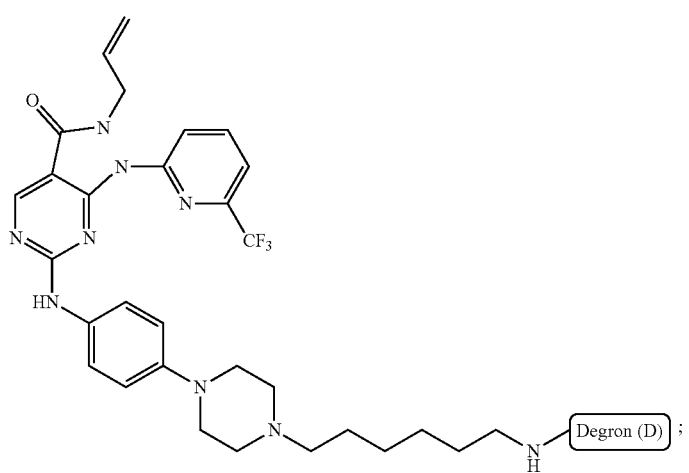
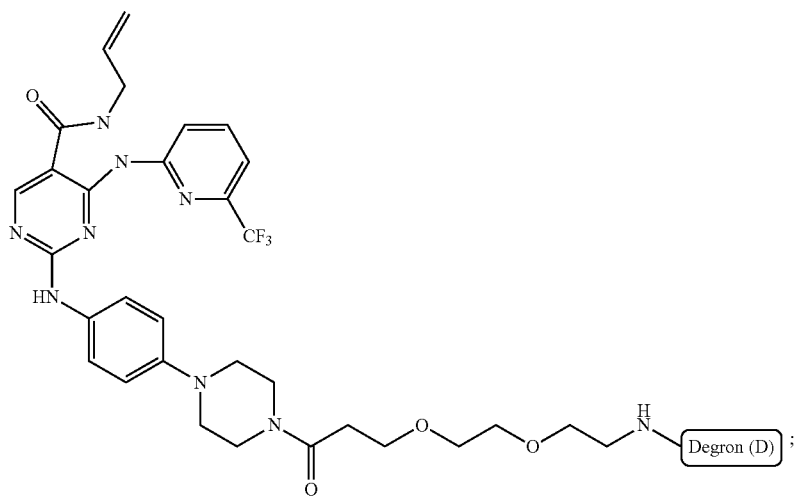

-continued
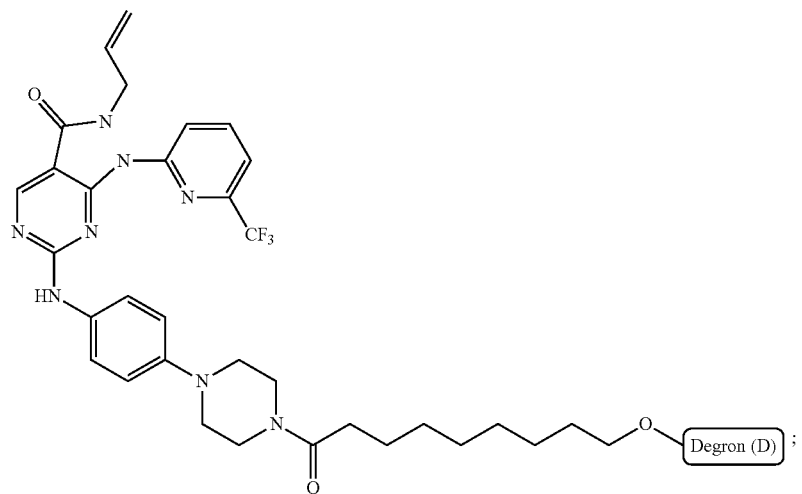
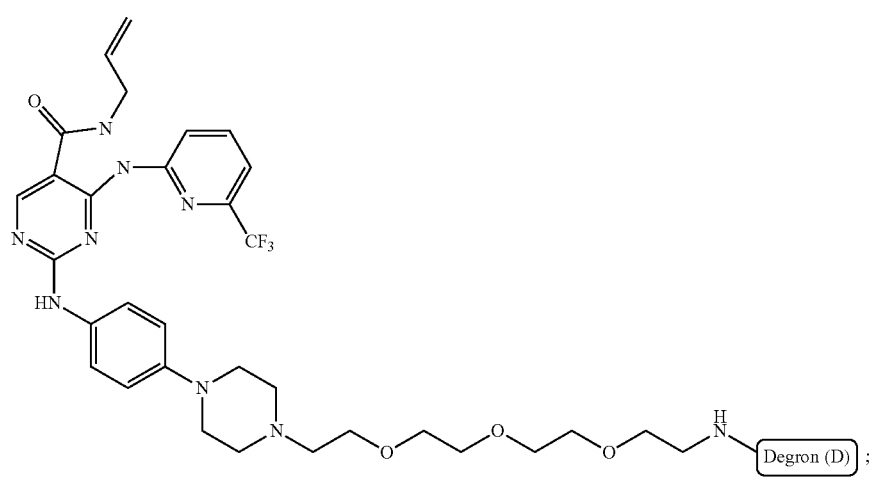
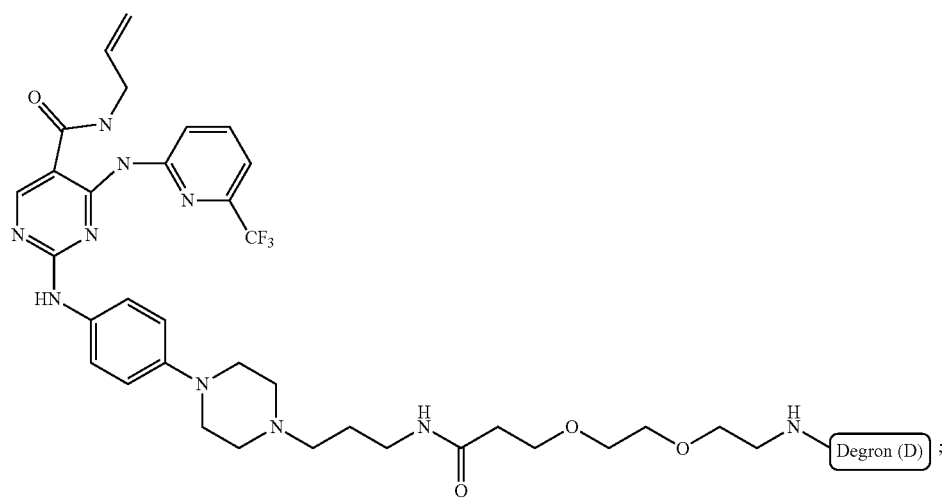

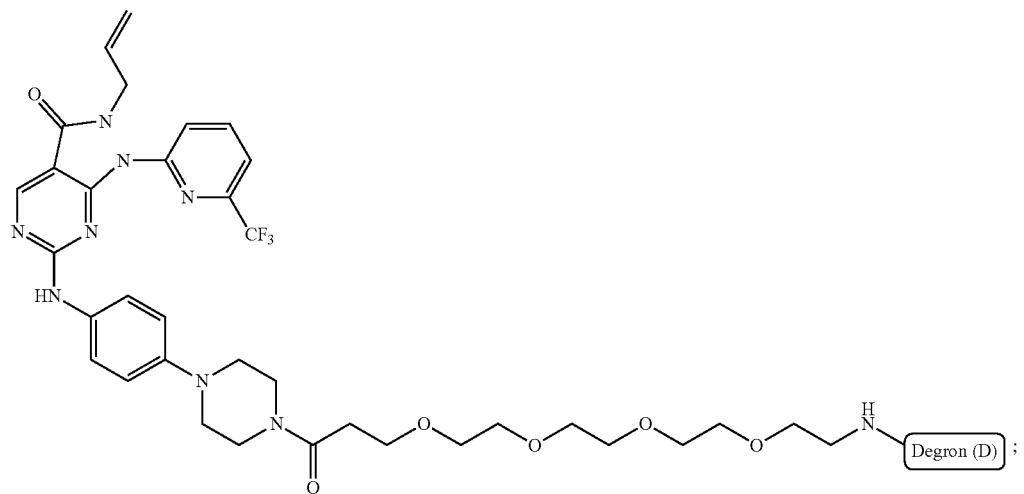
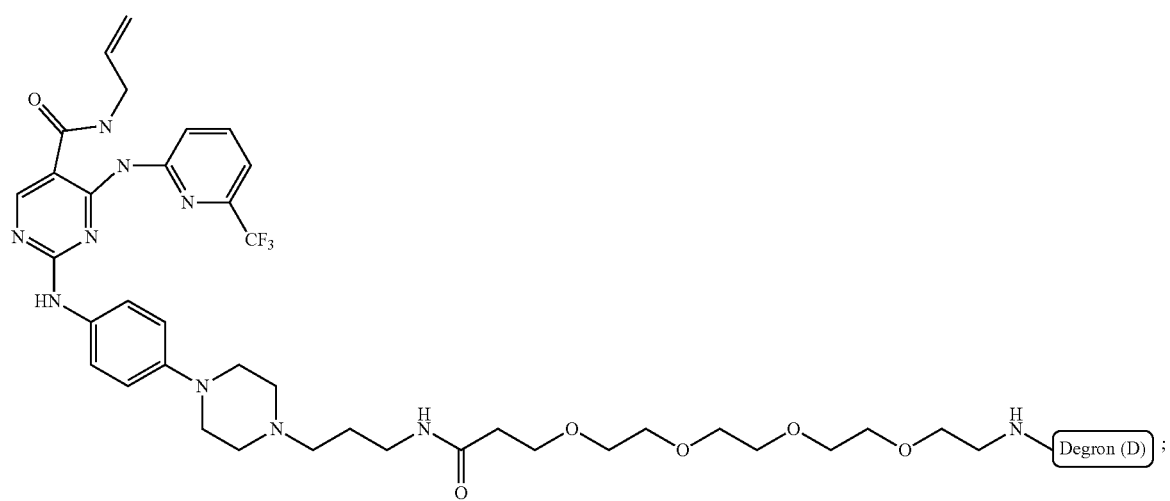
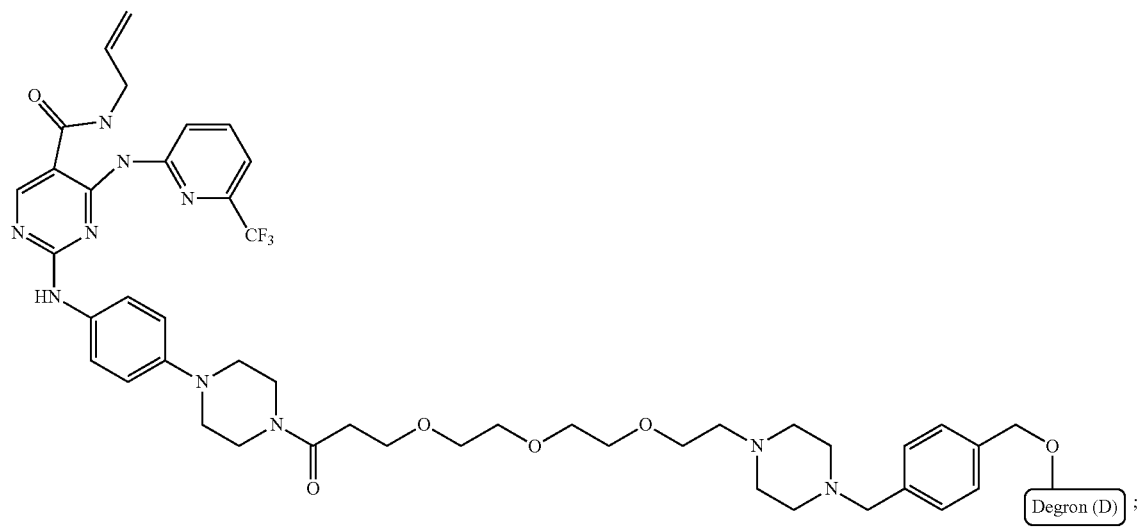

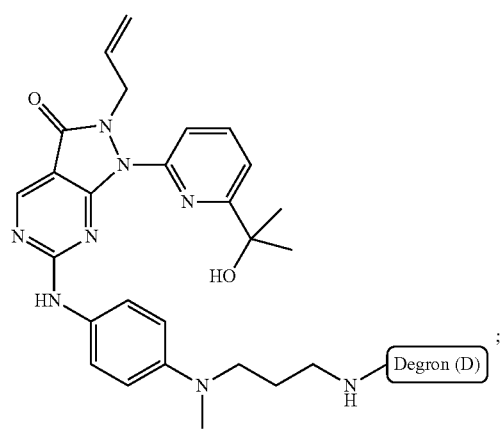
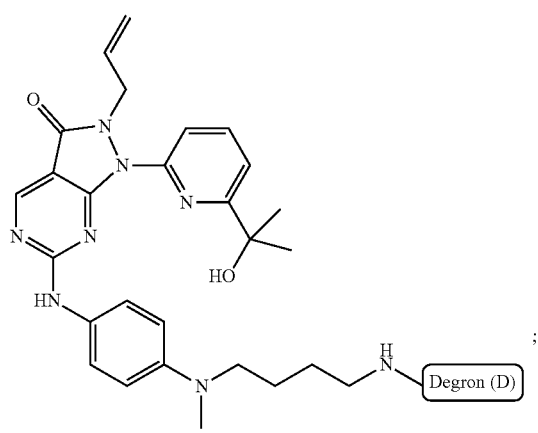
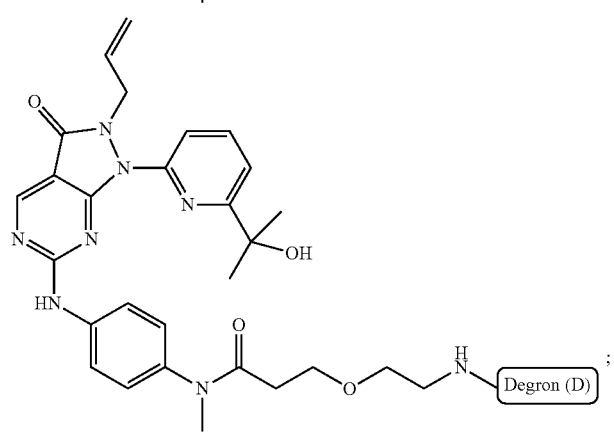
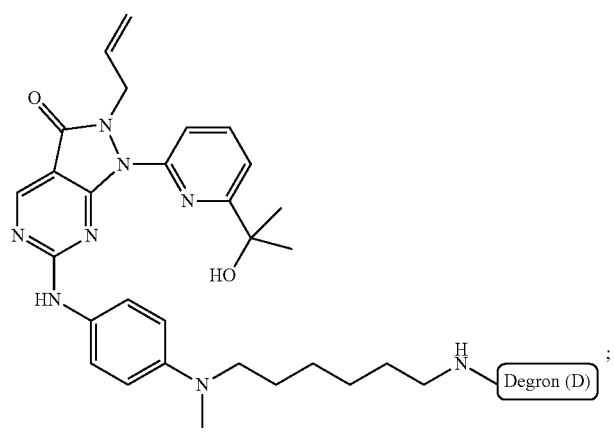
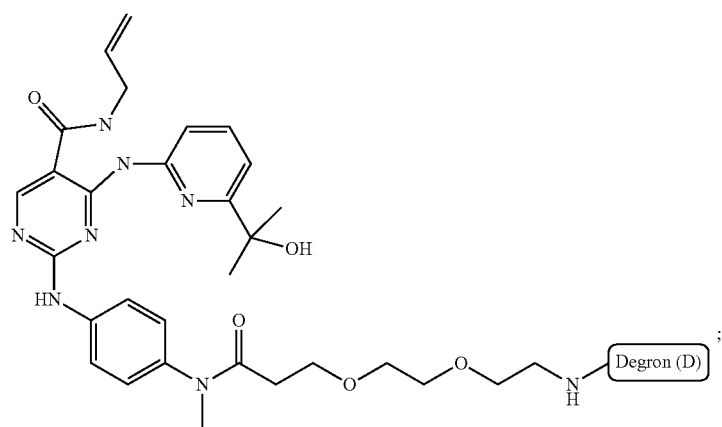

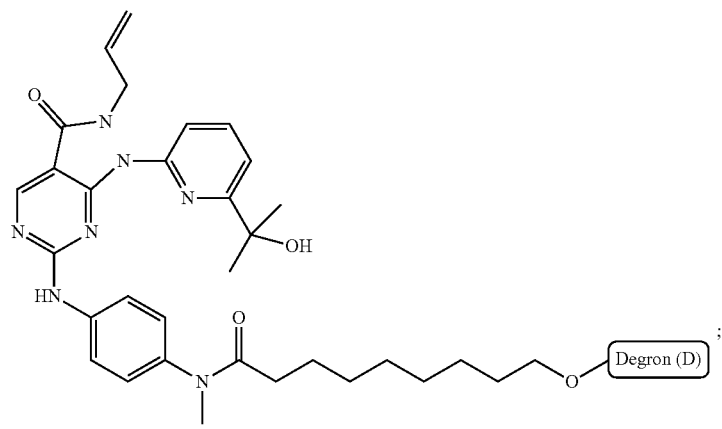
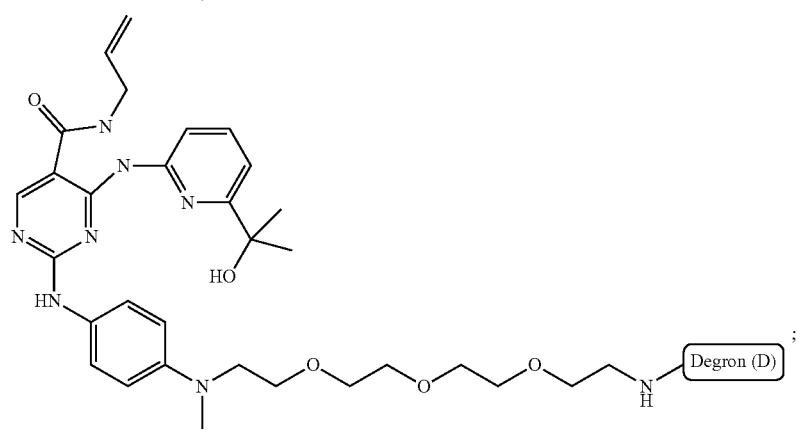
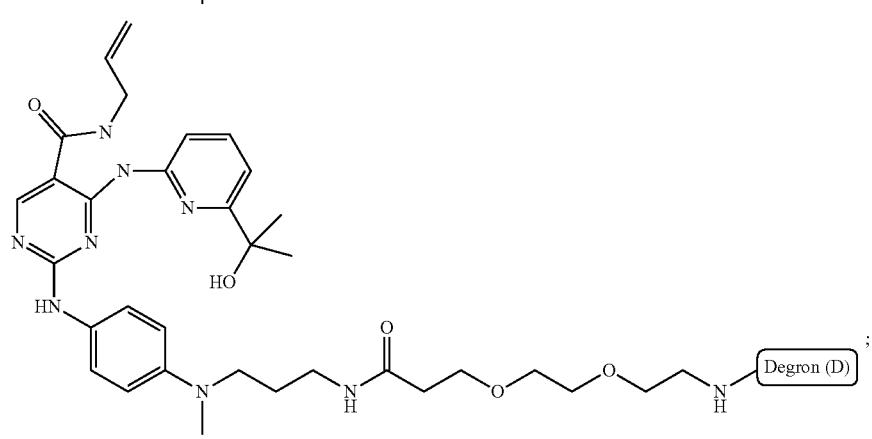
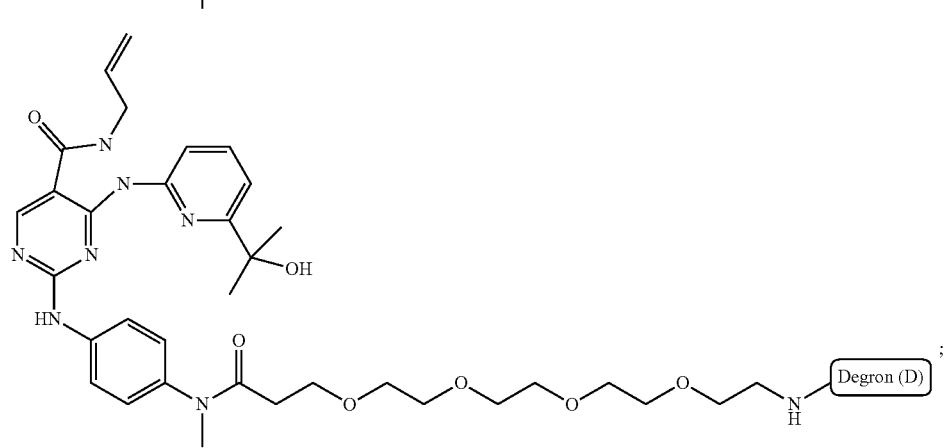

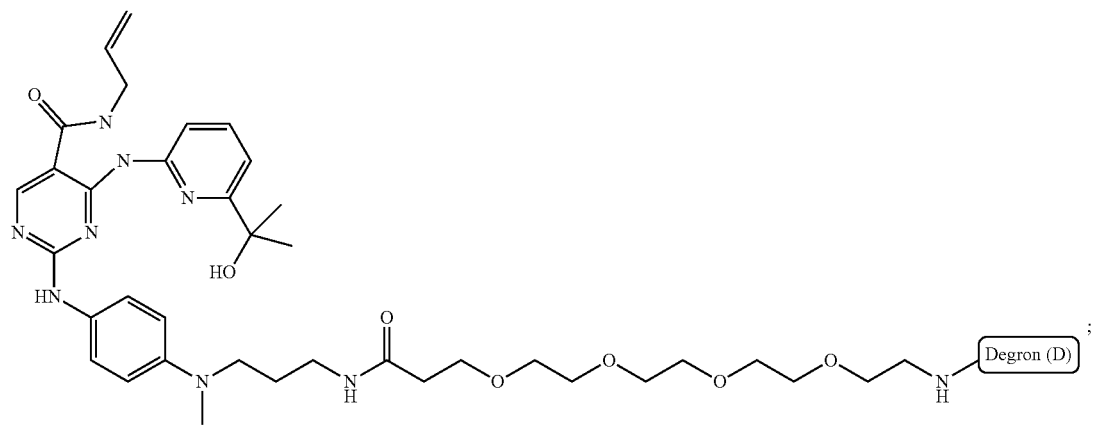
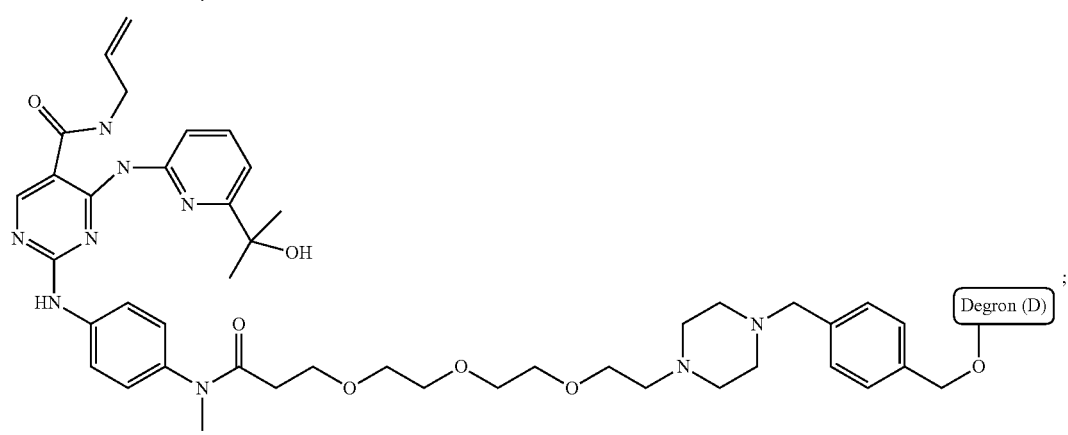
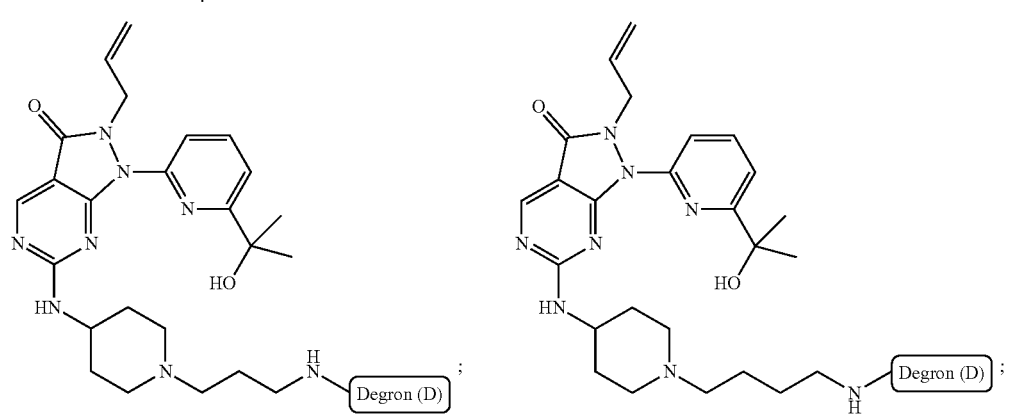
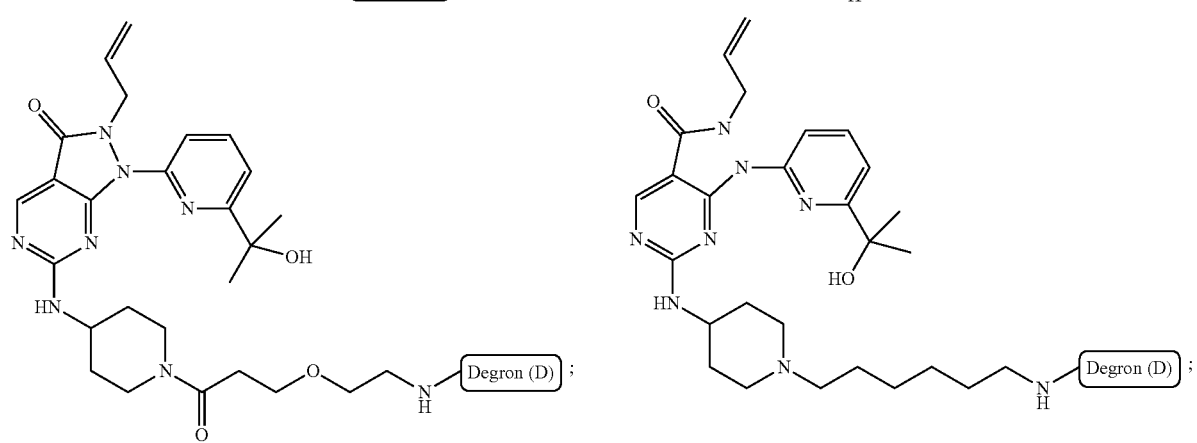

-continued
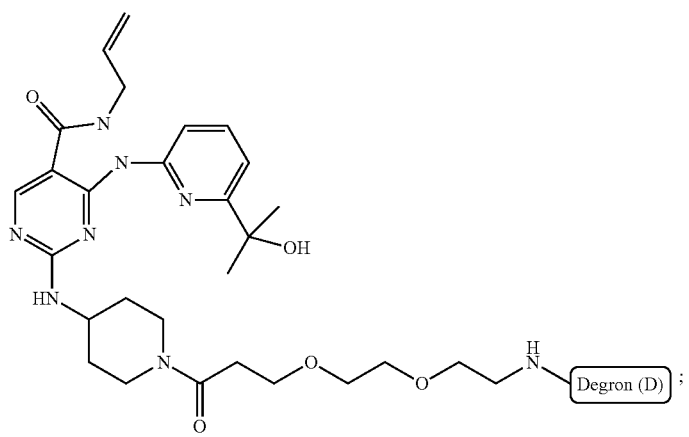
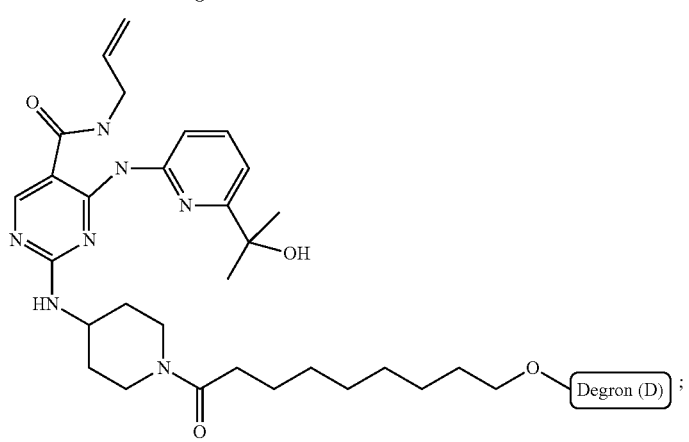
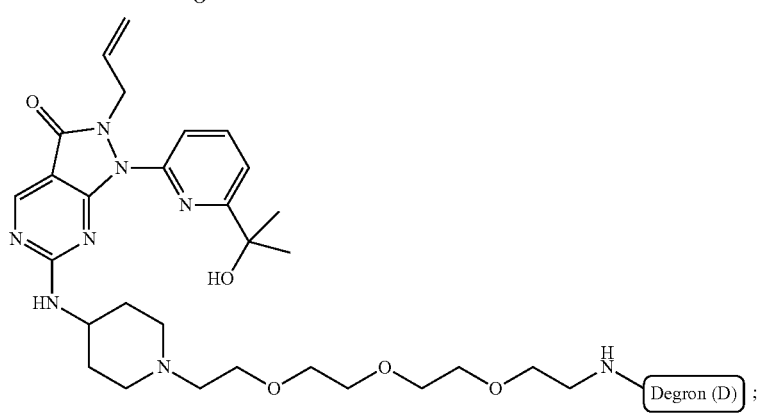
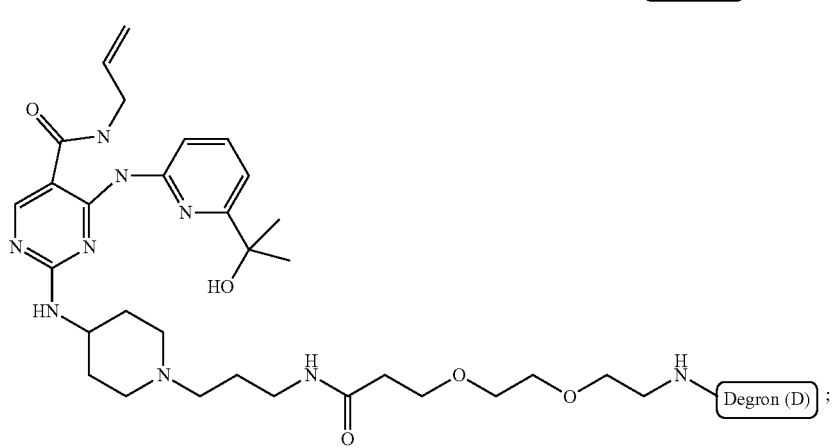

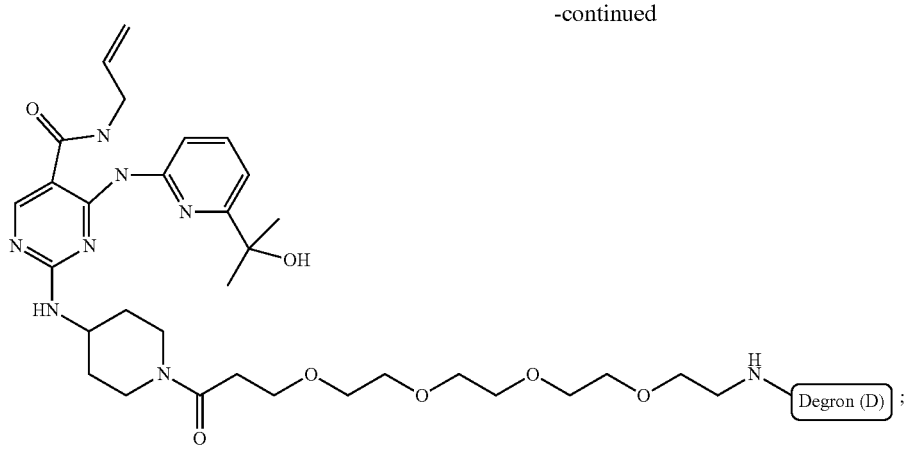

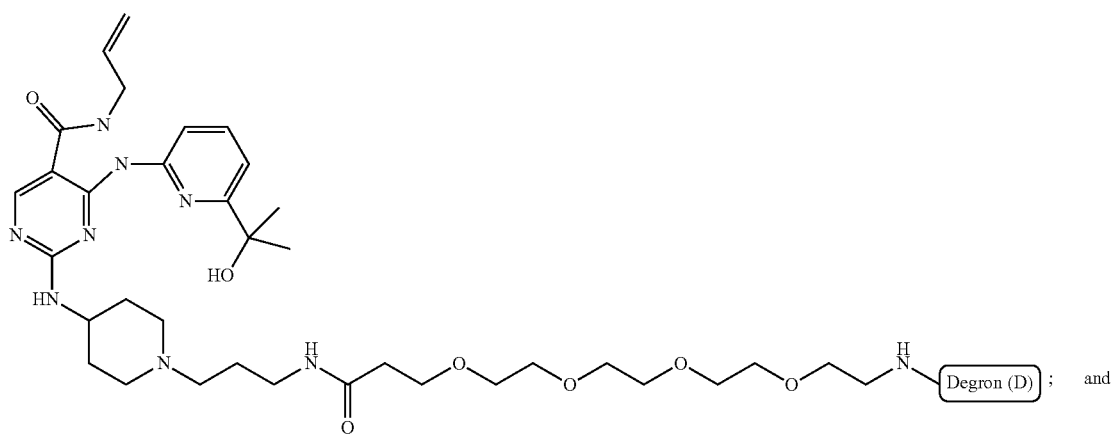

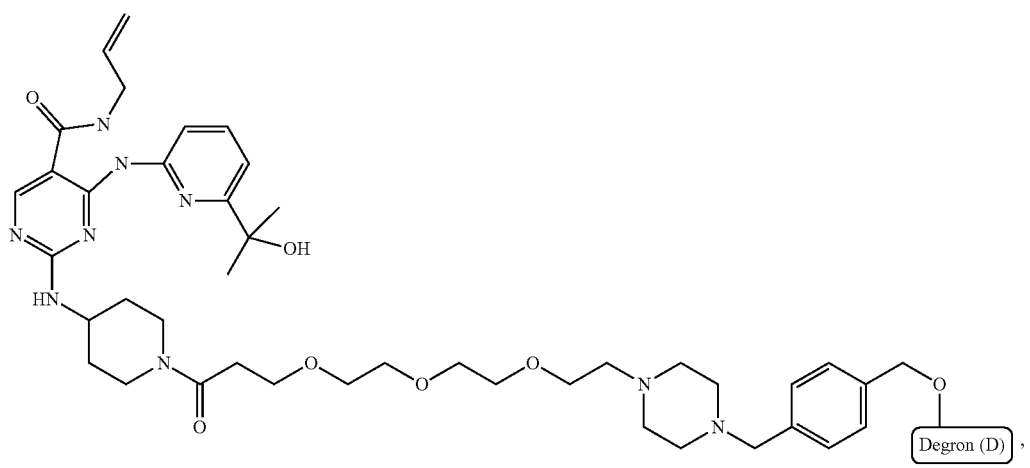

or a pharmaceutically acceptable salt or stereoisomer thereof.

Degrons

The Ubiquitin-Proteasome Pathway (UPP) is a critical cellular pathway that regulates key regulator proteins and degrades misfolded or abnormal proteins. UPP is central to multiple cellular processes. The covalent attachment of ubiquitin to specific protein substrates is achieved through the action of E3 ubiquitin ligases. These ligases include over 500 different proteins and are categorized into multiple classes defined by the structural element of their E3 functional activity.

In some embodiments, the degron binds the E3 ubiquitin ligase which is cereblon (CRBN), and is represented by any one of the following structures:

(D1-a)
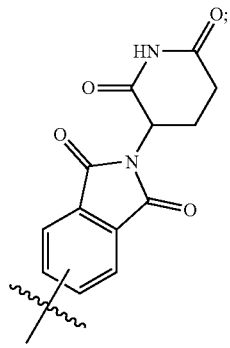

(D1-b)
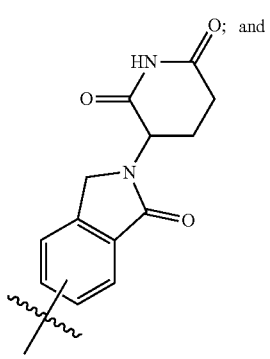

(D1-c)
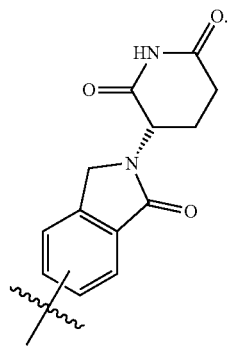

Thus, in some embodiments, the bifunctional compounds of the present invention are represented by any one of the following structures:

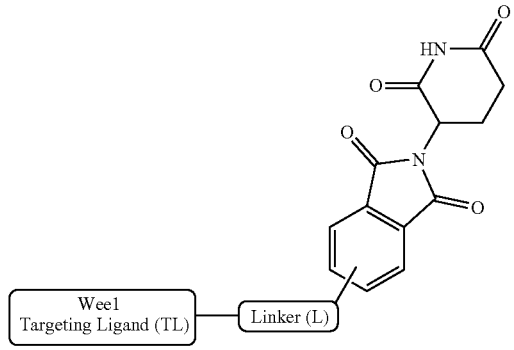
and

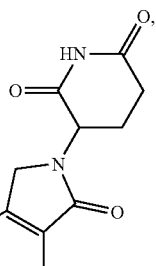

or a pharmaceutically acceptable salt or stereoisomer thereof.

In some embodiments, the bifunctional compounds of the present invention are represented by any one of the following structures:

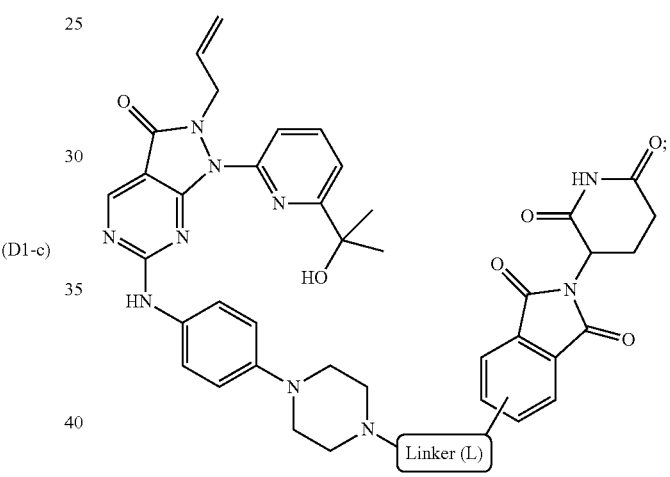

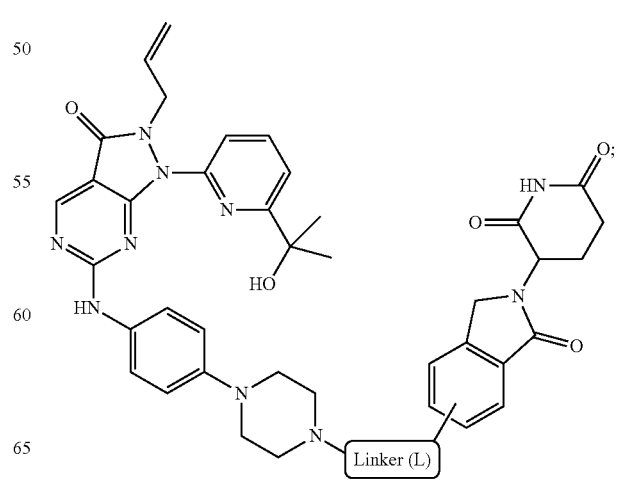

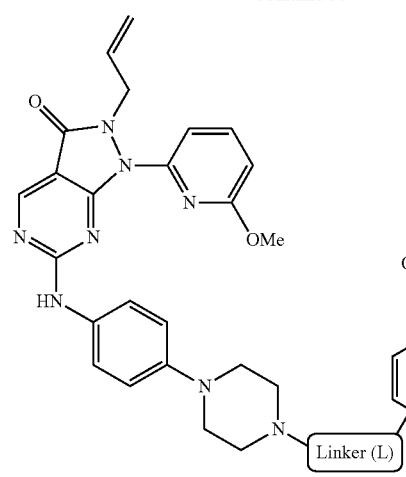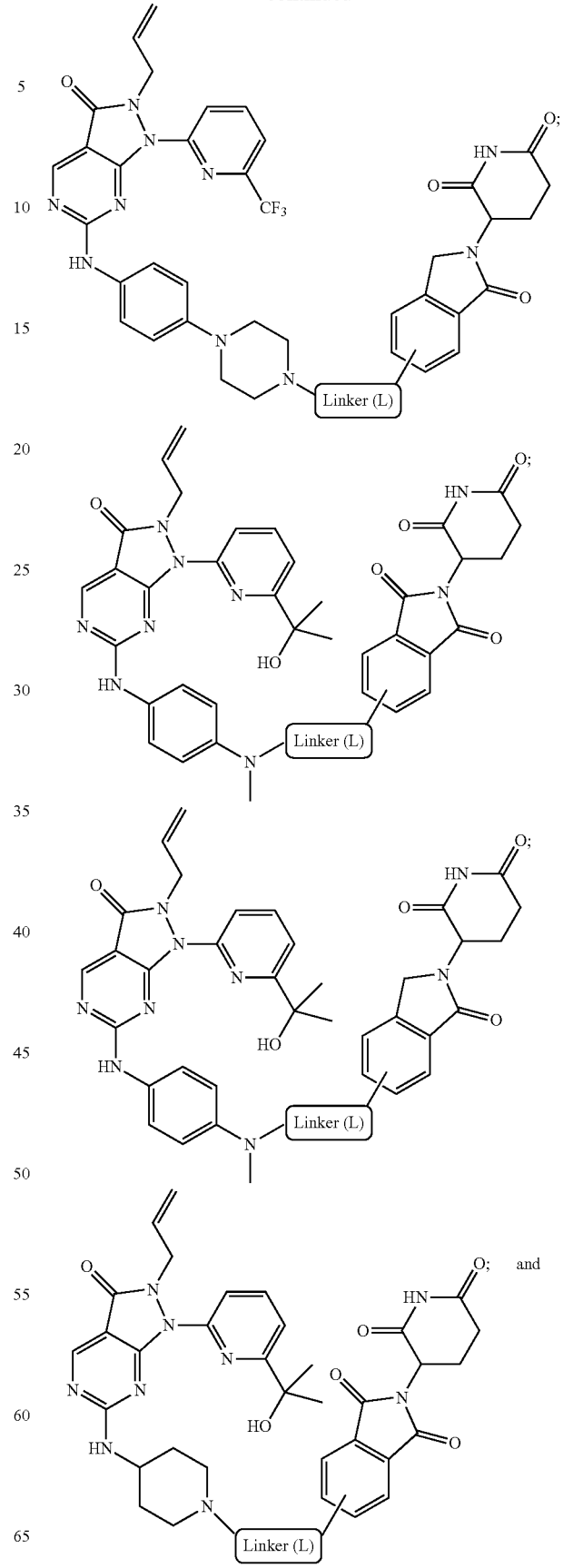

-continued

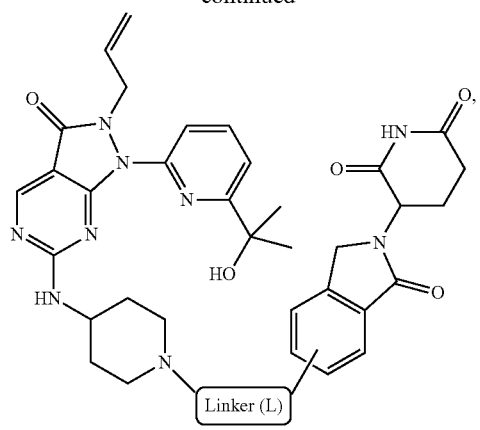

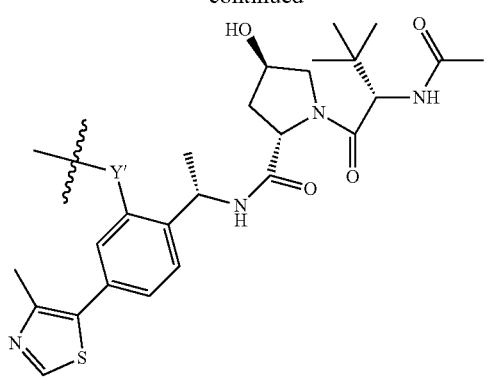

wherein Y' is a bond, N, O or C;

or a pharmaceutically acceptable salt or stereoisomer thereof.

Yet other degrons that bind cereblon and which may be suitable for use in the present invention are described in U.S. Patent Application Publication 2018/0015085 (e.g., the indolinones such as isoindolinones and isoindoline-1,3-diones embraced by formulae IA ad IA' therein, and the bridged cycloalkyl compounds embraced by formulae IB and IB' therein).

In some embodiments, the E3 ubiquitin ligase that is bound by the degron is the von Hippel-Lindau (VHL) tumor suppressor. See, Iwai et al., Proc. Nat'l. Acad. Sci. USA 96:12436-41(1999).

Representative examples of degrons that bind VHL are as follows:

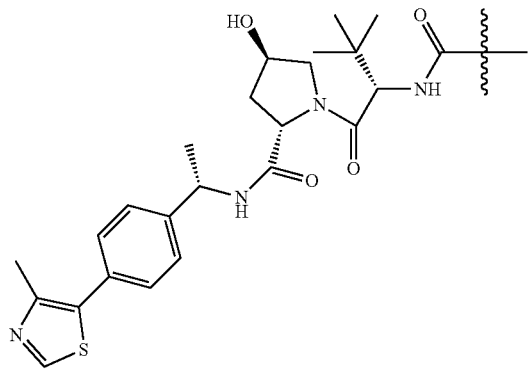

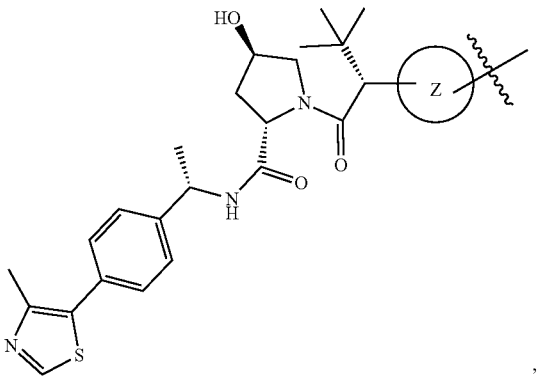

wherein Z is a cyclic group such as a $C_5$-$C_6$ carbocyclic or heterocyclic group; and

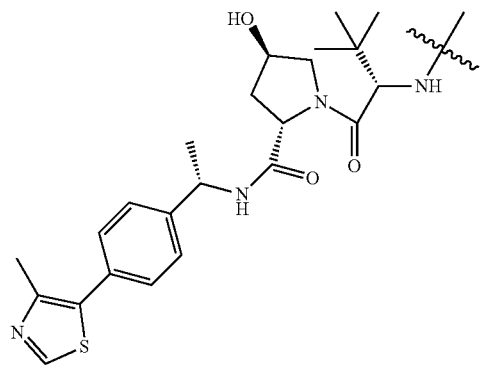

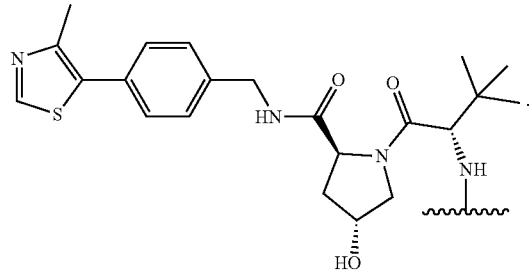 [SMILES: *N[C@H](C(=O)N1C[C@H](O)C[C@H]1C(=O)NCc1ccc(-c2scnc2C)cc1)C(C)(C)C]

Thus, in some embodiments, the bifunctional compounds of the present invention are represented by any one of the following structures:
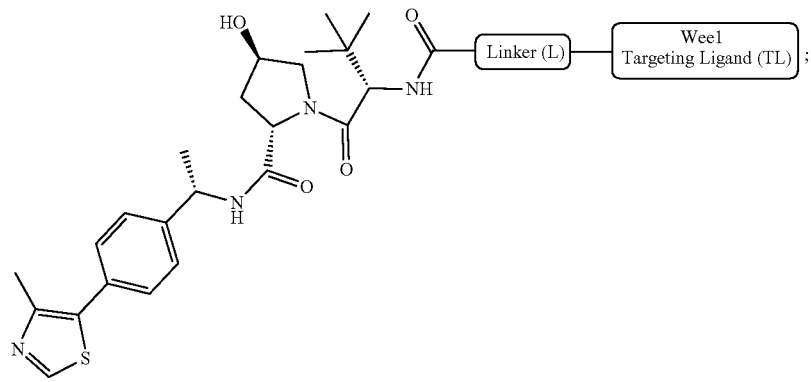
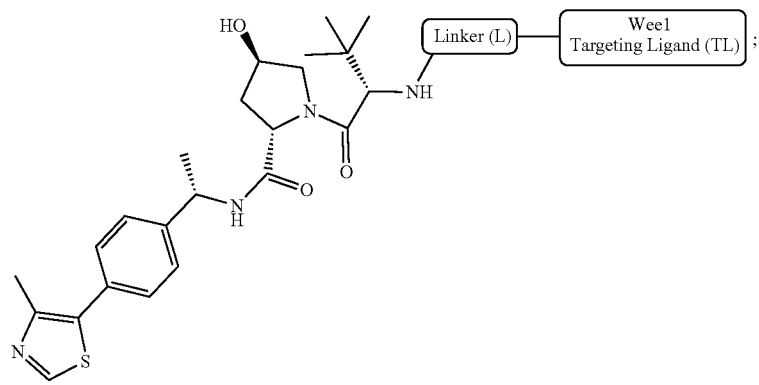
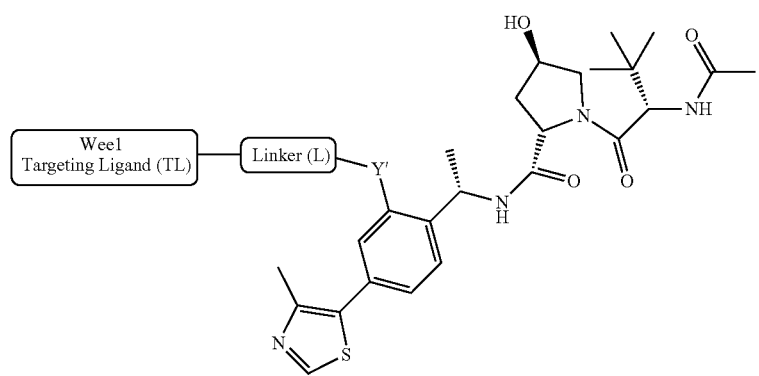

wherein Y' is a bond, N, O or C,
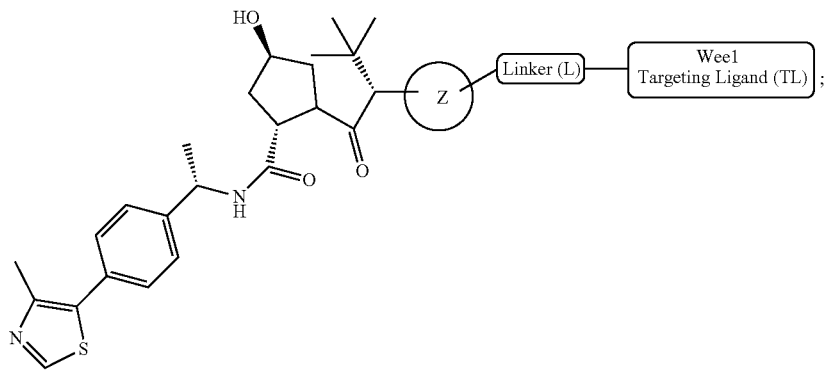
$C_5$-$C_6$ carbocyclic or heterocyclic group; and
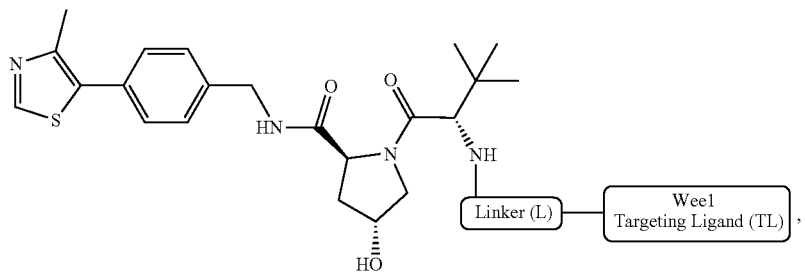
or a pharmaceutically acceptable salt or stereoisomer thereof.
In some embodiments, the bifunctional compounds of the present invention are represented by any one of the following structures:
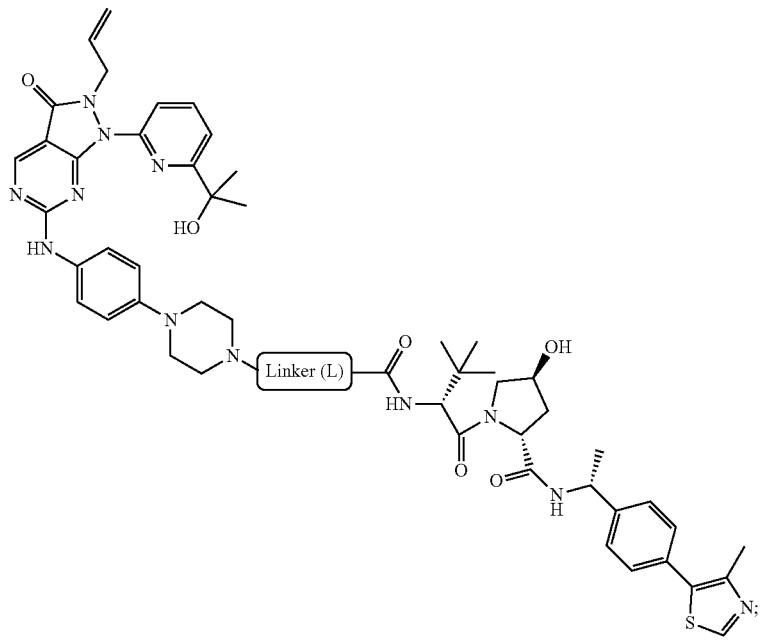

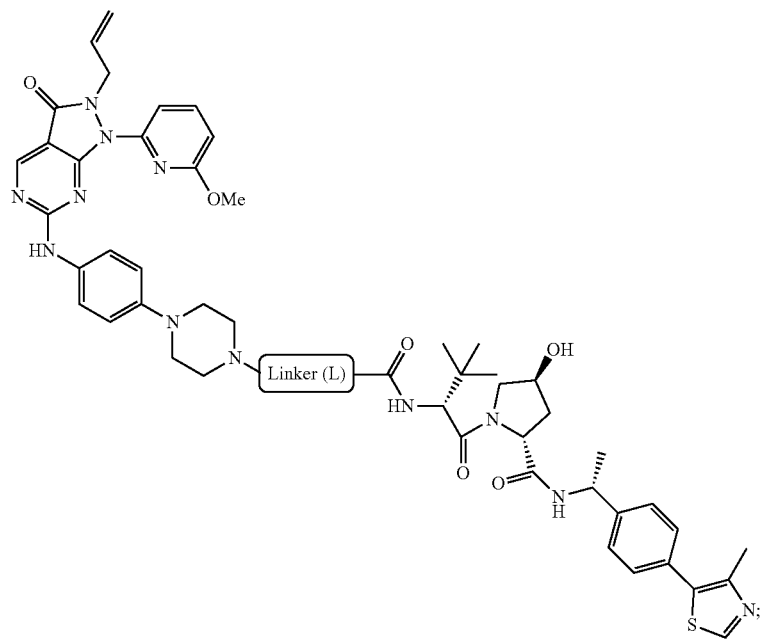
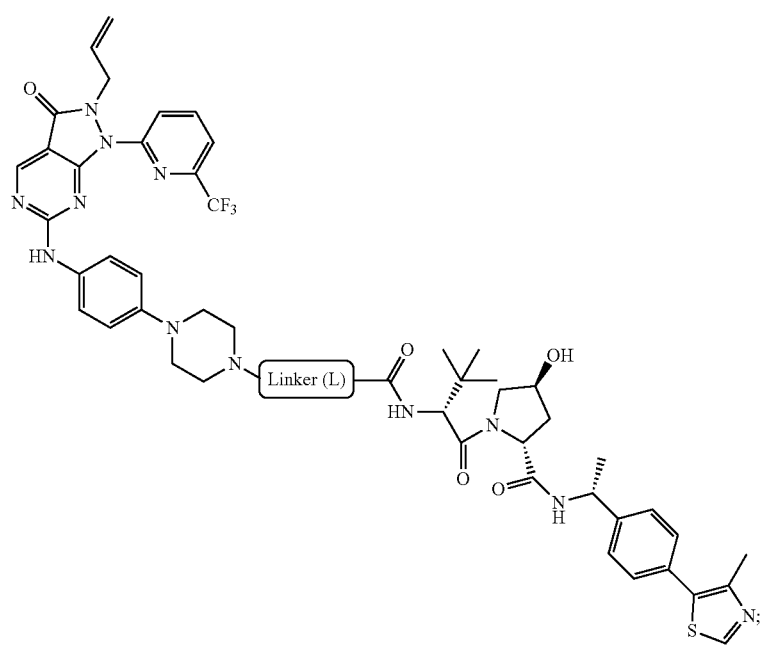

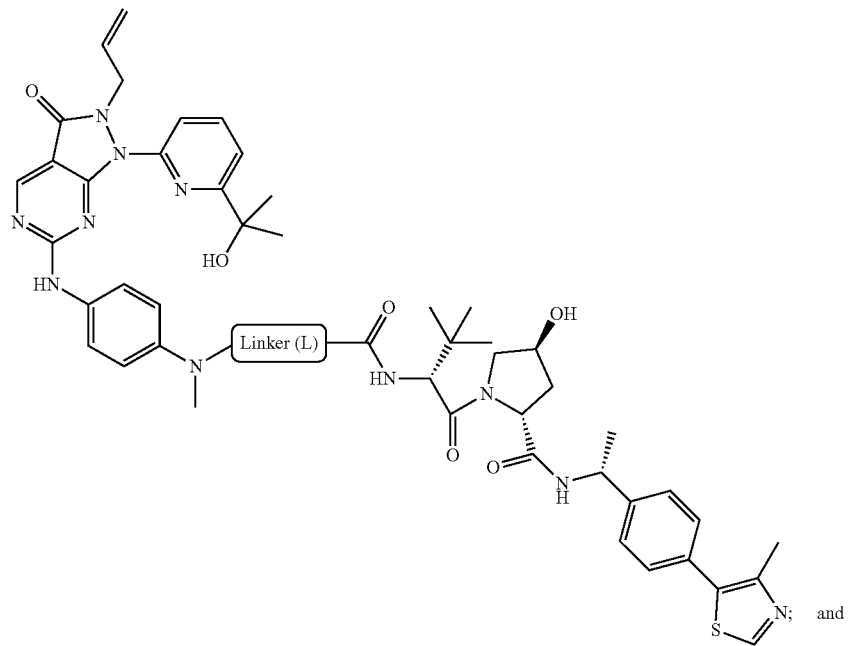
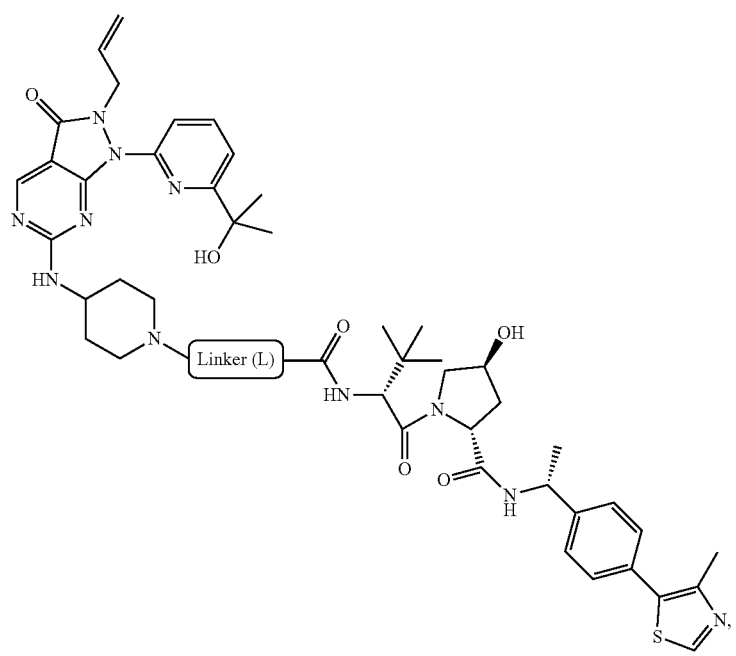 [SMILES: C=CCn1c(=O)c2cnc(NC3CCN(C)CC3)nc2n1-c1cccc(C(C)(C)O)n1 ; CC(=O)N[C@@H](C(=O)N1C[C@@H](O)C[C@@H]1C(=O)N[C@H](C)c1ccc(-c2scnc2C)cc1)C(C)(C)C]
or a pharmaceutically acceptable salt or stereoisomer thereof.

Yet other degrons that bind VHL and which may be suitable for use in the present invention are disclosed in U.S. Patent Application Publication 2017/0121321 A1.
In some embodiments, the bifunctional compounds of the present invention are represented by any one of the following structures:
(1)
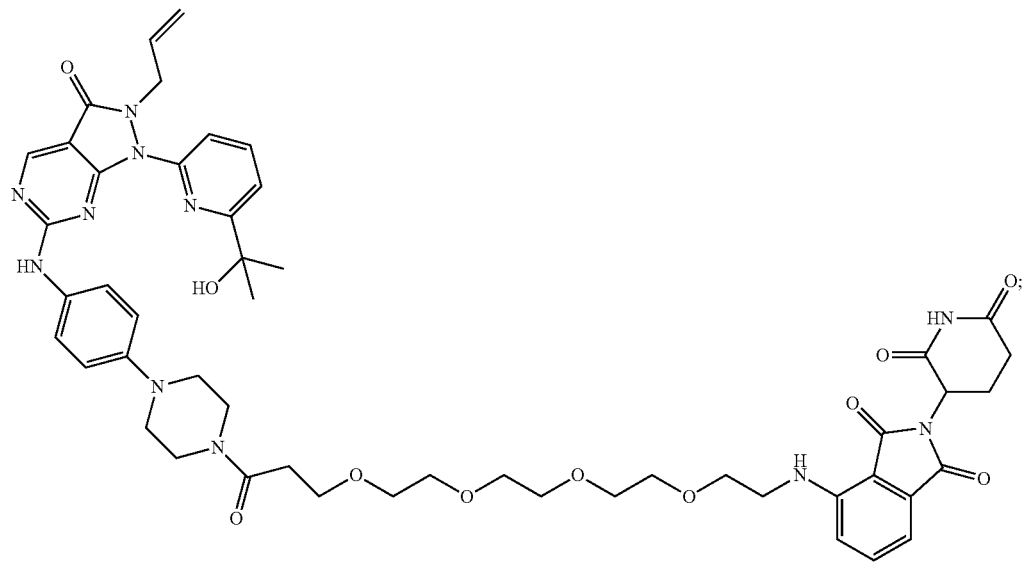
(2)
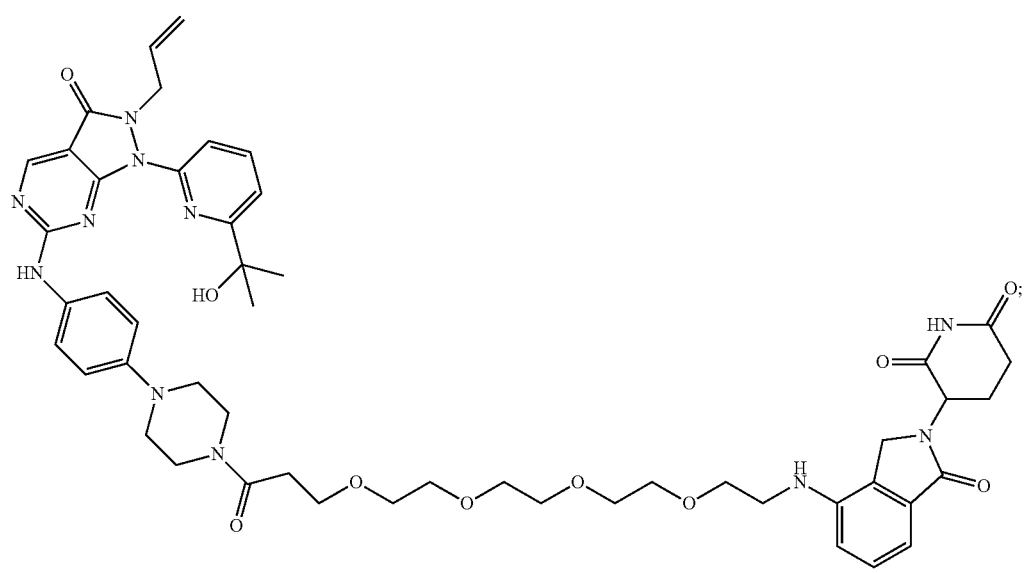

(3)
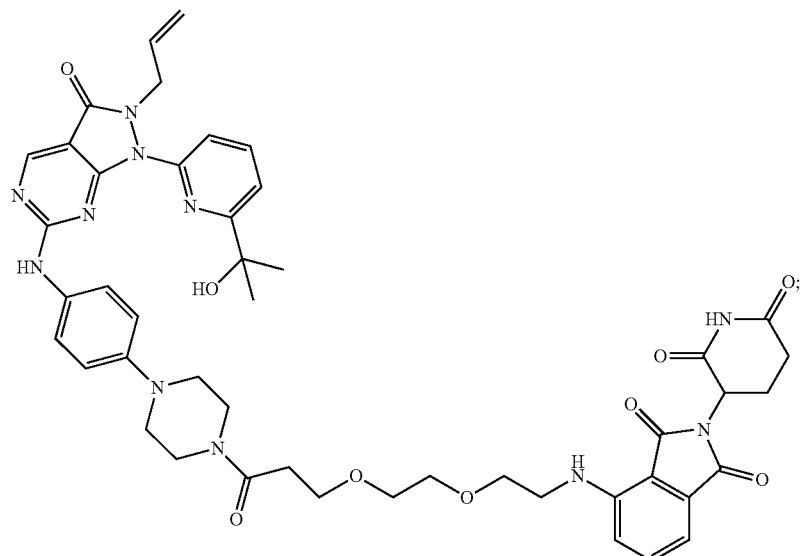
(4)
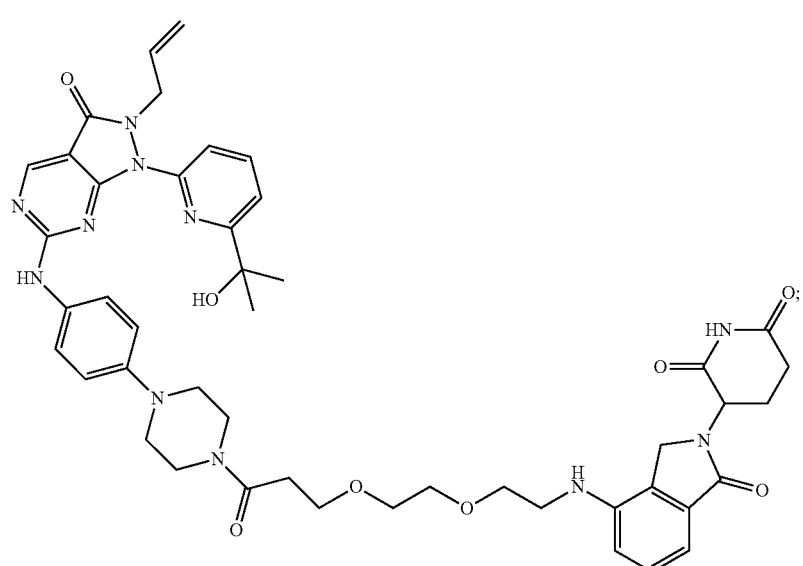
(5)
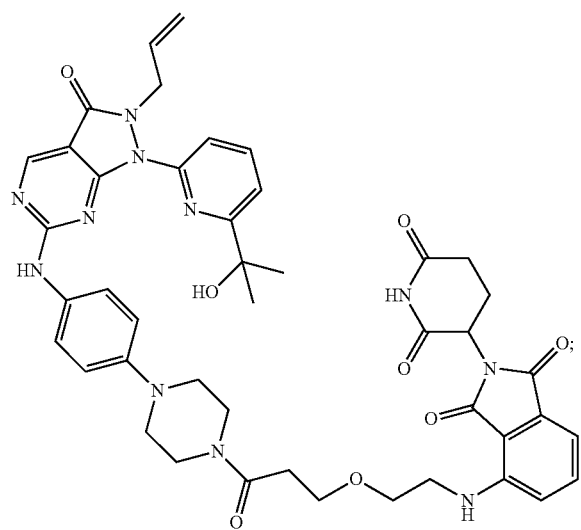

-continued
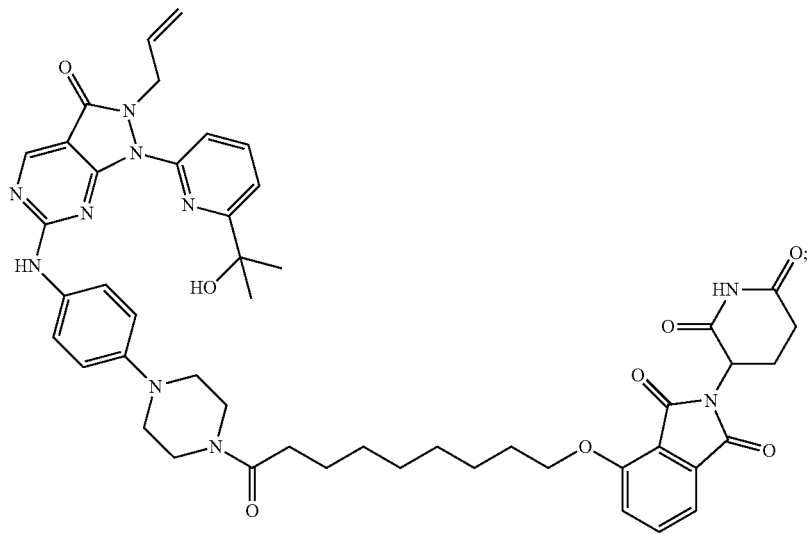
(6)
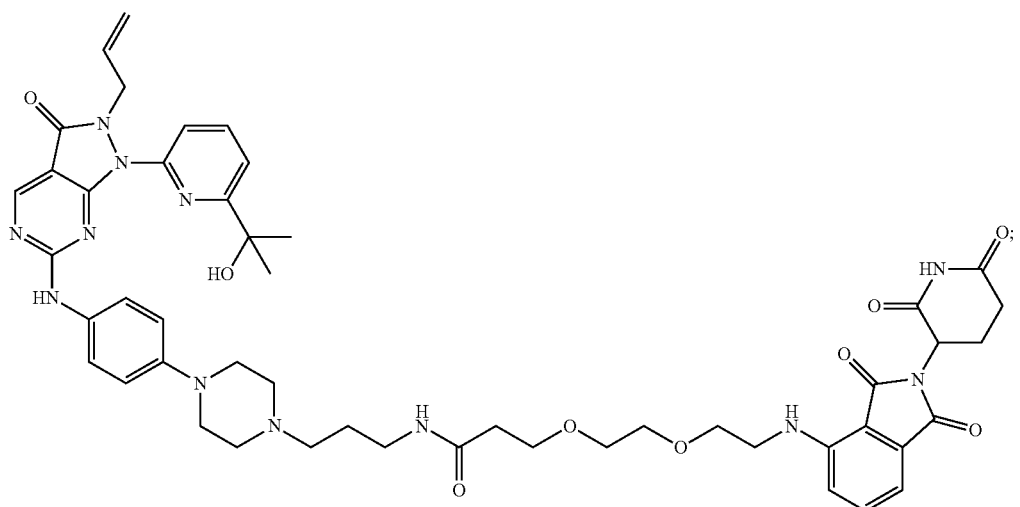
(7)
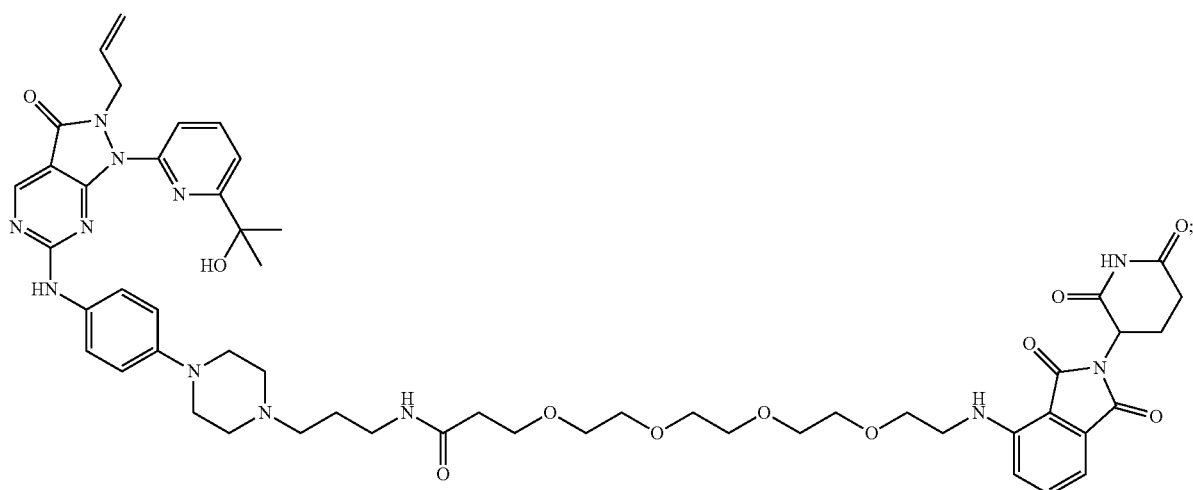
(8)

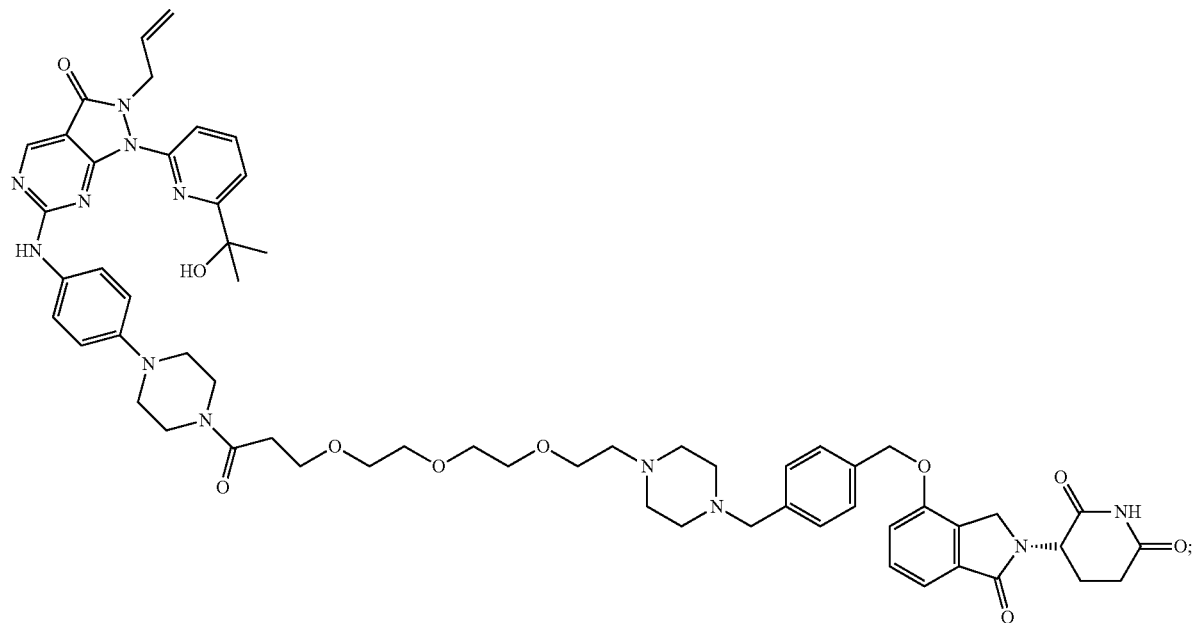
(9)
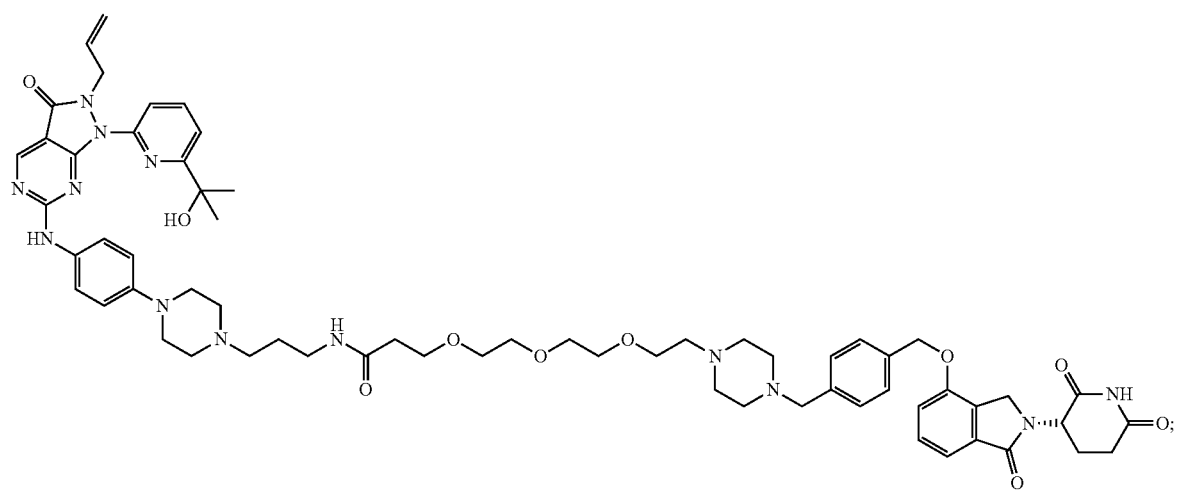
(10)
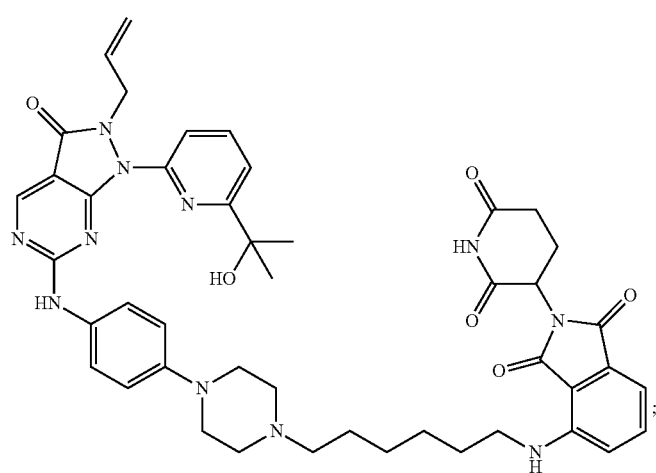
(11)

(12)
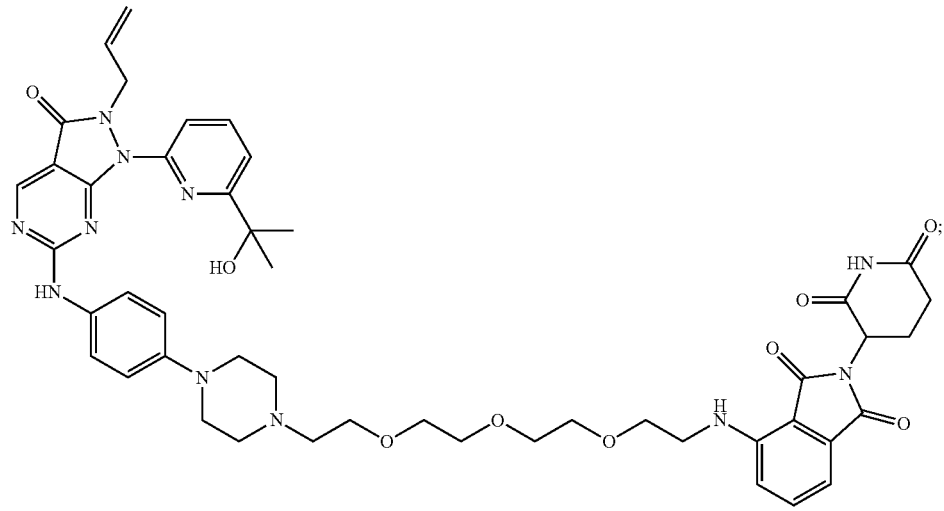
(13)
(14)
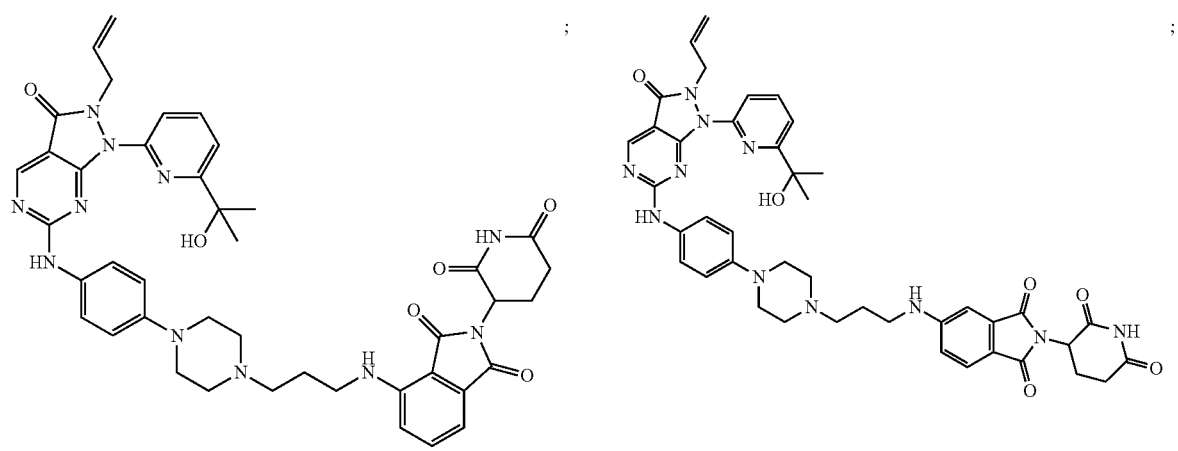
(15)
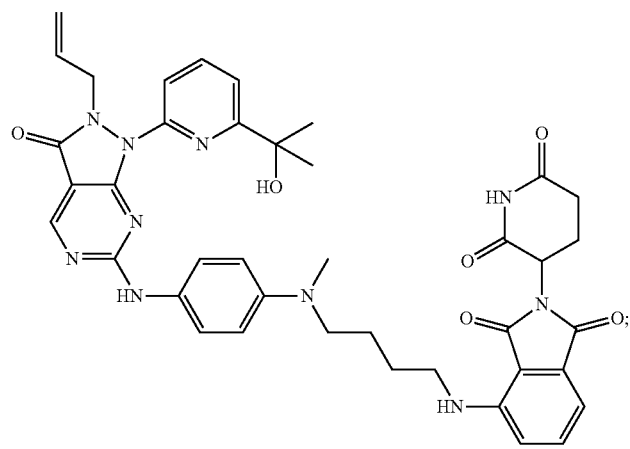

-continued
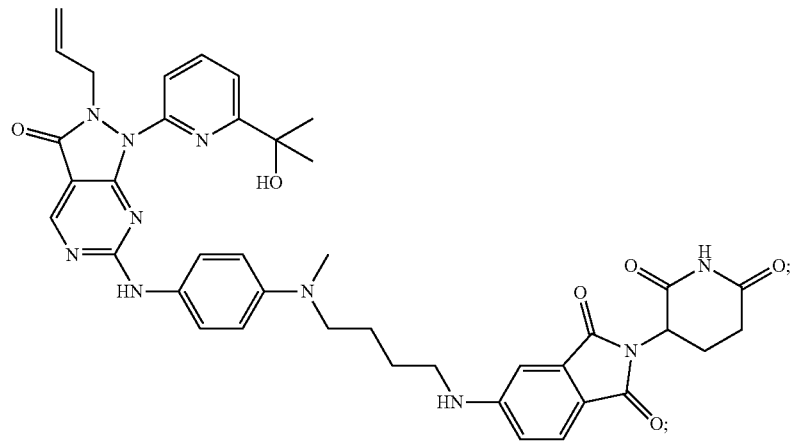
(16)
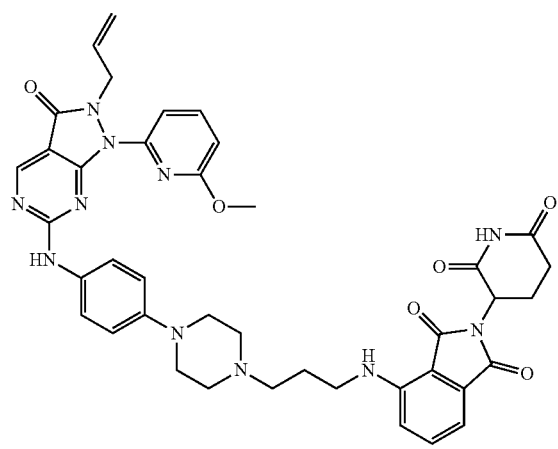
(17)
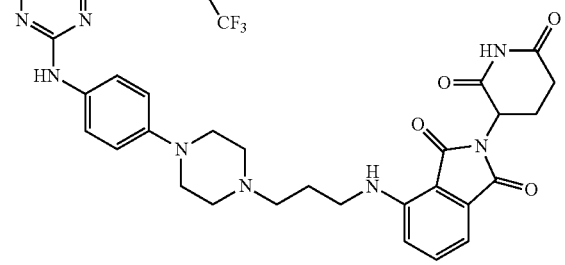
(18)
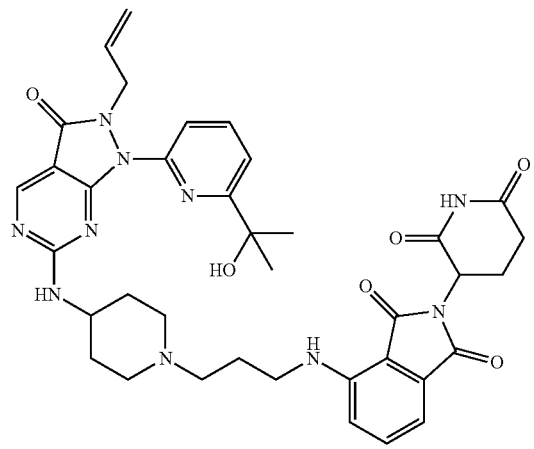
(19)
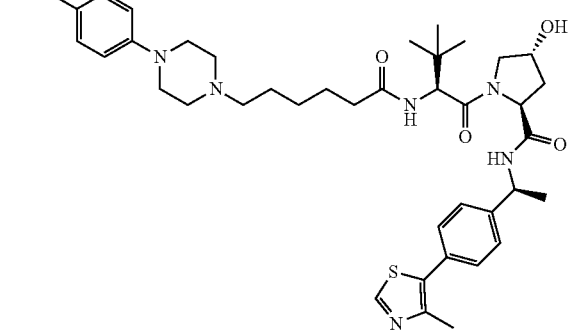
(21)

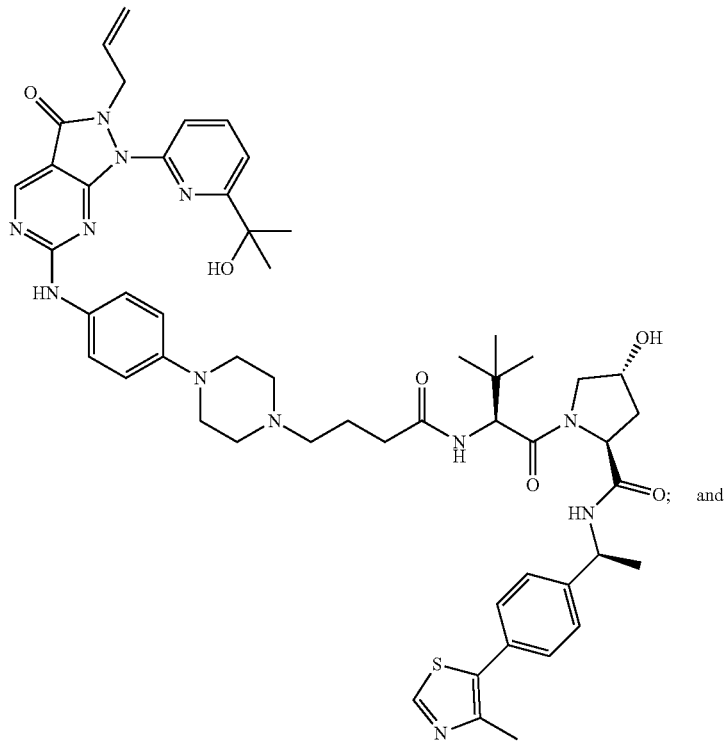

(22)

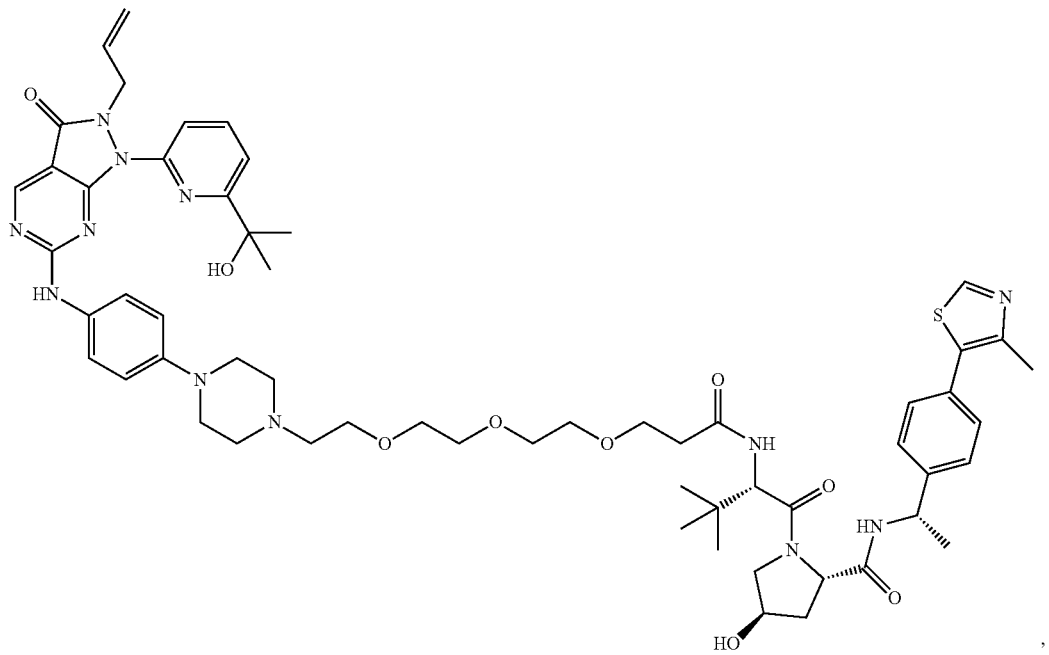

(23)

and pharmaceutically acceptable salts and stereoisomers thereof.

Bifunctional compounds of the present invention may be in the form of a free acid or free base, or a pharmaceutically acceptable salt. As used herein, the term "pharmaceutically acceptable" in the context of a salt refers to a salt of the compound that does not abrogate the biological activity or properties of the compound, and is relatively non-toxic, i.e., the compound in salt form may be administered to a subject without causing undesirable biological effects (such as dizziness or gastric upset) or interacting in a deleterious manner with any of the other components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the bifunctional compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^2$H, may afford certain therapeutic advantages resulting from greater metabolic stability, for example, increased in vivo half-life or reduced dosage requirements, and thus may be advantageous in some circumstances.

Bifunctional compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present invention may be made and used in the form of individual isomers and substantially free of other isomers, or in the form of a mixture of various isomers, e.g., racemic mixtures of stereoisomers.

In addition, bifunctional compounds of formula (I) embrace the use of N-oxides, crystalline forms (also known as polymorphs), active metabolites of the compounds having the same type of activity, tautomers, and unsolvated as well as solvated forms with pharmaceutically acceptable solvents such as water, ethanol, and the like, of the compounds. The solvated forms of the conjugates presented herein are also considered to be disclosed herein.

Methods of Synthesis

In another aspect, the present invention is directed to a method for making a bifunctional compound of formula (I), or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate nonlimiting methods by which the compounds of the invention may be prepared.

Pharmaceutical Compositions

Another aspect of the present invention is directed to a pharmaceutical composition that includes a therapeutically effective amount of the bifunctional compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may include one or more pharmaceutically acceptable excipients.

Broadly, bifunctional compounds of formula (I) may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i.v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the bifunctional compound may be administered relatively quickly such as in the case of a single-dose treatment and/or an acute condition.

In some embodiments, the bifunctional compounds are formulated for oral or intravenous administration (e.g., systemic intravenous injection).

Accordingly, bifunctional compounds of the present invention may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, bifunctional compounds of the present invention may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, bifunctional compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The bifunctional compounds may be formulated for buccal or sublingual administration, examples of which include tablets, lozenges and gels.

The bifunctional compounds may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Bifunctional compounds of formula (I) may be formulated for topical administration which as used herein, refers to administration intradermally by application of the formulation to the epidermis. These types of compositions are typically in the form of ointments, pastes, creams, lotions, gels, solutions and sprays.

Representative examples of carriers useful in formulating compositions for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerine, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a bifunctional compound of formula I or a pharmaceutically acceptable salt or a stereoisomer thereof effective in producing the desired therapeutic response in a particular patient suffering from a disease or disorder mediated by aberrant Wee1 activity. The term "therapeutically effective amount" thus includes the amount of the bifunctional compound or a pharmaceutically acceptable salt or a stereoisomer thereof, that when administered, induces a positive modification in the disease or disorder to be treated (e.g., to selectively inhibit/degrade Wee1), or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of Wee1 in diseased cells.

The total daily dosage of the compounds and usage thereof may be decided in accordance with standard medical practice, e.g., by the attending physician using sound medical judgment. The specific therapeutically effective dose for any particular subject will depend upon a variety of factors including the disease or disorder being treated and the severity thereof (e.g., its present status); the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed; and like factors well known in the medical arts (see, for example, *Goodman and Gilman's The Pharmacological Basis of Therapeutics,* 10th Edition, A. Gilman, J. Hardman and L. Limbird, eds., McGraw-Hill Press, 155-173, 2001).

Bifunctional compounds of formula (I) may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, from about 5 to about 40 mg per day, and in yet other embodiments from about 10 to about 30 mg per day. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, the compound may be administered at a dose in range from about 0.01 mg to about 200 mg/kg of body weight per day. In some embodiments, a dose of from 0.1 to 100, e.g. from 1 to 30 mg/kg per day in one or more dosages per day may be effective. By way of example, a suitable dose for oral administration may be in the range of 1-30 mg/kg of body weight per day, and a suitable dose for intravenous administration may be in the range of 1-0 ng/kg of body weight per day.

In some embodiments, the bifunctional compound is administered in a dose between 100 mg per day and 250 mg per day. In other embodiments the bifunctional compound is administered in a dose between 200 mg per day and 400 mg per day, e.g., 250-350 mg per day.

Methods of Use

In some aspects, the present invention is directed to methods of treating diseases or disorders involving aberrant Wee1 activity, that entails administration of a therapeutically effective amount of a bifunctional compound formula (I) or a pharmaceutically acceptable salt or stereoisomer thereof, to a subject in need thereof.

The diseases or disorders are characterized or mediated by aberrant (e.g., dysfunctional or dysregulated) Wee1 activity (e.g., elevated levels of protein or otherwise functionally abnormal relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the animal's state of health. In some embodiments, bifunctional compounds of formula (I) may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

Exemplary types of non-cancerous (e.g., cell proliferative) diseases or disorders that may be amenable to treatment with the bifunctional compounds of the present invention include inflammatory diseases and conditions, autoimmune diseases, neurodegenerative diseases, heart diseases, viral diseases, chronic and acute kidney diseases or injuries, metabolic diseases, and allergic and genetic diseases.

Representative examples of specific non-cancerous diseases and disorders include rheumatoid arthritis, alopecia areata, lymphoproliferative conditions, autoimmune hematological disorders (e.g. hemolytic anemia, aplastic anemia, anhidrotic ectodermal dysplasia, pure red cell anemia and idiopathic thrombocytopenia), cholecystitis, acromegaly, rheumatoid spondylitis, osteoarthritis, gout, scleroderma, sepsis, septic shock, dacryoadenitis, cryopyrin associated periodic syndrome (CAPS), endotoxic shock, endometritis, gram-negative sepsis, keratoconjunctivitis sicca, toxic shock syndrome, asthma, adult respiratory distress syndrome, chronic obstructive pulmonary disease, chronic pulmonary inflammation, chronic graft rejection, hidradenitis suppurativa, inflammatory bowel disease, Crohn's disease, Behcet's syndrome, systemic lupus erythematosus, glomerulonephritis, multiple sclerosis, juvenile-onset diabetes, autoimmune uveoretinitis, autoimmune vasculitis, thyroiditis, Addison's disease, lichen planus, appendicitis, bullous pemphigus, pemphigus vulgaris, pemphigus foliaceus, paraneoplastic pemphigus, myasthenia gravis, immunoglobulin A nephropathy, autoimmune thyroiditis or Hashimoto's disease, Sjogren's syndrome, vitiligo, Wegener granulomatosis, granulomatous orchitis, autoimmune oophoritis, sarcoidosis, rheumatic carditis, ankylosing spondylitis, Grave's disease, autoimmune thrombocytopenic purpura, psoriasis, psoriatic arthritis, eczema, dermatitis herpetiformis, ulcerative colitis, pancreatic fibrosis, hepatitis, hepatic fibrosis, CD14 mediated sepsis, non-CD14 mediated sepsis, acute and chronic renal disease, irritable bowel syndrome, pyresis, restenosis, cerebral malaria, cervicitis, stroke and ischemic injury, neural trauma, acute and chronic pain, allergic rhinitis, allergic conjunctivitis, chronic heart failure, congestive heart failure, acute coronary syndrome, cachexia, malaria, leprosy, leishmaniasis, Lyme disease, Reiter's syndrome, acute synovitis, muscle degeneration, bursitis, tendonitis, tenosynovitis, herniated, ruptured, or prolapsed intervertebral disk syndrome, osteopetrosis, rhinosinusitis, thrombosis, silicosis, pulmonary sarcoidosis, bone resorption diseases, such as osteoporosis, graft-versus-host reaction, fibromyalgia, AIDS and other viral diseases such as Herpes Zoster, Herpes Simplex I or II, influenza virus and cytomegalovirus, diabetes Type I and II, obesity, insulin resistance and diabetic retinopathy, 22q1 1.2 deletion syndrome, Angelman syndrome, Canavan disease, celiac disease, Charcot-Marie-Tooth disease, color blindness, Cri du chat, Down syndrome, cystic fibrosis, Duchenne muscular dystrophy, haemophilia, Klinefleter's syndrome, neurofibromatosis, phenylketonuria, Prader-Willi syndrome, sudden infant death syndrome, sickle cell disease, Tay-Sachs disease, Turner syndrome, urea cycle disorders, thalassemia, otitis, pancreatitis, parotitis, pericarditis, peritonitis, pharyngitis, pleuritis, phlebitis, pneumonitis, cystic fibrosis, uveitis, polymyositis, proctitis, interstitial lung fibrosis, dermatomyositis, arteriosclerosis, amyotrophic lateral sclerosis, asocality, immune response, varicosis, vaginitis, including chronic recurrent yeast vaginitis, depression, and Sudden Infant Death Syndrome.

In some embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinemia, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue), mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver (hepatocellular), brain, lung, colorectal (e.g., colon), pancreas, prostate, ovary, breast, skin (e.g., melanoma), and endometrium.

As used herein, "cell proliferative diseases or disorders of the hematologic system" include lymphoma, leukemia, myeloid neoplasms, mast cell neoplasms, myelodysplasia, benign monoclonal gammopathy, lymphomatoid papulosis, polycythemia vera, chronic myelocytic leukemia, angiogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the brain may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, bifunctional compounds of the present invention may be used to treat non-metastatic or metastatic lung cancer (e.g., NSCLC, ALK-positive NSCLC, NSCLC harboring ROS1 rearrangement, lung adenocarcinoma, and squamous cell carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell types).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The bifunctional compounds of formula (I) may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been partially successful but who became intolerant to the particular treatment. Therapy may also be given as an adjuvant treatment, i.e., to prevent reoccurrence of cancer in patients with no currently detectable disease or after surgical removal of a tumor. Thus, in some embodiments, the bifunctional compounds may be administered to a patient who has received another therapy, such as chemotherapy, radioimmunotherapy, surgical therapy, immunotherapy, radiation therapy, targeted therapy or any combination thereof.

The methods of the present invention may entail administration of bifunctional compounds of formula (I) or pharmaceutical compositions thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days). In other embodiments, the bifunctional compound may be dosed twice a day (BID) over the course of two and a half days (for a total of 5 doses) or once a day (QD) over the course of two days (for a total of 2 doses). In other embodiments, the bifunctional compound may be dosed once a day (QD) over the course of five days.

Combination Therapy

Bifunctional compounds of formula (I) may be used in combination or concurrently with at least one other active agent, e.g., anti-cancer agent or regimen, in treating diseases and disorders. The terms "in combination" and "concurrently in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically to provide an increased benefit than if they were administered otherwise). For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; *Physician's Desk Reference* 60th ed., 2006. For example, anti-cancer agents that may be used in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, the bifunctional compound of formula (I) and the additional anticancer therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more anticancer therapeutics may be administered within the same patient visit.

In some embodiments involving cancer treatment, the bifunctional compound of formula (I) and the additional anti-cancer or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

In some embodiments, a bifunctional compound of the present invention may be used in combination with Gemcitabine and radiation therapy (e.g., for adenocarcinoma of the pancreas), Irinotecan Hydrochloride (e.g., for childhood central nervous system neoplasm, recurrent childhood medulloblastoma, recurrent childhood supratentorial embryonal tumor, recurrent malignant solid neoplasm, recurrent neuroblastoma, metastatic colorectal cancer, and recurrent rhabdomyosarcoma), poly ADP ribose polymerase (PARP) inhibitor Olaparib (e.g., for refractory solid tumors, relapsed small cell lung cancer (SCLC), recurrent fallopian tube carcinoma, recurrent primary peritoneal carcinoma, refractory ovarian carcinoma, platinum refractory extensive-stage small cell lung carcinoma, and metastatic triple negative breast cancer), Carboplatin and Paclitaxel (e.g., for advanced solid tumors, lung cancer, and ovarian cancer), CYP1A2 (caffeine), CYP2C19 (omeprazole), CYP3A (midazolam), and Kytril (Granisetron) (e.g., for solid tumors), Cisplatin (e.g., for triple-negative metastatic breast cancer, recurrent hypopharyngeal squamous cell carcinoma, recurrent laryngeal squamous cell carcinoma, recurrent laryngeal verrucous carcinoma, recurrent lip and oral cavity squamous cell carcinoma, recurrent metastatic squamous cell carcinoma in the neck with occult primary, recurrent nasal cavity and paranasal sinus squamous cell carcinoma, recurrent oral cavity verrucous carcinoma, recurrent oropharyngeal squamous cell carcinoma and tongue carcinoma), Docetaxel (e.g., for non-small cell lung cancer), MEDI4736 (e.g., for advanced solid tumors and muscle invasive bladder cancer), Paclitaxel, Carboplatin, and Gemcitabine (e.g., for advanced solid tumors in ovarian, fallopian tube, and peritoneal cancer), Cytarabine (e.g., for chronic myelomonocytic leukemia, myelodysplastic syndrome with isolated Del(5q), myelodysplastic/myeloproliferative neoplasm, previously treated myelodysplastic syndrome, and recurrent and untreated adult acute myeloid leukemia), Paclitaxel (e.g., for advanced gastric adenocarcinoma), local radiation therapy (e.g., for anaplastic astrocytoma, anaplastic oligoastrocytoma, diffuse intrinsic pontine glioma, H3 K27M-Mutant diffuse midline glioma, glioblastoma, gliosarcoma, untreated childhood anaplastic astrocytoma, untreated childhood anaplastic oligoastrocytoma, untreated childhood glioblastoma, and untreated childhood gliosarcoma, metastatic pancreatic adenocarcinoma), Docetaxel and Cisplatin (e.g., for head and neck squamous cell carcinoma), Paclitaxel Albumin-Stabilized Nanoparticle Formulation and Gemcitabine Hydrochloride (e.g., for metastatic pancreatic adenocarcinoma, pancreatic cancer and unresectable pancreatic carcinoma), Carboplatin (e.g., for epithelial ovarian cancer), 5-FU or 5-FU/CDDP (e.g., for prostate cancer), Gemcitabine Hydrochloride (e.g., for ovarian Brenner tumor, ovarian carcinosarcoma, ovarian clear cell cystadenocarcinoma, ovarian endometrioid adenocarcinoma, ovarian mucinous cystadenocarcinoma, ovarian seromucinous carcinoma, ovarian serous cystadenocarcinoma, ovarian serous surface papillary adenocarcinoma, recurrent fallopian tube carcinoma, recurrent and undifferentiated ovarian carcinoma, and recurrent primary peritoneal carcinoma), external beam radiation therapy and Cisplatin (e.g., for endometrioid adenocarcinoma, recurrent cervical carcinoma, uterine corpus cancer, and vaginal cancer), radiation therapy and Temozolomide (e.g., for adult and recurrent glioblastoma), and Savolitinib and Darolutamide (e.g., for solid tumors).

In some embodiments, a bifunctional compound of the invention may be used combination with a CHK1 inhibitor. CHK1 is an essential serine/threonine kinase involved in two cell cycle checkpoints, the intra-S and G2/M checkpoints. In response to DNA replication stress during S-phase of the cell cycle, CHK1 activity prevents stalled replication forks from collapsing and causing genomic damage (Feijoo et al., J. Cell Biol. 154(5):913-23 (2001)). Also, CHK1 activity following DNA damage is necessary for arrest at the G2/M cell cycle boundary, preventing cells from prematurely entering mitosis before damaged DNA has been repaired (O'Connell et al., EMBO J. 16(3):545-54 (1997); Liu et al., Genes & Devel. 14(12):1448-59 (2000)).

In an embodiment of the invention, the CHK1 inhibitor is MK-8776, the structure of which is as shown below.

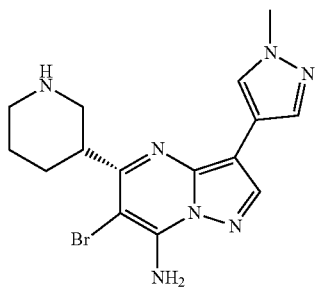

MK-8776 is also known as (R)-(−)-6-bromo-3-(1-methyl-1H-pyrazol-4-yl)-5-piperidin-3-yl-pyrazolo[1,5-a]pyrimidin-7-ylamine, or SCH900776. MK-8776 has been described in U.S. Pat. No. 7,196,078, and PCT International Publications WO 2007/044449 and WO 2011/1 19457.

In an embodiment, the CHK1 inhibitor is SCH900444, the structure of which is as shown below.

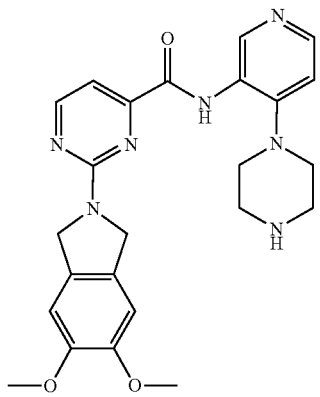 [SMILES: COc1cc2c(cc1OC)CN(c1nccc(C(=O)Nc3cnccc3N3CCNCC3)n1)C2]

SCH 900444 is also known as 2-(1,3-dihydro-5,6-dimethoxy-2H-isoindol-2-yl)-N-4-(1-piperazinyl)-3-pyridinyl-4-pyrimidinecarboxamide, or SCH1396195. SCH900444 has been described in PCT International Publication WO 2009/014637.

Other CHK1 inhibitors that may be useful in methods of the present invention are described in U.S. Patent Application Publication 2016/037502 A1.

Pharmaceutical Kits

The present compositions may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain the bifunctional compound of the present invention or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

Example 1: Preparation of Intermediates

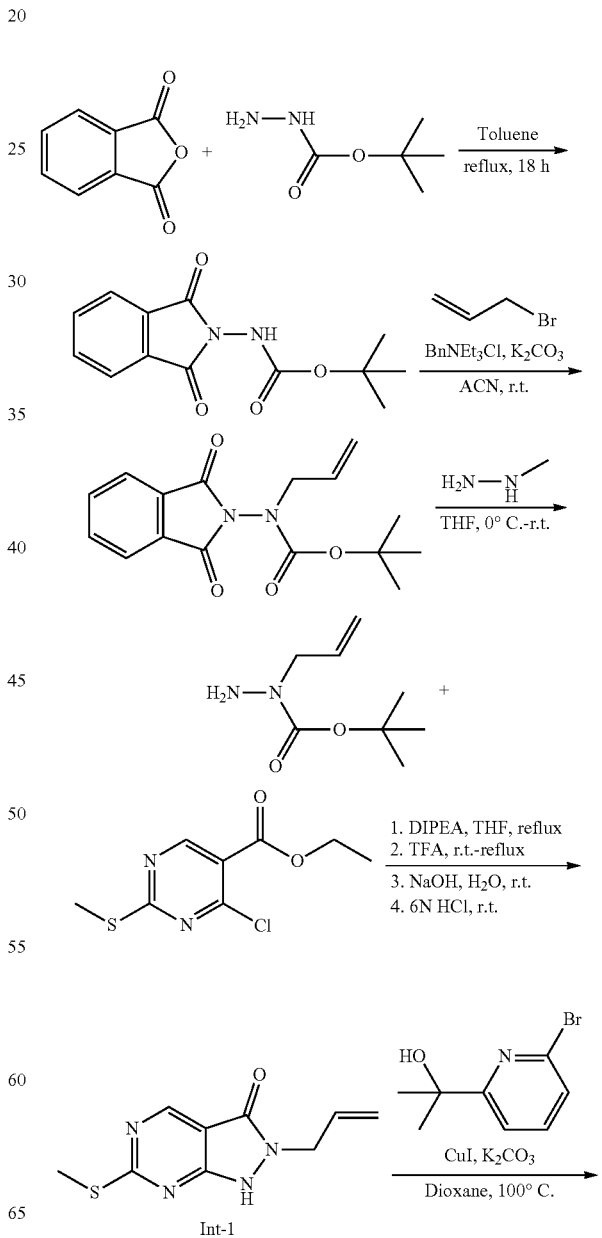

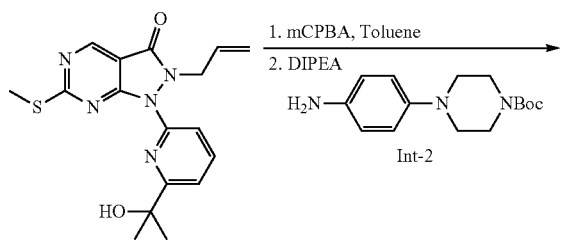
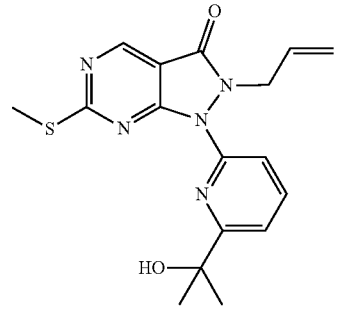 [SMILES: C=CCn1c(=O)c2cnc(SC)nc2n1-c1cccc(C(C)(C)O)n1]

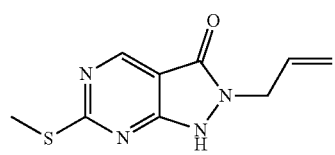

(Int-1)

The key intermediate Int-1 was prepared from phthalic anhydride and ethyl 4-chloro-2-(methylthio)pyrimidine-5-carboxylate according to the procedures described in U.S. Patent Application Publication 2007/0254892 A1.

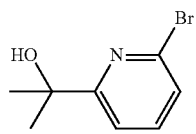

2-(6-Bromopyridin-2-yl)propan-2-ol

Methylmagnesium chloride (3M in THF, 5 mL, 15 mmol) was added to a solution of 2-acetyl-6-bromopyridine (2.0 g, 10 mmol) in dry THF (50 mL) at 0° C. The reaction mixture was stirred at room temperature and after 2 hours was quenched with 1M HCl (20 mL) and extracted with EtOAc (30 mL×3). The organic extract was washed with saturated NaHCO$_3$ solution (50 mL), brine (50 mL), dried over MgSO$_4$, and concentrated in vacuo to give title compound as a yellow oil (1.9 g, 89%) which was used without further purification.

2-Allyl-1-(6-(2-hydroxypropan-2-yl)pyridin-2-yl)-6-(methylthio)-1,2-dihydro-3H-pyrazolo[3,4-d]pyrimidin-3-one A mixture of dimethylethylenediamine (700 mg, 8.0 mmol), Int-1 (888 mg, 4.0 mmol), 2-(6-bromopyridin-2-yl)propan-2-ol (1.1 g, 5.2 mmol), copper iodide (750 mg, 4.0 mmol) and K$_2$CO$_3$ (830 mg, 6.0 mmol) in 1,4-dioxane (12 mL) was heated at 100° C. overnight. The reaction mixture was cooled to room temperature, diluted with NH$_4$OH (10 mL) and extracted with EtOAc (30 mL×2). The combined organic extracts were washed with brine (20 mL), dried over MgSO$_4$ and evaporated to dryness under reduced pressure. The crude material was purified via silica gel chromatography (20:1 DCM:MeOH) to afford the title compound (1 g, 70%).

MS m/z 358.12 [M+H]$^+$.

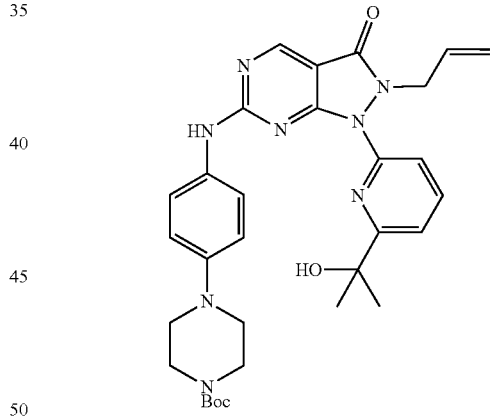

tert-Butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate m-Chloroperoxybenzoic acid (145 mg, 0.65 mmol) was added to a solution of 2-allyl-1-(6-(2-hydroxypropan-2-yl)pyridin-2-yl)-6-(methylthio)-1,2-dihydro-3H-pyrazolo[3,4-d]pyrimidin-3-one (220 mg, 0.6 mmol) in toluene, and the reaction mixture was stirred for 1 hour. N,N-diisopropylethylamine and Int-2 (205 mg, 0.74 mmol) were added and the reaction mixture was stirred overnight. Saturated NaHCO$_3$ (10 mL) was added, and the mixture was extracted with EtOAc (15 mL×2). The organic phase was washed with brine, dried over MgSO$_4$, filtered, and concentrated in vacuo. The crude material was purified via silica gel chromatography (20:1 DCM:MeOH) to afford the title compound (255 mg, 73%).

MS m/z 587.34 [M+H]⁺.

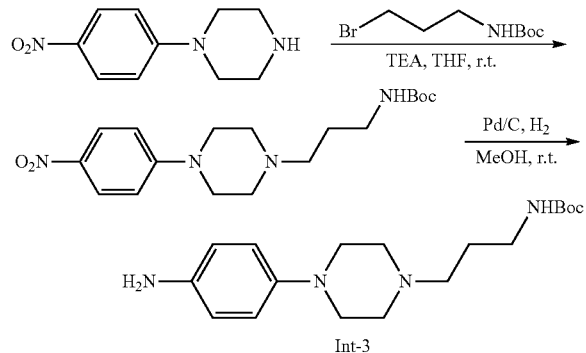

Int-3 was prepared from 1-(4-nitrophenyl)piperazine according to the procedures described in Wright et al. ACS Chem. Biol. 12:1883-1892 (2017).

tert-Butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate m-Chloroperoxybenzoic acid (180 mg, 0.8 mmol) was added to a solution of 2-allyl-1-(6-(2-hydroxypropan-2-yl)pyridin-2-yl)-6-(methylthio)-1,2-dihydro-3H-pyrazolo [3,4-d]pyrimidin-3-one (210 mg, 0.57 mmol) in toluene, and the reaction mixture was stirred for 1 hour. N,N-diisopropylethylamine and Int-3 (230 mg, 0.68 mmol) were added and the reaction mixture was stirred overnight. Saturated NaHCO₃ (10 mL) was added and the mixture was extracted with EtOAc (15 mL×2). The organic phase was washed with brine, dried over MgSO₄, filtered, and concentrated in vacuo. The crude material was purified via silica gel chromatography (20:1 DCM:MeOH) to afford the title compound (370 mg, 70%).

MS m/z 644.44 [M+H]⁺.

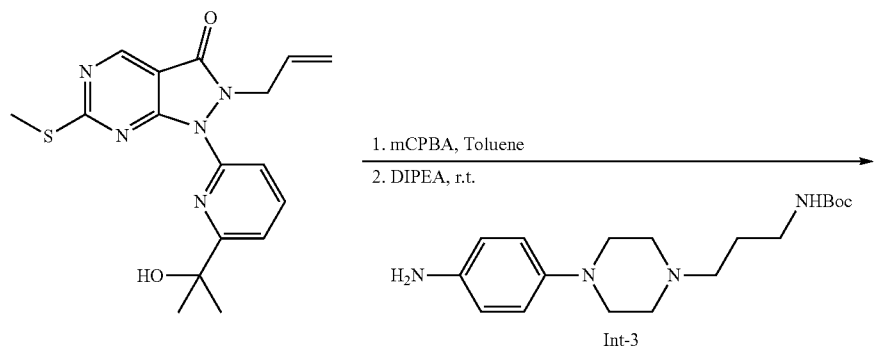

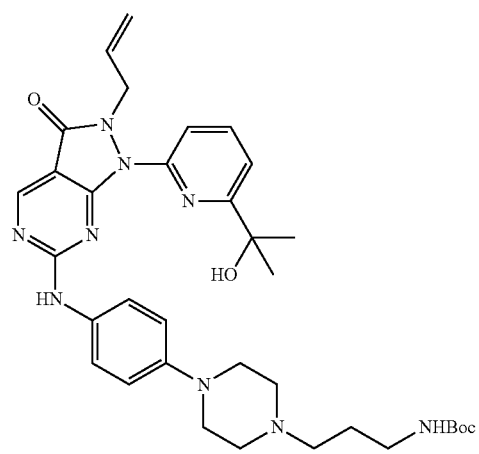

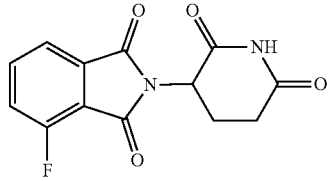 [SMILES: O=C1CCC(N2C(=O)c3cccc(F)c3C2=O)C(=O)N1]

2-(2,6-Dioxopiperidin-3-yl)-4-fluoroisoindoline-1,3-dione was prepared according to the procedures described in U.S. Patent Application Publication 2016/0058872 A1.

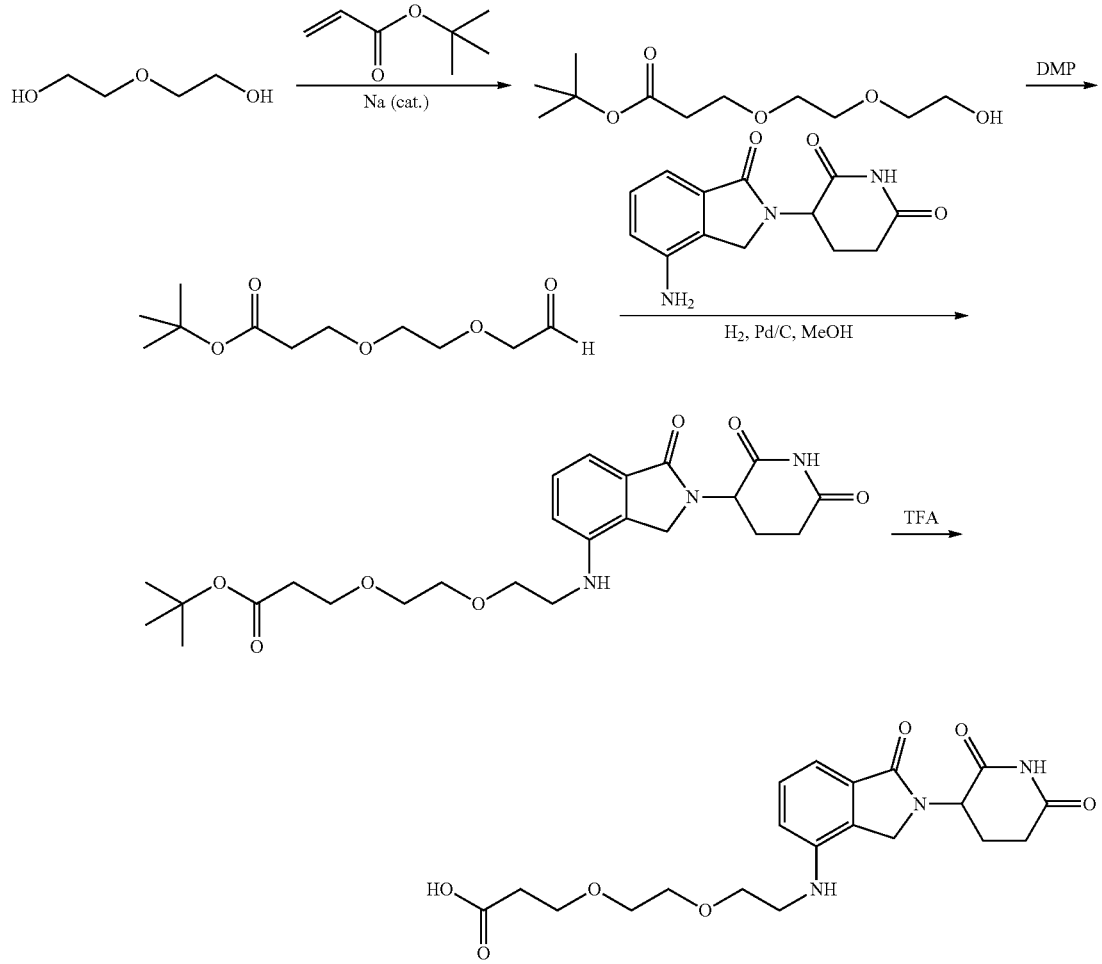

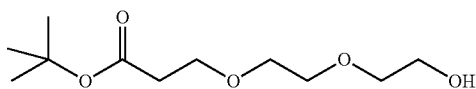 [SMILES: CC(C)(C)OC(=O)CCOCCOCCO]

tert-Butyl 3-(2-(2-hydroxyethoxy)ethoxy)propanoate

Sodium metal (64 mg, 0.03 eq) was added to a solution of diethylene glycol (29.5 g, 0.278 mmol) in THF (100 mL). The mixture was stirred for 1 hour to dissolve the sodium, then tert-butyl acrylate (12.4 g, 97 mmol) was added. The resulting mixture was stirred for 2 days, then concentrated under reduced pressure and the residue purified by silica chromatography (1:1 hexane:EtOAc) to give the title compound (9.1 g, 40%) as a colorless oil.

$^1$H NMR (400 MHz, CDCl$_3$): δ 3.75 (m, 4H), 3.64 (m, 6H), 2.53 (t, 2H), 2.40 (s, 1H), 1.45 (s, 9H).

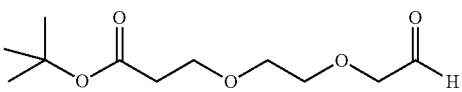 [SMILES: CC(C)(C)OC(=O)CCOCCOCC=O]

tert-Butyl 3-(2-(2-oxoethoxy)ethoxy)propanoate tert-Butyl 3-(2-(2-hydroxyethoxy)ethoxy)propanoate (8.6 g, 37 mmol) was added to a suspension of Dess-Martin periodinane (DMP) (18.8 g, 44 mmol) and pyridine (7.0 g, 88 mmol) in DCM (150 mL) at 0° C. The resulting mixture was stirred at room temperature for 16 hours, then filtered, and washed with DCM (3×50 mL). The filtrate and washings were combined and washed with saturated NaHCO$_3$ solution and brine, dried over anhydrous sodium sulfate, filtered and concentrated in vacuo. The residue was purified by silica chromatography (10:1-3:1 hexane:EtOAc) to give the title compound (4.1 g, 48%) as a yellow oil.

$^1$H NMR (400 MHz, CDCl$_3$): δ 9.76 (s, 1H), 4.16 (s, 2H), 3.50-3.80 (m, 6H), 2.53 (t, 2H), 1.46 (s, 9H).

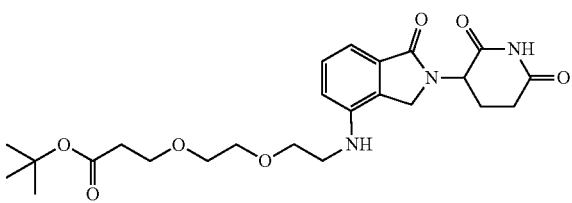 [SMILES: CC(C)(C)OC(=O)CCOCCOCCNc1cccc2c1CN(C1CCC(=O)NC1=O)C2=O]

tert-Butyl 3-(2-(2-((2-(2,6-dioxopiperidin-3-yl)-1-oxoisoindolin-4-yl)amino)ethoxy) ethoxy)propanoate 10% Pd/C (100 mg) was added to a solution of lenalidomide (1.0 g, 3.9 mmol) and tert-butyl 3-(2-(2-oxoethoxy)ethoxy)propanoate (1.8 g, 7.7 mmol) in MeOH (200 mL). The mixture was stirred at room temperature under an atmosphere of hydrogen for 16 hours. The suspension was filtered, and the filtrate was concentrated under reduced pressure. The residue was purified by silica chromatography (30:1-20:1 DCM:MeOH), followed by HPLC to give the title compound (425 mg, 23%).

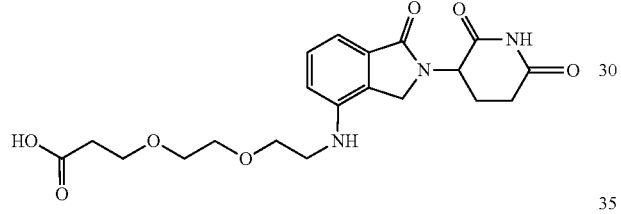

3-(2-(2-((2-(2,6-Dioxopiperidin-3-yl)-1-oxoisoindolin-4-yl)amino)ethoxy)ethoxy)propanoic acid Trifluoroacetic acid (TFA) (1.5 mL) was added to a solution of tert-butyl 3-(2-(2-((2-(2,6-dioxopiperidin-3-yl)-1-oxoisoindolin-4-yl)amino)ethoxy)ethoxy) propionate (400 mg, 0.84 mmol) in DCM (6 mL) at 0° C. The mixture was stirred at room temperature for 1 hour, and the solvent was removed under reduced pressure to give the title compound (380 mg, 92% yield) as TFA salt.

$^1$H NMR (400 MHz, DMSO): δ 11.00 (s, 1H), 7.30 (d, 1H), 6.95 (d, 1H), 6.80 (d, 1H), 5.10 (m, 1H), 4.15 (2d, 2H), 3.60 (m, 2H), 3.50 (m, 2H), 3.36 (m, 6H), 2.95 (m, 1H), 2.62 (m, 1H), 2.44 (t, 2H), 2.30 (m, 1H), 2.00 (m, 1H).

MS m/z 420.7 [M+H]$^+$.

1-((2-(2,6-Dioxopiperidin-3-yl)-1-oxoisoindolin-4-yl)amino)-3,6,9,12-tetraoxapentadecan-15-oic acid The title compound was prepared in an analogous manner to 3-(2-(2-((2-(2,6-dioxopiperidin-3-yl)-1-oxoisoindolin-4-yl)amino)ethoxy)ethoxy)propanoic acid from 2,2'-((oxybis(ethane-2,1-diyl))bis(oxy))bis(ethan-1-ol) and lenalidomide (above).

$^1$H NMR (400 MHz, DMSO): δ 12.30 (br s, 1H), 11.04 (s, 1H), 7.28 (m, 1H), 6.94 (d, 1H), 6.80 (d, 1H), 5.64 (m, 1H), 5.10 (m, 1H), 4.21 (d, 1H) 4.15 (d, 1H), 3.50 (m, 16H), 3.31 (m, 2H), 2.92 (m, 1H), 2.63 (m, 1H), 2.42 (t, 2H), 2.32 (m, 1H), 2.03 (m, 1H).

MS m/z [M+1]$^+$:507.95.

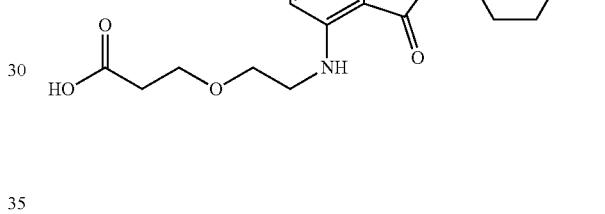

3-(2-((2-(2,6-Dioxopiperidin-3-yl)-1,3-dioxoisoindolin-4-yl)amino)ethoxy)propanoic acid The title compound was prepared in an analogous manner to 3-(2-(2-((2-(2,6-dioxopiperidin-3-yl)-1-oxoisoindolin-4-yl)amino)ethoxy)ethoxy)propanoic acid from ethane-1,2-diol and pomalidomide.

$^1$H NMR (400 MHz, CDCl$_3$): δ 8.60 (s, 1H), 7.50 (m, 1H), 7.11 (d, 1H), 6.92 (d, 1H), 4.95 (m, 1H), 3.78 (t, 2H), 3.71 (t, 2H), 3.47 (t, 2H), 2.88 (m, 1H), 2.78 (m, 2H), 2.62 (t, 2H), 2.13 (m, 1H).

MS m/z 387.6 [M-H]$^-$.

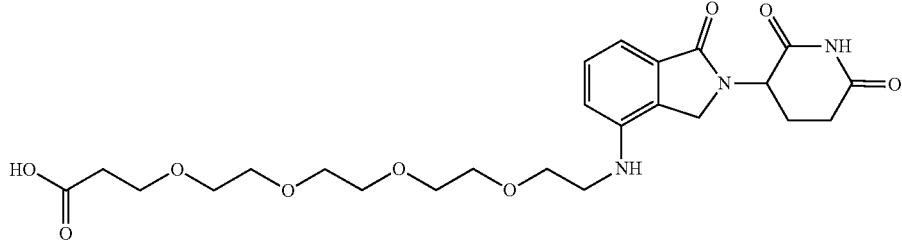 [SMILES: O=C(O)CCOCCOCCOCCOCCNc1cccc2c1CN(C1CCC(=O)NC1=O)C2=O]

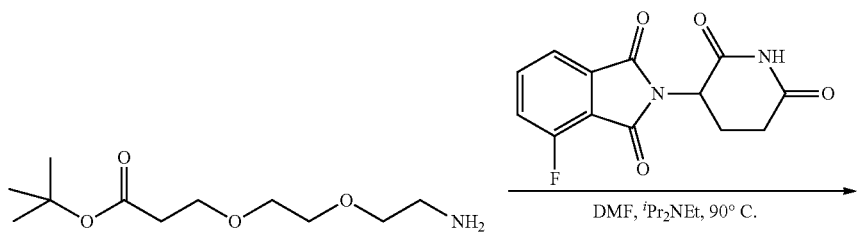

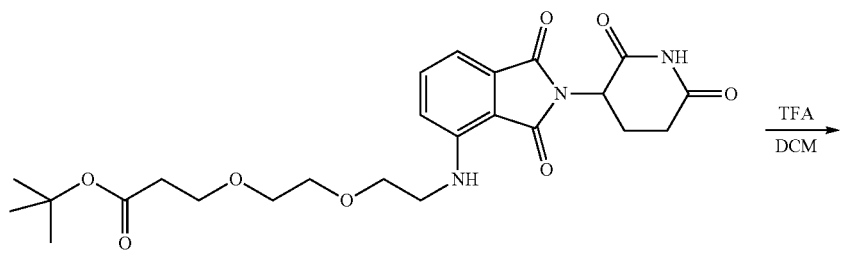

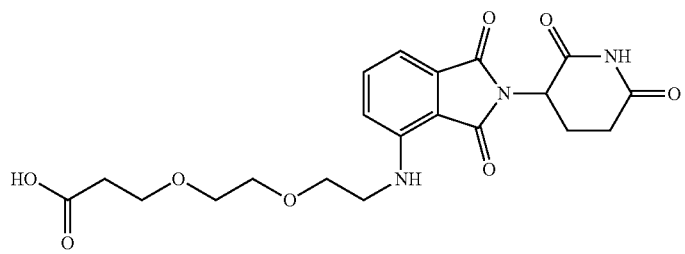 [SMILES: O=C(O)CCOCCOCCNc1cccc2c1C(=O)N(C1CCC(=O)NC1=O)C2=O]

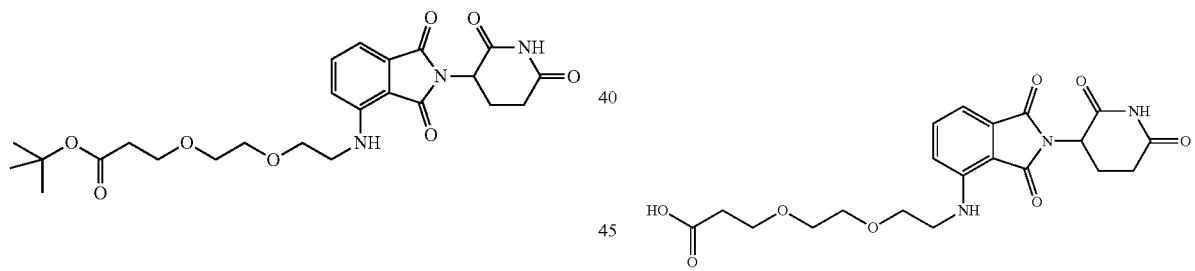

tert-Butyl 3-(2-(2-(2-(2,6-dioxopiperidin-3-yl)-1,3-dioxoisoindolin-4-ylamino)ethoxy)ethoxy) propanoate Diisopropylethylamine (10 mL) was added to a solution of 2-(2,6-dioxopiperidin-3-yl)-4-fluoroisoindoline-1,3-dione (1.2 g, 4.3 mmol) and $NH_2$-PEG2-tBu (1 g, 4.3 mmol) in DMF (10 mL). The solution was heated at 90° C. for 2 hours, then cooled, diluted with water (50 mL) and acidified to pH 4-5 with 10% $KHSO_4$. The mixture was extracted with ethyl acetate (3×50 mL) and the combined organic extracts were washed with brine, dried over anhydrous sodium sulfate and concentrated in vacuo. The residue was purified by silica chromatography (2:1 petroleum ether:EtOAc) to give the title compound (470 mg, 22% yield) as a yellow solid.

$^1$H NMR (400 MHz, $CDCl_3$): δ 8.09 (s, 1H), 7.49 (m, 1H), 7.10 (d, 1H), 6.92 (d, 1H), 4.92 (m, 1H), 3.72 (m, 4H), 3.64 (m, 4H), 3.46 (t, 2H), 2.67-2.94 (m, 3H), 2.51 (t, 2H), 2.13 (m, 1H), 1.44 (s, 9H).

MS m/z 512.17 $(M+Na)^+$.

3-(2-(2-((2-(2,6-Dioxopiperidin-3-yl)-1,3-dioxoisoindolin-4-yl)amino)ethoxy)ethoxy) propanoic acid TFA (6 mL) was added to a solution of tert-butyl 3-(2-(2-(2-(2,6-dioxopiperidin-3-yl)-1,3-dioxoisoindolin-4-ylamino)ethoxy)ethoxy)propanoate (740 mg, 1.51 mmol) in DCM (20 mL), and the solution was stirred for 2 hours. The solvent was removed under reduced pressure to give the title compound (615 mg, 94% yield) as a yellow solid.

$^1$H NMR (400 MHz, $CDCl_3$): δ 8.62 (s, 1H), 7.48 (m, 1H), 7.10 (d, 1H), 6.91 (d, 1H), 6.54 (br s, 1H), 4.93 (m, 1H), 3.77 (t, 2H), 3.73 (t, 2H), 3.67 (s, 4H), 3.46 (t, 2H), 2.86 (m, 1H), 2.77 (m, 2H), 2.65 (t, 2H), 2.13 (m, 1H).

MS m/z 434.25 $[M+H]^+$.

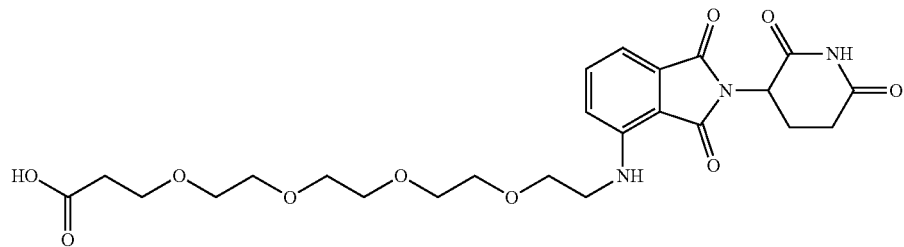 [SMILES: O=C(O)CCOCCOCCOCCOCCNc1cccc2c1C(=O)N(C1CCC(=O)NC1=O)C2=O]
1-((2-(2,6-Dioxopiperidin-3-yl)-1,3-dioxoisoindolin-4-yl)amino)-3,6,9,12-tetraoxapentadecan-15-oic acid
Title compound was prepared in an analogous manner to 3-(2-(2-((2-(2,6-dioxopiperidin-3-yl)-1,3-dioxoisoindolin-4-yl)amino)ethoxy)ethoxy) propanoic acid, employing tert-butyl 1-amino-3,6,9,12-tetraoxapentadecan-15-oate and 2-(2,6-dioxopiperidin-3-yl)-4-fluoroisoindoline-1,3-dione.
MS m/z [M+1]$^+$: 522.4.
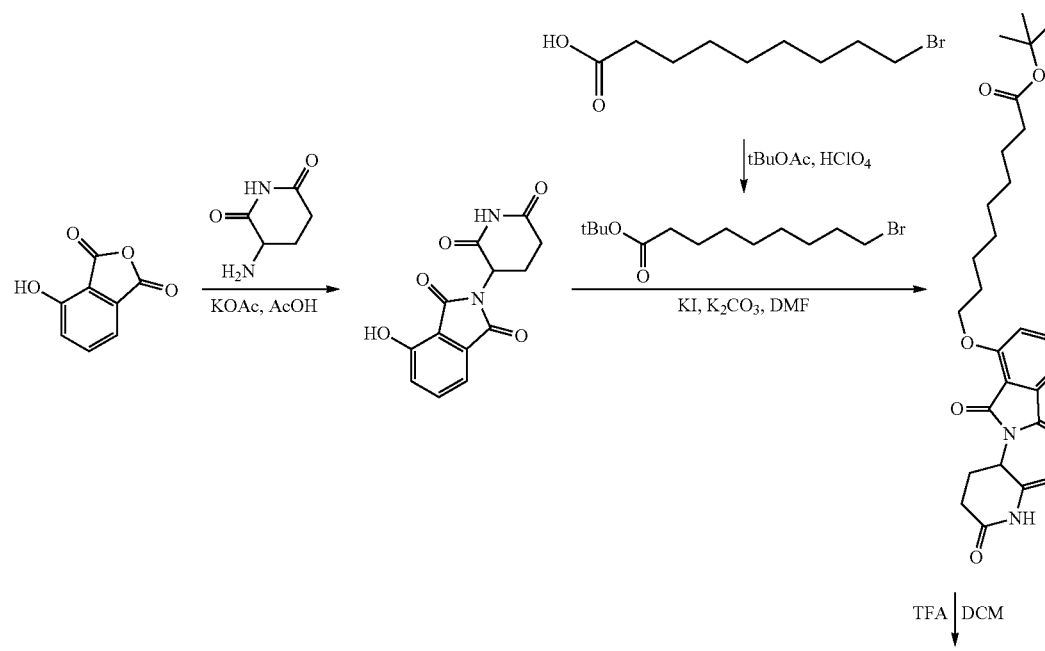
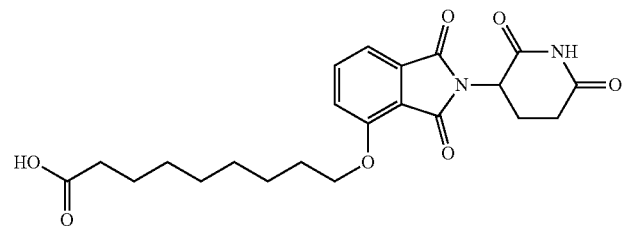

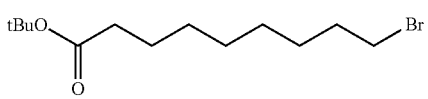 [SMILES: CC(C)(C)OC(=O)CCCCCCCCBr]

tert-Butyl 9-bromononanoate

9-Bromononanoic acid (5.5 g, 23.2 mmol) was dissolved in tert-butyl acetate (70 mL). $HClO_4$ (1.8 g) was added to the solution and the mixture was stirred overnight then quenched by addition of aqueous (aq.) $NaHCO_3$ (50 mL). The mixture was filtered and the filtrate was extracted with EtOAc (2×50 mL). The combined organic extracts were washed with brine, dried over $Na_2SO_4$ and concentrated in vacuo. The residue was purified by silica chromatography (petroleum ether:EtOAc 50:1) to give the title compound (3.6 g, 49% yield) as a colorless oil.

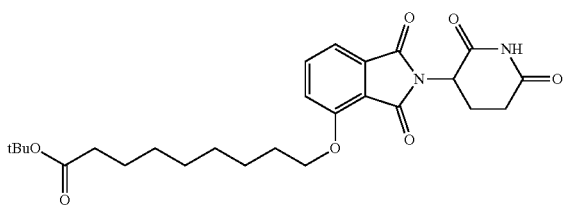 [SMILES: CC(C)(C)OC(=O)CCCCCCCCOc1cccc2c1C(=O)N(C1CCC(=O)NC1=O)C2=O]

2-(2,6-Dioxopiperidin-3-yl)-4-hydroxyisoindoline-1,3-dione

4-Hydroxyisobenzofuran-1,3-dione (3.6 g, 22 mmol), 3-aminopiperidine-2,6-dione (3.6 g, 22 mmol) and KOAc (8.6 g, 88 mmol) were dissolved in acetic acid (70 mL). The reaction mixture was stirred at 120° C. for 1 hour then cooled and diluted with water (100 mL). The resulting mixture was extracted with EtOAc (2×100 mL). The combined organic extracts were washed with $NaHCO_3$ and brine, dried over $Na_2SO_4$ and filtered. The solvents were removed under reduced pressure to give the title compound (4.0 g, 67% yield) as a blue solid.

$^1$H NMR (400 MHz, DMSO): δ 11.30 (br s, 1H), 11.10 (s, 1H), 7.65 (dd, 1H), 7.30 (d, 1H), 7.24 (d, 1H), 5.07 (m, 1H), 2.87 (m, 1H), 2.53 (m, 2H), 2.02 (m, 1H).

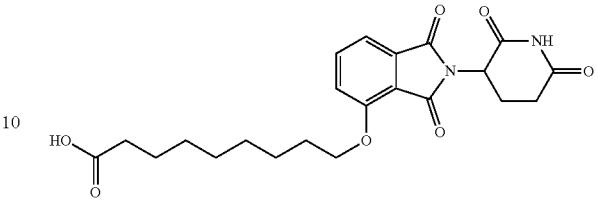

9-((2-(2,6-Dioxopiperidin-3-yl)-1,3-dioxoisoindolin-4-yl)oxy)nonanoic acid

A mixture of tert-butyl 9-bromononanoate (2.5 g, 8.53 mmol), 2-(2,6-dioxopiperidin-3-yl)-4-hydroxy isoindoline-1,3-dione (2.34 g, 8.53 mmol), $K_2CO_3$ (2.35 g, 17.06 mmol) and KI (0.71 g, 4.27 mmol) in DMF (100 mL) was stirred for 24 hours then diluted with water (200 mL). The resulting mixture was extracted with EtOAc (3×100 mL). The combined organic extracts were washed with $NaHCO_3$ and brine, dried over $Na_2SO_4$, and the residue was purified by prep-HPLC to give tert-butyl 9-((2-(2,6-dioxopiperidin-3-yl)-1,3-dioxoisoindolin-4-yl)oxy)nonanoate (0.73 g) as a white solid. This material was dissolved in a mixture of DCM (70 mL) and TFA (7 mL). The mixture was stirred for 5 hours then diluted with water (200 mL). The mixture was separated and the aqueous phase was extracted with DCM (2×100 mL). The combined organic extracts were washed with brine, dried over $Na_2SO_4$ and concentrated in vacuo to give the title compound (0.64 g, 17% yield over two steps) as a white solid.

$^1$H NMR (400 MHz, DMSO): δ 12.00 (br s, 1H), 11.1 (s, 1H), 7.79 (dd, 1H), 7.51 (d, 1H), 7.44 (d, 1H), 5.08 (m, 1H), 4.20 (t, 2H), 2.87 (m, 1H), 2.55 (m, 2H), 2.19 (t, 2H), 2.02 (m, 1H), 1.77 (m, 2H), 1.45 (m, 4H), 1.29 (m, 6H).

MS m/z 429.3 [M−H]$^-$.

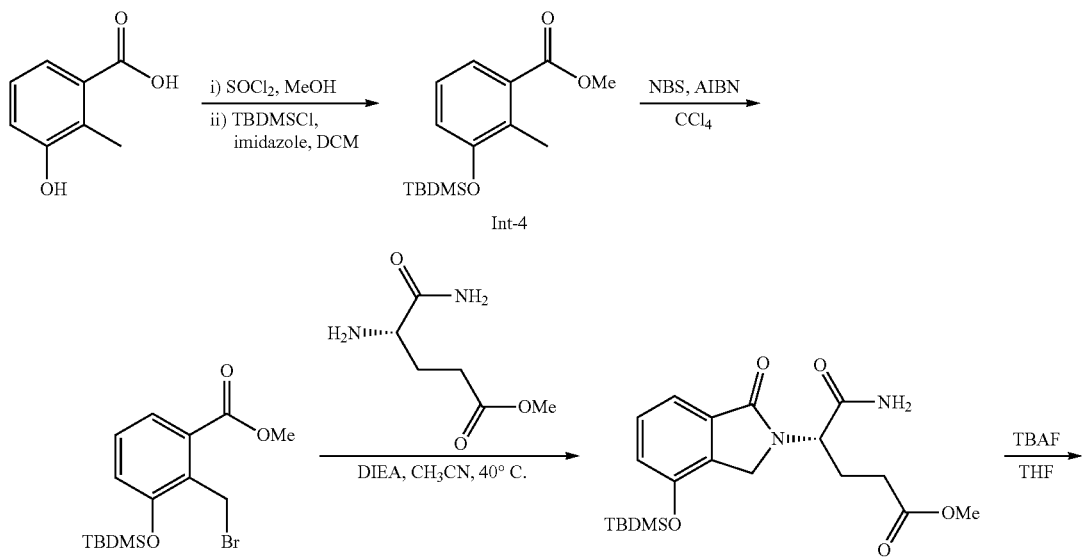

115 116
-continued
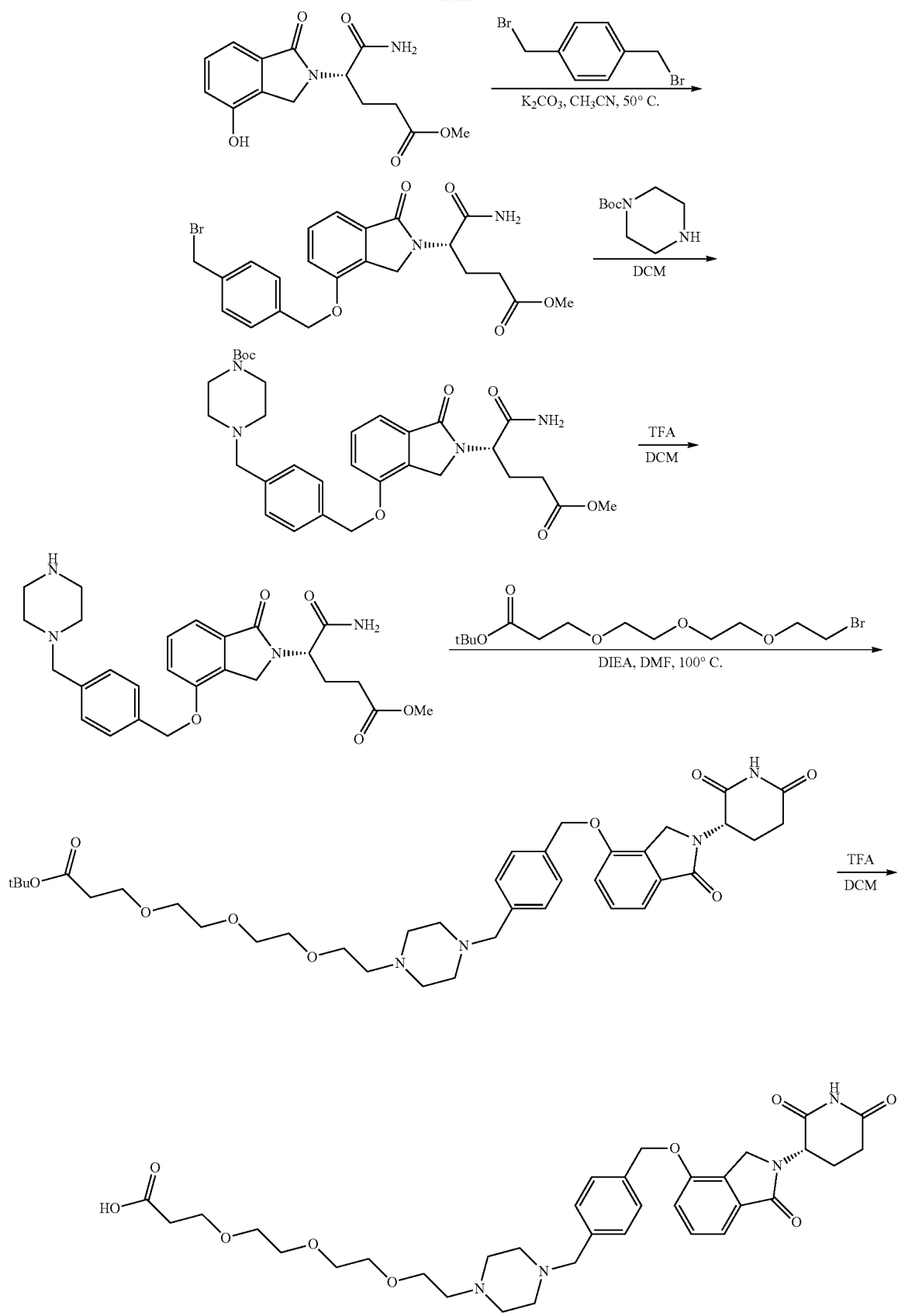

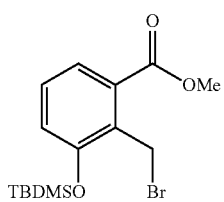 [SMILES: COC(=O)c1cccc(O[Si](C)(C)C(C)(C)C)c1CBr]

Methyl 2-(bromomethyl)-3-(tert-butyldimethylsilyloxy)benzoate

Thionyl chloride (26.2 g, 0.22 mol) was added dropwise to a solution of 3-hydroxy-2-methylbenzoic acid (20 g, 0.13 mol) in methanol (60 mL) at 0° C. The reaction was refluxed for 1 hour, and the solvent was removed to give the corresponding methyl ester (22.3 g, quantitative yield). The ester (22.3 mol, 0.13 mol) was dissolved in DCM (100 mL) and cooled to 0° C. Imidazole (26.5 g, 0.39 mol) and tert-butyldimethylsilyl chloride (TBDMSCl) (24.2 g, 0.16 mol) were added while keeping the internal temperature between 0-5° C., and the reaction was stirred for 1 hour at 0° C. The mixture was poured into water (100 mL) and extracted with DCM (3×100 mL). The combined organic extracts were washed with brine, dried over anhydrous sodium sulfate, and concentrated under reduced pressure. The residue was purified by silica chromatography (100:1 petroleum ether:EtOAc) to give TBS-protected methyl ester (Int-4) (37.9 g, quantitative yield). A mixture of Int-4 (37.9 g, 0.13 mol) and N-bromosuccinimide (NBS) (26.7 g, 0.15 mol) in CCl$_4$ (200 mL) was degassed and purged with N$_2$. Azobisisobutyronitrile (AIBN) (2.3 g, 14 mmol) was added and the reaction was refluxed overnight. After allowing the reaction to cool to room temperature, the precipitate was filtered and washed with CCl$_4$ (50 mL). The filtrate was concentrated, and the residue was suspended in water (200 mL) and extracted with EtOAc (3×200 mL). The combined organic extracts were washed with brine, dried over anhydrous sodium sulfate, and concentrated to give the title compound (52 g, quantitative yield), which was used without further purification.

$^1$H NMR (400 MHz, CDCl$_3$): δ 7.51 (dd, 1H), 7.23 (m, 1H), 7.00 (dd, 1H), 5.02 (s, 2H), 3.93 (s, 3H), 1.26 (s, 9H), 0.31 (s, 6H).

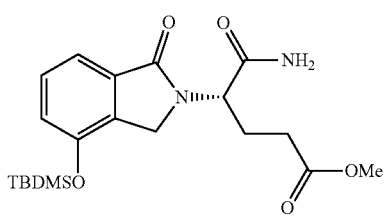 [SMILES: COC(=O)CC[C@@H](C(N)=O)N1Cc2c(O[Si](C)(C)C(C)(C)C)cccc2C1=O]

(S)-Methyl 5-amino-4-(4-(tert-butyldimethylsilyloxy)-1-oxoisoindolin-2-yl)-5-oxopentanoate A mixture of methyl 2-(bromomethyl)-3-(tert-butyldimethylsilyloxy)benzoate (7.29 g, 20.3 mmol), (S)-methyl 4,5-diamino-5-oxopentanoate hydrochloride (4 g, 20.3 mmol), and N,N-diisopropylethylamine (DIEA) (5.24 g, 40.6 mmol) in acetonitrile (50 mL) was heated at 40° C. overnight. The mixture was cooled, diluted with EtOAc (200 mL), washed with 1 N HCl, saturated sodium bicarbonate and brine, dried over anhydrous sodium sulfate, and concentrated in vacuo. The residue was purified by silica chromatography (100:1 DCM:methanol) to give the title compound (4.2 g, 51% yield) as a light yellow powder.

$^1$H NMR (400 MHz, CDCl$_3$): δ 7.44 (d, 1H), 7.34 (m, 1H), 6.96 (d, 1H), 6.38 (br s, 1H), 5.37 (br s, 1H), 4.90 (m, 1H), 4.35 (dd, 2H), 3.65 (s, 3H), 2.44 (m, 3H), 2.35 (m, 1H), 1.00 (s, 9H), 0.26 (s, 6H).

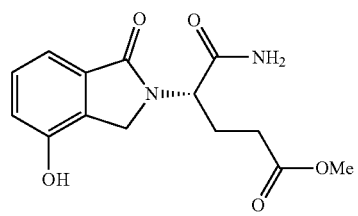 [SMILES: COC(=O)CC[C@@H](C(N)=O)N1Cc2c(O)cccc2C1=O]

(S)-Methyl 5-amino-4-(4-hydroxy-1-oxoisoindolin-2-yl)-5-oxopentanoate

Tetrabutylammonium fluoride (TBAF) (6.3 g, 20.0 mmol) was added to a solution of (S)-methyl 5-amino-4-(4-(tert-butyldimethylsilyloxy)-1-oxoisoindolin-2-yl)-5-oxopentanoate (4.2 g, 10.0 mmol) in THF (20 mL) and the reaction mixture was stirred for 2 hours. The solution was poured into water (50 mL) and extracted with EtOAc (3×50 mL). The combined organic extracts were washed with brine, dried over anhydrous sodium sulfate, and concentrated under reduced pressure to give the title compound (3.6 g, quantitative yield), which was used without further purification.

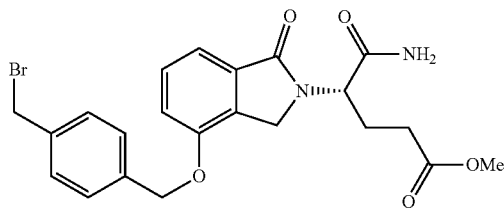 [SMILES: COC(=O)CC[C@@H](C(N)=O)N1Cc2c(OCc3ccc(CBr)cc3)cccc2C1=O]

(S)-Methyl 5-amino-4-(4-(4-(bromomethyl)benzyloxy)-1-oxoisoindolin-2-yl)-5-oxo pentanoate A mixture of (S)-methyl 5-amino-4-(4-hydroxy-1-oxoisoindolin-2-yl)-5-oxopentanoate (3.6 g, 12.3 mmol), 1,4-bis(bromomethyl)benzene (9.7 g, 36.9 mmol), and potassium carbonate (1.7 g, 12.3 mmol) in acetonitrile (20 mL) was heated at 50° C. overnight. The mixture was cooled, filtered, and washed with acetonitrile (10 mL). The filtrate was concentrated and the residue purified by silica chromatography (100:1 DCM:methanol) to give the title compound (1.28 g, 22% yield).

MS m/z 475.34 [M+H]$^+$

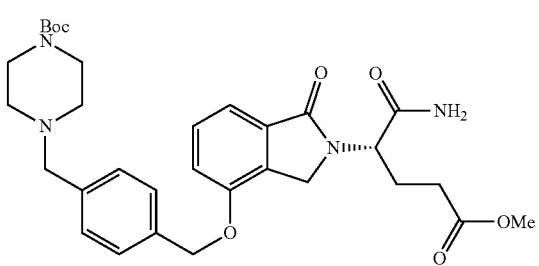 [SMILES: COC(=O)CC[C@@H](C(N)=O)N1Cc2c(OCc3ccc(CN4CCNCC4)cc3)cccc2C1=O]

(S)-tert-Butyl 4-(4-((2-(1-amino-5-methoxy-1,5-dioxopentan-2-yl)-1-oxoisoindolin-4-yloxy)methyl)benzyl)piperazine-1-carboxylate tert-Butyl piperazine-1-carboxylate (1.69 g, 9.1 mmol) was added to a solution of (S)-methyl 5-amino-4-(4-(4-(bromomethyl)benzyloxy)-1-oxoisoindolin-2-yl)-5-oxopentanoate (1.23 g, 2.6 mmol) in DCM (10 mL). The reaction was stirred for 5 hours. The solvent was removed in vacuo and the residue was purified by silica gel chromatography (20:1 DCM/methanol) to give the title compound (1.1 g, 73% yield).

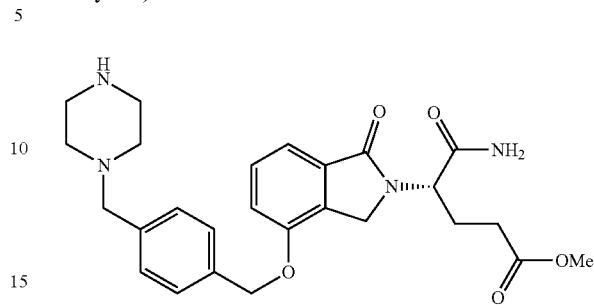

(S)-Methyl 5-amino-5-oxo-4-(1-oxo-4-(4-(piperazin-1-ylmethyl)benzyloxy) isoindolin-2-yl) pentanoate TFA (3 mL) was added to a solution of (S)-tert-butyl 4-(4-((2-(1-amino-5-methoxy-1,5-dioxopentan-2-yl)-1-oxoisoindolin-4-yloxy)methyl)benzyl)piperazine-1-carboxylate (1.1 g, 1.9 mmol) in DCM (6 mL). The reaction was stirred for 2 hours. The solvent was removed in vacuo to give the title compound as the TFA salt (1.1 g, 86% yield).

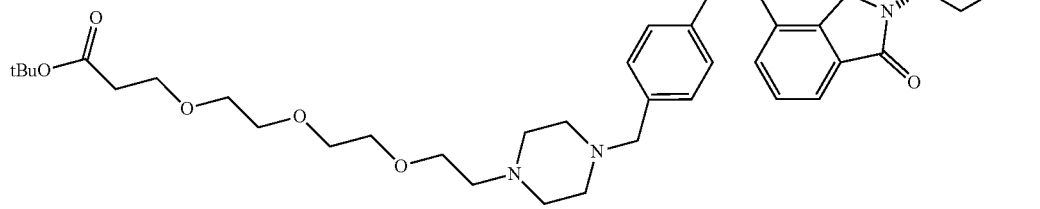

(S)-tert-Butyl 3-(2-(2-(2-(4-(4-((2-(2,6-dioxopiperidin-3-yl)-1-oxoisoindolin-4-yloxy)methyl) benzyl) piperazin-1-yl)ethoxy)ethoxy)ethoxy)propanoate A solution of (S)-methyl 5-amino-5-oxo-4-(1-oxo-4-(4-(piperazin-1-ylmethyl) benzyloxy)isoindolin-2-yl)pentanoate (173 mg, 0.26 mmol), tert-butyl 3-(2-(2-(2-bromoethoxy)ethoxy)ethoxy)propanoate (122 mg, 0.34 mmol), and DIEA (139 mg, 1.08 mmol) in DMF (5 mL) was heated at 100° C. overnight. The mixture was cooled, poured into water (30 mL), and extracted with EtOAc (3×30 mL). The combined organic extracts were washed with brine, dried over anhydrous sodium sulfate, and concentrated in vacuo. The residue was purified by silica gel chromatography (20:1 DCM/methanol) to give the title compound (130 mg, 67% yield).

MS m/z 709.52 [M+H]$^+$

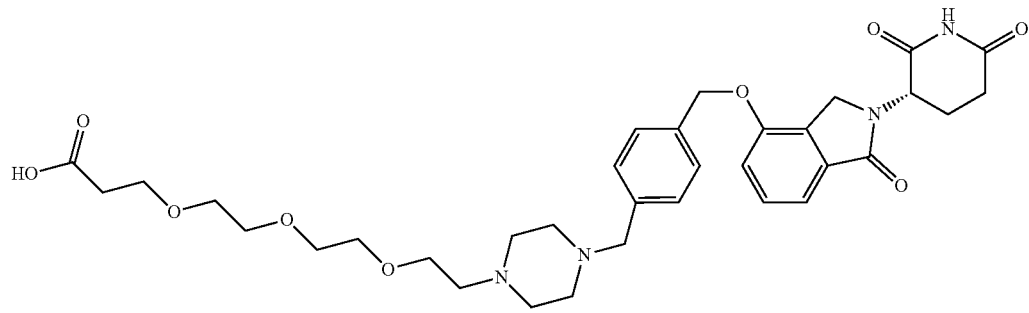 [SMILES: O=C(O)CCOCCOCCOCCN1CCN(Cc2ccc(COc3cccc4c3CN([C@H]3CCC(=O)NC3=O)C4=O)cc2)CC1]

(S)-3-(2-(2-(2-(4-(4-(((2-(2,6-Dioxopiperidin-3-yl)-1-oxoisoindolin-4-yl)oxy)methyl)benzyl) piperazin-1-yl)ethoxy)ethoxy)ethoxy)propanoic acid TFA (5 mL) was added to a solution of (S)-tert-butyl 3-(2-(2-(2-(4-(4-((2-(2,6-dioxopiperidin-3-yl)-1-oxoisoindolin-4-yloxy)methyl)benzyl)piperazin-1-yl)ethoxy)ethoxy)ethoxy)propanoate (130 mg, 0.18 mmol) in DCM (5 mL). The reaction was stirred for 2 hours and the solvent was removed under reduced pressure to give the title compound (160 mg, ~quantitative yield).

MS m/z 653.6 [M+H]⁺.

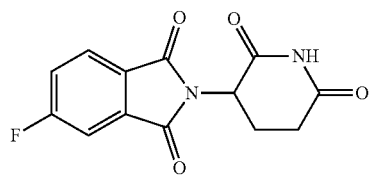 [SMILES: O=C1CCC(N2C(=O)c3ccc(F)cc3C2=O)C(=O)N1]

2-(2,6-Dioxopiperidin-3-yl)-5-fluoroisoindoline-1,3-dione was prepared according to the procedures described in U.S. Patent Application Publication 2016/0058872 A1.

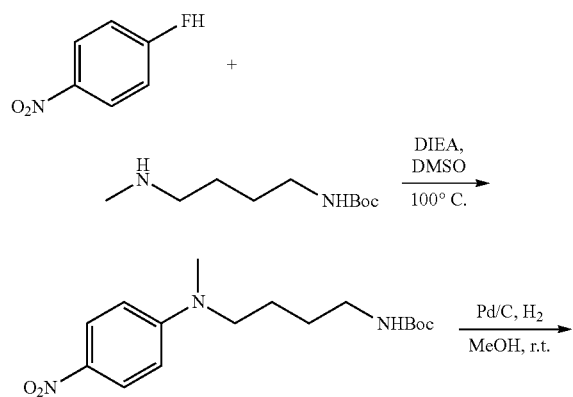

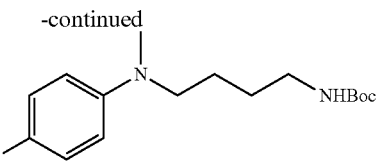

tert-Butyl (4-((4-aminophenyl)(methyl)amino)butyl) carbamate

1-Fluoro-4-nitrobenzene (350 mg, 2.5 mmol), tert-butyl (4-(methylamino)butyl)carbamate (500 mg, 2.5 mmol) and DIEA (870 μL, 5.0 mmol) were added to DMSO (5 mL). The mixture was heated to 100° C. for 3 hours, then cooled to room temperature. The mixture was diluted with EtOAc (50 mL) and water (50 mL), and extracted with EtOAc (3×20 mL). The organic extract was washed with brine (30 mL), dried over MgSO₄, and concentrated under reduced pressure. The residue was purified via silica gel chromatography (Hexane:EtOAc 3:1) to give tert-butyl (4-(methyl(4-nitrophenyl)amino)butyl)carbamate (780 mg, 96% yield).

MS m/z 324.19[M+H]⁺.

tert-Butyl (4-(methyl(4-nitrophenyl)amino)butyl)carbamate (780 mg, 2.4 mmol) in MeOH (25 mL) was purged with argon, and 10% Pd on C (80 mg) was added. The reaction was purged with hydrogen and the mixture stirred under hydrogen for 6 hours. The mixture was filtered using a pad of Celite®, washed with methanol, and the filtrate was concentrated under reduced pressure to give the title compound (610 mg, 87%) as a brown solid, used in the next step without further purification.

MS m/z 294.24 [M+H]⁺.

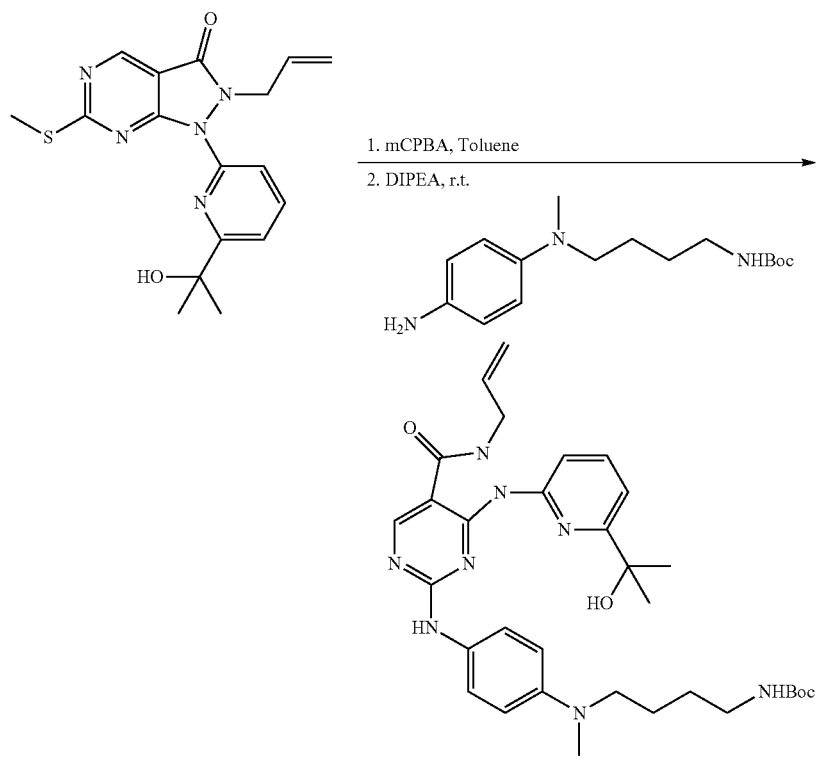

tert-Butyl (4-((4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)(methyl)amino)butyl)carbamate m-Chloroperoxybenzoic acid (280 mg, 1.25 mmol) was added to a solution of 2-allyl-1-(6-(2-hydroxypropan-2-yl)pyridin-2-yl)-6-(methylthio)-1,2-dihydro-3H-pyrazolo [3,4-d]pyrimidin-3-one (320 mg, 0.9 mmol) in toluene, and the reaction mixture was stirred for 1 hour. N,N-diisopropylethylamine (1 mL, 4 mmol) and tert-butyl (4-((4-aminophenyl)(methyl)amino)butyl) carbamate (320 mg, 1.1 mmol) were added and the reaction mixture was stirred overnight. Saturated $NaHCO_3$ (10 mL) was added and the mixture was extracted with EtOAc (2×15 mL). The organic phase was washed with brine, dried over $MgSO_4$, filtered, and concentrated in vacuo. The crude material was purified via silica gel chromatography (20:1 DCM:MeOH) to give the title compound (490 mg, 85%).

MS m/z 603.45 $[M+H]^+$.

Benzyl (1-(3-((tert-butoxycarbonyl)amino)propyl)piperidin-4-yl)carbamate

Benzyl piperidin-4-ylcarbamate (500 mg, 2.1 mmol), tert-butyl (3-bromopropyl)carbamate (560 mg, 2.3 mmol), NaI (345 mg, 2.3 mmol) and K₂CO₃ (580 mg, 4.2 mmol) were added to acetone (15 mL). The mixture was refluxed for 2 hours, the solvent was removed under reduced pressure and the residue was dissolved in water and ethyl acetate. The mixture was extracted with EtOAc (3×30 mL). The organic extract was washed with brine (30 ml), dried over MgSO₄, and concentrated under reduced pressure. The residue was purified via silica gel chromatography (DCM: MeOH 10:1) to give the title compound (580 mg, 75% yield).

MS m/z 392.97 [M+H]⁺.

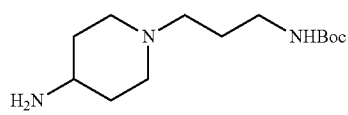

tert-Butyl (3-(4-aminopiperidin-1-yl)propyl)carbamate

Benzyl (1-(3-((tert-butoxycarbonyl)amino)propyl) piperidin-4-yl)carbamate (410 mg, 1.0 mmol) in MeOH (10 mL) was purged with argon, and 10% Pd on C (40 mg) was added. The reaction was purged with hydrogen and the mixture stirred under hydrogen for 12 hours. The mixture was filtered using a pad of celite, washed with methanol, and the filtrate was concentrated under reduced pressure to give the title compound (230 mg, 90% yield) as a brown oil, used in the next step without further purification.

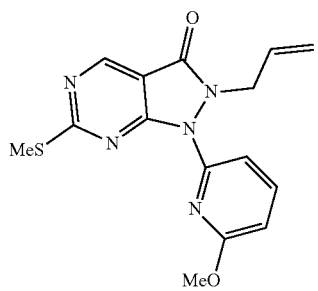 [SMILES: C=CCn1c(=O)c2cnc(SC)nc2n1-c1cccc(OC)n1]

2-Allyl-1-(6-methoxypyridin-2-yl)-6-(methylthio)-1,2-dihydro-3H-pyrazolo[3,4-d]pyrimidin-3-one The title compound was prepared in an analogous manner to 2-allyl-1-(6-(2-hydroxypropan-2-yl)pyridin-2-yl)-6-(methylthio)-1,2-dihydro-3H-pyrazolo [3,4-d]pyrimidin-3-one, from Int-1 and 2-bromo-6-methoxypyridine.

MS m/z [M+1]⁺: 330.12

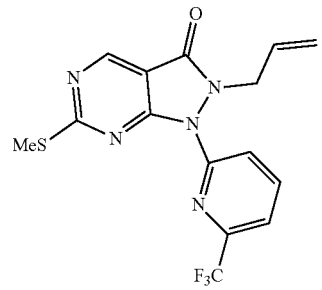 [SMILES: C=CCn1c(=O)c2cnc(SC)nc2n1-c1cccc(C(F)(F)F)n1]

2-Allyl-6-(methylthio)-1-(6-(trifluoromethyl)pyridin-2-yl)-1,2-dihydro-3H-pyrazolo[3,4-d]pyrimidin-3-one The title compound was prepared in an analogous manner to 2-allyl-1-(6-(2-hydroxypropan-2-yl)pyridin-2-yl)-6-(methylthio)-1,2-dihydro-3H-pyrazolo [3,4-d]pyrimidin-3-one, from Int-1 and 2-bromo-6-(trifluoromethyl)pyridine.

MS m/z [M+1]⁺: 368.07.

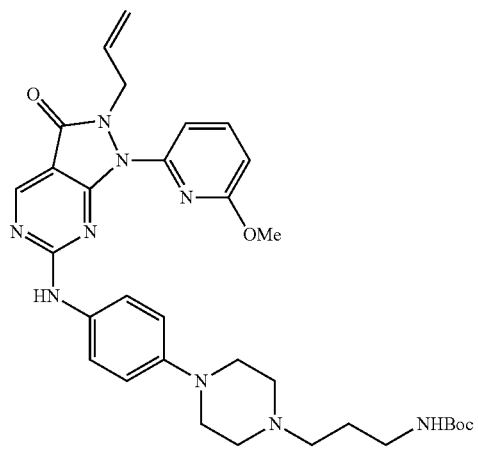 [SMILES: C=CCn1c(=O)c2cnc(Nc3ccc(N4CCN(CCCNC(=O)OC(C)(C)C)CC4)cc3)nc2n1-c1cccc(OC)n1]

tert-Butyl (3-(4-(4-((2-allyl-1-(6-methoxypyridin-2-yl)-3-oxo-2,3-dihydro-1H-pyrazolo[3,4-d]pyrimidin-6-yl)amino)phenyl)piperazin-1-yl)propyl)carbamate The title compound was prepared in an analogous manner to tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate, from Int-3 and 2-allyl-1-(6-methoxypyridin-2-yl)-6-(methylthio)-1,2-dihydro-3H-pyrazolo[3,4-d]pyrimidin-3-one.

MS m/z [M+1]⁺: 616.48.

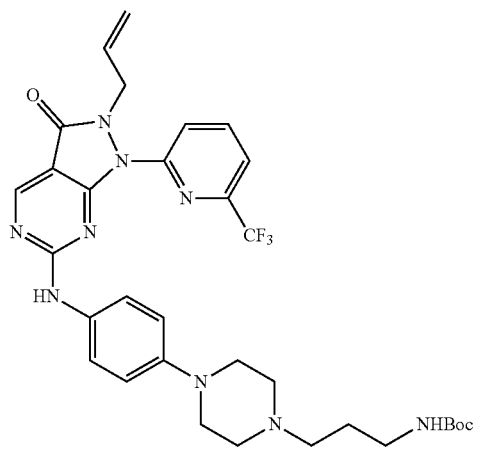 [SMILES: C=CCn1c(=O)c2cnc(Nc3ccc(N4CCN(CCCNC(=O)OC(C)(C)C)CC4)cc3)nc2n1-c1cccc(C(F)(F)F)n1]

tert-Butyl (3-(4-(4-((2-allyl-3-oxo-1-(6-(trifluoromethyl)pyridin-2-yl)-2,3-dihydro-1H-pyrazolo[3,4-d]pyrimidin-6-yl)amino)phenyl)piperazin-1-yl)propyl)carbamate The title compound was prepared in an analogous manner to tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate, from Int-3 and 2-allyl-6-(methylthio)-1-(6-(trifluoromethyl)pyridin-2-yl)-1,2-dihydro-3H-pyrazolo[3,4-d]pyrimidin-3-one.

MS m/z [M+1]+: 654.38.

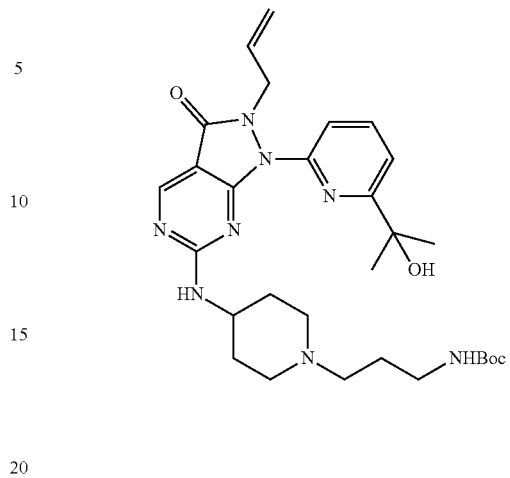

tert-Butyl (3-(4-((2-allyl-1-(6-(2-hydroxypropan-2-yl)pyridin-2-yl)-3-oxo-2,3-dihydro-1H-pyrazolo[3,4-d]pyrimidin-6-yl)amino)piperidin-1-yl)propyl)carbamate The title compound was prepared in an analogous manner to tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate, from 2-allyl-1-(6-(2-hydroxypropan-2-yl)pyridin-2-yl)-6-(methylthio)-1,2-dihydro-3H-pyrazolo[3,4-d]pyrimidin-3-one and tert-butyl (3-(4-aminopiperidin-1-yl)propyl)carbamate.

MS m/z [M+1]+: 567.54.

Example 2: Synthesis of 4-((15-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-15-oxo-3,6,9,12-tetraoxapentadecyl)amino)-2-(2,6-dioxopiperidin-3-yl)isoindoline-1,3-dione (1)

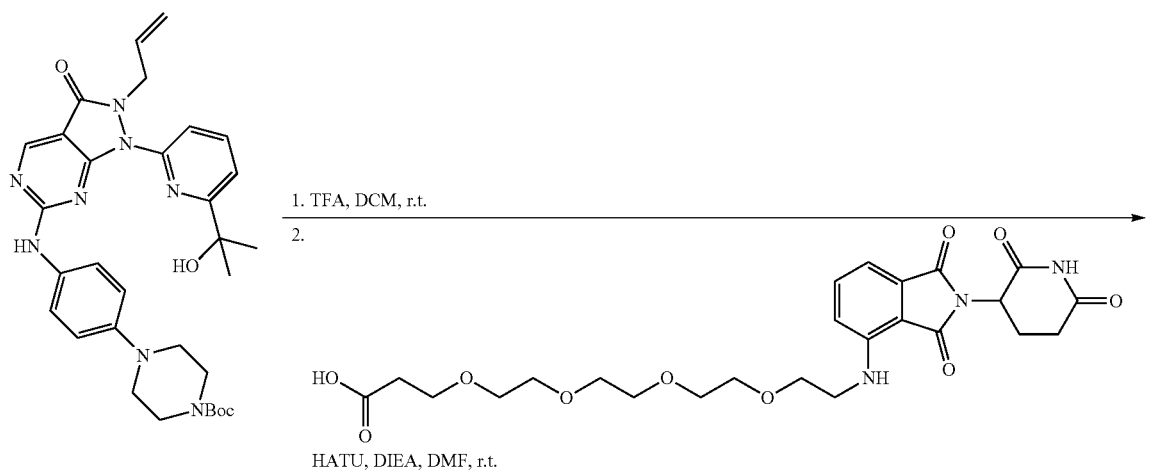

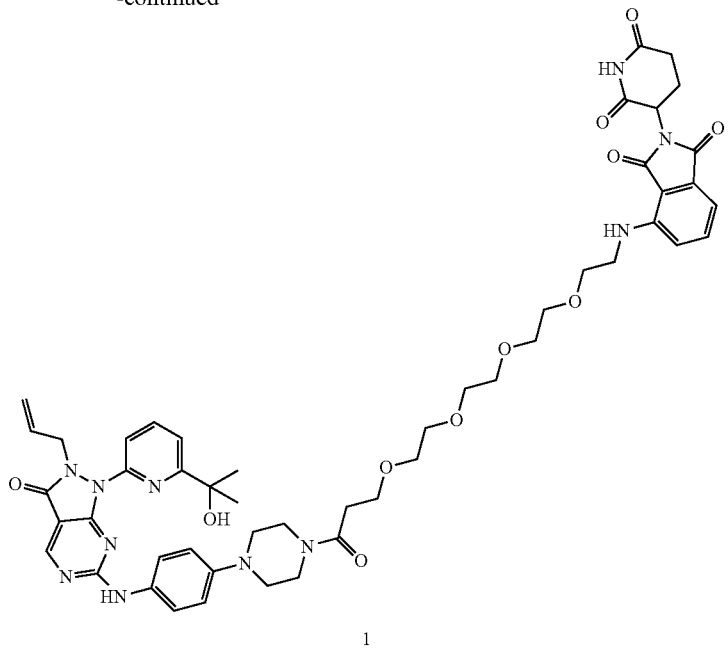

TFA (0.5 mL) was added to a solution of tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate (15 mg, 0.025 mmol) in DCM (2 mL). The reaction was stirred for 2 hours. The solvent was removed under reduced pressure to obtain the TFA salt of the Boc-deprotected amine. 1-[Bis(dimethylamino)methylene]-1H-1,2,3-triazolo[4,5-b]pyridinium 3-oxide hexafluorophosphate (HATU) (20 mg, 0.05 mmol), 1-((2-(2,6-dioxopiperidin-3-yl)-1,3-dioxoisoindolin-4-yl)amino)-3,6,9,12-tetraoxapentadecan-15-oic acid (13 mg, 0.025 mmol) and DIEA (25 μL, 0.13 mmol) were added to a solution of the TFA salt in DMF (1.5 mL). The reaction was stirred for 1 h and the mixture was purified by HPLC to obtain compound 1 (20 mg, 80%) as a yellow solid.

MS m/z 990.51 [M+H]⁺.

Example 3: Synthesis of 4-((2-(2-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-3-oxopropoxy)ethoxy)ethyl)amino)-2-(2,6-dioxopiperidin-3-yl)isoindoline-1,3-dione (2)

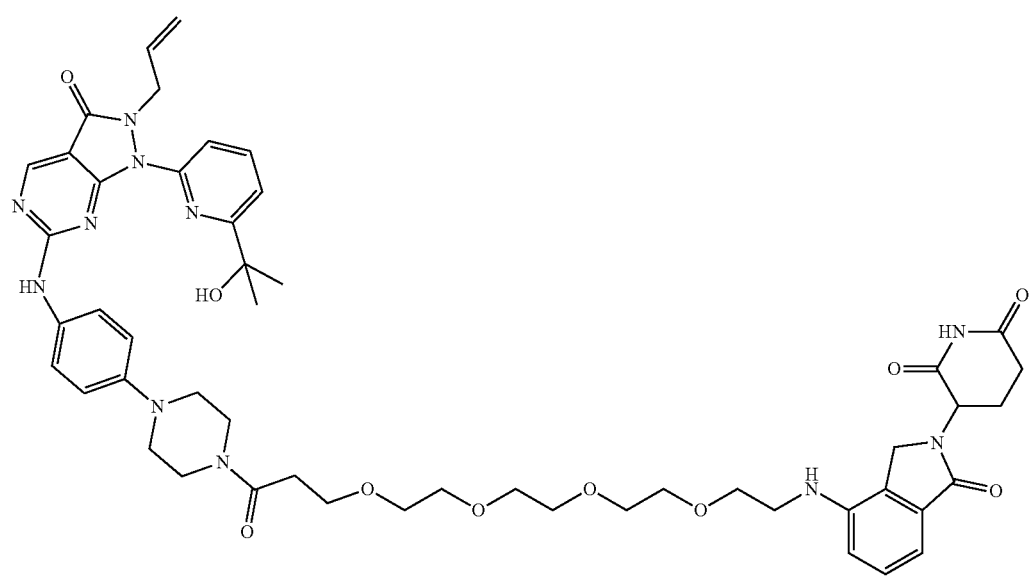

Compound 2 was prepared in an analogous manner to compound 1 in Example 2, from tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and 1-((2-(2,6-dioxopiperidin-3-yl)-1-oxoisoindolin-4-yl)amino)-3,6,9,12-tetraoxapentadecan-15-oic acid.

MS m/z [M+1]$^+$: 976.57.

Example 4: Synthesis of 4-((2-(2-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-3-oxopropoxy)ethoxy)ethyl)amino)-2-(2,6-dioxopiperidin-3-yl)isoindoline-1,3-dione (3)

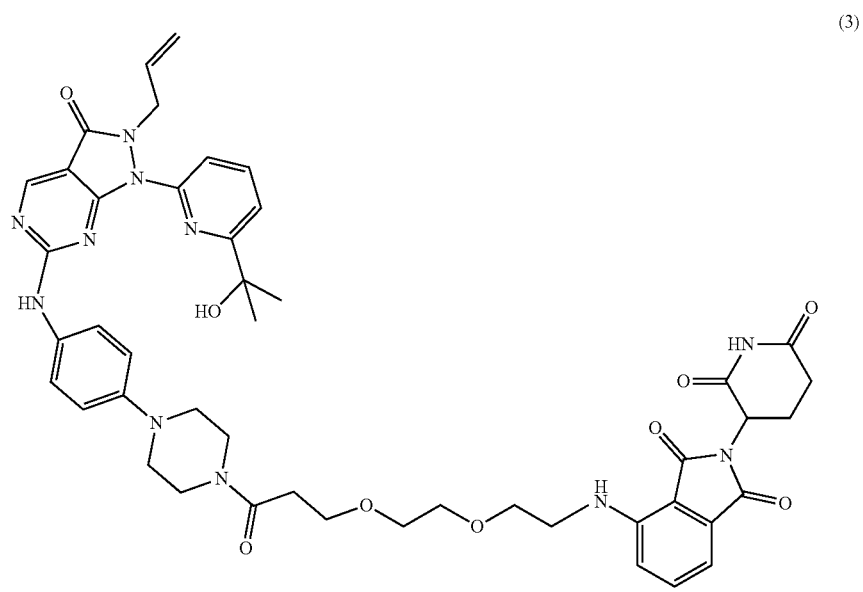

(3)

Compound 3 was prepared in an analogous manner to compound 1 in Example 2, from tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and 3-(2-(2-((2-(2,6-dioxopiperidin-3-yl)-1,3-dioxoisoindolin-4-yl)amino)ethoxy)ethoxy)propanoic acid.

MS m/z [M+1]$^+$: 902.55.

Example 5: Synthesis of 3-(4-((2-(2-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-3-oxopropoxy)ethoxy)ethyl)amino)-1-oxoisoindolin-2-yl)piperidine-2,6-dione (4)

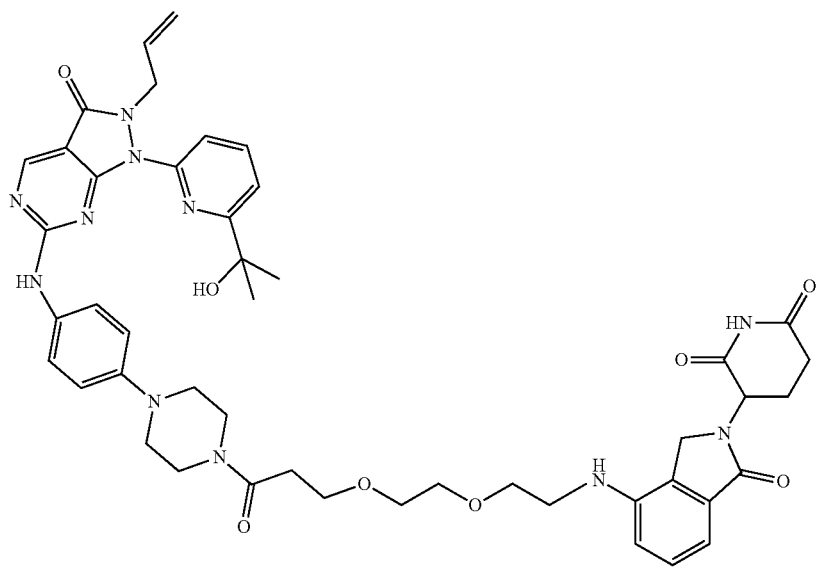

(4)

Compound 4 was prepared in an analogous manner to compound 1 in Example 2, from tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and 3-(2-(2-((2-(2,6-dioxopiperidin-3-yl)-1-oxoisoindolin-4-yl)amino)ethoxy)ethoxy)propanoic acid.

MS m/z [M+1]⁺: 888.56.

Example 6: Synthesis of 4-((2-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-3-oxopropoxy)ethyl)amino)-2-(2,6-dioxopiperidin-3-yl)isoindoline-1,3-dione (5)

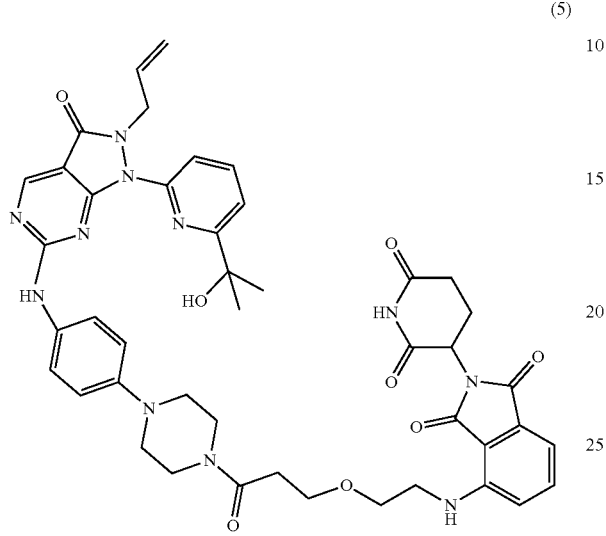

(5)

Compound 5 was prepared in an analogous manner to compound 1 in Example 2, from tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and 3-(2-((2-(2,6-dioxopiperidin-3-yl)-1,3-dioxoisoindolin-4-yl)amino)ethoxy)propanoic acid.
MS m/z [M+1]$^+$: 858.54.

Example 7: Synthesis of 4-((9-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-9-oxononyl)oxy)-2-(2,6-dioxopiperidin-3-yl)isoindoline-1,3-dione (6)

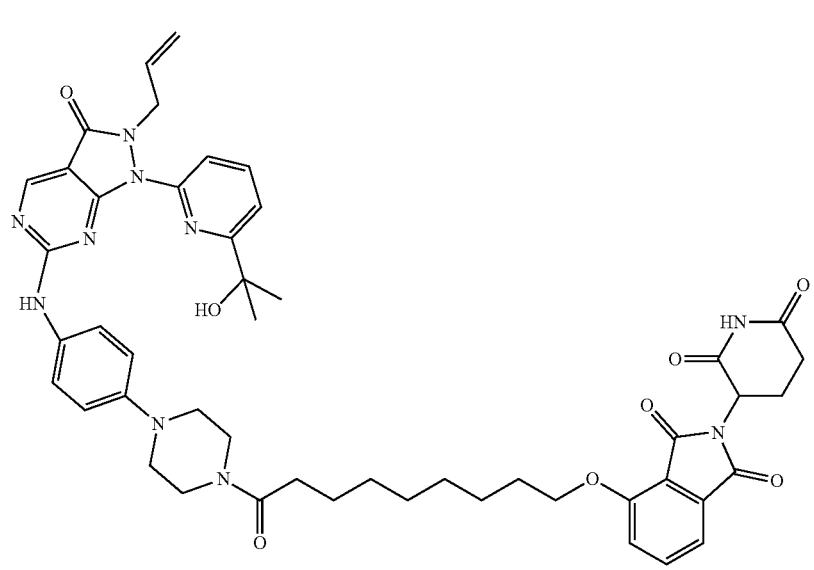

(6)

Compound 6 was prepared in an analogous manner to compound 1 in Example 2, from intermediates tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and 9-((2-(2,6-dioxopiperidin-3-yl)-1,3-dioxoisoindolin-4-yl)oxy)nonanoic acid.

MS m/z [M+1]⁺: 899.56.

Example 8: Synthesis of N-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)-3-(2-(2-((2-(2,6-dioxopiperidin-3-yl)-1,3-dioxoisoindolin-4-yl)amino)ethoxy)ethoxy)propanamide (7)

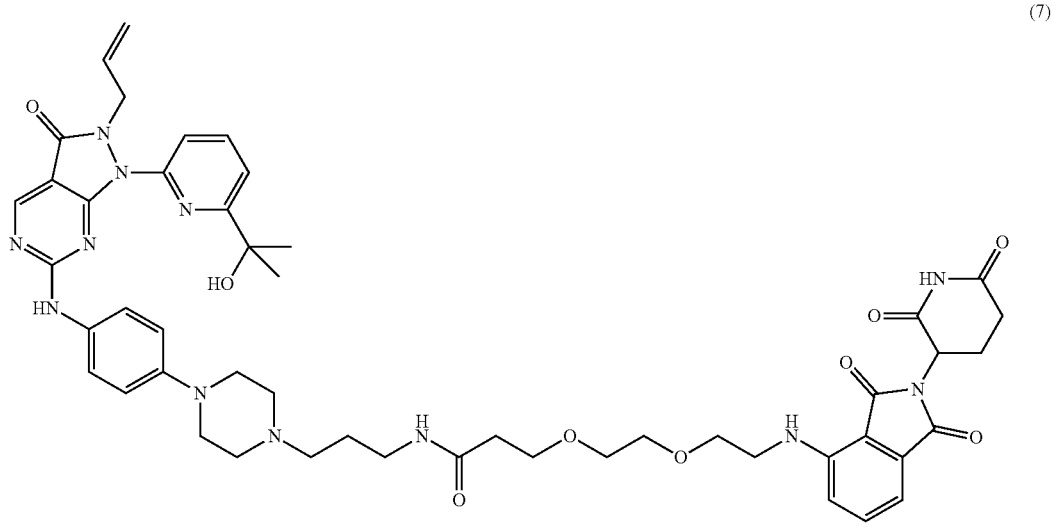 [SMILES: C=CCn1c(=O)c2cnc(Nc3ccc(N4CCN(CCCNC(=O)CCOCCOCCNc5cccc6c5C(=O)N(C5CCC(=O)NC5=O)C6=O)CC4)cc3)nc2n1-c1cccc(C(C)(C)O)n1]

(7)

Compound 7 was prepared in an analogous manner to compound 1 in Example 2, from tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate and 3-(2-(2-((2-(2,6-dioxopiperidin-3-yl)-1,3-dioxoisoindolin-4-yl)amino)ethoxy)ethoxy) propanoic acid.

MS m/z [M+1]⁺: 959.70.

Example 9: Synthesis of N-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)-1-((2-(2,6-dioxopiperidin-3-yl)-1,3-dioxoisoindolin-4-yl)amino)-3,6,9,12-tetraoxapentadecan-15-amide (8)

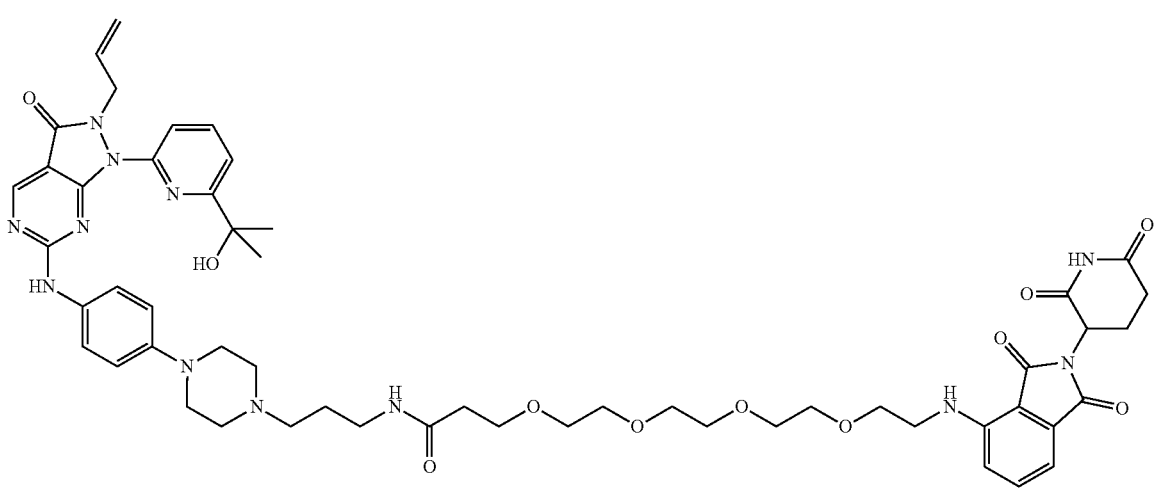

(8)

Compound 8 was prepared in an analogous manner to compound 1 in Example 2, from tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate and 1-((2-(2,6-dioxopiperidin-3-yl)-1,3-dioxoisoindolin-4-yl)amino)-3,6,9,12-tetraoxapentadecan-15-oic acid.

MS m/z [M+1]$^+$: 1047.72.

Example 10: Synthesis of (S)-3-(4-((4-((4-(2-(2-(2-(3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-3-oxopropoxy)ethoxy)ethoxy)ethyl)piperazin-1-yl)methyl)benzyl)oxy)-1-oxoisoindolin-2-yl)piperidine-2,6-dione (9)

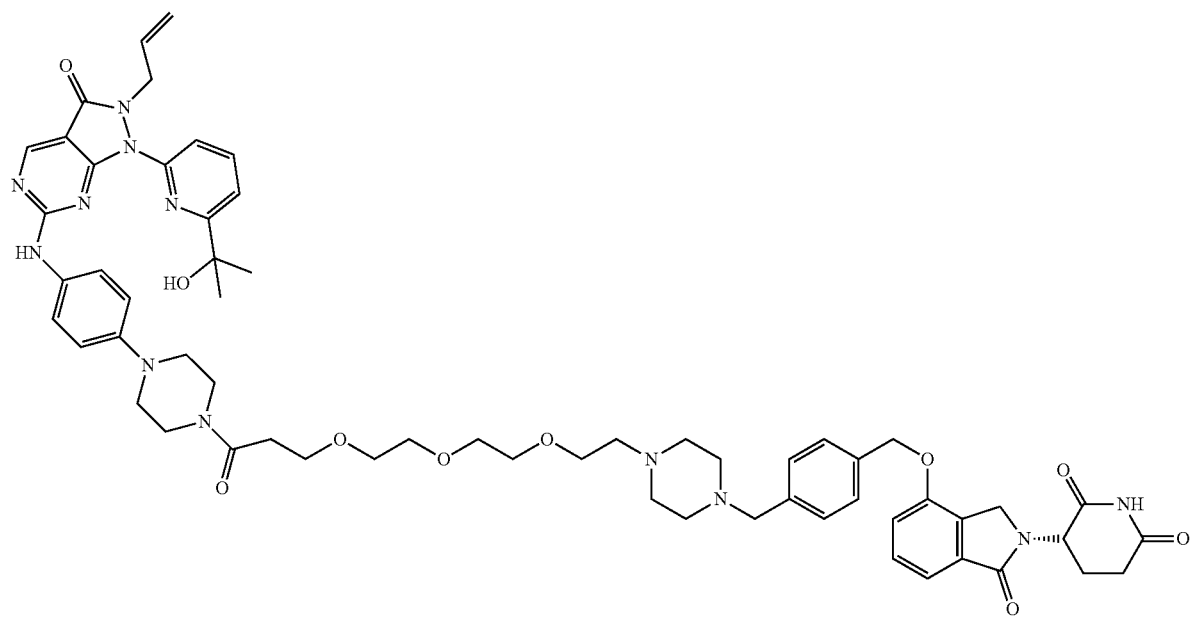

(9)

Compound 9 was prepared in an analogous manner to compound 1 in Example 2, from tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and (S)-3-(2-(2-(2-(4-(4-(((2-(2,6-dioxopiperidin-3-yl)-1-oxoisoindolin-4-yl)oxy)methyl)benzyl) piperazin-1-yl)ethoxy)ethoxy)ethoxy)propanoic acid.

MS m/z [M+1]$^+$: 1121.76.

Example 11: Synthesis of (S)—N-(3-(4-(4-((2-Allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)-3-(2-(2-(2-(4-(4-(((2-(2,6-dioxopiperidin-3-yl)-1-oxoisoindolin-4-yl)oxy)methyl)benzyl)piperazin-1-yl)ethoxy)ethoxy)ethoxy)propanamide (10)

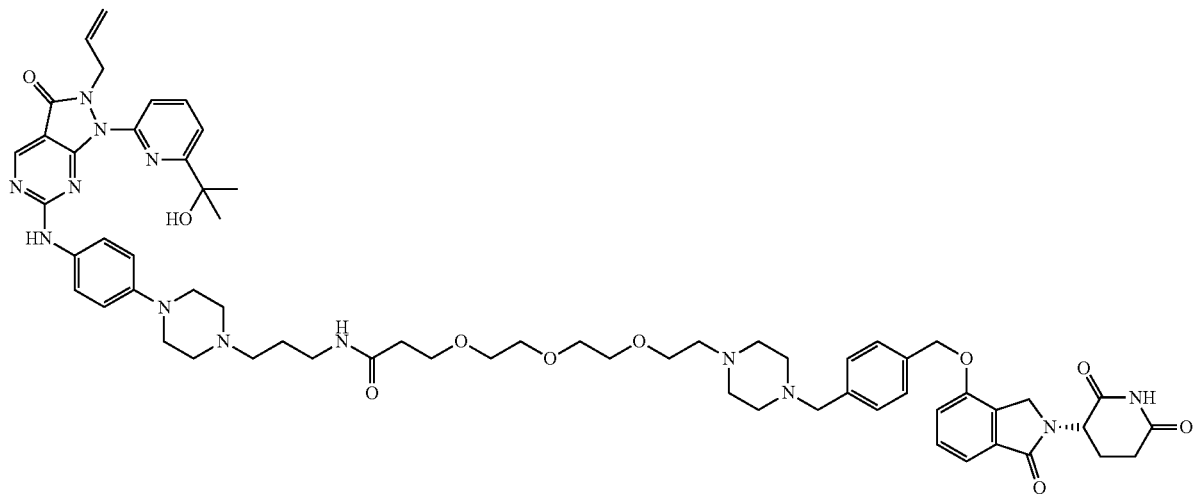

(10)

Compound 10 was prepared in an analogous manner to compound 1 in Example 2, from tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate and (S)-3-(2-(2-(2-(4-(4-(((2-(2,6-dioxopiperidin-3-yl)-1-oxoisoindolin-4-yl)oxy)methyl)benzyl) piperazin-1-yl)ethoxy)ethoxy)ethoxy)propanoic acid.

MS m/z [M+1]⁺: 1178.93.

Example 12: Synthesis of 4-((6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexyl)amino)-2-(2,6-dioxopiperidin-3-yl)isoindoline-1,3-dione (11)

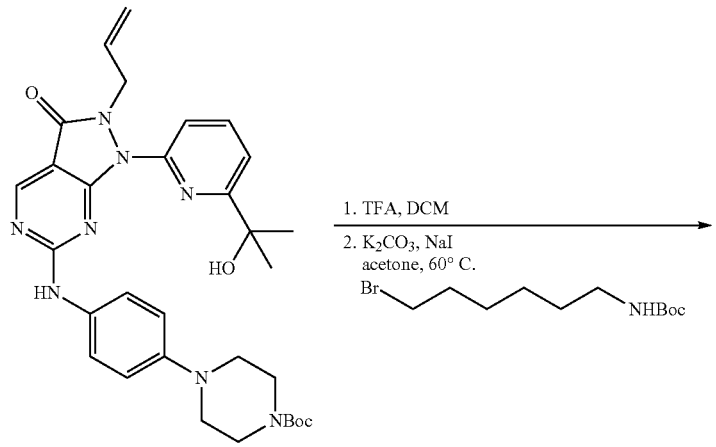

-continued
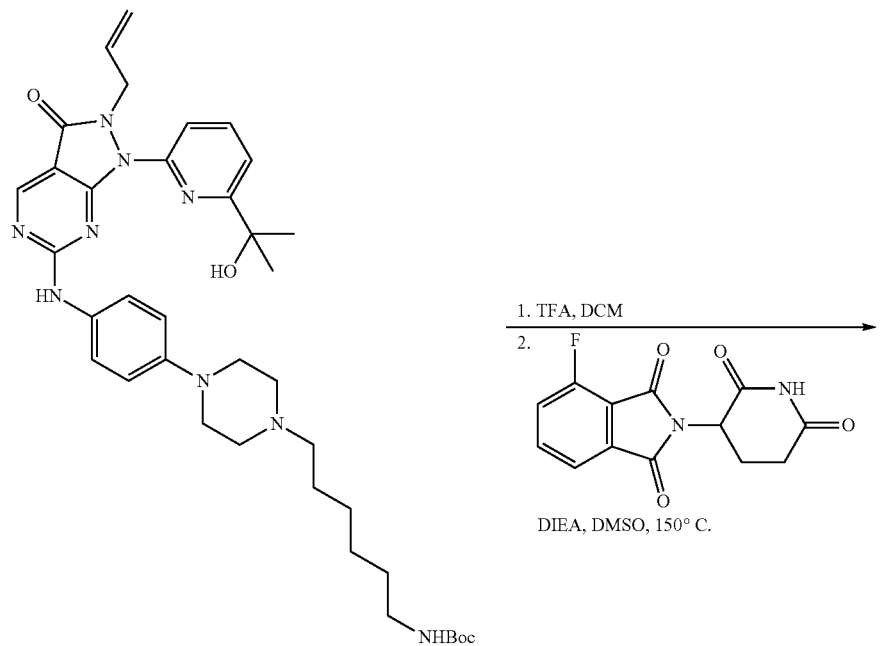
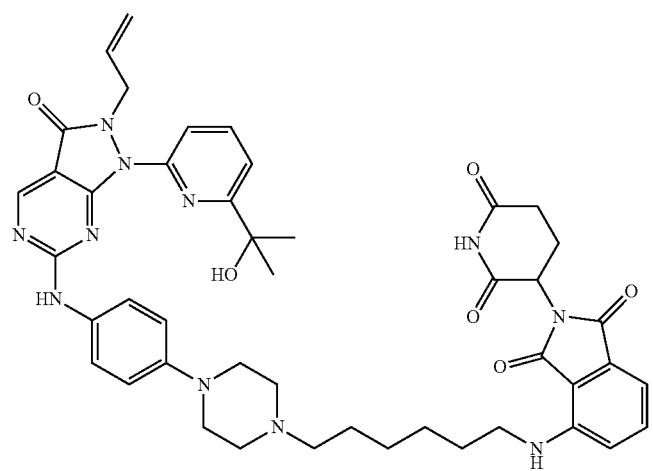

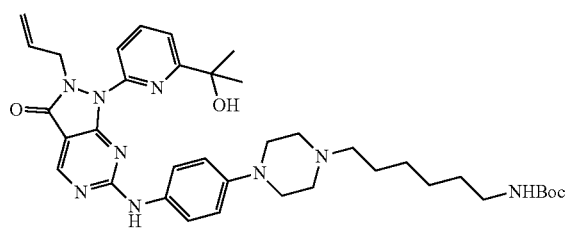 [SMILES: C=CCn1c(=O)c2cnc(Nc3ccc(N4CCN(CCCCCCNC(=O)OC(C)(C)C)CC4)cc3)nc2n1-c1cccc(C(C)(C)O)n1]

tert-Butyl (6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexyl)carbamate tert-Butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate (35 mg, 0.073 mmol) was dissolved in DCM (3 mL). TFA (1 mL) was added and the mixture was stirred for 30 minutes. The solvent was removed under reduced pressure and the residue was dissolved in acetone (5 mL). tert-Butyl (6-bromohexyl) carbamate (25 mg, 0.08 mmol), NaI (11 mg, 0.073 mmol), and K$_2$CO$_3$ (20 mg, 0.15 mmol) were added. The mixture was refluxed overnight. After allowing the reaction to cool to room temperature, the solvent was removed under reduced pressure, and the residue was dissolved in water and ethyl acetate. The mixture was extracted with EtOAc (3×10 mL). The organic extract was washed with brine (20 mL), dried over MgSO$_4$, and concentrated under reduced pressure. The residue was purified via silica gel chromatography (1:1 Hexane:EtOAc) to give the title compound (40 mg, 80%).

MS m/z 686.47 [M+H]$^+$.

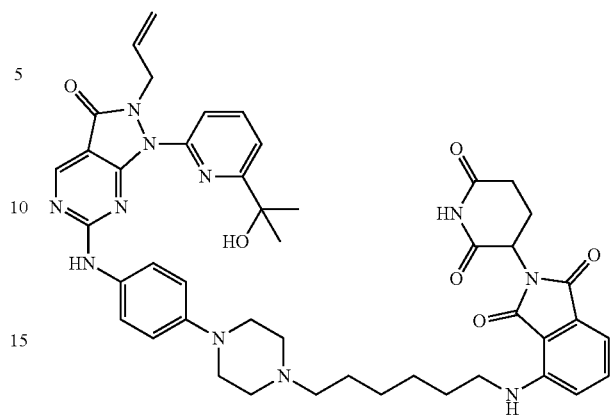

tert-Butyl (6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexyl)carbamate (20 mg, 0.03 mmol) was dissolved in DCM (3 mL). TFA (1 mL) was added and the mixture was stirred for 30 minutes. The solvent was removed under reduced pressure and the residue was dissolved in DMSO (1 mL). 2-(2,6-Dioxopiperidin-3-yl)-4-fluoroisoindoline-1,3-dione (10 mg, 0.035 mmol) and N,N-Diisopropylethylamine (15 µL, 0.09 mmol) were added, and the mixture was stirred at 150° C. for 30 min. The mixture was purified by HPLC to give compound 11 (8 mg, 30%) as a yellow solid.

MS m/z 842.52 [M+H]$^+$.

Example 13: Synthesis of 4-((2-(2-(2-(2-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)ethoxy)ethoxy)ethoxy)ethyl)amino)-2-(2,6-dioxopiperidin-3-yl)isoindoline-1,3-dione (12)

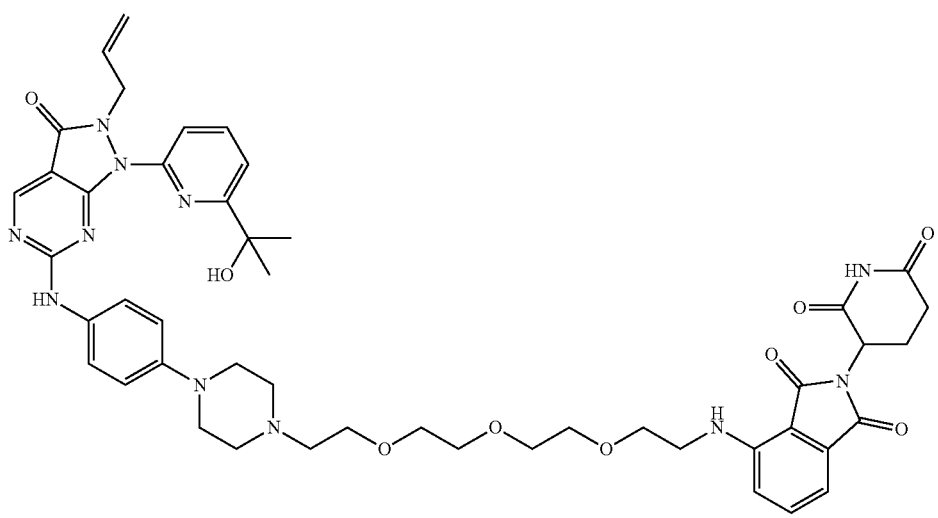

Compound 12 was prepared in an analogous manner to compound 11 in Example 12, from tert-butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate and tert-butyl (2-(2-(2-(2-bromoethoxy)ethoxy)ethyl)carbamate.

MS m/z 918.46 [M+H]$^+$.

Example 14. Synthesis of 4-((3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)amino)-2-(2,6-dioxopiperidin-3-yl)isoindoline-1,3-dione (13)

tert-Butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)carbamate (35 mg, 0.05 mmol) was dissolved in DCM (3 mL). TFA (1 mL) was added, and the mixture was stirred for 30 minutes. The solvent was removed under reduced pressure, and the residue was dissolved in DMSO (1.5 mL). 2-(2,6-dioxopiperidin-3-yl)-4-fluoroisoindoline-1,3-dione (20 mg, 0.075 mmol) and N, N-diisopropylethylamine (35 µL, 0.09 mmol) were added, and the mixture was stirred at 150° C. for 1.5 hours. The mixture was purified by HPLC to obtain compound 13 (10 mg, 25%) as a yellow solid.

MS m/z 800.52 [M+H]$^+$.

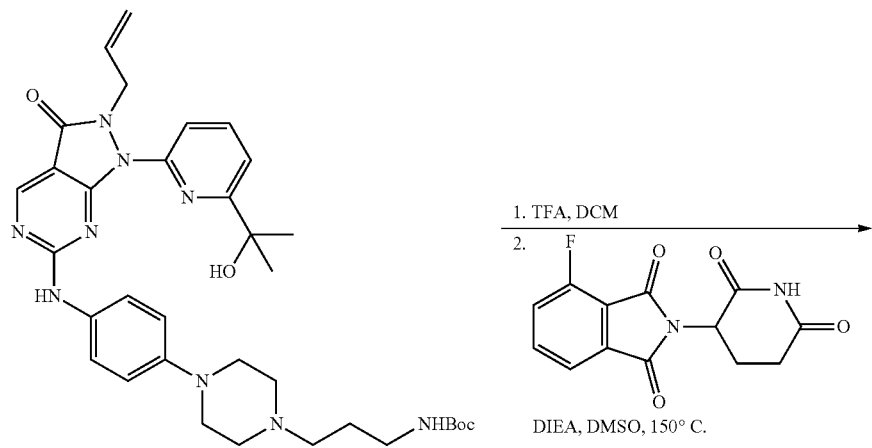

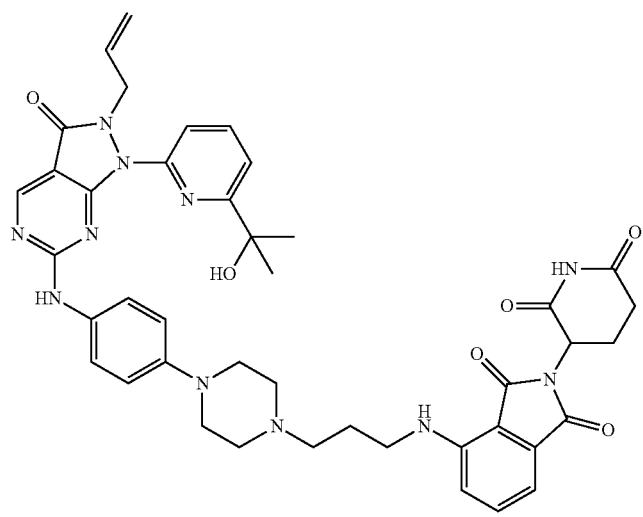

Example 15. Synthesis of 4-((6-(4-(4-((2-Allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexyl)amino)-2-(2,6-dioxopiperidin-3-yl)isoindoline-1,3-dione (14)

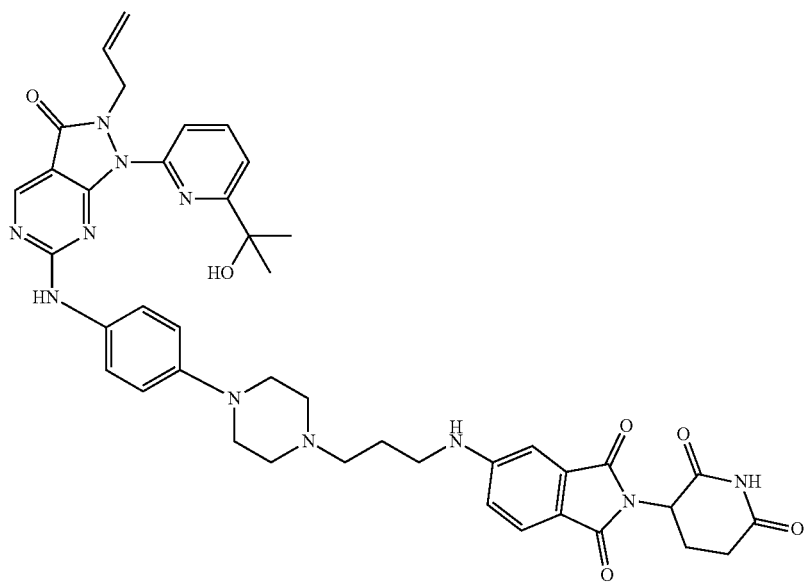

(14)

Compound 14 was prepared in an analogous manner to compound 13 in Example 14, from tert-butyl (3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl) piperazin-1-yl)propyl)carbamate and 2-(2,6-dioxopiperidin-3-yl)-5-fluoroisoindoline-1,3-dione.

MS m/z 800.52 [M+H]$^{+}$.

Example 16. Synthesis of 4-((4-((4-((2-Allyl-1-(6-(2-hydroxypropan-2-yl)pyridin-2-yl)-3-oxo-2,3-dihydro-1H-pyrazolo[3,4-d]pyrimidin-6-yl)amino)phenyl)(methyl)amino)butyl)amino)-2-(2,6-dioxopiperidin-3-yl)isoindoline-1,3-dione (15)

(15)

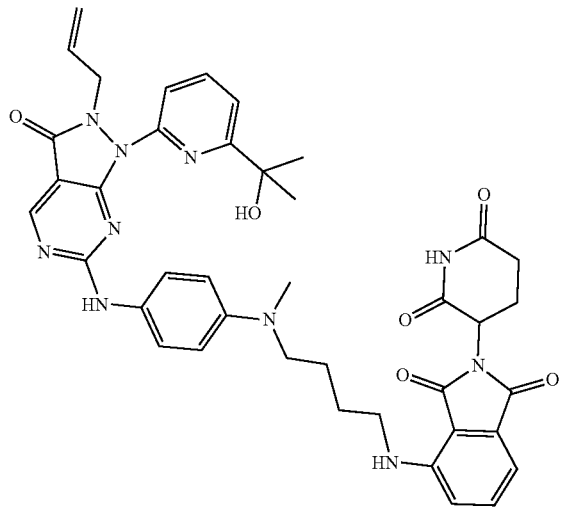

Compound 15 was prepared in an analogous manner to compound 13 in Example 14, from tert-butyl (4-((4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)(methyl)amino)butyl)carbamate and 2-(2,6-dioxopiperidin-3-yl)-4-fluoroisoindoline-1,3-dione.

MS m/z 759.41 [M+H]⁺.

Example 17. Synthesis of 5-((4-((4-((2-Allyl-1-(6-(2-hydroxypropan-2-yl)pyridin-2-yl)-3-oxo-2,3-dihydro-1H-pyrazolo[3,4-d]pyrimidin-6-yl)amino)phenyl)(methyl)amino)butyl)amino)-2-(2,6-dioxopiperidin-3-yl)isoindoline-1,3-dione (16)

(16)

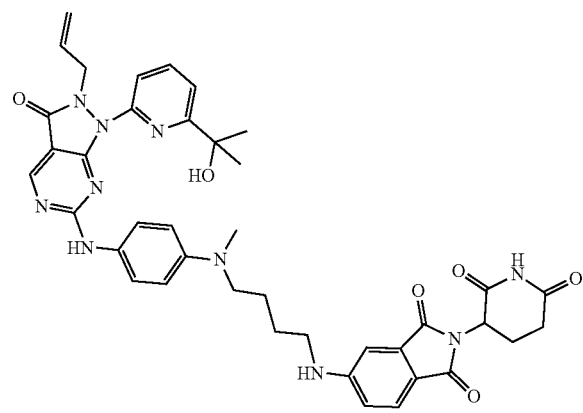

Compound 16 was prepared in an analogous manner to compound 13 in Example 14, from tert-butyl (4-((4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)(methyl)amino)butyl)carbamate and 2-(2,6-dioxopiperidin-3-yl)-5-fluoroisoindoline-1,3-dione.

MS m/z 759.46 [M+H]⁺.

Example 18. Synthesis of 4-((3-(4-(4-((2-Allyl-1-(6-methoxypyridin-2-yl)-3-oxo-2,3-dihydro-1H-pyrazolo[3,4-d]pyrimidin-6-yl)amino)phenyl)piperazin-1-yl)propyl)amino)-2-(2,6-dioxopiperidin-3-yl)isoindoline-1,3-dione (17)

(17)

Compound 17 was prepared in an analogous manner to compound 13 in Example 14, from tert-butyl (3-(4-(4-((2-allyl-1-(6-methoxypyridin-2-yl)-3-oxo-2,3-dihydro-1H-pyrazolo[3,4-d]pyrimidin-6-yl)amino)phenyl)piperazin-1-yl)propyl)carbamate and 2-(2,6-dioxopiperidin-3-yl)-3-fluoroisoindoline-1,3-dione.

MS m/z 772.43 [M+H]⁺.

Example 19. Synthesis of 4-((3-(4-(4-((2-Allyl-3-oxo-1-(6-(trifluoromethyl)pyridin-2-yl)-2,3-dihydro-1H-pyrazolo[3,4-d]pyrimidin-6-yl)amino)phenyl)piperazin-1-yl)propyl)amino)-2-(2,6-dioxopiperidin-3-yl)isoindoline-1,3-dione (18)

(18)

Compound 18 was prepared in an analogous manner to compound 13 in Example 14, from tert-butyl (3-(4-(4-((2-allyl-3-oxo-1-(6-(trifluoromethyl)pyridin-2-yl)-2,3-dihydro-1H-pyrazolo[3,4-d]pyrimidin-6-yl)amino)phenyl)piperazin-1-yl)propyl)carbamate and 2-(2,6-dioxopiperidin-3-yl)-3-fluoroisoindoline-1,3-dione.

MS m/z 810.45 [M+H]+.

Example 20. Synthesis of 4-((3-(4-((2-allyl-1-(6-(2-hydroxypropan-2-yl)pyridin-2-yl)-3-oxo-2,3-dihydro-1H-pyrazolo[3,4-d]pyrimidin-6-yl)amino)piperidin-1-yl)propyl)amino)-2-(2,6-dioxopiperidin-3-yl)isoindoline-1,3-dione (19)

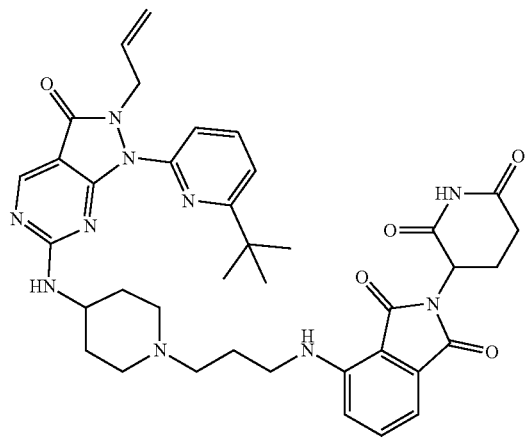

(19)

Compound 19 was prepared in an analogous manner to compound 13 in Example 14, from tert-butyl (3-(4-((2-allyl-1-(6-(2-hydroxypropan-2-yl)pyridin-2-yl)-3-oxo-2,3-dihydro-1H-pyrazolo[3,4-d]pyrimidin-6-yl)amino)piperidin-1-yl)propyl)carbamate and 2-(2,6-dioxopiperidin-3-yl)-3-fluoroisoindoline-1,3-dione.

MS m/z 723.48 [M+H]+.

Example 21: Synthesis of 4-((3-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)propyl)amino)-2-(1-methyl-2,6-dioxopiperidin-3-yl)isoindoline-1,3-dione (20

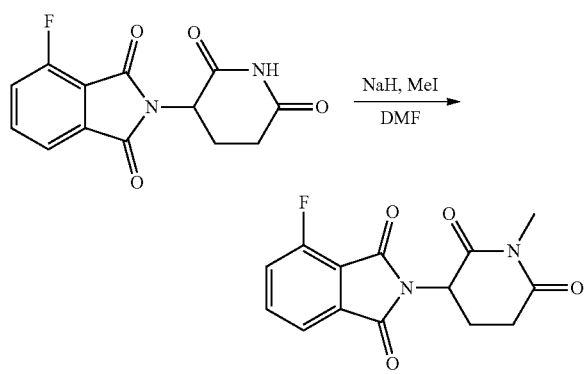

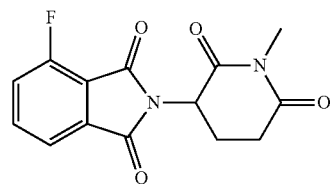 [SMILES: CN1C(=O)CCC(N2C(=O)c3cccc(F)c3C2=O)C1=O]

4-Fluoro-2-(1-methyl-2,6-dioxopiperidin-3-yl)isoindoline-1,3-dione

To DMF (3 mL) was added NaH 60% (21 mg, 0.54 mmol), then 2-(2,6-dioxopiperidin-3-yl)-4-fluoroisoindoline-1,3-dione (100 mg, 0.36 mmol) was dissolved in DMF (1 mL) was dropped at 0° C., the mixture was stirred for 15 minutes, MeI (35 uL, 0.54 mmol) was added and the mixture was stirred for 8 h warming to room temperature. The mixture was diluted with EtOAc (20 mL) and water (30 mL), and extracted with EtOAc (3×10 mL). The organic extract was washed with brine (20 ml), dried (MgSO4) and concentrated under reduced pressure, and the residue was purified via silica gel chromatography (DCM:MeOH=10:1) to give 4-fluoro-2-(1-methyl-2,6-dioxopiperidin-3-yl) isoindoline-1,3-dione (80 mg, 76% yield).

LC-MS: m z 291.09 [M+1]+.

(20)

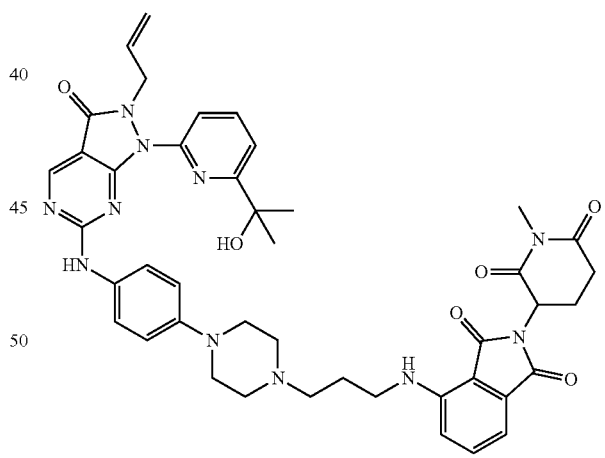

Compound 20 was prepared in an analogous manner to compound 13 in Example 14, from tert-butyl (3-(4-((2-allyl-1-(6-(2-hydroxypropan-2-yl)pyridin-2-yl)-3-oxo-2,3-dihydro-1H-pyrazolo[3,4-d]pyrimidin-6-yl)amino)piperidin-1-yl)propyl)carbamate and 4-Fluoro-2-(1-methyl-2,6-dioxopiperidin-3-yl)isoindoline-1,3-dione.

LC-MS: m z 814.46 [M+1]+.

Example 22: Synthesis of tert-butyl (2S,4R)-1-((S)-2-(6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexanamido)-3,3-dimethylbutanoyl)-4-hydroxy-N—((S)-1-(4-(4-methylthiazol-5-yl)phenyl)ethyl)pyrrolidine-2-carboxamide (21)
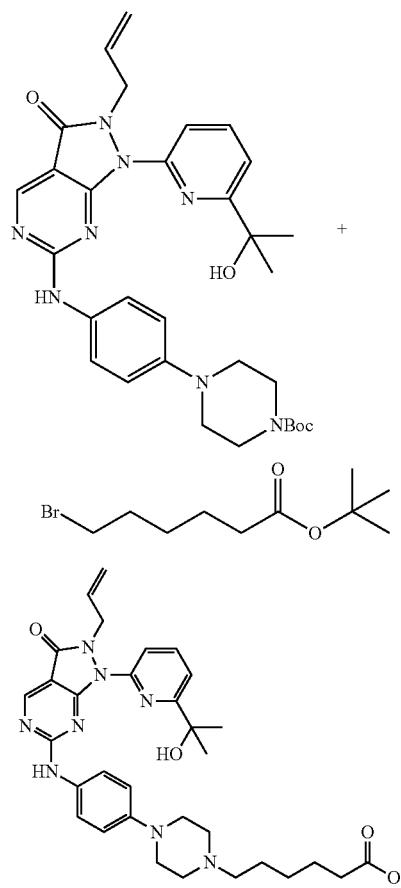
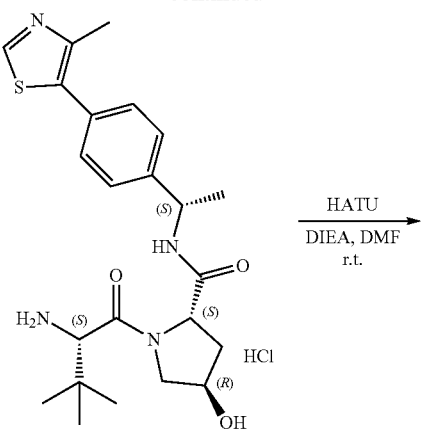
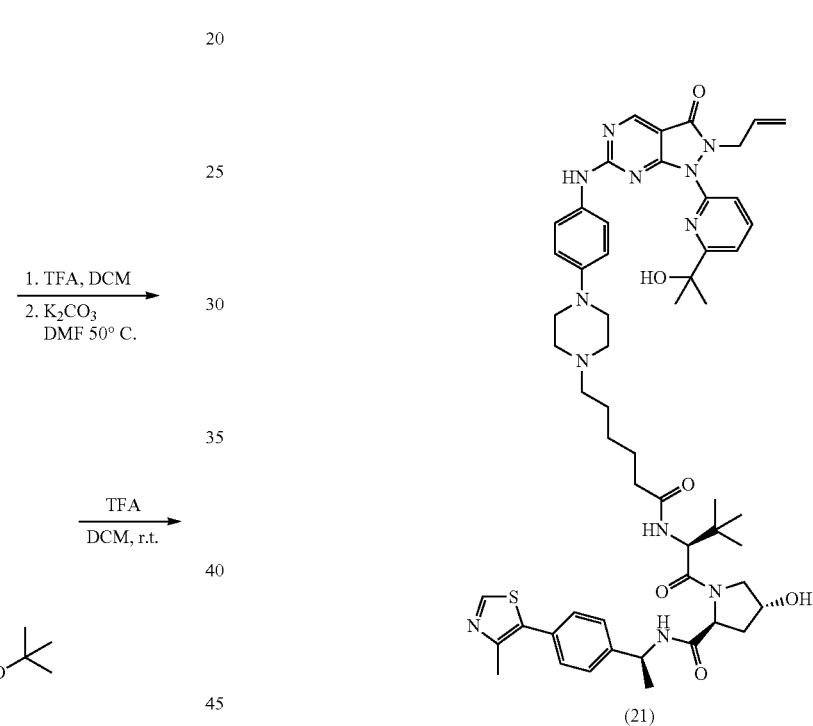
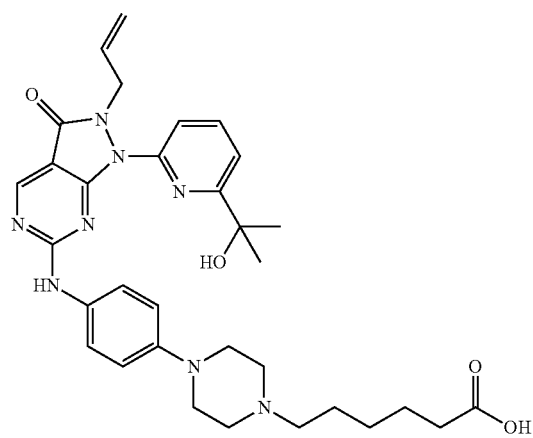
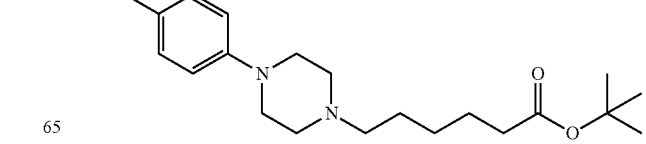

tert-Butyl 6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexanoate tert-Butyl 4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazine-1-carboxylate (60 mg, 0.1 mmol) was dissolved in DCM (3 mL), TFA (1 mL) was added and the mixture was stirred for 30 minutes. The solvent was removed under reduced pressure and the residue was dissolved in acetone (5 mL). tert-Butyl 6-bromohexanoate (38 mg, 0.15 mmol) and K$_2$CO$_3$ (28 mg, 0.2 mmol) were added. The mixture was refluxed overnight. After allowing the reaction to cool to room temperature, the solvent was removed under reduced pressure, and the residue was dissolved in water and ethyl acetate. The mixture was extracted with EtOAc (3×10 mL). The organic extract was washed with brine (20 mL), dried over MgSO$_4$, and concentrated under reduced pressure. The residue was purified via silica gel chromatography (1:1 Hexane:EtOAc) to give the title compound (56 mg, 82%)

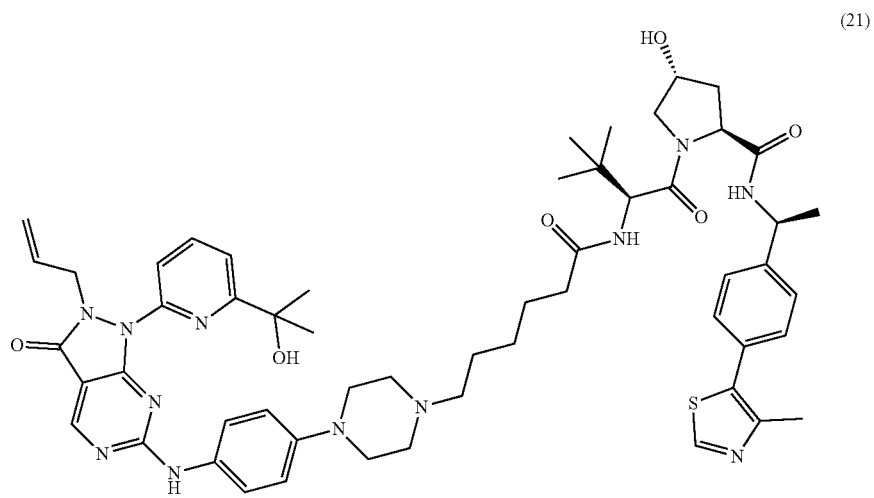 [SMILES: C=CCn1c(=O)c2cnc(Nc3ccc(N4CCN(CCCCCC(=O)N[C@H](C(=O)N5C[C@H](O)C[C@H]5C(=O)N[C@@H](C)c5ccc(-c6scnc6C)cc5)C(C)(C)C)CC4)cc3)nc2n1-c1cccc(C(C)(C)O)n1]

(21)

tert-butyl 6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexanoate(22 mg, 0.033 mmol) was dissolved in DCM (2 mL), TFA (0.5 mL) was added and the mixture was stirred for 1 hour. The solvent was removed under reduced pressure and the residue was dissolved in DMF (1.5 mL). Then (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride(16 mg, 0.033 mmol), HATU(25 mg, 0.066 mmol), N,N-diisopropylethylamine(30 µL, 0.165 mmol) were added, and the mixture was stirred at room temperature for 30 min. The mixture was purified by HPLC to give compound 21 (28 mg, 85%).

MS m/z 1028.3 [M+H]$^+$.

Example 23: Synthesis of (2S,4R)-1-((S)-2-(4-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)butanamido)-3,3-dimethylbutanoyl)-4-hydroxy-N—((S)-1-(4-(4-methylthiazol-5-yl)phenyl)ethyl)pyrrolidine-2-carboxamide (22)
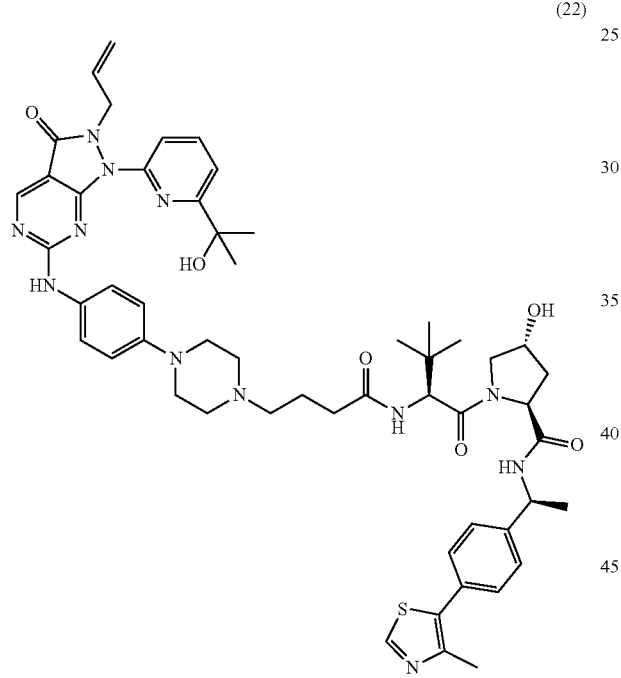
(22)
Compound 22 was prepared in an analogous manner to compound 21 in Example 22.
MS m/z 999.74 [M+H]$^+$.

Example 24: Synthesis of (2S,4R)-1-((S)-1-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)-14-(tert-butyl)-12-oxo-3,6,9-trioxa-13-azapentadecan-15-oyl)-4-hydroxy-N—((S)-1-(4-(4-methylthiazol-5-yl)phenyl)ethyl)pyrrolidine-2-carboxamide (23)
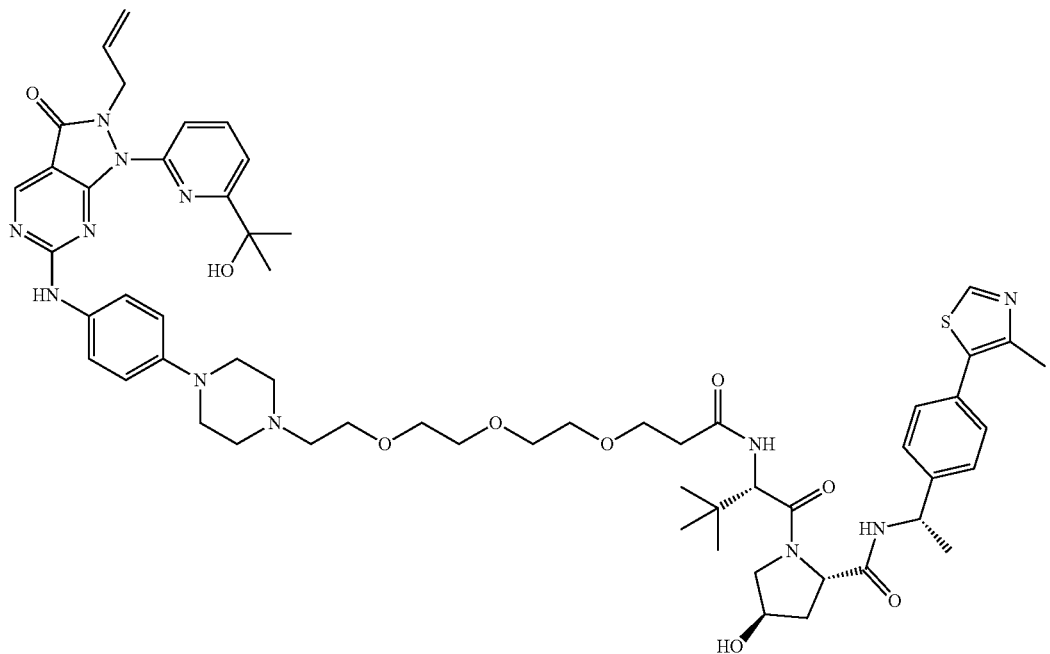 [SMILES: C=CCn1c(=O)c2cnc(Nc3ccc(N4CCN(CCOCCOCCOCCC(=O)N[C@H](C(=O)N5C[C@H](O)C[C@H]5C(=O)N[C@@H](C)c5ccc(-c6scnc6C)cc5)C(C)(C)C)CC4)cc3)nc2n1-c1cccc(C(C)(C)O)n1]
Compound 23 was prepared in an analogous manner to compound 21 in Example 22.
MS m/z 1117.52 [M+H]+.

Example 25: Synthesis of (2R,4S)-1-((S)-2-(6-(4-(4-((2-allyl-1-(6-(2-hydroxypropan-2-yl)pyridin-2-yl)-3-oxo-2,3-dihydro-1H-pyrazolo[3,4-d]pyrimidin-6-yl)amino)phenyl)piperazin-1-yl)hexanamido)-3,3-dimethylbutanoyl)-4-hydroxy-N—((S)-1-(4-(4-methylthiazol-5-yl)phenyl)ethyl)pyrrolidine-2-carboxamide (24)

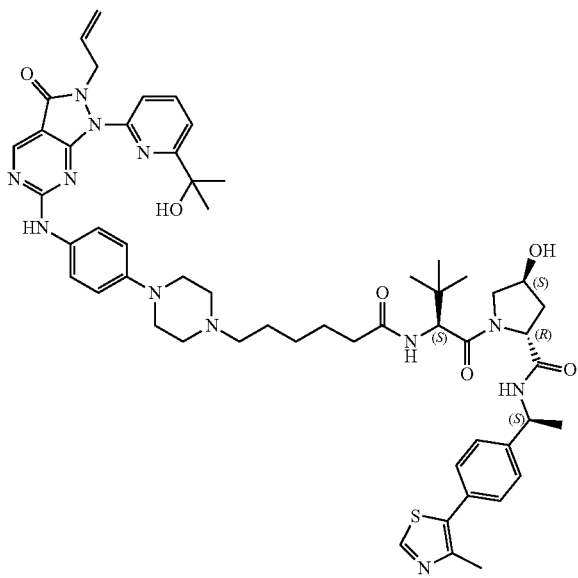

Compound 24 was prepared in an analogous manner to compound 21 in Example 22.

MS m/z 1028.34 [M+H]$^+$.

Example 26: General Methods

Cell Culture and Reagents

All cell lines were purchased from American Type Cell Collection (ATCC). They were routinely tested for the absence of *Mycoplasma* infection. MOLT4 and Kuramochi cells were cultured in RPMI-1640 medium supplemented with 10% fetal bovine serum (FBS, Sigma) and 1% penicillin/streptomycin. OVCAR8 cells were cultured in Dulbecco's Modified Eagle's Medium (DMEM) supplemented with 10% fetal bovine serum (FBS, Sigma) and 1% penicillin/streptomycin. COV382 cells were cultured in DMEM supplemented with 10% FBS, L-glutamine (300 mg/L), and 1% penicillin/streptomycin. All cell lines were cultured at 37° C. in a humidified chamber. Antibodies used against various proteins were as follows: Wee1 (1:1,000, Cell Signaling Technology® cat #4936), β-Actin (1:1000, Cell Signaling Technology® cat #3700), phoshpo-cdc2 (Tyr15) (1:1000, Cell Signaling Technology® cat #4539S), PLK1 (1:1000, Abcam® cat #ab17056), γ-H2AX, poly ADP ribose polymerase (PARP) (1:1000, Cell Signaling Technology® cat #9542), cleaved PARP (1:1000, Cell Signaling Technology® cat #5625), Ikaros (1:1000, Cell Signaling Technology® cat #9034), Aiolos (1:1000, Cell Signaling Technology® cat #15103).

Immunoblotting

Whole cell lysates for immunoblotting were prepared by pelleting cells from each cell line at 4° C. (300 g) for 5 minutes. The resulting cell pellets were washed 1x with ice-cold PBS and then resuspended in RIPA lysis buffer (Sigma, cat #R0278) supplemented with protease and phosphatase inhibitor tablets (Roche cat #4906845001). Lysates were clarified at 14,000 rpm for 15 minutes at 4° C. prior to quantification by BCA assay (Pierce™, cat #23225). Whole cell lysates were loaded into Bolt 4-12% Bis-Tris Gels (Thermo Fisher, cat #NW04120BOX) and separated by electrophoreses at 95 V for 1.5 hours. The gels were transferred to a nitrocellulose membrane using the iBlot® Gel Transfer at P3 for 7 minutes (Thermo Fisher, cat #IB23001) and then blocked for 1 hour at room temperature in Odyssey® blocking buffer (LICOR® Biosciences, cat #927-50010). Membranes were probed using antibodies against the relevant proteins at 4° C. overnight in 20% Odyssey® Blocking Buffer in 1xTBST. Membranes were then washed three times with 1xTBST (at least 5 minutes per wash) followed by incubation with the IRDye® goat anti-mouse (LICOR®, cat #926-32210) or goat anti-rabbit (LICOR®, cat #926-32211) secondary antibody (diluted 1:10,000) in 20% Odyssey® Blocking Buffer in 1xTBST for 1 hour at room temperature. After three washes with 1xTBST (at least 5 minutes per wash), the immunoblots were visualized using the ODYSSEY® Infrared Imaging System (LICOR®).

Cell Viability Assays

The indicated cell lines were plated in flat bottom 384-well plates (Corning® cat #3570). MOLT4 cells were plated at a density of 3,000 cells per well in 50 μL media, while OVCAR8, COV362, and Kuramochi cells were plated at a density of 750 cells per well in 50 μL media. Cells were treated the next day (except for MOLT4 cells, which were treated the same day as plating) with 0.1 μL of the indicated compounds in a four-fold dilution series using the Janus pinner. Cells were incubated with compounds for 72 hours at 37° C. 5% $CO_2$. Anti-proliferative effects were then assessed by CellTiter-Glo® Luminescent Cell Viability Assay (Promega™ cat #G7570) according to the manufacturer's standards, measuring luminescence using an EnVision® plate-reader. $IC_{50}$ values were determined using a non-linear regression curve fit in GraphPad Prism 8. N=4 biological replicates were used for each treatment condition.

Cell Cycle Analysis

MOLT4 cells were plated at 1.5 million cells per well in a 6-well plate, with 3 mL of media per well. Immediately after plating, cells were treated with the indicated concentrations of the indicated compound. At the indicated time points, cells were collected by transferring each well to a 15 mL conical, centrifuging (1000 rpm for 3 min), and then washing the cell pellet 3x with cold PBS. Cell pellets were then fixed with 1 mL cold 80% ethanol in PBS at 4° C. overnight. The cell pellets were then washed by adding 1 mL of PBS and then centrifuging (1500 rpm for 5 minutes), followed by aspiration of the PBS/ethanol mix. Cells were resuspended in cell cycle staining solution (100 μg/mL of RNAse A (Roche, 10109169001) and 50 μg/mL propidium iodide (Life Technologies™, P1304MP), diluted in PBS, and incubated for 10 minutes at room temperature. Cell cycle data was acquired by flow cytometry on a Guava® easyCyte™ flow cytometer (Millipore™) using the InCyte™ software. Data was analyzed using FlowJo®. N=3 biological replicates were used for each treatment condition.

In Vitro Kinase Assays

LanthaScreen™ assays were conducted for Wee1 in a 10-point dose response as performed in the commercial assay service by Life Technologies™. Z'-LYTE™ assays were conducted for PLK1 as performed in the commercial assay service by Life Technologies™ in a 10-point dose response using $K_m$ ATP concentrations.

Inhibitor Treatment and Western Blotting Experiments

MOLT4 cells were plated at 1.5 million cells per well in a 6-well plate, with 3 mL of media per well. Cells were then immediately treated with the indicated concentration of the indicated compound and incubated for the indicated amount of time. Cells were collected by transferring each well to a 15 mL conical, centrifuging (1000 rpm for 3 min), then washing the cell pellet 2× with cold PBS. Each cell pellet was then lysed in 100 µL of RIPA lysis buffer (+protease/phosphatase inhibitors). Samples were normalized and prepped in 4×LDS+10% β-mercaptoethanol and boiled for 5 min at 95° C. Lysates were probed for specified proteins by western blotting using the Bolt® system (Life Technologies™)

Synergy Experiment (a) Plate Cells

OVCAR8 cells were plated at a density of 750 cells per well in 50 µL media in a white 384-well plate (Corning® cat #3570).

(b) Prepare Compound Plates and Treat Cells

Figure 12:
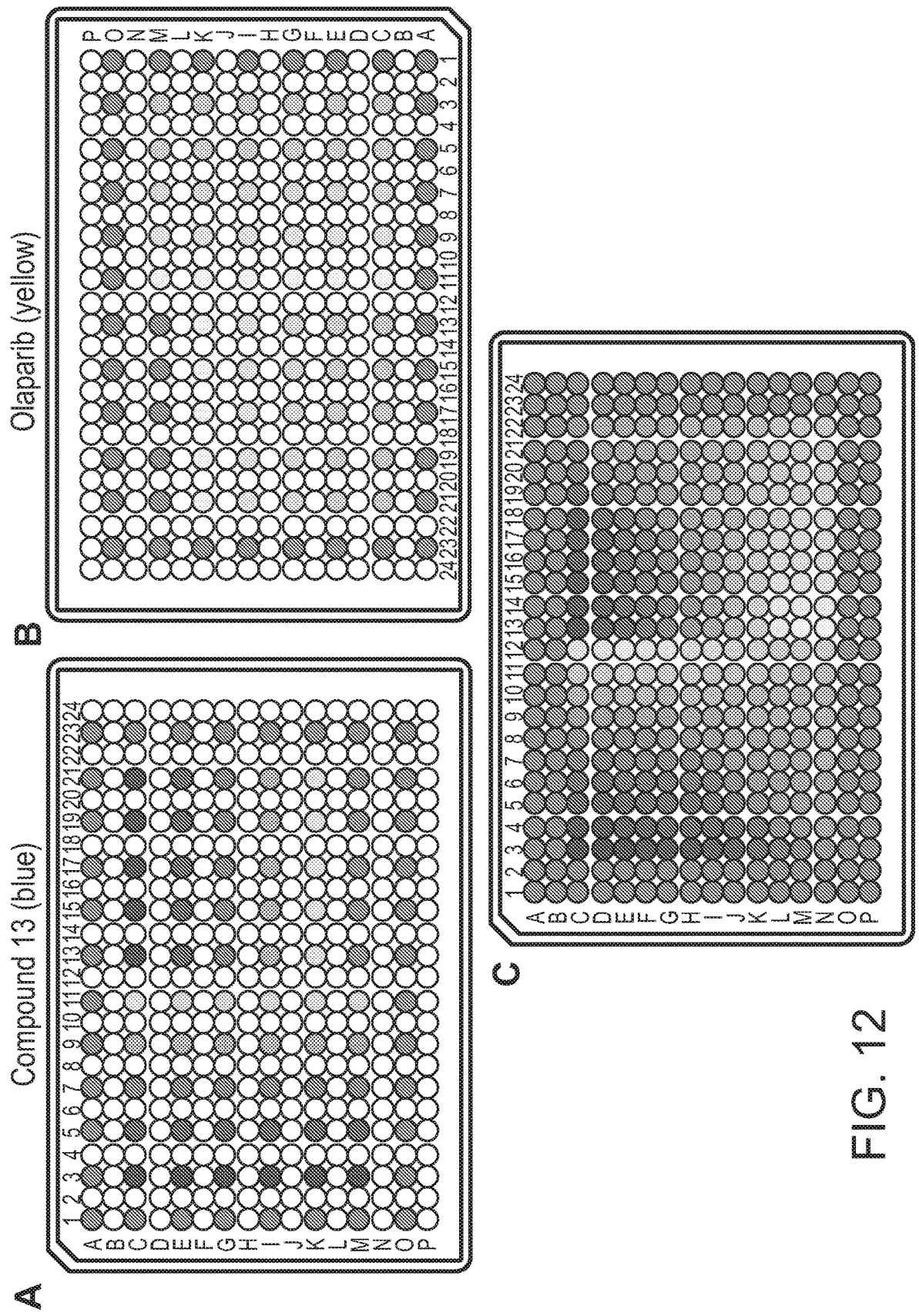
FIG. 12 is an image of the plate setup in the synergy experiments, wherein blue represents compound 13 (A), yellow represents Olaparib (B), gray and white represents DMSO, dark blue or yellow represents the highest compound concentration and light blue or light yellow represents dilutions.

Each compound was plated in a 384-well plate in a 5-point, four-fold dilution curve as illustrated in FIG. 12 (where blue is compound 13 (A, below), yellow is Olaparib (B, below), gray and white is DMSO; dark blue or yellow is the highest compound concentration, with dilutions represented by the gradations to light blue or yellow). Cells were treated the day after plating with 0.1 µL from each compound plate using the Janus pinner (compound 20 plate pinned with orientation A1 to back left (A, below); Olaparib plate pinned with orientation A1 to front right (B, below), to give the co-treatment pattern (C, below) in which green represents co-treatment regions).

(c) Incubate Cells with Compound

Cells were incubated with compounds for 72 hours at 37° C. 5% $CO_2$. Anti-proliferative effects were then assessed by CellTiter-Glo® Luminescent Cell Viability Assay (Promega™ cat #G7570) according to the manufacturer's standards, measuring luminescence using an EnVision® platereader. $IC_{50}$ values were determined using a non-linear regression curve fit in GraphPad Prism 8. N=4 biological replicates were used for each treatment condition.

Proteomics (a) Sample Preparation TMT LC-MS3 Mass Spectrometry

MOLT4 cells were treated with DMSO or 100 nM of compound 13 for 2 or 4 hours in biological triplicates and lenalidomide in biological duplicates for 4 hours and cells were harvested by centrifugation. Lysis buffer (8 M Urea, 50 mM NaCl, 50 mM 4-(2hydroxyethyl)-1-piperazineethanesulfonic acid (EPPS) pH 8.5, Protease and Phosphatase inhibitors from Roche) was added to the cell pellets and homogenized by 20 passes through a 21 gauge (1.25 in. long) needle to achieve a cell lysate with a protein concentration between 1-4 mg mL$^{-1}$. A micro-BCA assay (Pierce™) was used to determine the final protein concentration of protein in the cell lysate. 200 µg of protein for each sample were reduced and alkylated as previously described in Donovan et al., Elife 7:e38430 (2018).

Proteins were precipitated using methanol/chloroform. In brief, four volumes of methanol were added to the cell lysate, followed by one volume of chloroform, and finally three volumes of water. The mixture was vortexed and centrifuged to separate the chloroform phase from the aqueous phase. The precipitated protein was washed with three volumes of methanol, centrifuged and the resulting washed precipitated protein was allowed to air dry. Precipitated protein was resuspended in 4 M Urea, 50 mM HEPES pH 7.4, followed by dilution to 1 M urea with the addition of 200 mM EPPS, pH 8. Proteins were first digested with LysC (1:50; enzyme: protein) for 12 hours at room temperature. The LysC digestion was diluted down to 0.5 M Urea with 200 mM EPPS pH 8 and then digested with trypsin (1:50; enzyme:protein) for 6 hours at 37° C. Tandem mass tag (TMT) reagents (Thermo Fisher Scientific) were dissolved in anhydrous acetonitrile (ACN) according to manufacturer instructions. Anhydrous ACN was added to each peptide sample to a final concentration of 30% v/v, and labeling was induced with the addition of TMT reagent to each sample at a ratio of 1:4 peptide:TMT label. The 10-plex labeling reactions were performed for 1.5 hours at room temperature and the reaction quenched by the addition of hydroxylamine to a final concentration of 0.3% for 15 minutes at room temperature. The sample channels were combined at a 1:1:1:1:1:1:1:1:1:1 ratio, desalted using C18 solid phase extraction cartridges (Waters®) and analyzed by LC-MS for channel ratio comparison. Samples were then combined using the adjusted volumes determined in the channel ratio analysis and dried down in a speed vacuum. The combined sample was then resuspended in 1% formic acid and acidified (pH 2-3) before being subjected to desalting with C18 SPE (Sep-Pak®, Waters®). Samples were then offline fractionated into 96 fractions by high pH reverse-phase HPLC (Agilent LC1260) through an aeris peptide xb-c18 column (Phenomenex®) with mobile phase A containing 5% acetonitrile and 10 mM $NH_4HCO_3$ in LC-MS grade $H_2O$, and mobile phase B containing 90% acetonitrile and 10 mM $NH_4HCO_3$ in LC-MS grade $H_2O$ (both pH 8.0). The 96 resulting fractions were then pooled in a non-continuous manner into 24 fractions and these fractions were used for subsequent mass spectrometry analysis.

Data were collected using an Orbitrap Fusion™ Lumos™ mass spectrometer (Thermo Fisher Scientific, San Jose, CA, USA) coupled with a Proxeon EASY-nLC™ 1200 LC pump (Thermo Fisher Scientific). Peptides were separated on an EasySpray™ ES803 75 m inner diameter microcapillary column (ThermoFisher Scientific). Peptides were separated using a 190 min gradient of 6-27% acetonitrile in 1.0% formic acid with a flow rate of 350 nL/min. Each analysis used an MS3-based TMT method as described previously[2] The data were acquired using a mass range of m z 340-1350, resolution 120,000, automatic gain control (AGC) target 5×105, maximum injection time 100 ms, dynamic exclusion of 120 seconds for the peptide measurements in the Orbitrap. Data dependent MS2 spectra were acquired in the ion trap with a normalized collision energy (NCE) set at 35%, AGC target set to 1.8×104 and a maximum injection time of 120 ms. MS3 scans were acquired in the mass spectrometer with a higher energy collision dissociation (HCD) set to 55%, AGC target set to 2×105, maximum injection time of 150 ms, resolution at 50,000 and with a maximum synchronous precursor selection (SPS) precursors set to 10.

b) LC-MS Data Analysis. Proteome Discoverer 2.2

(Thermo Fisher) was used to for RAW file processing and controlling peptide and protein level false discovery rates, assembling proteins from peptides, and protein quantification from peptides. MS/MS spectra were searched against a Uniprot human database (September 2016) with both the forward and reverse sequences. Database search criteria are as follows: tryptic with two missed cleavages, a precursor mass tolerance of 20 ppm, fragment ion mass tolerance of 0.6 Da, static alkylation of cysteine (57.02146 Da), static TMT labelling of lysine residues and N-termini of peptides (229.16293 Da), and variable oxidation of methionine (15.99491 Da). TMT reporter ion intensities were measured using a 0.003 Da window around the theoretical m/z for each reporter ion in the MS3 scan. Peptide spectral matches with poor quality MS3 spectra were excluded from quantitation (summed signal-to-noise across 11 channels<200 and precursor isolation specificity <0.5).

Reporter ion intensities were normalized and scaled using in-house scripts in the R framework (R Development Core Team (2008). R: A language and environment for statistical computing. R Foundationfor Statistical Computing, Vienna, Austria. ISBN 3-900051-07-0, URL http://www.R-project.org). Statistical analysis was carried out using the limma package within the R framework (Ritchie et al., Nucleic Acids Res. 43:e47 (2015).

Measurement of Cell Viability and Cell Cycle Perturbation

HCC1806, BT549, and Kuramochi cells were maintained in RPMI (Corning®, Corning, NY) supplemented with 10% fetal bovine serum (FBS) (Life Technologies™, Carlsbad, CA) and 1% penicillin/streptomycin (Corning, Corning®, NY). OVCAR8 cells were maintained as above with the addition of 2 mM L-glutamine (Life Technologies™, Carlsbad, CA). MCF10A cells were maintained in a 1:1 mix of DMEM:F12 supplemented with 5% horse serum (Life Technologies™ Carlsbad, CA), 1% penicillin/streptomycin (Corning®, Corning, NY), 20 ng/ml EGF (Peprotech®, Rocky Hill, NJ), 500 ng/ml hydrocortisone (Sigma-Aldrich®, St. Louis, MO), 10 µg/ml insulin (Sigma-Aldrich®, St. Louis, MO), and 100 ng/ml cholera toxin (Sigma-Aldrich®, St. Louis, MO). COV362 cells were maintained in DMEM (Corning®, Corning, NY) supplemented with 10% FBS (Life Technologies™, Carlsbad, CA), 1% penicillin/streptomycin (Corning®, Corning, NY) and 2 mM L-glutamine (Life Technologies™, Carlsbad, CA). The OCE1 cells were maintained in FOMI (Wit-Fo) (PMID: 24303006) supplemented with 25 ng/ml cholera toxin (Sigma-Aldrich®, St. Louis, MO). Cell line identities were confirmed by STR profiling and were maintained free of *mycoplasma* at 37° C. and 5% $CO_2$.

Breast cancer cell lines, BT549, HCC1806, and MCF 10A cells were plated at a density of 1000 cells per well in 384-well Cell Carrier plates (PerkinElmer®, Waltham, MA) using a Multidrop™ Combi Reagent Dispenser (Thermo Fisher Scientific, Waltham, MA) and allowed to adhere to for 24 hours prior to drug treatment. Ovarian cancer cells were platted similarly at the following densities: COV362 and OVCAR8 500 cells/well, Kuramochi 1500 cells per well and, OCE1 1000 cells per well. Cells were treated with a dilution series of the indicated drugs using a D300 Digital Dispenser (Hewlett-Packard, Palo Alto, CA). Cells were stained and fixed for analysis at the time of drug delivery and after 24, 48 or 72 hours of incubation. Cells were pulsed for one hour with 5-ethynyl-2'-deoxyuridine (EdU) (Lumiprobe, Hunt Valley, MD) and stained with 1:2000 LIVE/DEAD™ Far Red Dead Cell Stain (LDR) (Thermo Fisher Scientific, Waltham, MA). Cells were then fixed with 3.7% formaldehyde (Sigma-Aldrich®, St. Louis, MO) for 30 minutes and permeabilized with 0.5% Triton X-100 in PBS. The EdU was labeled with cy3-azide (Lumiprobe, Hunt Valley, MD) for 30 min. The cells were then blocked for one hour with Odyssey blocking buffer (LI-COR®, Lincoln, NE), and stained overnight at 4° C. with 2 µg/ml Hoechst 33342 (Sigma-Aldrich®, St. Louis, MO) and a 1:1000 dilution of anti-phospho-histone H3 (pHH3) Alexa 488® (Ser10, clone $D2C_8$) conjugated antibody (Cell Signaling Technologies™, Danvers, MA).

Fixed cells were imaged with a 10× objective using an Operetta microscope and analyzed using the Columbus image data storage and analysis system (PerkinElmer®, Waltham, MA). Nuclei were segmented using Columbus software (PerkinElmer®, Waltham, MA) based on their Hoechst signal. DNA content was defined by the total Hoechst intensity within the nuclear mask to identify cells in the G1 and G2 phases of the cell cycle. The average LDR, EdU and phospho-histone H3 intensities within the nuclear masks were determined. The LDR signal was used to classify cells as live or dead, the EdU and pHH3 signals to identify S and M phase cells respectively. Cells with intermediate DNA content and no EdU signal were classified as S phase dropout cells. Live cell counts were normalized to DMSO-treated controls on the same plates to yield normalized growth rate inhibition (GR) values as described previously (Hafner et al., Nat. Methods 13:521 (2016)). Experiments in breast cancer cell lines were performed as technical triplicates in biological duplicate, and as technical and biological triplicates in ovarian cancer cell lines.

Rosetta Docking

All protein docking was carried out using Rosetta 3.8 provided through SBGrid (Morin et al., Elife 2:e01456 (2013)). Input models were downloaded from the PDB (CRBN bound lenalidomide pdb: 5fqd, chain B; Wee1 pdb: 3cr0, chain A with inhibitor, glycerol and Cl removed). Ligand parameters for lenalidomide were generated using OpenEye Omega™ (OpenEye Scientific) and parameter files generated using Rosetta 'molfile to_params.py'. Pdb structure coordinates were combined into a single file and prepared for docking using the Rosetta 'docking_prepack_protocol' program. Initial global docking was performed by running Rosetta 'docking_protocol' 80 times (total 40,000 poses) with the following command line options: -partners A_B -dock_pert 5 25 -randomize2 -ex1 -ex2aro -nstruct 500 -beta, providing the combined pdb, lenalidomide specific parameter files and database file as input.

To assess the landscape of possible low energy binding modes for Wee1, the top 200 lowest I_sc scoring docking decoys were selected. X-ray crystal structure model of Wee1 bound AZD1775 (pdb: 5v5y) was superimposed to each of the docked poses of Wee1 using Pymol 'align' command (The PyMOL Molecular Graphics System, Version 1.8.6.0 Schrödinger, LLC). The shortest pairwise distance between selected atoms on lenalidomide and AZD1775 (see, highlighted atoms in FIG. 8) was calculated in Pymol as Euclidean distance for each of the top 200 poses. The histogram was obtained in GraphPad Prism 7 using Column Analysis—Frequency Distribution. Data analysis and statistics for all steps were performed using GraphPad Prism 7.

Statistical Methods

For all experiments, number of replicates and error bars are described in the respective figure legends. All biological experiments were performed at least twice.

Example 27: Development and Optimization of Wee1 Bifunctional Degraders

To develop a Wee1-targeted bifunctional degrader, AZD1775 was modified by conjugating it to pomalidomide, which binds to the ubiquitously expressed cereblon (CRBN), the substrate receptor of the CUL4-DDB1-RBX1 E3 ubiquitin ligase complex (Chanan-Khan et al., Blood Cancer J. 3:e143 (2013); Chamberlain et al., Nat. Struct. Mol. Biol. 21:803-809 (2014)). Based on the reported co-crystal structure of AZD1775 bound to Wee1 (PDB 5V5Y), the N-methyl piperazine is solvent-exposed and therefore provides a potential site for attaching a linker without compromising Wee1 binding (FIG. 1A).

To assess whether bifunctional degraders derived from AZD1775 could successfully degrade Wee1, propylamine was installed on the piperazine of AZD1775, and coupled to a polyethylene glycol (PEG) chain conjugated to pomalidomide (compound 7). To reduce the number of hydrogen bond donors with the goal of enhanced cell penetration, a derivative without the amide bond (compound 12) was also synthesized.

Using the Fluorescence Resonance Energy Transfer (FRET)-based LanthaScreen biochemical binding assay (Invitrogen™), it was demonstrated that both compound 7 and compound 12 showed similar potency against Wee1, with $IC_{50}$ values of 1-10 nM (Table 1). Both compounds also successfully induced Wee1 degradation following a 5-hr treatment in MOLT4 cells, an acute lymphoblastic leukemia (ALL) cell line that is sensitive to single agent AZD1775 treatment (Di Rorá et al., J. Hematol. Oncol. 11:99 (2018). While a 1 µM treatment of compound 7 was required to achieve maximal Wee1 degradation, 100 nM of compound 12 was sufficient to degrade Wee1, likely due to its increased hydrophobicity and enhanced cell permeability (FIG. 7A-FIG. 7D). These data validated the N-methyl piperazine of AZD1775 as a suitable linker attachment site.

TABLE 1

Enzymatic $IC_{50}$ of inventive compounds 7, 11, 12 and 13 and negative control 20.

| Compound ID | IC50s (nM) | |
| --- | --- | --- |
| | Wee1[a] | PLK1[b] |
| AZD1775 | 1.52 ± 0.17 | 212 ± 12 |
| Compound 7 | 7.28 ± 0.67 | 118 ± 6 |
| Compound 11 | 4.46 ± 0.95 | 23.6 ± 4.0 |
| Compound 12 | 3.18 ± 0.52 | 285 ± 14 |
| Compound 13 | 3.58 ± 0.36 | 102 ± 6 |
| Compound 20 | 7.38 ± 0.47 | 43 ± 4 |
| Pomalidomide | >10000 | >10000 |

[a]$IC_{50}$s against Wee1 was obtained with LanthaScreen™ Binding activity assays and reported as the average of two replicates ± SD.
[b]$IC_{50}$s against PLK1 was obtained with ZLYTE activity assay and reported as the average of two replicates ± SD.

Figure 1B:
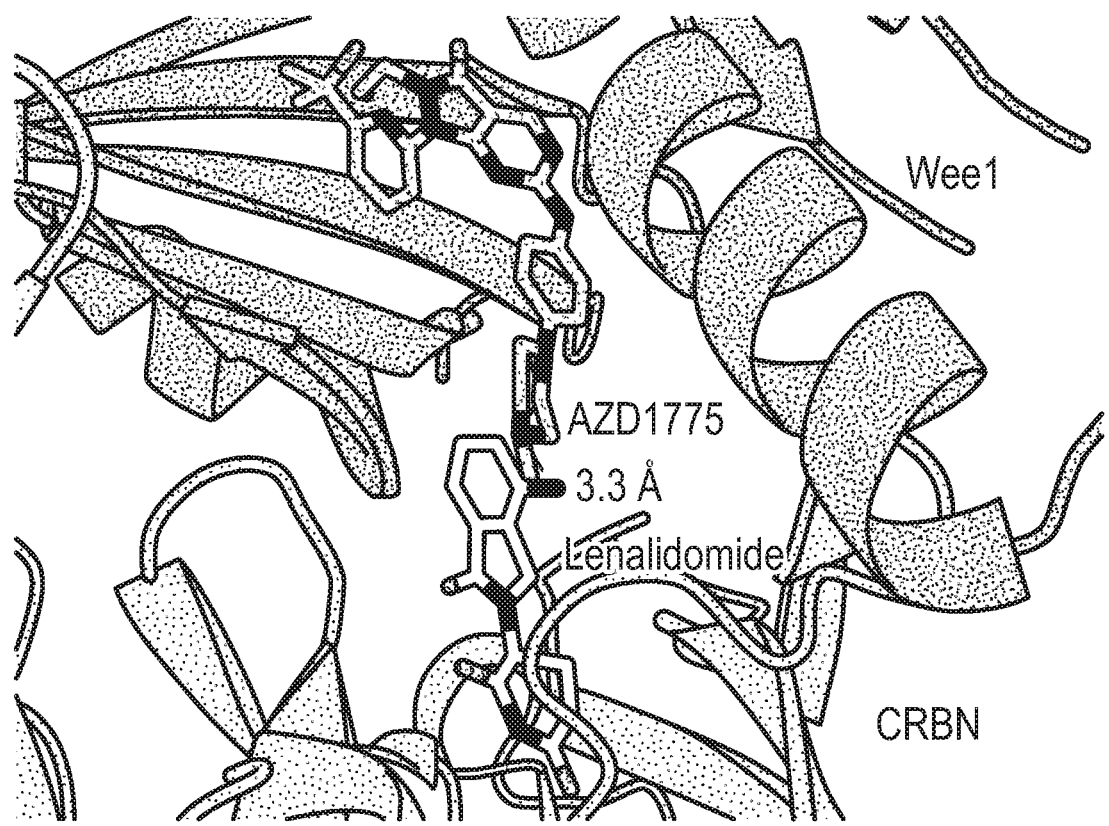
FIG. 1B is an image showing the shortest pairwise distance docking pose between lenalidomide and AZD1775 using Rosetta.
Figure 1C:
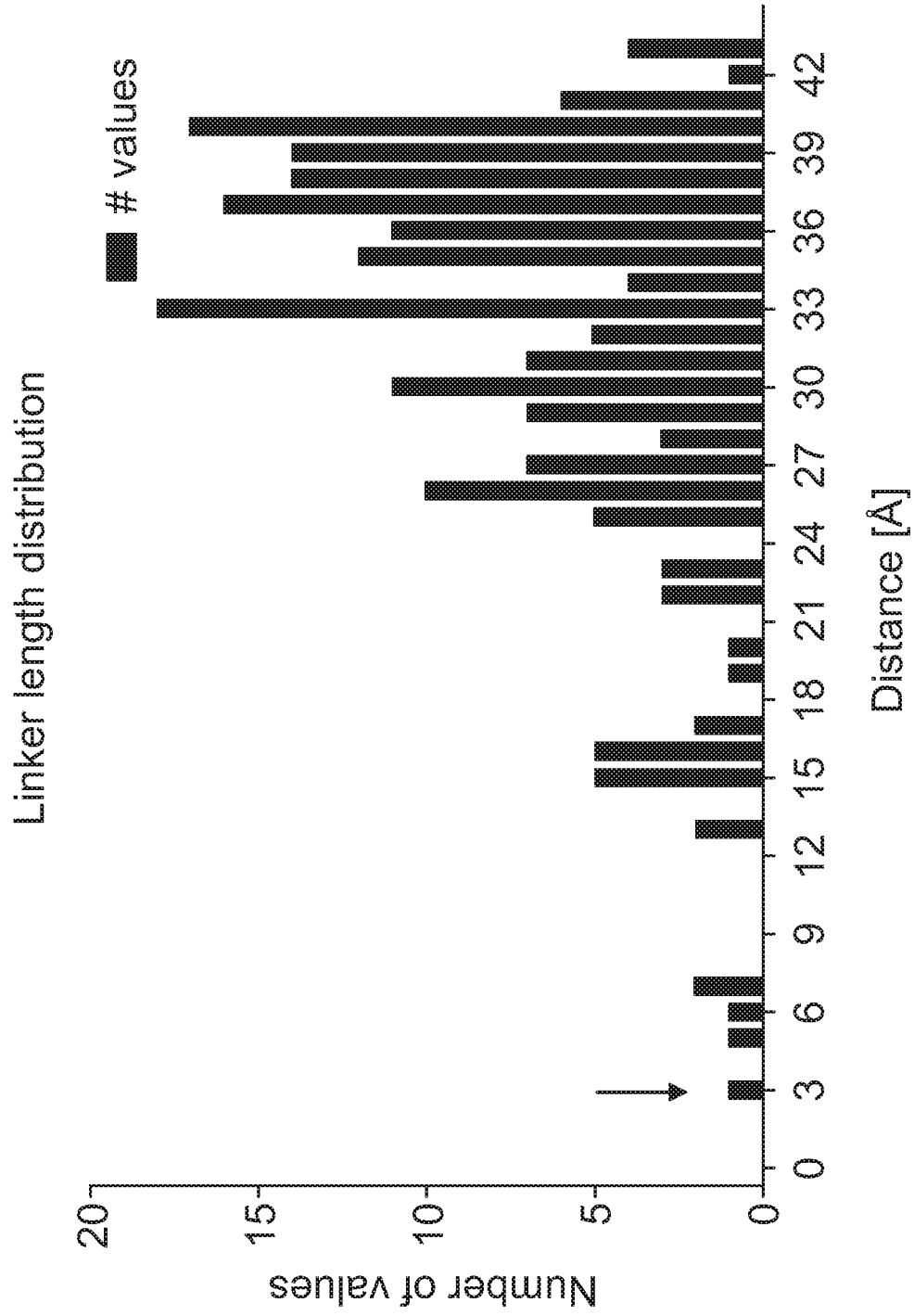
FIG. 1C is a histogram of the shortest pairwise distances between lenalidomide and AZD1775, with the red arrow corresponding to the docking pose depicted in panel.
Figure 8:
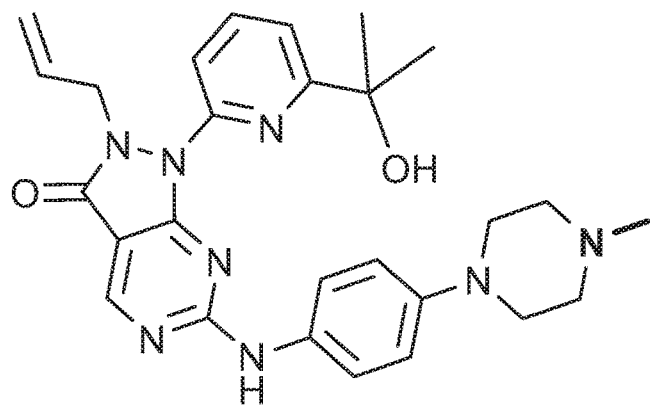
FIG. 8 is an image showing atom selection (highlighted in red) of AZD1775 and lenalidomide used for the Rosetta pairwise distance calculation.
Figure 8:
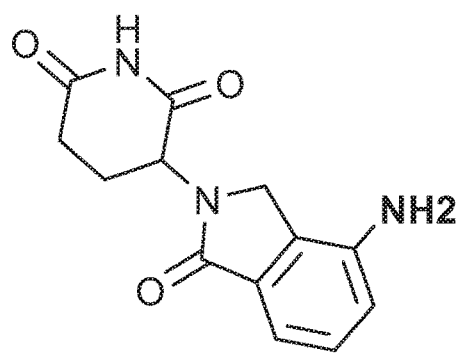

The linker length and composition of bifunctional degraders is often critical for achieving successful ternary complex formation, transfer of ubiquitin, and subsequent target degradation (Smith et al., Nat. Commun. 10:1-13 (2019)). To determine whether shorter linkers could be tolerated, the minimum required linker length to enable ternary complex formation was assessed. To do this, we used a recently described computational approach in which Rosetta docking can predict degrader-mediated protein-protein interactions (Nowak et al., Nat. Chem. Biol. 14:706-714 (2018)). A docking experiment was performed using 40,000 models (see, Example 23) based on the X-ray crystal structures of lenalidomide bound to CRBN (PDB 5FQD) and apo Wee1 (PDB 3CR0) to identify the top 200 low energy minima conformations. The structure of AZD1775 bound to Wee1 (PDB 5V5Y) was then aligned to the docked poses of apo Wee1. This allowed the calculation of the shortest possible distances between the N-methyl piperazine of AZD1775 and lenalidomide (FIG. 8). Use of the apo structure to generate a docking model, followed by addition of the AZD1775 ligand post-docking, made possible the exploration of binding conformations that would otherwise have been excluded due to steric clashes. This approach thereby enabled the design of short linker degraders, including molecules in which the two ligands are directly fused. Accordingly, a cluster of linkers 3-7 Å in length, corresponding to 2-6 linker atoms, was identified as sufficient to connect the two moieties (FIG. 1B-FIG. 1C).

Figure 7A:
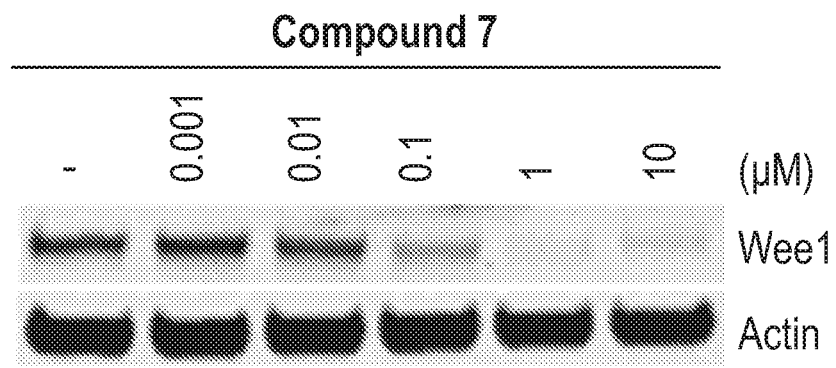
Figure 7B:
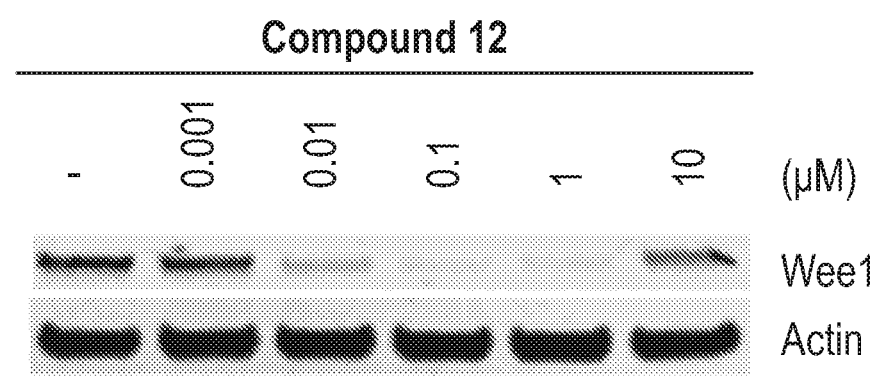
Figure 7C:
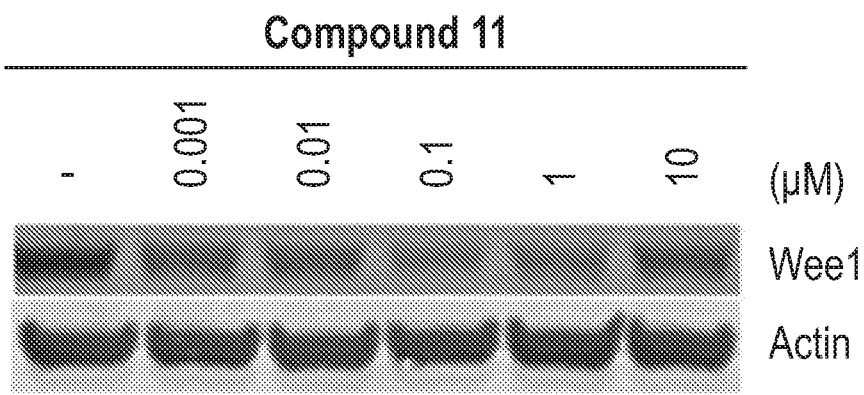
Figure 7D:
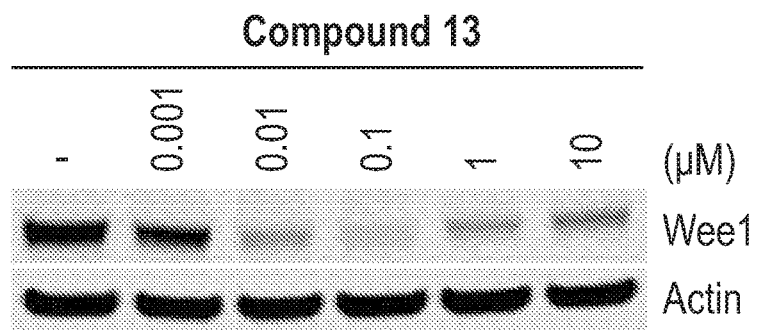

To test this prediction, two derivatives featuring short saturated carbon chain linkers, either 6 (compound 11) or 3 atoms in length (compound 13), were synthesized. Both compounds engaged recombinant Wee1 in the LanthaScreen™ binding assay (Table 1) and degraded Wee1 following a 5-hr exposure at 100 nM-10 µM concentrations in MOLT4 cells, but degradation was most pronounced for compound 13, which was selected as lead compound (FIG. 7A-FIG. 7G). To probe degradation-dependent phenotypes, compound 20 was also synthesized. Compound 20 is a negative control derivative of compound 13 featuring a methylated glutarimide ring, which is not capable of CRBN binding and therefore did not degrade Wee1 (FIG. 7E). Ultimately, the linker development strategy, informed by Rosetta docking, yielded compound 13 as a potent, nanomolar Wee1 bifunctional degrader.

The resulting lead compound, compound 13, induced potent and rapid Wee1 degradation, while sparing degradation of AZD1775's secondary target, PLK1, in cell-based assays. Compound 13 also induced premature mitotic entry, DNA damage and apoptosis, and synergized with the PARP inhibitor, Olaparib (see, Example 31).

The first clinical candidate degrader, an orally bioavailable small molecule targeting the androgen receptor, has entered a phase I clinical trial for prostate cancer this year (Neklesa et al., J. Clin. Oncol. 37:259-259 (2019)). In the clinic, degraders offer the exciting possibility of separating pharmacodynamics from pharmacokinetics, given that brief exposure to a degrader can have long-lasting effects, dependent on the rate of protein re-synthesis.

Example 28. Cellular Degradation of Wee1 Kinase

General Protocol: HT-29, MOLT4 wild type (WT) or $CRBN^{-/-}$ cells were plated in a 6 well plate and treated for 6 hours with the indicated concentrations of the inventive compounds and control. HT-29 cells were cultured in McCoy's Media supplemented with 10% FBS and 1% Penicillin/Streptomycin. MOLT4 WT and $CRBN^{-/-}$ cells were cultured in Roswell Park Memorial Institute (RPMI) medium supplemented with 10% FBS and 1% Penicillin/Streptomycin. Mycoplasma testing was performed every month and all lines were negative.

Immunoblotting: Cells were washed with phosphate-buffered saline (PBS) and then lysed using radioimmunoprecipitation assay (RIPA) buffer supplemented with protease and phosphatase inhibitor cocktail (Roche) on ice for 15 minutes. The lysates were centrifuged at 14,000 rpm for 15 minutes at 4° C. and protein was quantified by bicinchoninic acid (BCA) assay (Pierce™). Primary antibodies used include: Wee1 (D10D2) (Cell Signaling Technology®, 13084S), polo-like kinase 1 (PLK1) (Thermo Fisher Scientific, 37-7000), phosphor-cdc2 (Y15) (10A11) (Cell Signaling Technology®, 4539S), phospho-histone H3 (Ser10) (Cell Signaling Technology®, 9701S), Ikaros (D6N9Y) (Cell Signaling Technology®, 14859S), Aiolos (D1C1E) (Cell Signaling Technology®, 15103), casein kinase 1 alpha (Abcam®, 108296), β-actin (Cell Signaling Technology®, 8H10D10).

Figure 2A:
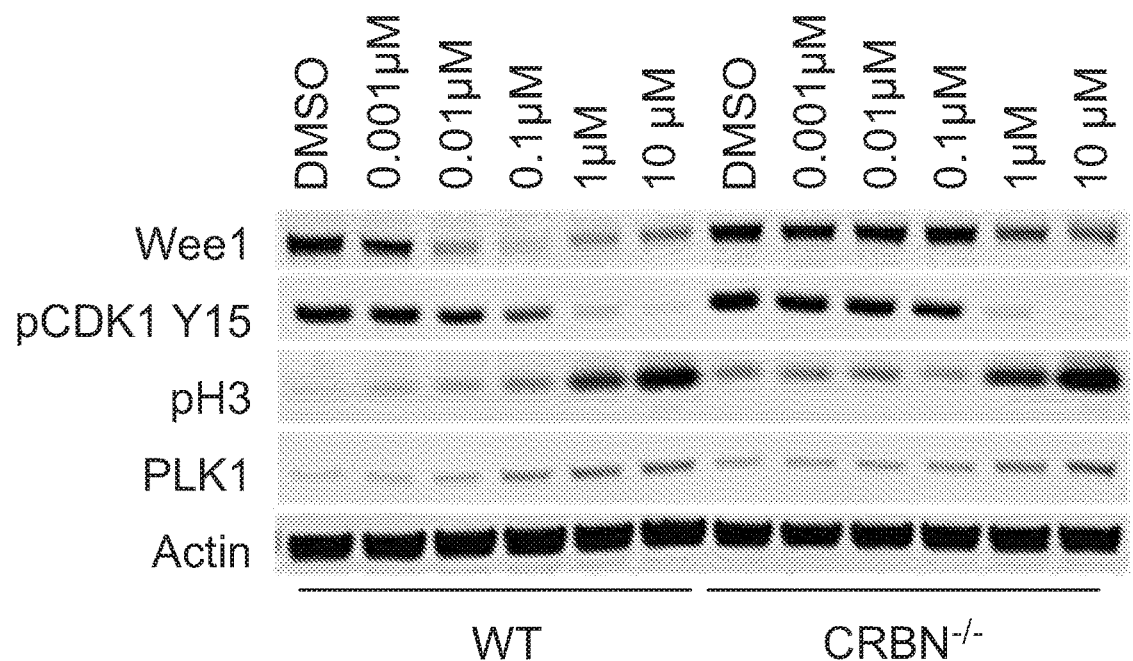
FIG. 2A is an immunoblot that shows the degradation of Wee1 in wild type and CRBN-MOLT4 cells following a 6-hour treatment with 0.001 µM-1 µM of inventive compound 13.

FIG. 2A is an immunoblot showing that compound 13 degraded Wee1 after a 6-hour treatment in MOLT4 cells, and induced the downstream changes expected from Wee1 loss—including a decrease in phosphorylated cyclin-dependent kinase 1 (pCDK1) (Y15) and an increase in pH 3. PLK1, an off-target of the parent scaffold, AZD1775, was not degraded by compound 13. Degradation of Wee1 by compound 13 was rescued in MOLT4 $CRBN^{-/-}$ cells.

MOLT4 WT and CRBN$^{-/-}$ cells were plated in a 6-well plate at 2.25 million cells per well in 3 mL media (RPMI+10% FBS+1% Penn/Strep). After treatment with the indicated concentrations of candidate compounds, cells were incubated for 6 hours at 37° C. 5% $CO_2$. To harvest, the cells were washed 1× with cold PBS, then collected by centrifugation. Cell pellets were lysed in RIPA buffer with protease and phosphatase inhibitors (Roche). Lysates were clarified by centrifugation, and protein concentrations were normalized using a BCA assay (Thermo Scientific™). The samples were diluted with 4×LDS+10% β-mercaptoethanol, and were boiled at 95° C. for 5 minutes. Proteins of interest were then assessed by western blotting. Degradation of Wee1 was also observed with inventive compound 21 via Von Hippel-Lindau (VHL) ubiquitin ligase-mediated Wee1 degradation (FIG. 2C).

Figure 2B:
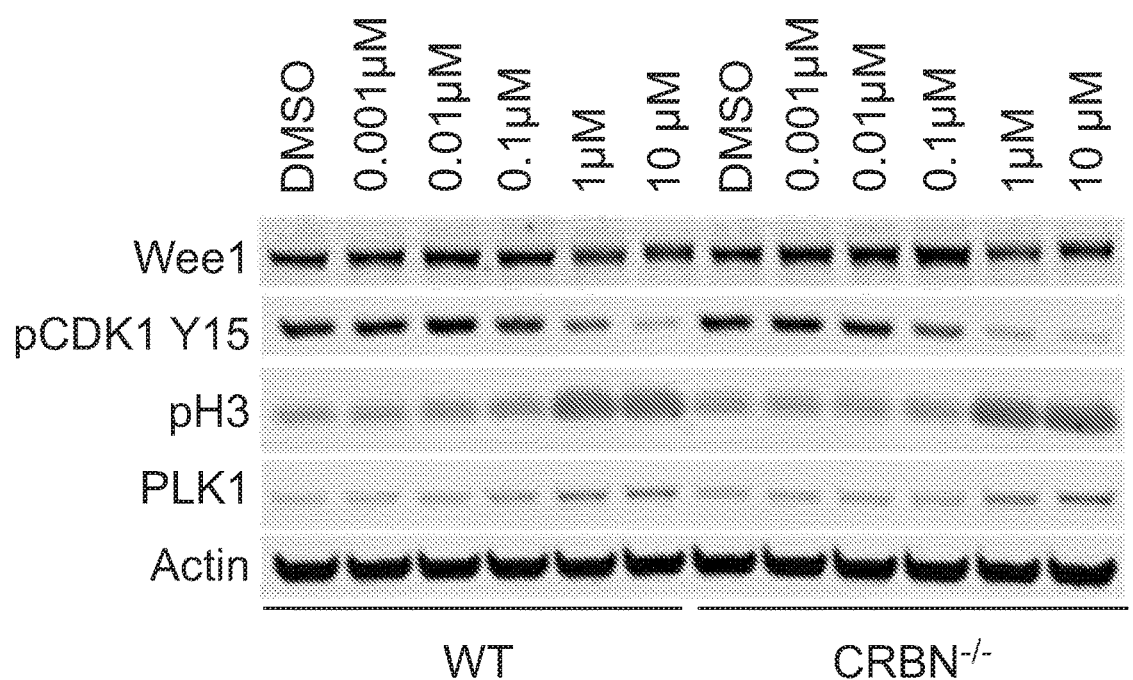
FIG. 2B is an immunoblot that shows the degradation of Wee1 in wild type and CRBN$^{-/-}$ MOLT4 cells following a 6-hour treatment with 0.001 µM-1 µM of compound 20 (negative control).
Figure 2C:
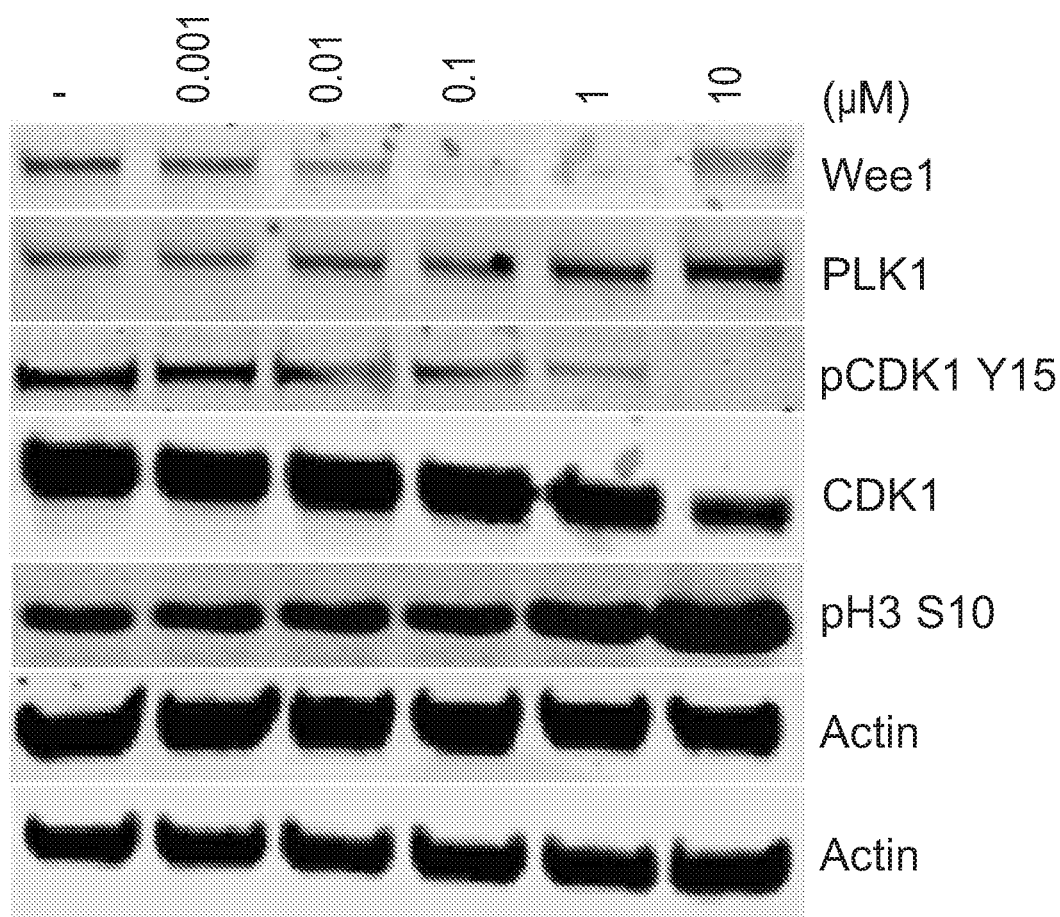
FIG. 2C is an image showing an immunoblot analysis MOLT4 cells treated for 5 hours with the indicated concentrations of inventive compound 21.

FIG. 2B is an immunoblot showing that compound 20 did not degrade Wee1 after a 6-hour treatment in MOLT4 cells.

FIG. 2D is an immunoblot showing that compound 20 did not degrade Wee1 after a 6-hour treatment in MOLT4 cells.

Figure 3A:
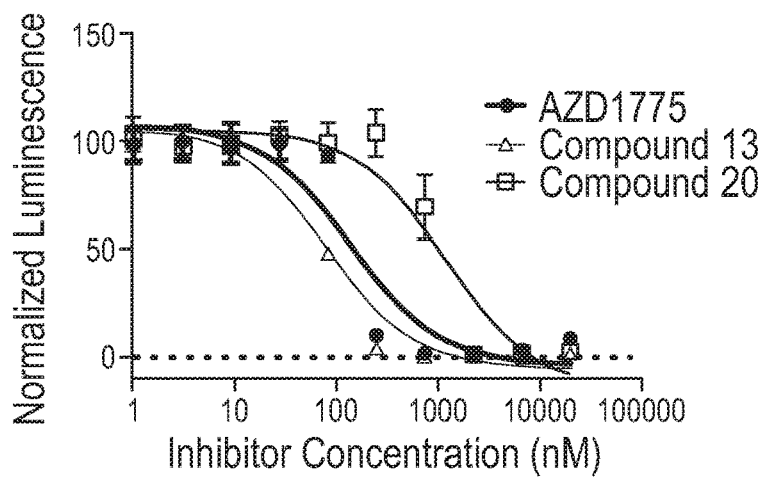
FIG. 3A is a graph showing the cell viability data for AZD1775 (parental inhibitor), inventive compound 13, and N-Me analog 20 in wild-type MOLT4 cells after a 72 hour treatment, as approximated by CellTiter-Glo®.

FIG. 3A shows the cell viability data for AZD1775, inventive compound 13, and compound 20 in MOLT4 WT cells. MOLT4 cells were plated in a 384-well plate at 5,000 cells per well in 50 μL media (RPMI+10% FBS+1% Penn/Strep) and treated with 0.1 μL of the candidate compounds in four-fold dilution series using the Janus pinner. Cells were incubated with compounds for 72 hours at 37° C. 5% $CO_2$. Anti-proliferative effects of these compounds were assessed 72 hours after compound addition using CellTiter-Glo® (Promega, cat #G7571). All proliferation assays were performed in biological quadruplicate. The results show that compound 13 has a significantly enhanced anti-proliferative effect than the corresponding N-Me analog (20), which is incapable of binding cereblon (CRBN) but has similar Wee1 inhibition activity. Effects upon cell viability for compound 13 in the MOLT4 WT cells are therefore likely driven in part by Wee1 inhibition, and in part by CRBN-mediated Wee1 degradation. Similar results were observed with compounds 21 and 24 in FIG. 3C. Degradation of Wee1 with compound 21 was mediated by VHL.

Compounds 13 and 20 showed similar anti-proliferative activity in the CRBN$^{-/-}$ cells, as effects from Wee1 degradation are no longer available in this cell line.

Figure 3B:
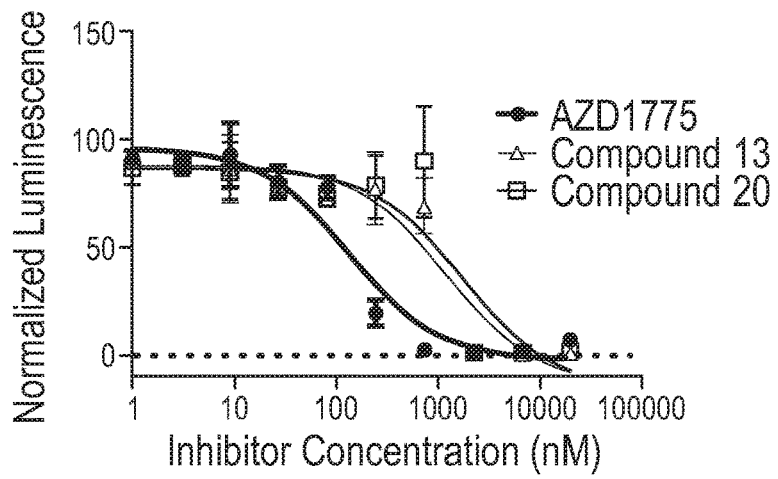
FIG. 3B is a graph showing the cell viability data for AZD1775 (parental inhibitor), inventive compound 13, and compound 20 in CRBN$^{-/-}$ MOLT4 cells after a 72 hour treatment, as approximated by CellTiter-Glo®.
Figure 3C:
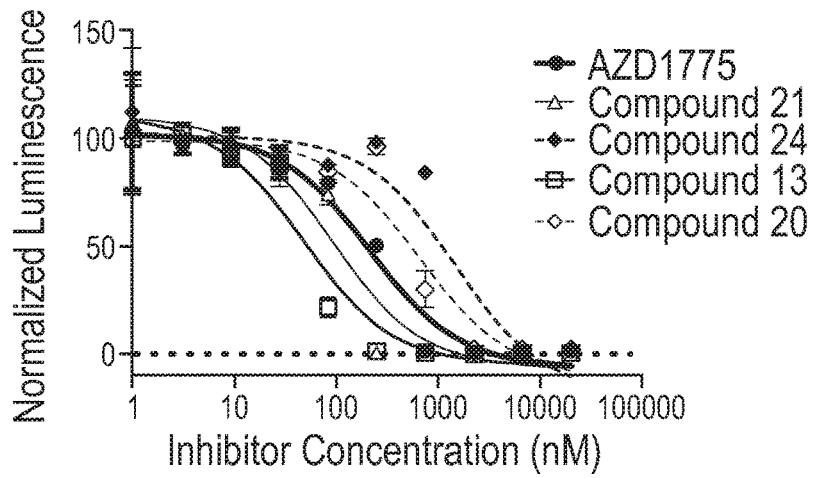
FIG. 3C is a graph showing the cell viability data for AZD1775 (parental inhibitor), inventive compounds 13 and 21, and negative control compounds 20 and 24 in wild-type MOLT4 cells after a 72 hour treatment, as approximated by CellTiter-Glo®.

FIG. 3B shows the cell viability data for AZD1775, compound 13, and compound 20 in MOLT4 CRBN$^{-/-}$ cells after a 72-hour treatment, as determined by CellTiter-Glo®. There was approximately a 15-fold rescue of compound 13's anti-proliferative activity in the CRBN$^{-/-}$ cells, as compared to the WT cells in FIG. 3A.

Example 29: Cellular Degradation of Wee1 with Inventive Compounds

The experimental protocol was the same as in Example 28.

Table 2 shows the extent to which compounds 1-21 induced degradation of Wee1 at 1 μM (as approximated by immunoblot in MOLT4 cells after a 6-hour treatment).

TABLE 2

Degradation of Wee1 by compounds 1-21.

| Compound | Extent of Degradation |
|---|---|
| 1 | <25% |
| 2 | <25% |
| 3 | >50% |
| 4 | 25-50% |
| 5 | >50% |
| 6 | 25-50% |
| 7 | >50% |
| 8 | >50% |
| 9 | >50% |
| 10 | 25-50% |
| 11 | 25-50% |
| 12 | >50% |
| 13 | >50% |
| 14 | >50% |
| 15 | 25-50% |
| 16 | >50% |
| 17 | >50% |
| 18 | >50% |
| 19 | <25% |
| 20 | <25% |
| 21 | <25% |

Figure 1D:
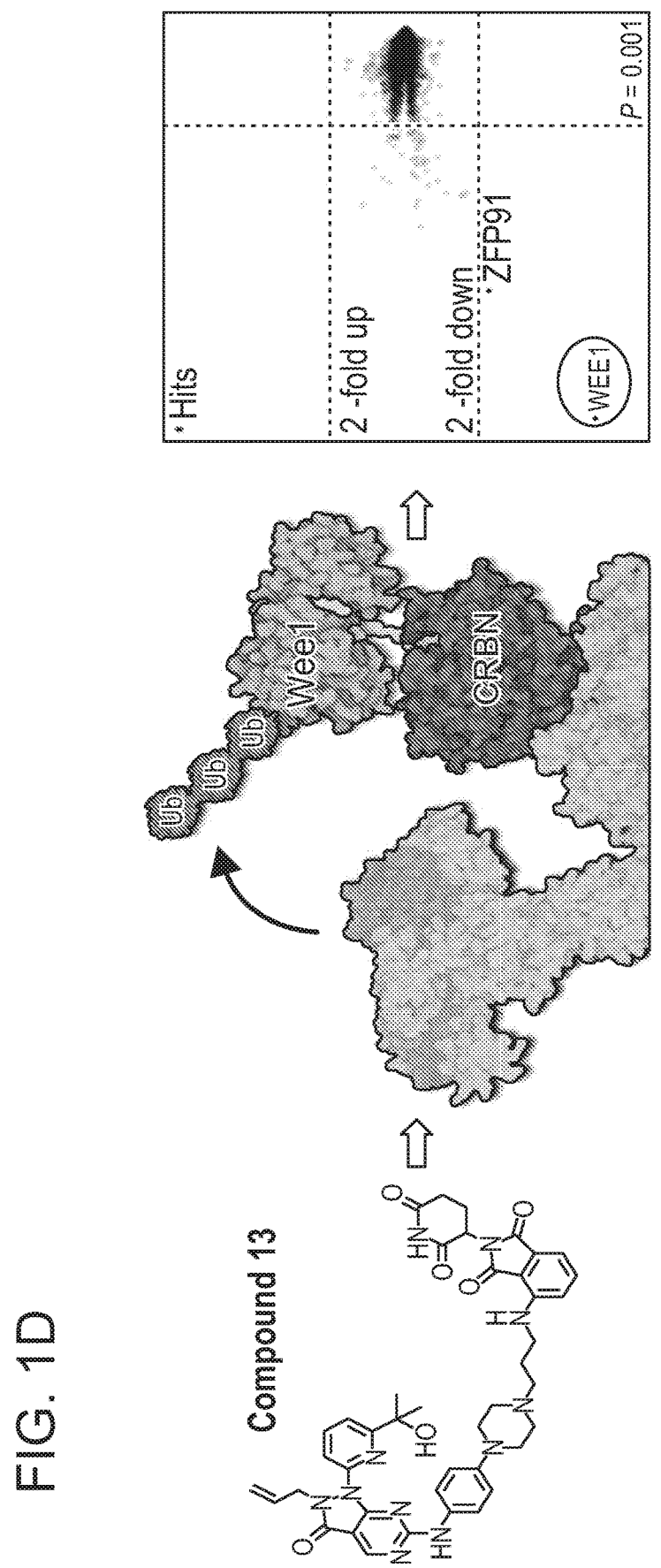
FIG. 1D is an image showing inventive compound 13, a schematic of the CR3N-dependent degradation of Wee1 by compound 13, and a scatter plot showing the selective degradation of Wee1 following a 2-hr treatment of MOLT4 cells with inventive compound 13 (100 nM), as measured using multiplexed quantitative-mass spectrometry-based proteomics.
Figure 4A:
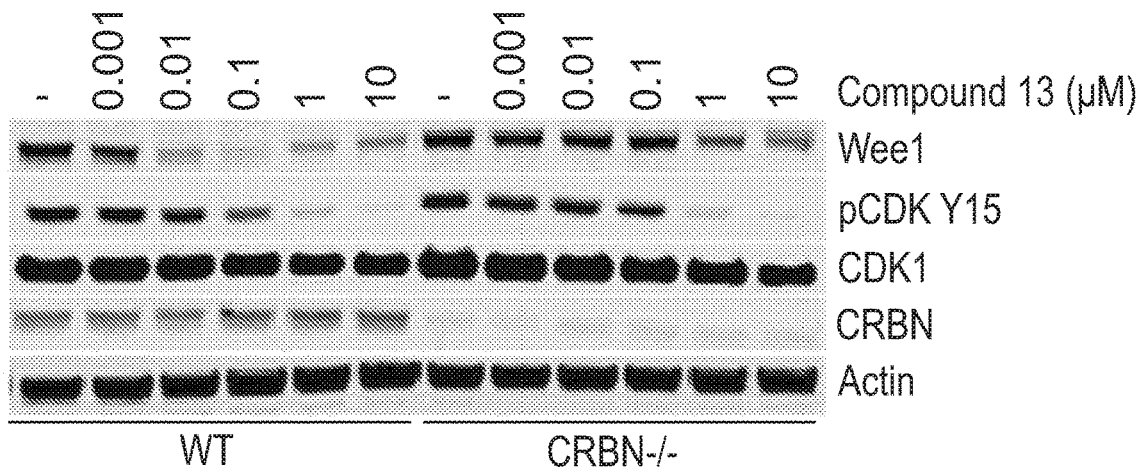
FIG. 4A-FIG. 4E are a set of immunoblots and scatter plot showing that inventive compound 13 induced potent, rapid, and selective Wee1 degradation in a CRBN-dependent manner.

Example 30: Compound 13 is a Rapid and Selective CRBN-Mediated Wee1 Bifunctional Degrader To confirm that compound 13-mediated Wee1 degradation is CRBN dependent (FIG. 1D), Wee1 degradation profiles in parental versus CRBN$^{-/-}$ MOLT4 cells were compared. In parental MOLT4 cells, compound 13 induced potent Wee1 degradation after 5 hours, with maximal degradation observed at 100 nM and a "hook effect" apparent at the top concentration of 10 μM, where compound 13:CRBN and compound 13-Wee1 binary complexes inhibit the formation of a productive ternary complex (Toure and Crews, Angew. Chem. 55:1966-1973 (2016)). By contrast, in CRBN$^{-/-}$ MOLT4 cells, compound 13 had no effect on Wee1 abundance, demonstrating that Wee1 degradation was CRBN-dependent (FIG. 4A).

Furthermore, treatment with compound 13 in the parental MOLT4 cells reduced the inhibitory phosphorylation of CDK1 at Tyr15 (pCDK1 Y15) starting at a 100 nM dose, while decreased pCDK1 Y15 was observed in the CRBN$^{-/-}$ MOLT4 cells starting at a 1 μM dose. Therefore, low concentrations of compound 13 (100 nM) yielded CRBN-dependent effects on pCDK1 Y15, while high concentrations (1 μM or above) resulted in the combined effects of inhibition and degradation.

Figure 4B:
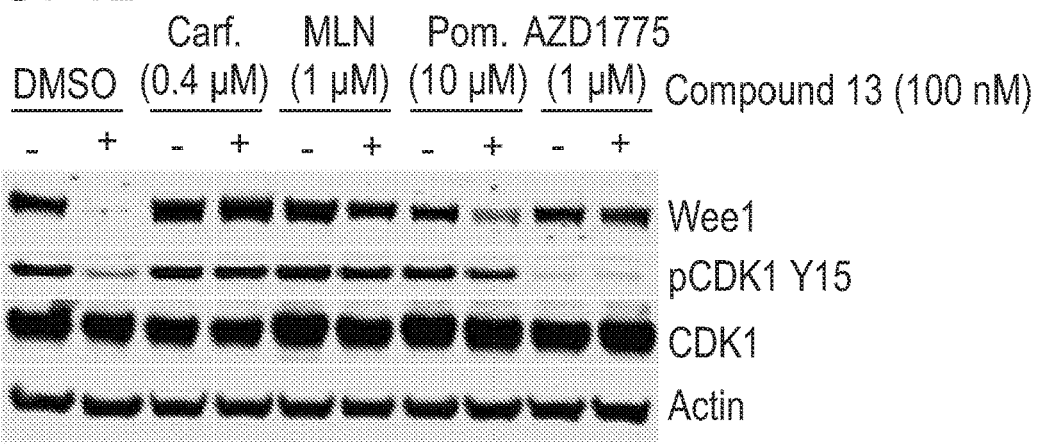

Next, the necessity of proteasome function, Wee1 binding, and CRBN binding for compound 13 activity, were evaluated. Degradation of Wee1 by compound 13 was rescued upon pretreatment of MOLT4 cells with the proteasome inhibitor, carfilzomib, establishing a requirement for proteasome function (FIG. 4B). Wee1 degradation was also prevented following pretreatment with the NEDD8-activating enzyme inhibitor, MHLN4924, indicating a dependence on Cullin-RING ligase (CRL) activity, given that CUL4 neddylation is required for E3 ligase activity (FIG. 2B). Finally, pretreatment with either an excess of AZD1775 or pomalidomide prevented compound 13-induced Wee1 degradation, demonstrating a requirement for both Wee1 and CRBN engagement (FIG. 4B), although pomalidomide pretreatment gave only partial rescue. Notably, the decrease in pCDK Y15 induced by 100 nM of compound 13 was similarly dependent on proteasome function and CRBN binding, as indicated by the complete rescue of this downstream phenotype upon pretreatment with carfilzomib, MLN4924, or pomalidomide. As expected, pretreatment with 1 µM of AZD1775 alone decreased pCDK1 Y15 by inhibiting Wee1, independent of compound 13 co-treatment (FIG. 4B).

Figure 4C:
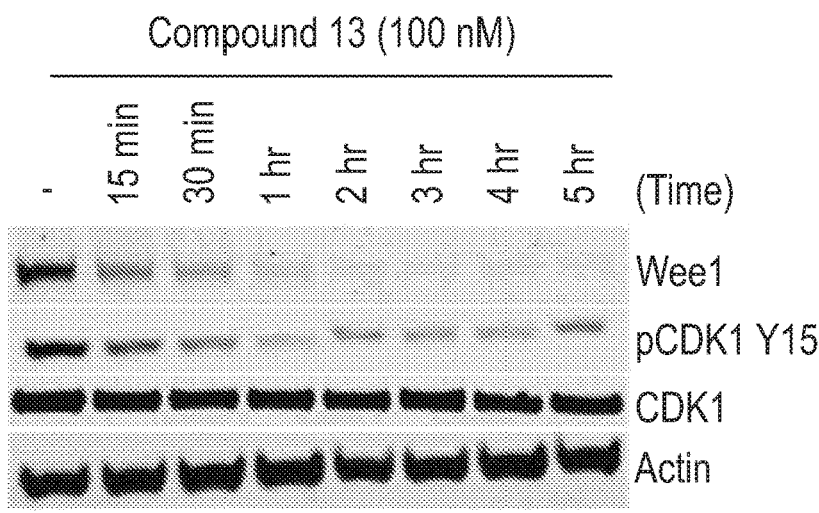
Figure 4D:
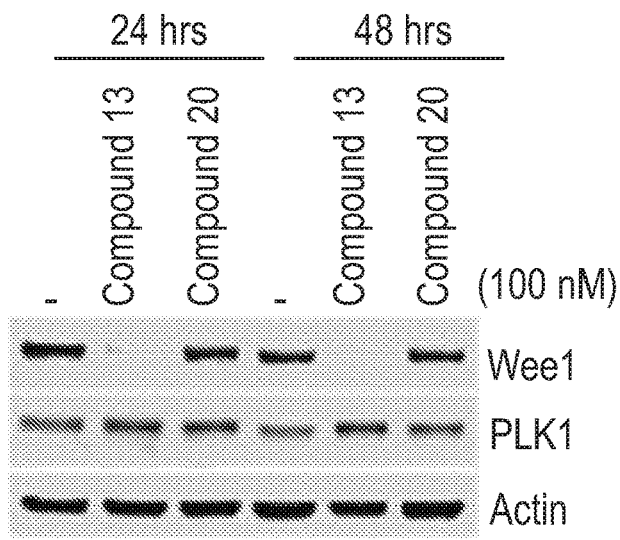

To evaluate the kinetics of Wee1 degradation, a time course study was performed in MOLT4 cells using 100 nM compound 13. Degradation occurred rapidly, with over 50% degradation achieved within 30 min, and complete degradation reached by 3 hr (FIG. 4C). In addition to being rapid, Wee1 degradation was also prolonged, with a single 100 nM treatment of compound 13 resulting in sustained loss of Wee1 for at least 48 hrs. The negative control compound, compound 20, had no effect on Wee1 protein levels (FIG. 4D).

Figure 4E:
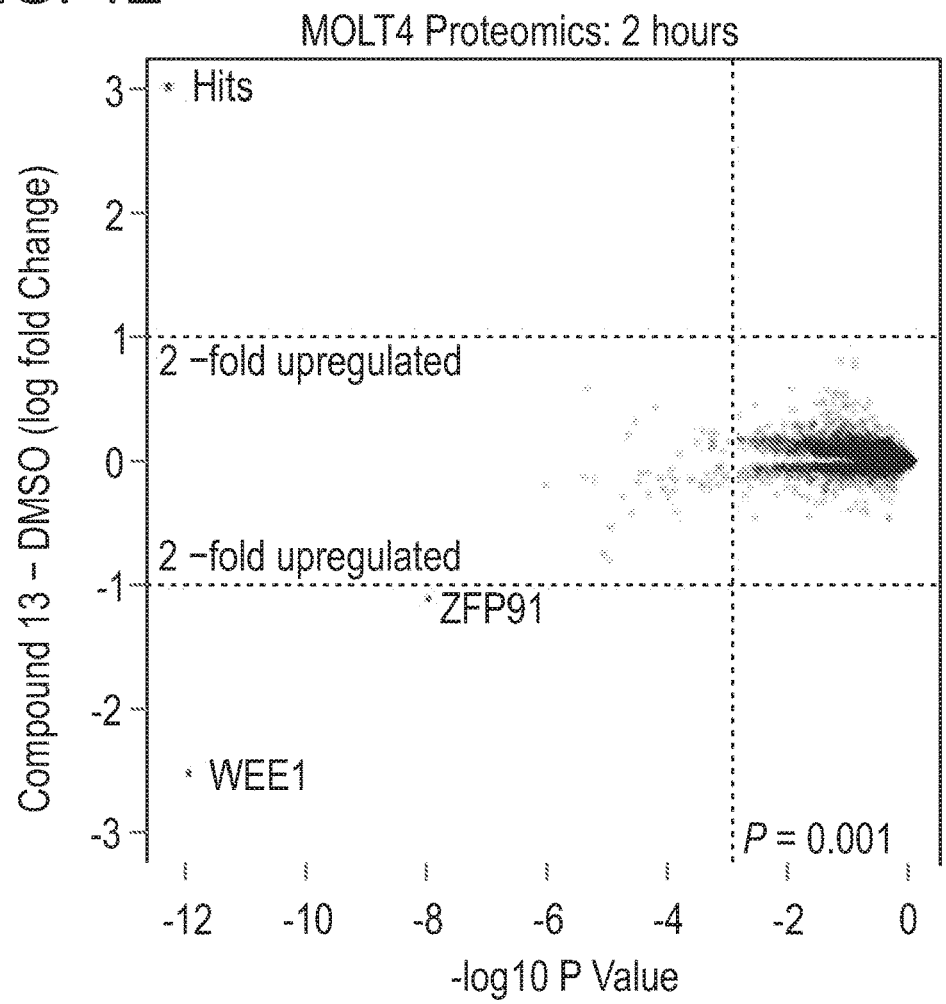
Figure 9A:
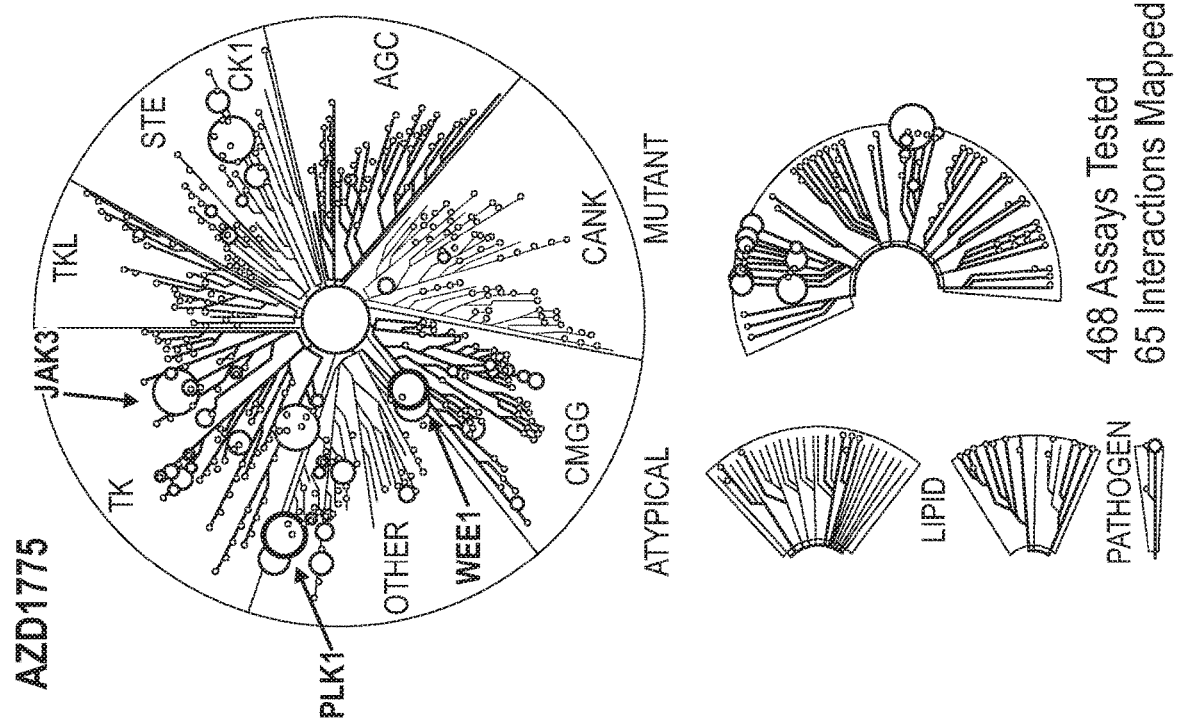
FIG. 9A is a set of kinase trees that represent kinome-wide selectivity of compound 13 and AZD1775 through KINOMEscan® profiling at 1 µM.
Figure 9A:
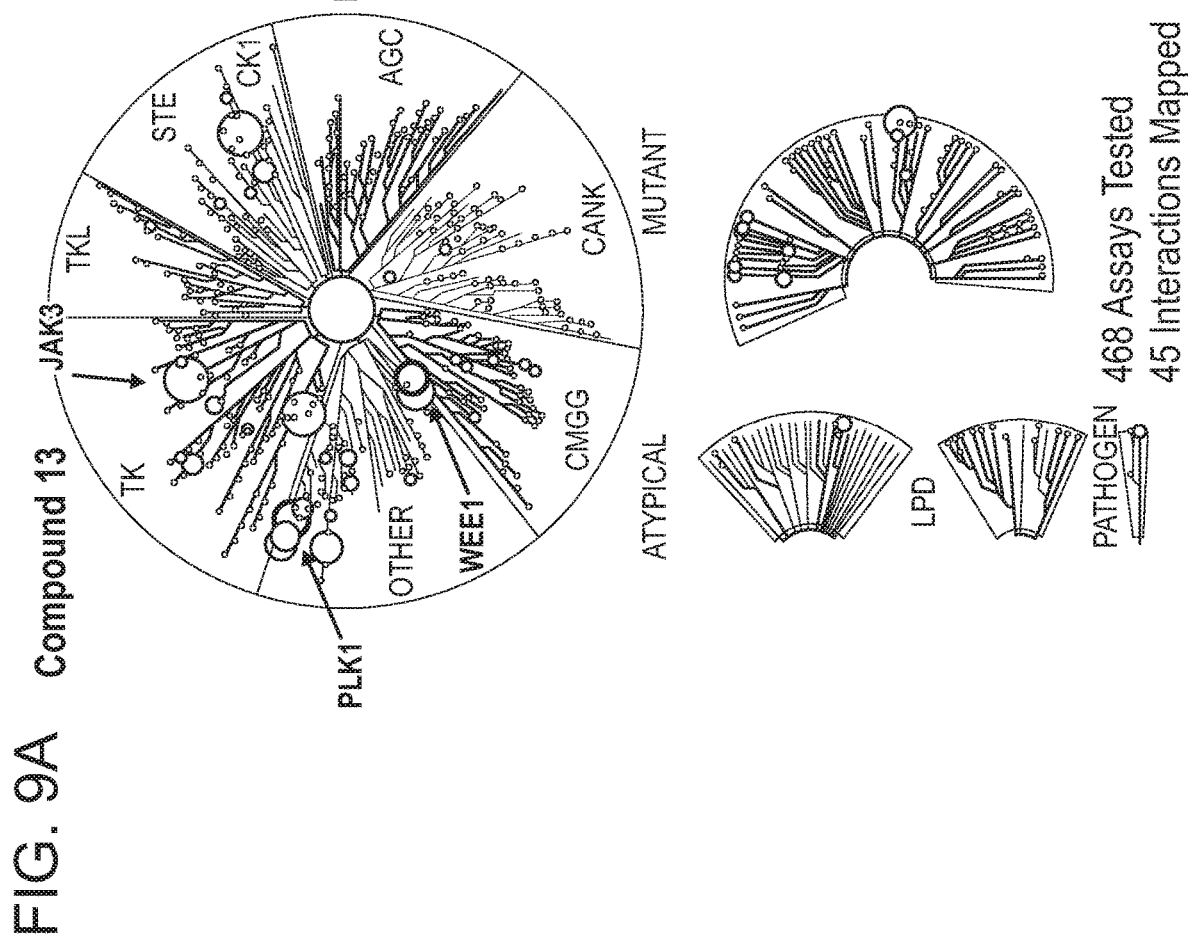

To compare their biochemical selectivity, compound 13 and AZD1775 were submitted for KINOMEscan® profiling (DiscoverX) at 1 µM. As expected, compound 13 had a similar off-target profile to AZD1775—for example, exhibiting strong engagement of both Wee1 and PLK1 (FIG. 9A). This result was confirmed in a FRET-based Z'-LYTE™ kinase assay (Invitrogen™) in which compound 13 demonstrated potent PLK1 inhibition ($IC_{50}$=102 nM; Table 1). Therefore, compound 13 exactly mirrored the biochemical selectivity of AZD1775, inhibiting both Wee1 and PLK1. The selectivity of Wee1 degradation was then assessed by performing multiplexed mass spectrometry (MS)-based proteomics in MOLT4 cells treated with 100 nM of compound 13 for 2 hours (Donovan et al., Elife 7:e38430 (2018)). Quantification across the MOLT4 proteome identified Wee1 as the only protein significantly downregulated (P=8.22E−09; Log2FC=−1.97), thus establishing compound 13 as a Wee1 degradation selective bifunctional compound. No downregulation of PLK1 was evident by proteomics. Immunoblotting confirmed that PLK1 levels were not reduced in MOLT4 cells treated with compound 13 for up to 48 hrs, indicating that compound 13 does not degrade PLK1 in cells (FIG. 4D-FIG. 4E).

Figure 9C:
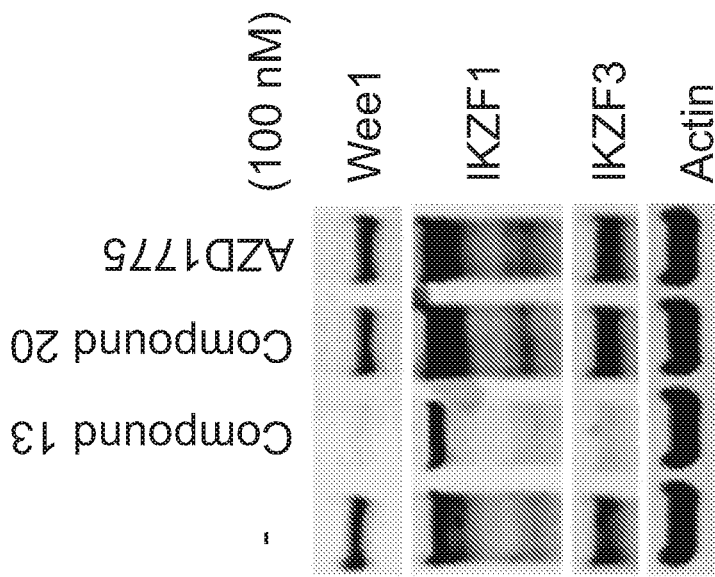
FIG. 9C is an image of an immunoblot analysis of MOLT4 cells after a 24-hour treatment with 100 nM of compound 13, compound 20, or AZD1775. Degradation of IKZF1 and IKZF3 is apparent after a 24-hr treatment, but not after a 5-hour treatment.
Figure 9B:
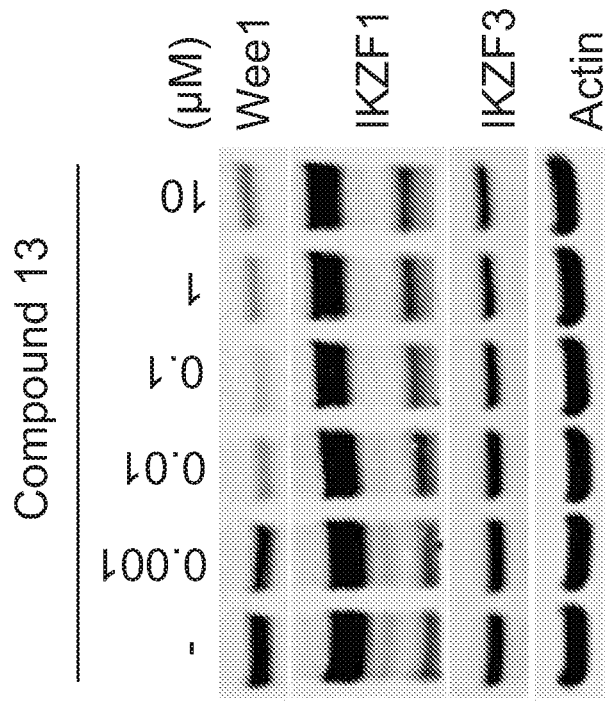
FIG. 9B is an image of an immunoblot analysis of MOLT4 cells after a 5-hour treatment with the indicated concentrations of compound 13.

Zinc-finger transcription factors such as Ikaros (IKZF1), Aiolos (IKZF3), and zinc finger protein 91 (ZFP91) are well-established off-targets of IMiD-based degraders (Donovan et al., Elife 7:e38430 (2018); Kronke et al., Oncoimmunology 3:e941742 (2014)). While low levels of ZFP91 degradation was evident in the proteomics experiment (FIG. 4E), no degradation of either IKZF1 or IKZF3 by compound 13 was observed at short time points. However, degradation of both IKZF1 and IKZF3 was apparent following 24 hrs of drug exposure, as assayed by immunoblotting (FIG. 9B-FIG. 9C).

Taken together, these data show that compound 13 induced potent degradation of Wee1 in a CRBN—and proteasome-dependent manner, with maximal degradation achieved at 100 nM. While compound 13 inhibited PLK1 in vitro, it did not degrade PLK1 in cells. Finally, while compound 13 induced selective Wee1 degradation at short time points (2-5 hrs), it degraded the common IMiD targets by 24 hrs post-treatment. Therefore, it was critical to include lenalidomide as a control in cell-based assays in order to distinguish between the phenotypes associated with Wee1 and IKZF1/3 degradation.

Figure 5A:
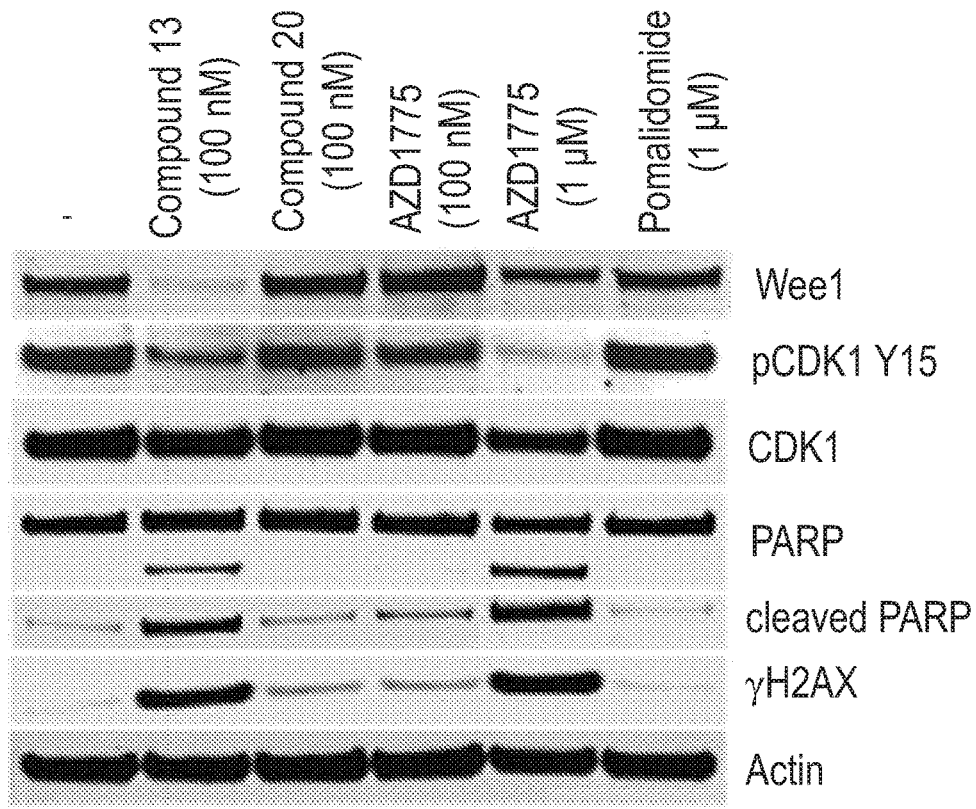
FIG. 5A-FIG. 5D are a set of graphs and an immunoblot showing that inventive compound 13 induced DNA damage, apoptosis, and premature mitotic entry.

Example 31: Compound 13 Induced DNA Damage, Apoptosis, and Deregulation of the G2/M Checkpoint The effects of targeted Wee1 degradation on the cell cycle were evaluated. Wee1 is required for the temporal regulation of CDK1 at the G2/M cell-cycle checkpoint, and Wee1 loss therefore increases the number of cells in G2/M via activation of CDK1. Following loss of Wee1 activity, cells are expected to enter mitosis before completing DNA repair, ultimately resulting in excessive unrepaired DNA damage, mitotic catastrophe, and apoptosis (Beck et al., Mol. Cell Biol. 32:4226-4236 (2012)). In support of this hypothesis, a 24-hr, 100 nM treatment of compound 13 in MOLT4 cells led to reduced pCDK1 Y15, increased apoptosis, as monitored by cleavage of poly (ADP-ribose) polymerase (PARP), and increased unrepaired DNA, as indicated by increased expression of the DNA double-strand break marker, γH2Ax. By contrast, treatment with an equivalent dose of compound 13 or AZD1775 did not produce any noticeable changes in downstream signalling. Rather, a 1 µM treatment of AZD1775 was necessary to induce the same downstream changes as 100 nM of compound 13. Serving as the IMiD control, 1 µM of pomalidomide did not affect phosphorylation of CDK1 Y15, apoptosis, or levels of DNA damage (FIG. 5A). These data indicate that compound 13 treatments mimicked the downstream effects of AZD1775 treatment, but at up to 10-fold lower doses, likely because the degrader's catalytic turnover enabled efficacy at lower doses than the inhibitor.

Figure 5B:
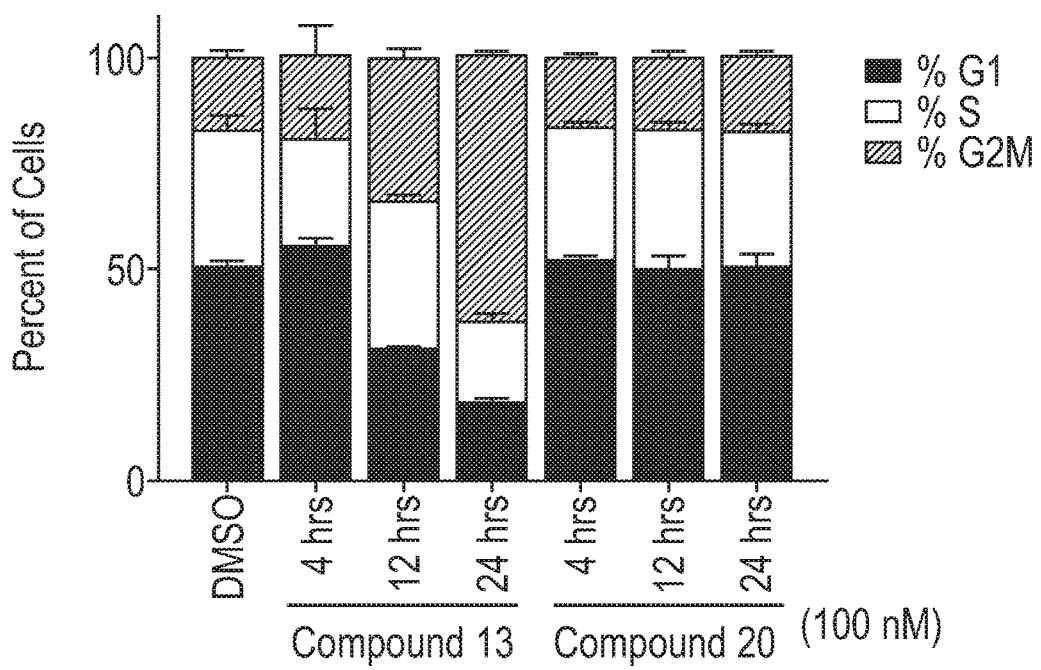
Figure 5C:
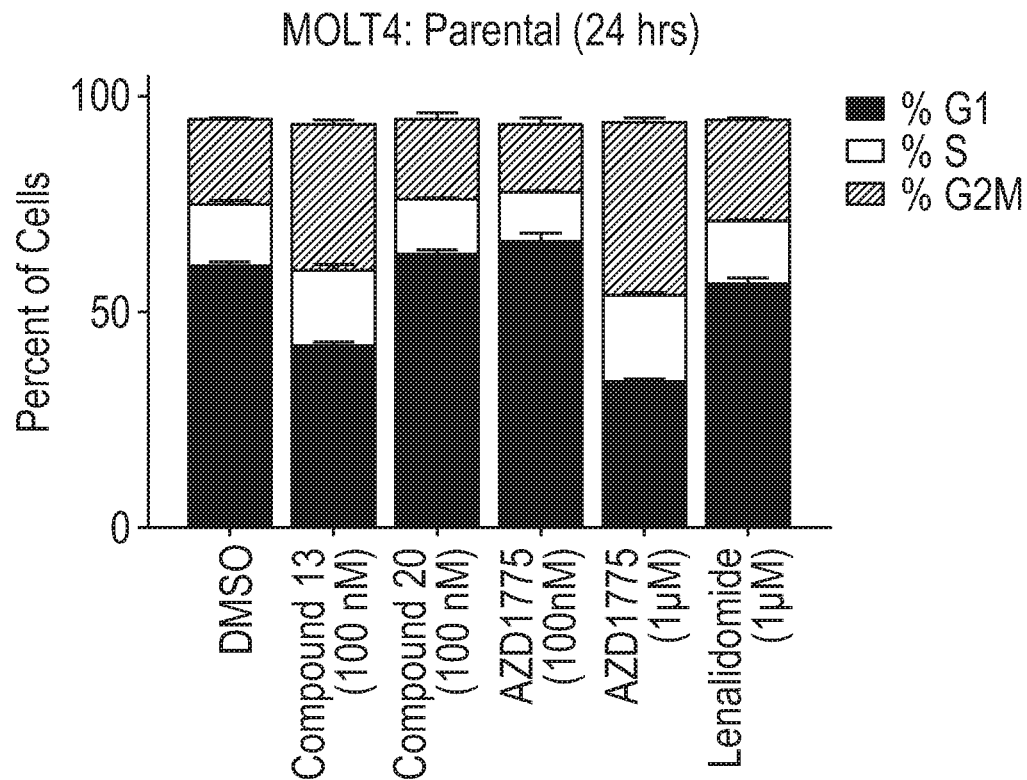
Figure 5D:
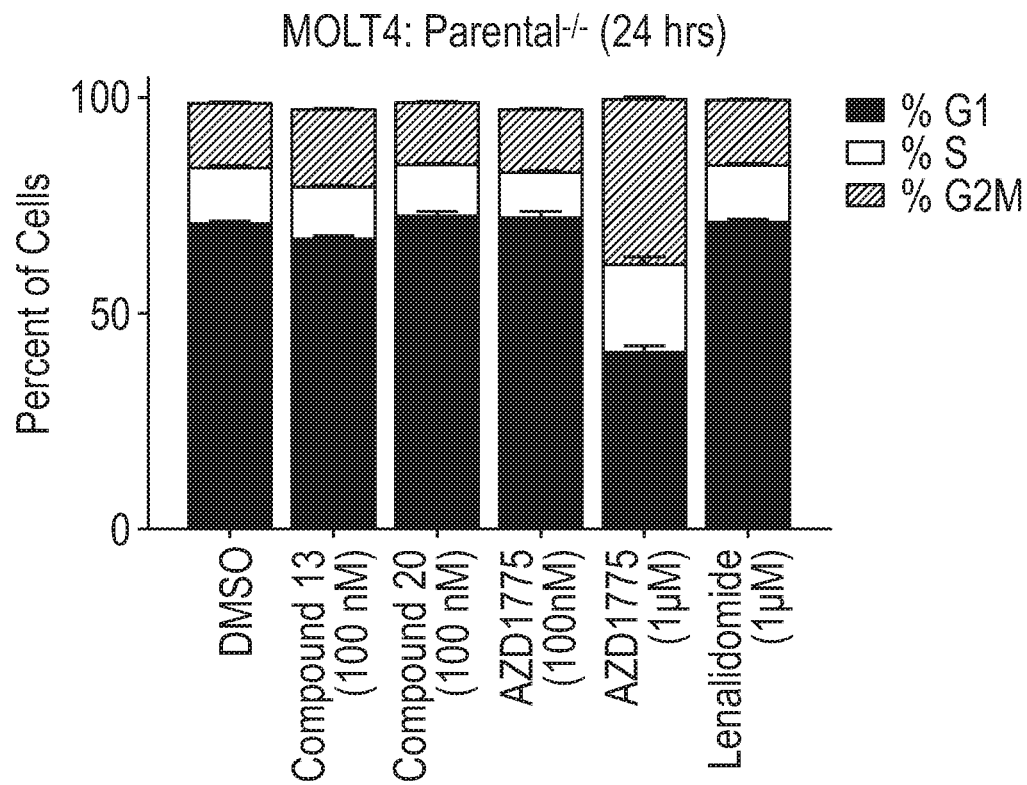

Treatment with 100 nM of compound 13 increased the proportion of MOLT4 cells in G2-M in a time-dependent manner, as measured by propidium iodide (PI) staining (FIG. 5B). A 24-hr treatment with 100 nM of compound 13 induced a dramatic increase in G2-M cells from 19% to 34%, but an equivalent dose of AZD1775 or compound 20 did not appreciably affect the cell cycle. A 10-fold higher dose of AZD1775 (1 µM) was needed to elicit the same changes in the cell cycle as 100 nM of compound 13. To control for the potentially complicating effects of concomitant IKZF1/3 degradation, lenalidomide was included as a control, which did not induce any significant changes in the cell-cycle at 1 µM. Furthermore, the increased mitotic entry mediated by compound 13 was absent in CRBN$^{-/-}$ MOLT4 cells, highlighting a requirement for CRBN-dependent degradation (FIG. 5C). By contrast, the cell cycle effects induced by AZD1775 at 1 µM are CRBN-independent and therefore were unchanged in the CRBN$^{-/-}$ MOLT4 cells.

To assess whether this observed cell-cycle phenotype could be extended to other cancer cell lines, compound 13 and AZD1775 were tested in triple-negative breast cancer (TNBC) cell lines using an image-based method to assay changes in cell cycle state (M. Hafner et al., *DeepDyeDrop: an image-based approach to quantify the phenotypic response of cancer cells to therapeutics* (Conference Presentation), Vol. 10475, SPIE, 2018). In the TNBC lines, BT549 and HCC1806, compound 13 induced greater changes in mitotic cell number than AZD1775, while having very little effect on the non-transformed mammary epithelial cell line, MCF10A (data not shown herein). Collectively, these data suggest that compound 13-mediated Wee1 degradation can achieve the same cell-cycle phenotype as AZD1775-mediated Wee1 inhibition, but at significantly lower doses.

Figure 6A:
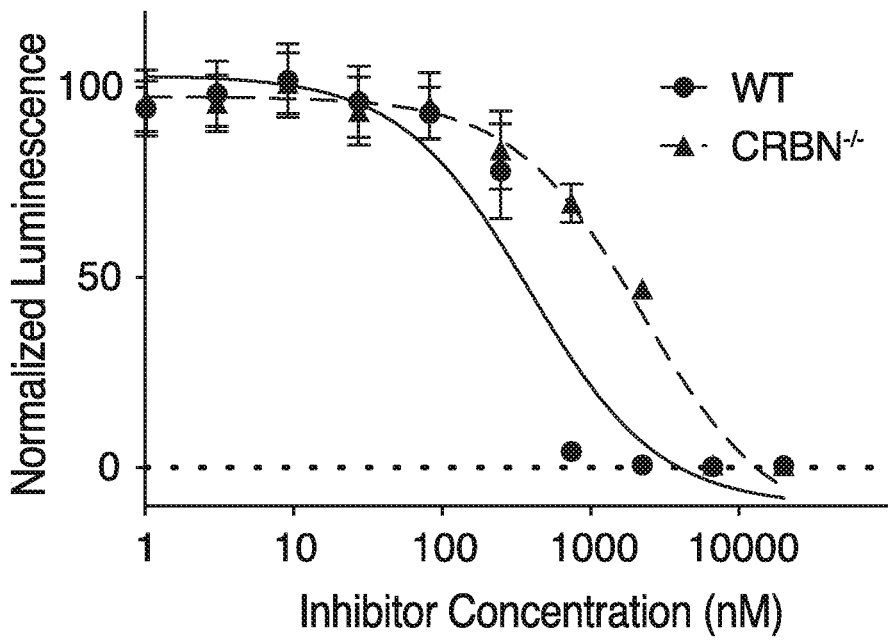
FIG. 6A-FIG. 6F are a set of graphs showing that inventive compound 13 induced potent anti-proliferative effects and synergized with Olaparib.
Figure 6B:
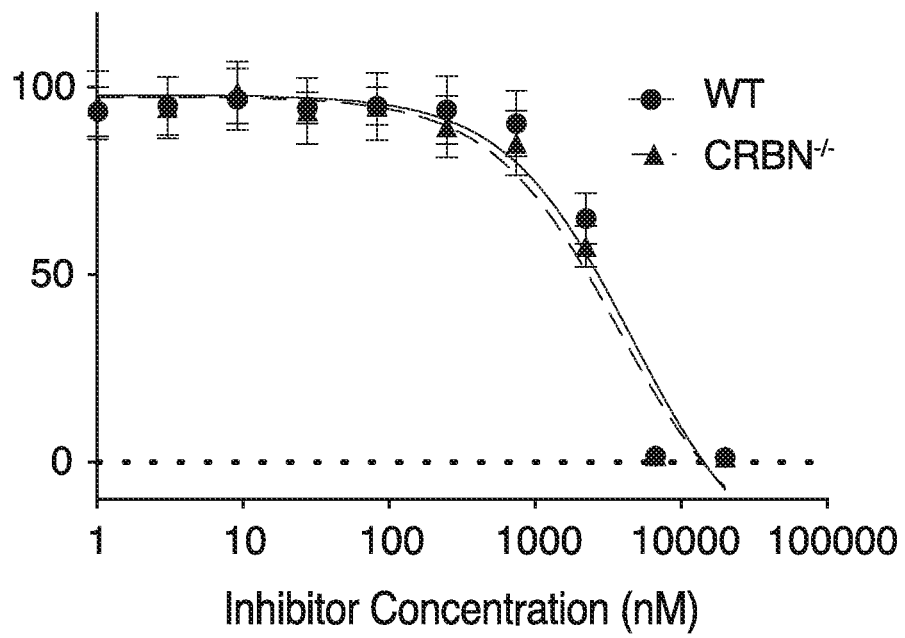
Figure 6C:
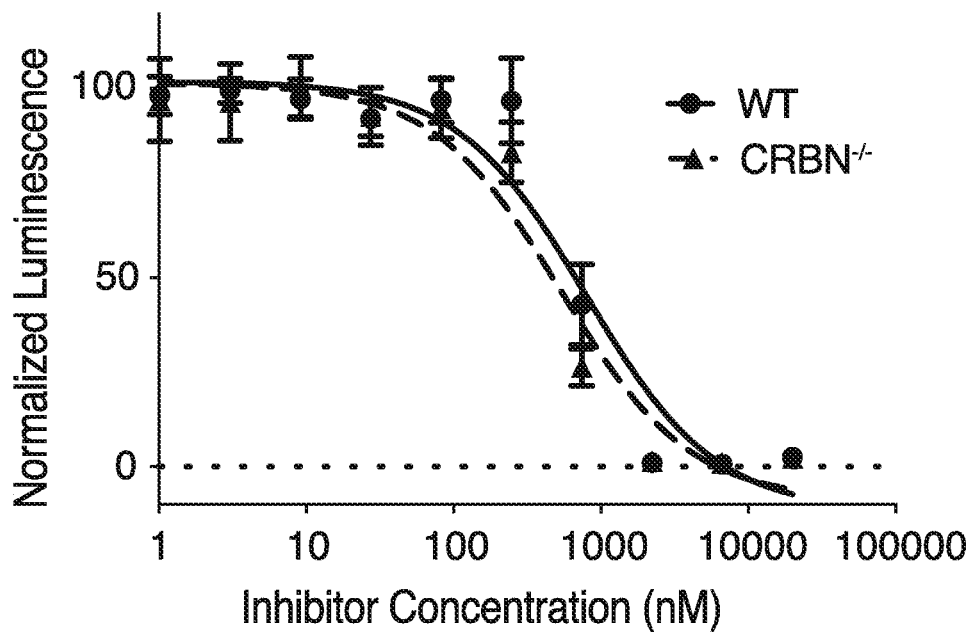
Figure 10A:
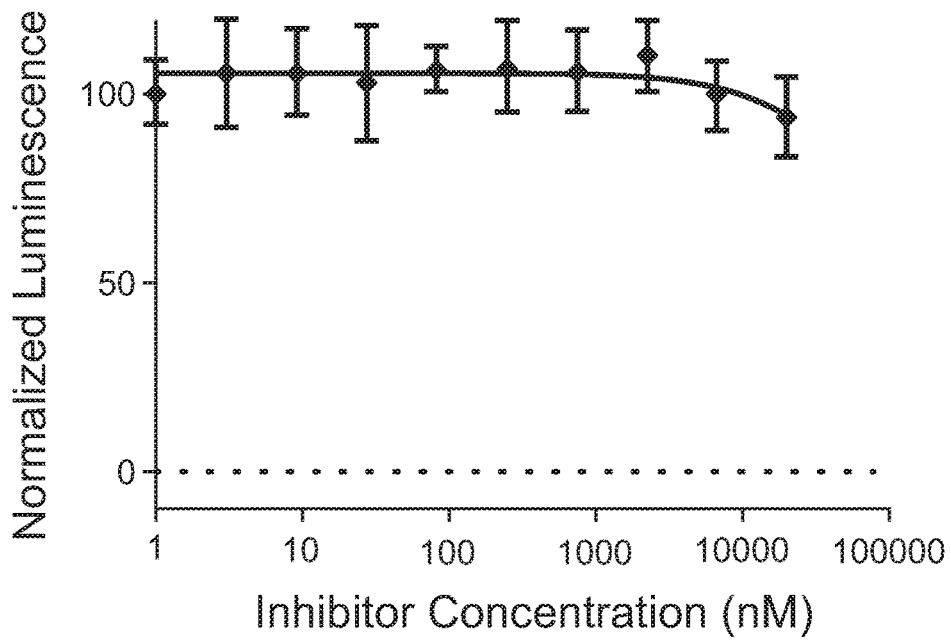
FIG. 10A is a graph showing antiproliferative effects of Pomalidomide in MOLT4 WT cells after a 72-hr treatment, as approximated by CellTiter-Glo. Data points are plotted as the average of three replicates ±SEM.
Figure 10B:
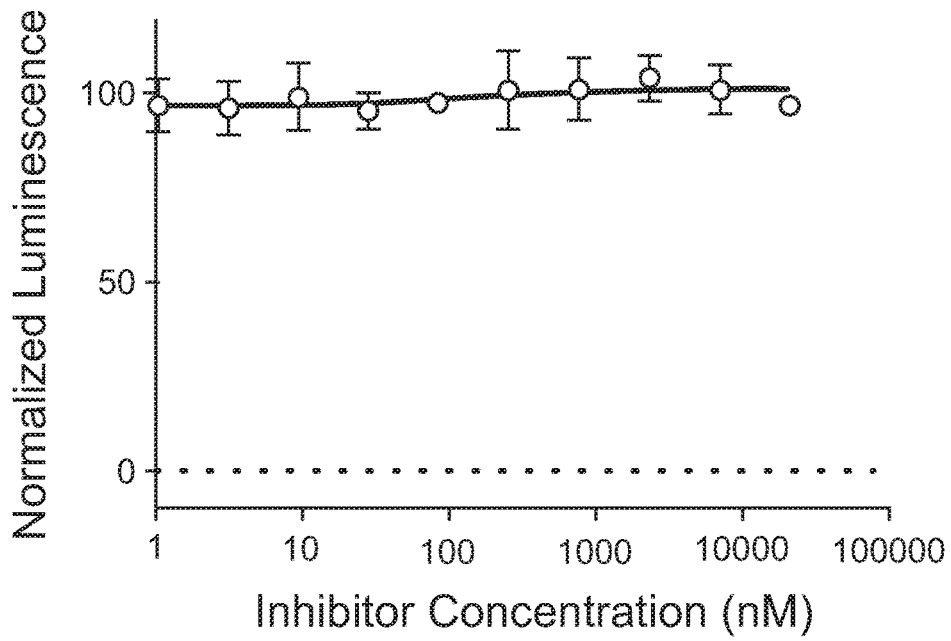
FIG. 10B is graph showing antiproliferative effects of Lenalidomide in MOLT4 WT cells after a 72-hr treatment, as approximated by CellTiter-Glo. Data points are plotted as the average of three replicates ±SEM.

Example 32: Compound 13 Induced CRBN-Dependent Antiproliferative Effects and Synergized with Olaparib The antiproliferative activity of compound 13 was profiled versus the parental compound, AZD1775. In MOLT4 cells, compound 13 exhibited slightly enhanced cytotoxicity as compared to AZD1775 (compound 13 $IC_{50}$=390 nM;

AZD1775 IC$_{50}$=800 nM), while the negative control, compound 20, was significantly less potent (IC$_{50}$=4557 nM). Given that compound 13 and compound 20 have similar chemical properties and cell permeability, this shift in their IC$_{50}$ values represents the CRBN-dependent contribution to the antiproliferative activity of compound 13. The CRBN-dependent cytotoxicity was further indicated by the approximately 6-fold shift in the cellular IC$_{50}$ of compound 13 in the MOLT4 CRBN$^{-/-}$ cells (IC$_{50}$=2220 nM) as compared to the parental MOLT4 cells. (FIG. 6A-FIG. 6C). Lenalidomide and pomalidomide, which were used to control for the effects of IKZF1/3 degradation, had no detectable antiproliferative activity in MOLT4 cells (FIG. 10A-FIG. 10B), suggesting that the CRBN-dependent antiproliferative activity of compound 13 is attributable to Wee1 degradation.

To more broadly profile the antiproliferative activity of compound 13, the bifunctional compound was submitted to the PRISM platform (Broad Institute), a pooled cytotoxicity assay, to evaluate its single-agent potency against 300 suspension and hematopoietic cancer cell lines (Yu et al., Nat. Biotechnol. 34:419-423 (2016). The negative control compound, compound 20, was also profiled to control for the contribution of CRBN-dependent degradation versus inhibition. Compound 13 exhibited sub-1 µM IC$_{50}$ values in almost all of the lines tested, demonstrating efficacy in a broad spectrum of cancer types, including ovarian cancer, while compound 20 was uniformly less potent. The largest shift in potency between compound 13 and compound 20 was observed in multiple myeloma (MM) cell lines, which may be partially attributable to IKZF1/3 degradation given the therapeutic efficacy of lenalidomide in MM patients (data not shown herein). Overall, these data highlight the enhanced anti-proliferative activity of Wee1 degradation by compound 13, as compared to Wee1 inhibition by compound 20. Moreover, cell lines dependent on IKZF1/3 exhibited particularly striking sensitivity to compound 13, likely due to the additional effects of IMiD-dependent protein degradation.

In general, ovarian cancer cell lines are insensitive to IKZF1/3 degradation. Therefore this cancer type was selected for follow-up studies. AZD1775 has demonstrated efficacy in ovarian cancer as a monotherapy and in combination with DNA-damaging agents, in both preclinical models and the clinic (Guertin et al., Mol. Cancer Ther. 12:1442-1452 (2013); Zhang et al., Oncol. Lett. 14:3580-3586 (2017)). In particular, AZD1775 has been reported to increase the sensitivity of ovarian cancer cells to the PARP inhibitor, Olaparib, and AZD1775/Olaparib combination therapy is currently being evaluated in a Phase 1b clinical trial in patients with refractory solid tumors (Meng et al., Cancers 10:149 (2018); Kim et al., Clin. Cancer Res. 21:4257-4261 (2015); ClinicalTrials.gov Identifier: NCT02511795).

Figure 6D:
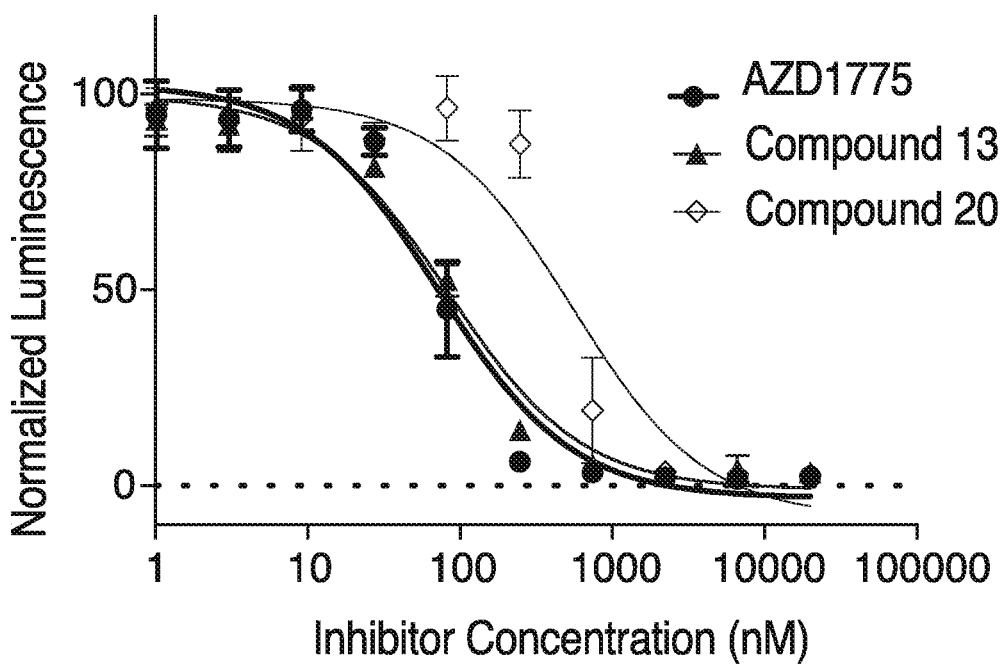
Figure 6E:
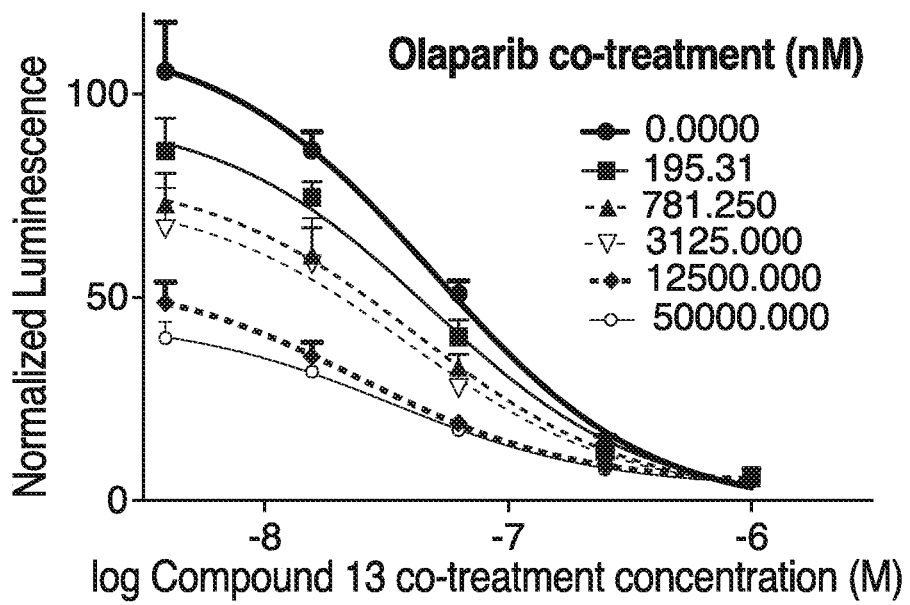
Figure 6F:
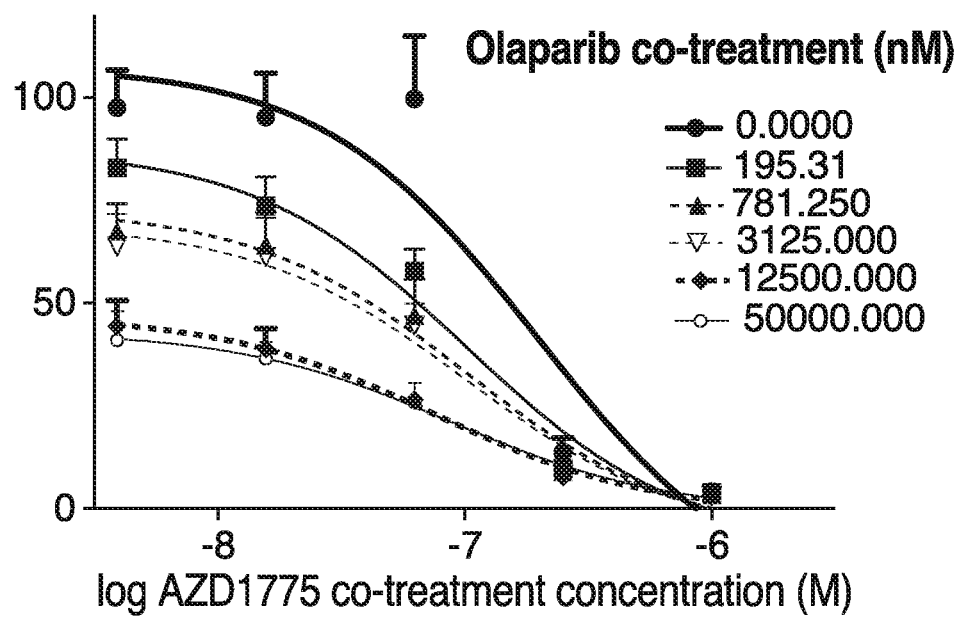
Figure 11E:
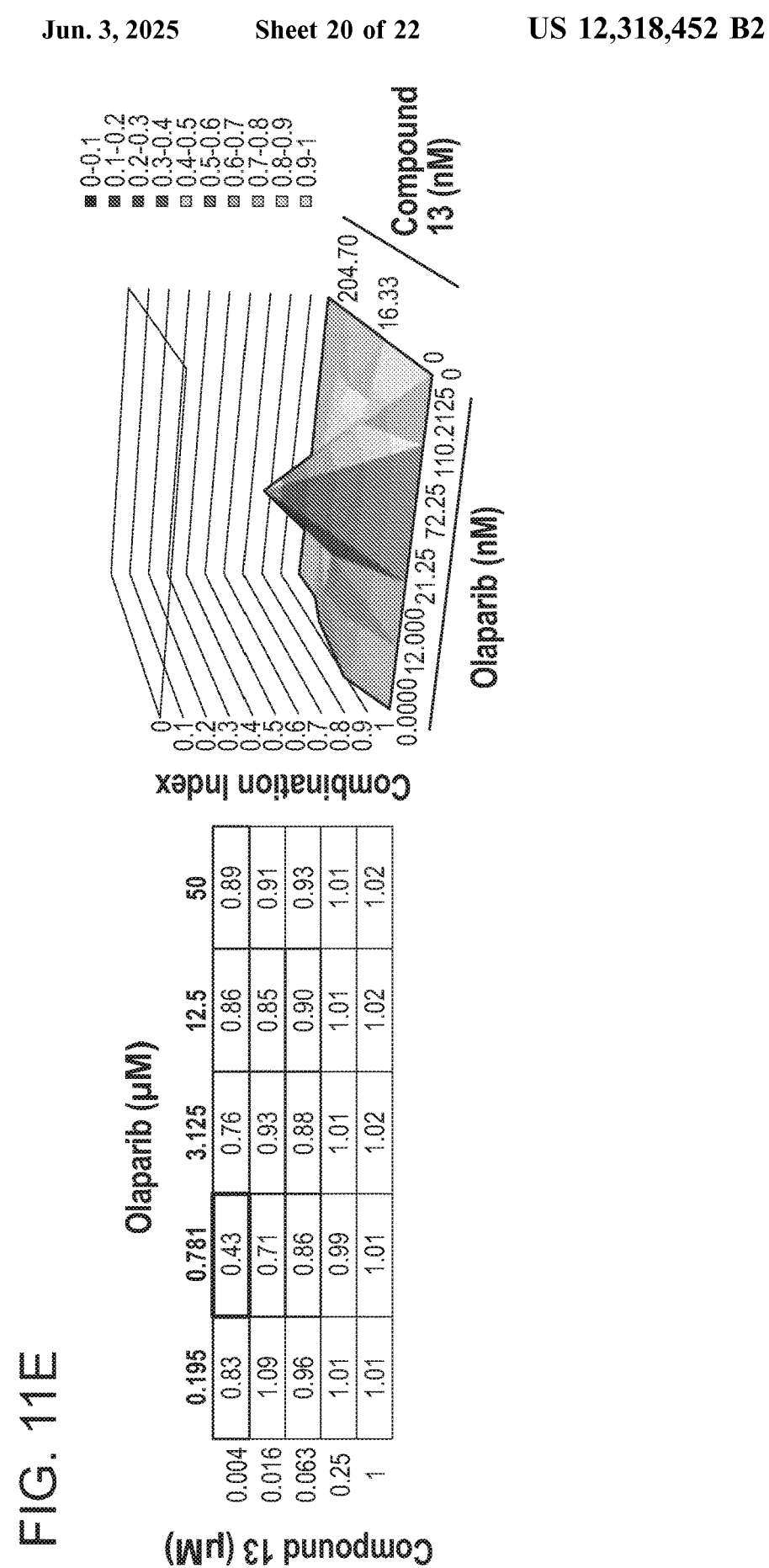
FIG. 11E is an image showing a combination index (CI) for compound 13 and Olaparib co-treatment for 72 hours in OVCAR8 cells, where CI=[A+B−A*B]/AB. Synergistic effect (CI<1), additive (CI=1), antagonism (CI>1).
Figure 11F:
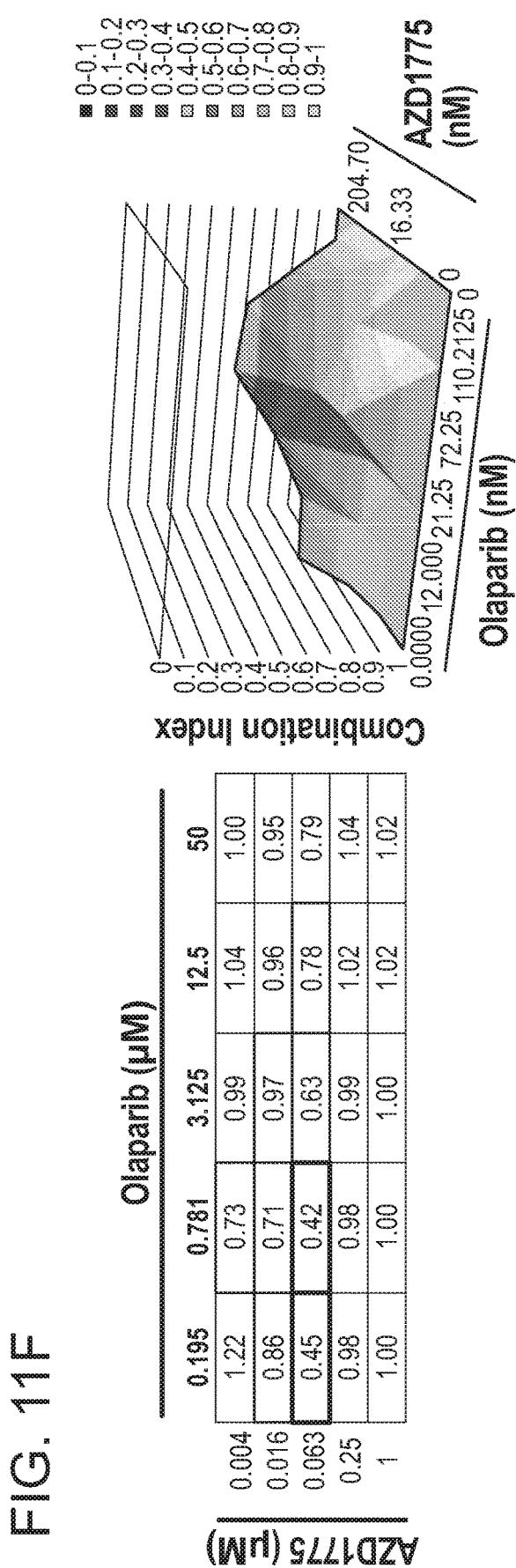
FIG. 11F is an image showing a combination index (CI) for AZD1775 and Olaparib co-treatment for 72 hours in OVCAR8 cells, where CI=[A+B−A*B]/AB. Synergistic effect (CI<1), additive (CI=1), antagonism (CI>1).

Compound 13 was profiled in three different ovarian cancer cell lines OVCAR8, COV362, and Kuramochi (FIG. 6C-FIG. 6E). The greatest potency was observed in OVCAR8 cells, which we selected for follow-up drug combination experiments. After confirming that Compound 13 degraded Wee1 in OVCAR8 cells, with maximal degradation observed at a 100 nM treatment (FIG. 11A), the efficacy of compound 13 and Olaparib combination treatments were evaluated. Compound 13 synergized with Olaparib in OVCAR8 cells following a 72-hr treatment, with similar synergy observed upon AZD1775 and Olaparib co-treatment (FIG. 6F; FIG. 11E-FIG. 11F). By contrast, low concentrations of compound 20 displayed less synergistic activity with Olaparib than compound 13 (FIG. 11B). To control for IKZF1/3 degradation, it was established that pomalidomide and Olaparib co-treatment was not synergistic, nor was pomalidomide and AZD1775 co-treatment. This was tested to ensure that IKZF1/3 degradation did not synergize with Wee1 inhibition (FIG. 11C-FIG. 11D). These data highlight that in certain cellular contexts, compound 13-mediated Wee1 degradation exhibited enhanced cytotoxicity as compared to AZD1775-mediated Wee1 inhibition. Furthermore, the potent synergy observed upon compound 13 and Olaparib co-treatment in ovarian cancer cell lines suggests that combination therapies of PARP inhibitors and targeted Wee1 degraders may have therapeutic value.

In summary, compound 13 exhibited rapid and sustained Wee1 degradation at sub-µM doses, potently induced premature mitotic entry, DNA damage, and apoptosis, and exhibited significant antiproliferative activity across a panel of 300 cancer cell lines. Comparing compound 13 directly to the existing clinical molecule, AZD1775, showed that the degrader induced premature mitotic entry at 10-fold lower doses in MOLT4 cells. Moreover, negative control, compound 20, inhibited Wee1 but was incapable of engaging CRBN, mirrored the phenotype of AZD1775 and was similarly unable to induce cell-cycle changes at nanomolar doses. These data suggest that targeted Wee1 degraders might be efficacious at lower doses than Wee1 inhibitors, potentially lessening the severity of the dose-limiting toxicities that have been associated with AZD1775 in the clinic. Collectively, the data presented herein revealed that Wee1 degradation may prove a viable therapeutic strategy in ovarian cancer, either as a monotherapy or in combination with a PARP inhibitor such as Olaparib.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound having a structure represented by formula I:

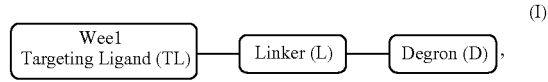

(I)

wherein the targeting ligand is a moiety that binds Wee1 kinase and is represented by a structure selected from the group consisting of:
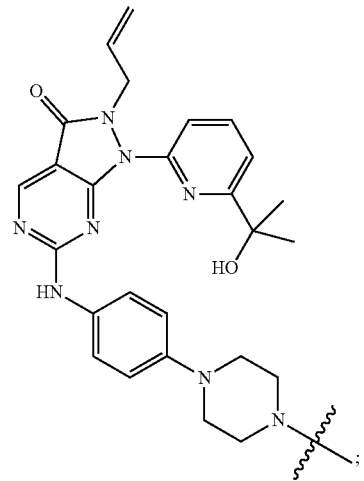
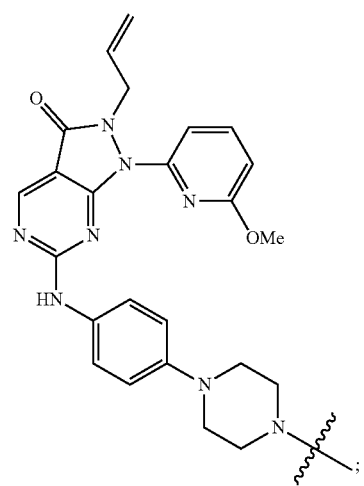
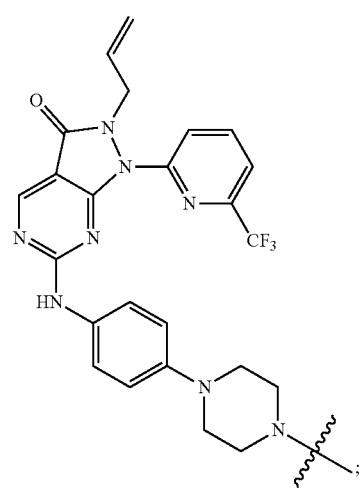
-continued
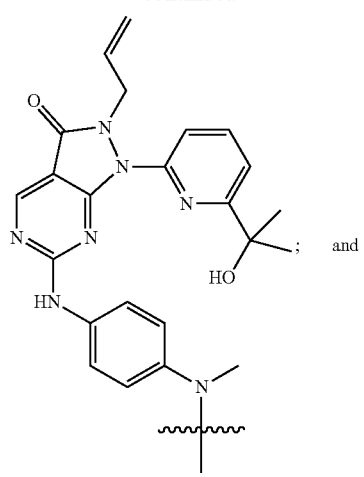
and
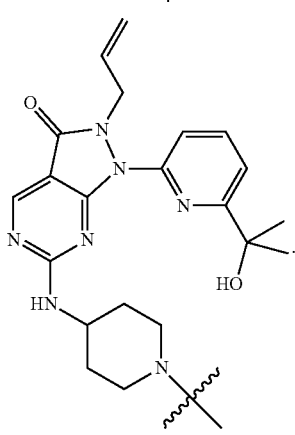
the degron is:
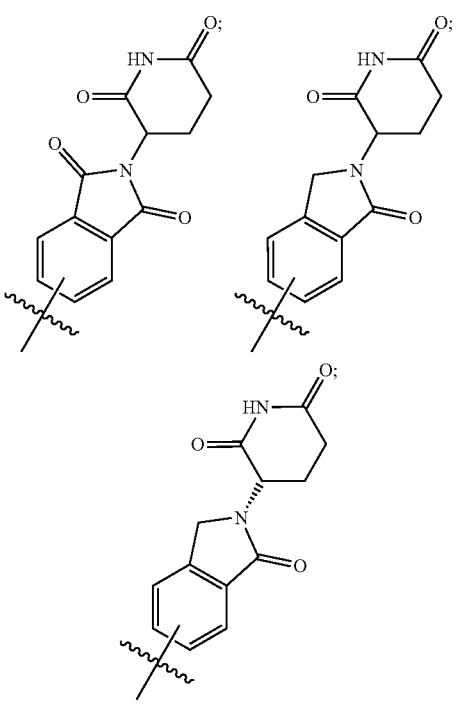

-continued

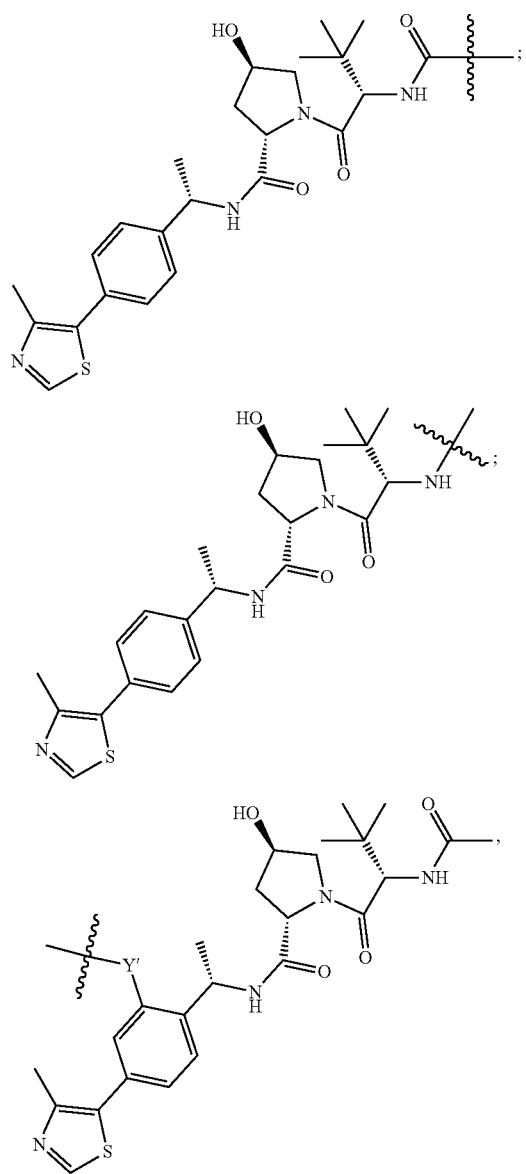

wherein Y' is a bond, N, O or C;

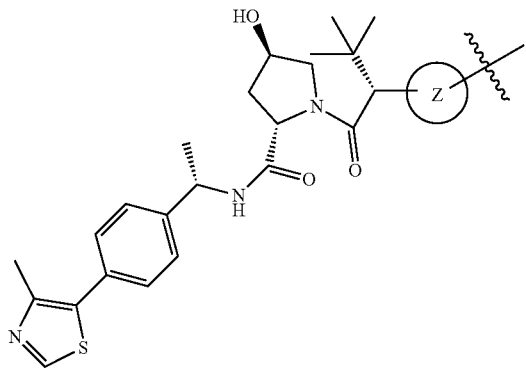

wherein Z is a $C_5$-$C_6$ carbocyclic or a $C_5$-$C_6$ heterocyclic group; or

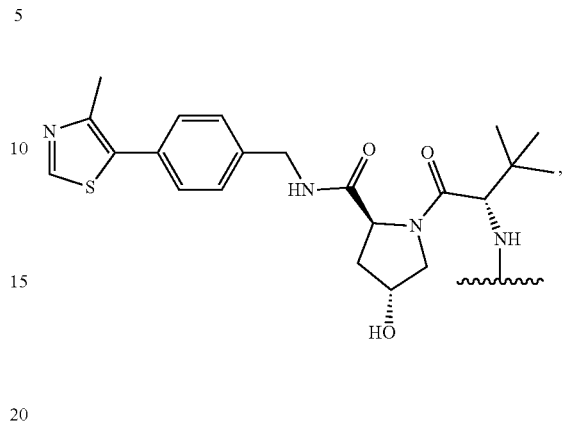

and the linker is an alkylene chain or a polyethylene glycol chain, either of which may be interrupted by and/or terminate (at either or both termini) in at least one of —O—, —S—, —N(R')—, —C≡C—, —C(O)—, —C(O)O—, —OC(O)—, —OC(O)O—, —C(NOR')—, —C(O)N(R')—, —C(O)N(R')C(O)—, —C(O)N(R')C(O)N(R')—, —N(R')C(O)—, —N(R')C(O)N(R')—, —N(R')C(O)O—, —OC(O)N(R')—, —C(NR')—, —N(R')C(NR')—, —C(NR')N(R')—, —N(R')C(NR')N(R')—, —OB(Me)O—, —S(O)$_2$—, —OS(O)—, —S(O)O—, —S(O)—, —OS(O)$_2$—, —S(O)$_2$O—, —N(R')S(O)$_2$—, —S(O)$_2$N(R')—, —N(R')S(O)—, —S(O)N(R')—, —N(R')S(O)$_2$N(R')—, —N(R')S(O)N(R')—, $C_3$-$C_{12}$ carbocyclene, 3- to 12-membered heterocyclene, 5- to 12-membered heteroarylene or any combination thereof, wherein R' is H or $C_1$-$C_6$ alkyl, wherein the interrupting and the one or both terminating groups may be the same or different, or a pharmaceutically acceptable salt or stereoisomer thereof.

2. The compound of claim 1, which is represented by a structure selected from the group consisting of:

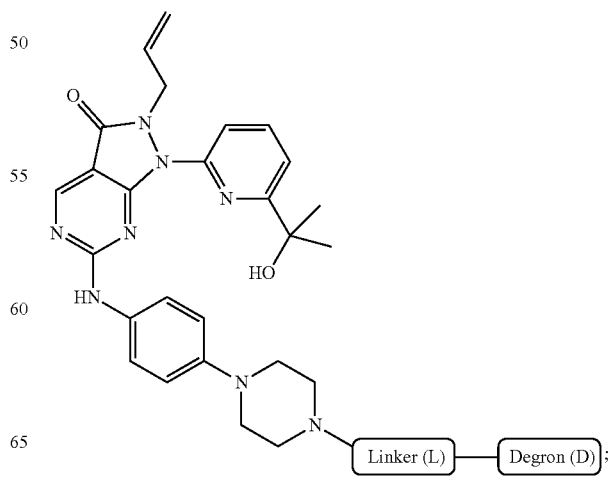

-continued

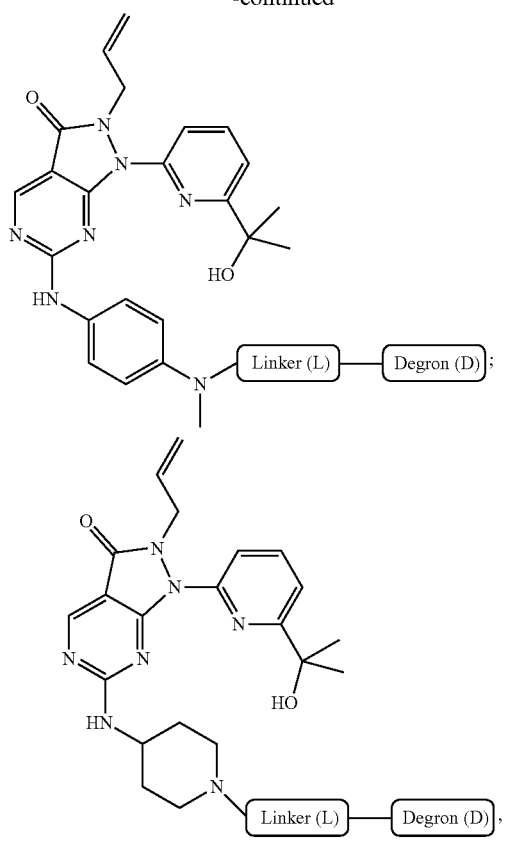

or a pharmaceutically acceptable salt or stereoisomer thereof.

3. The compound of claim 1, wherein the degron is

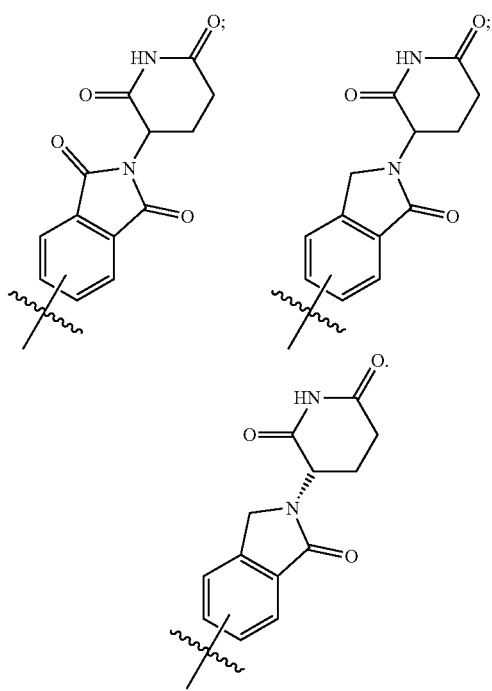

4. The compound of claim 3, which is represented by any one of the following structures:

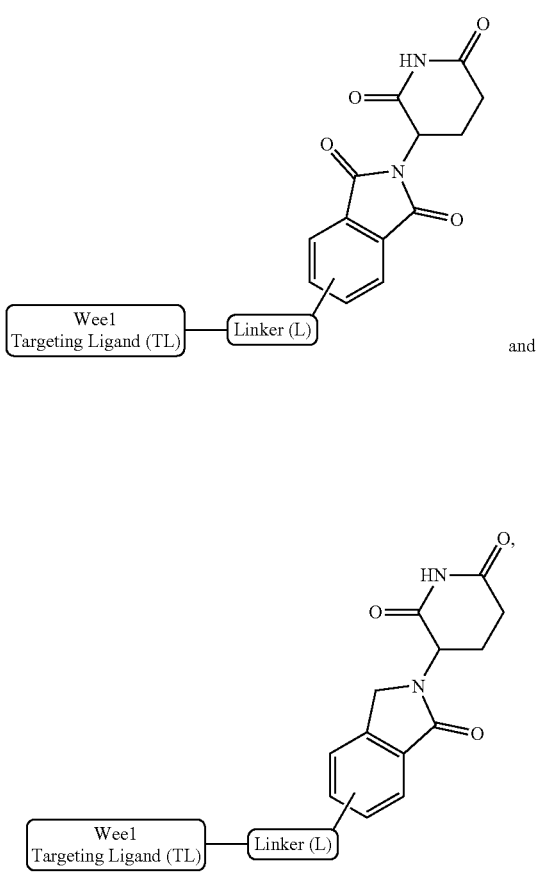

or a pharmaceutically acceptable salt or stereoisomer thereof.

5. The compound of claim 4, which is represented by a structure selected from the group consisting of:

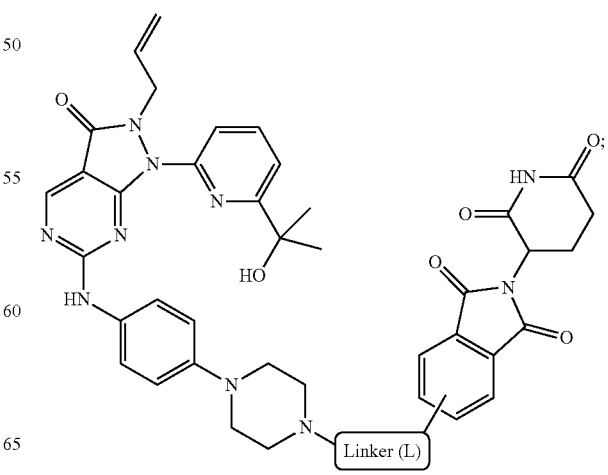

183
-continued
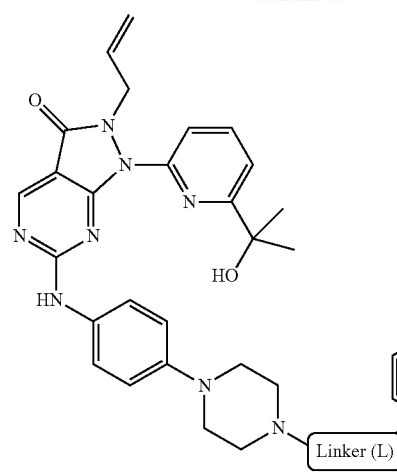
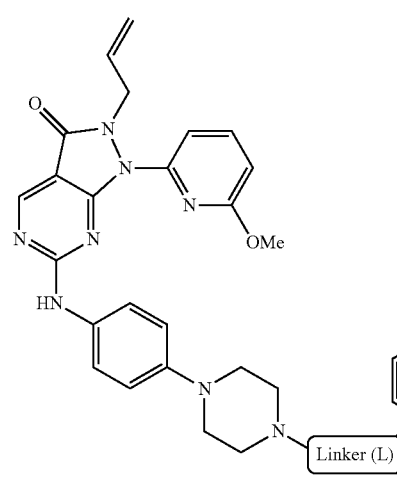
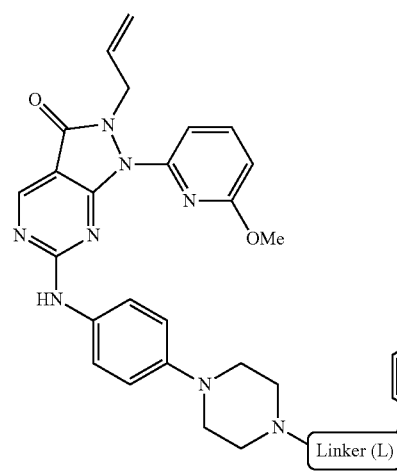
184
-continued
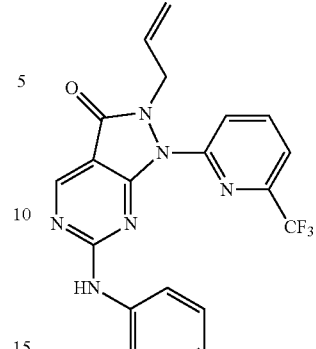
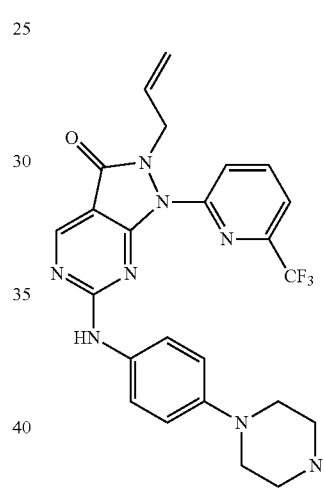
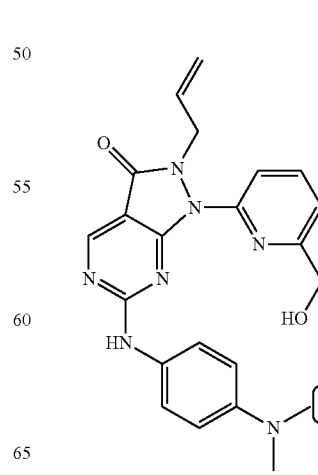

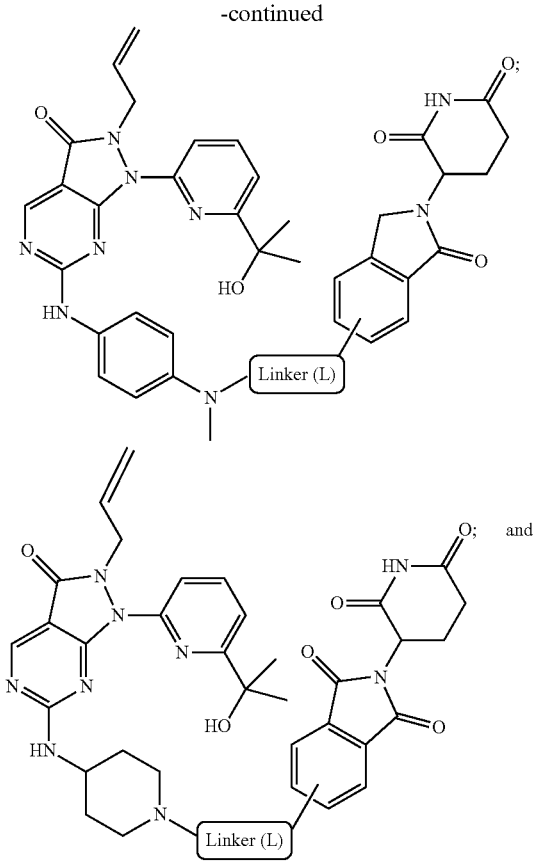
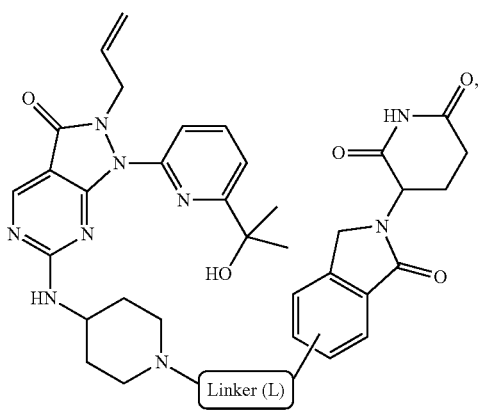
or a pharmaceutically acceptable salt or stereoisomer thereof.
6. The compound of claim 1, wherein the linker is represented by a structure selected from the group consisting of
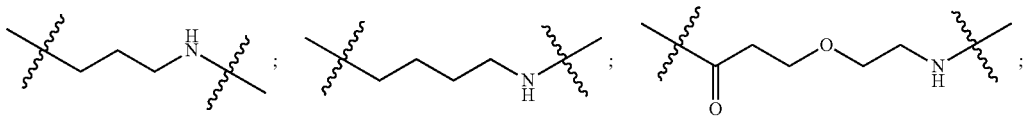
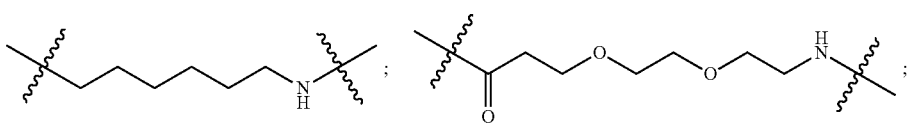
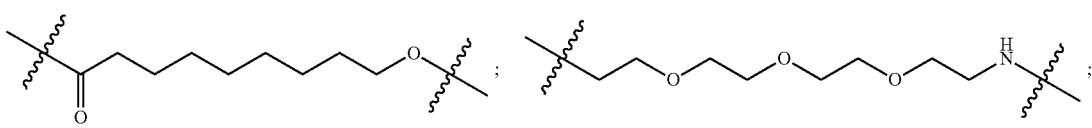
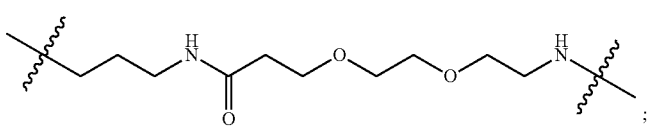

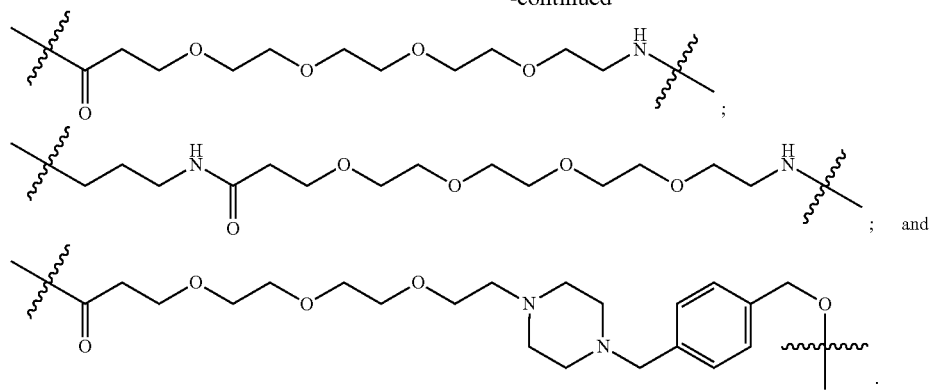
7. The compound of claim 1, wherein the degron is
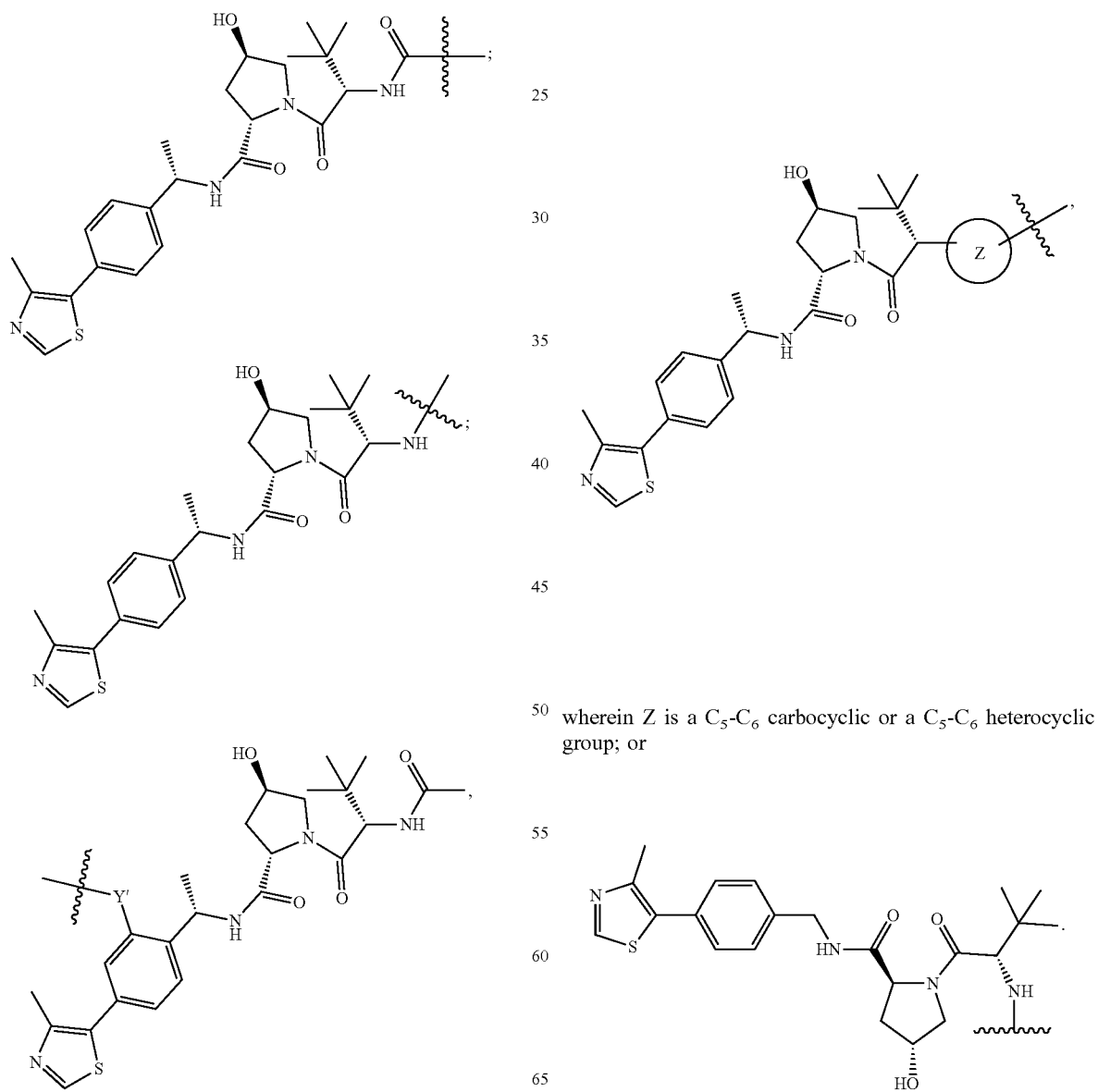
wherein Y' is a bond, N, O or C;
wherein Z is a $C_5$-$C_6$ carbocyclic or a $C_5$-$C_6$ heterocyclic group; or 8. The compound of claim 1, which is represented by a structure selected from the group consisting of:
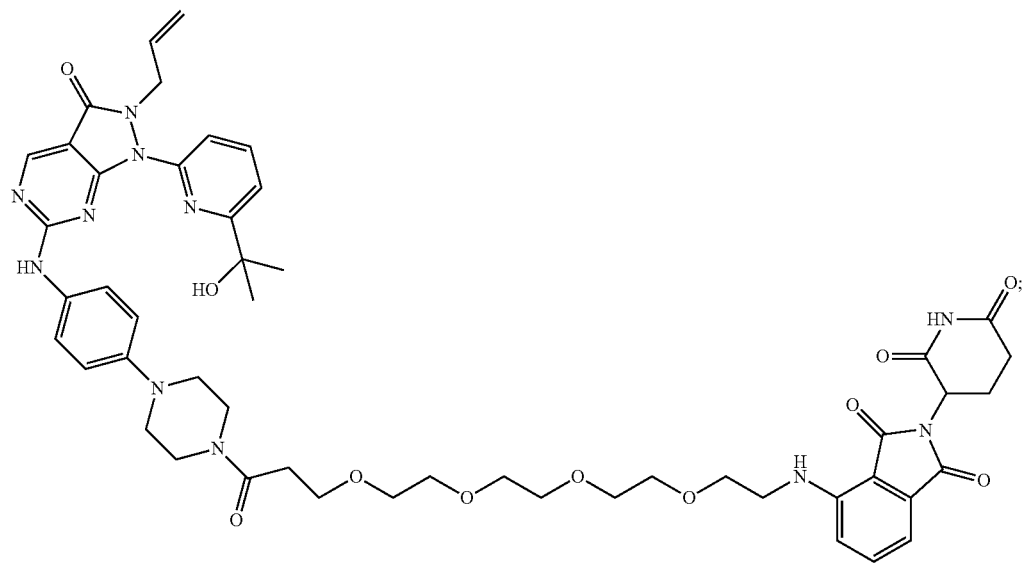
(1)
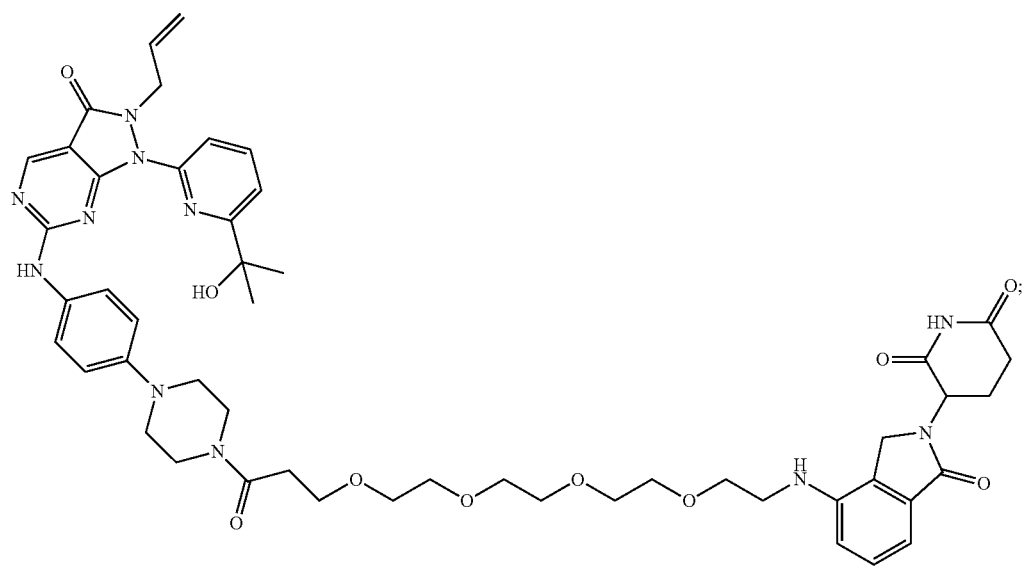
(2)

(3)
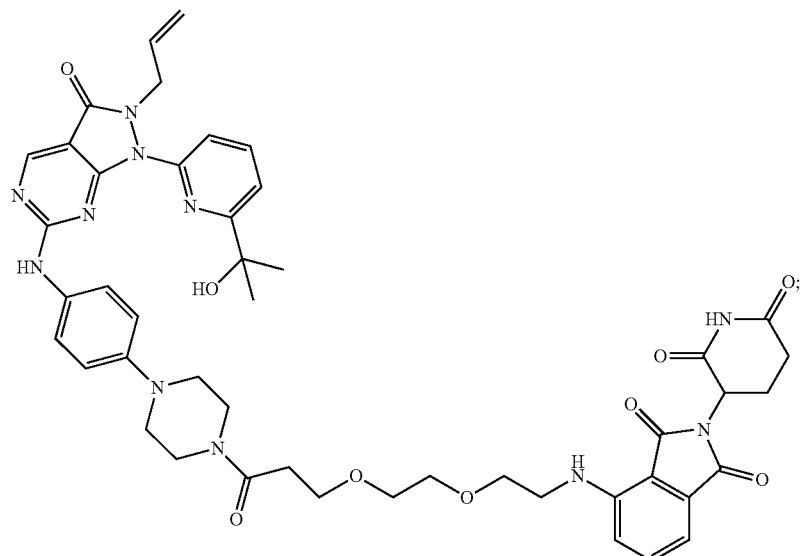
(4)
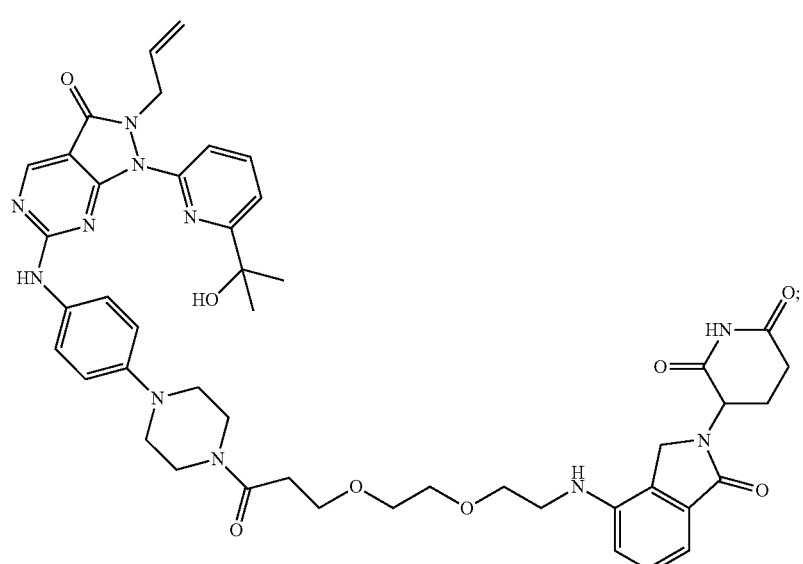
(5)
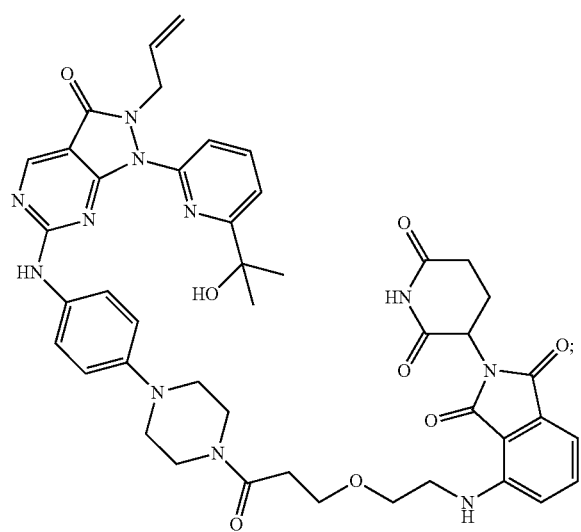

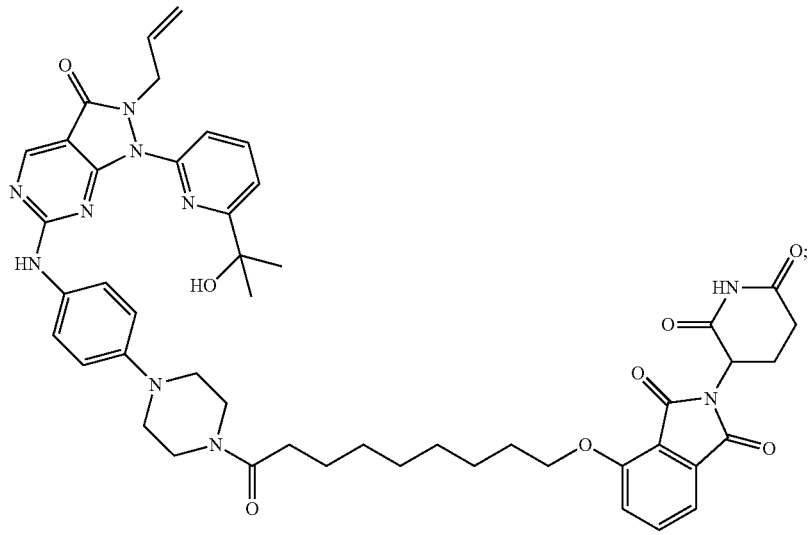
(6)
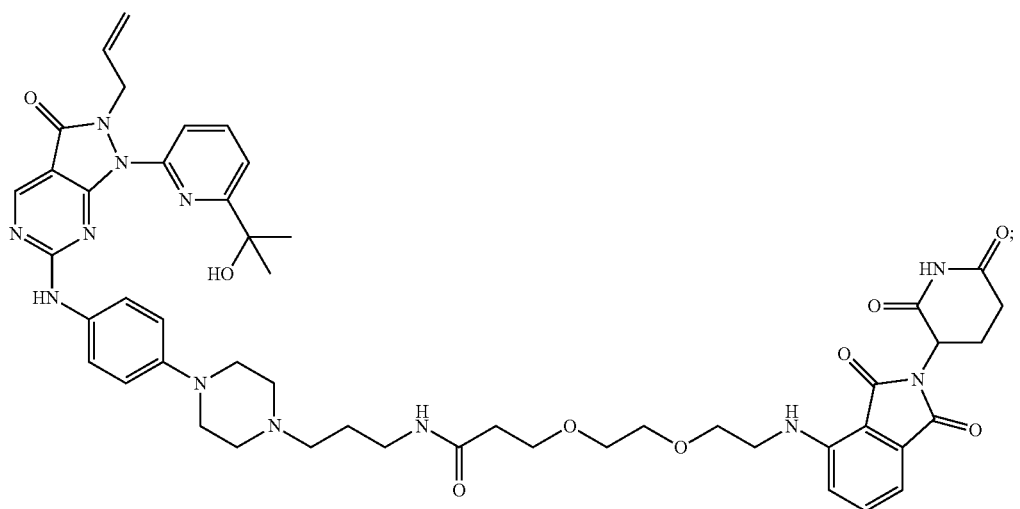
(7)
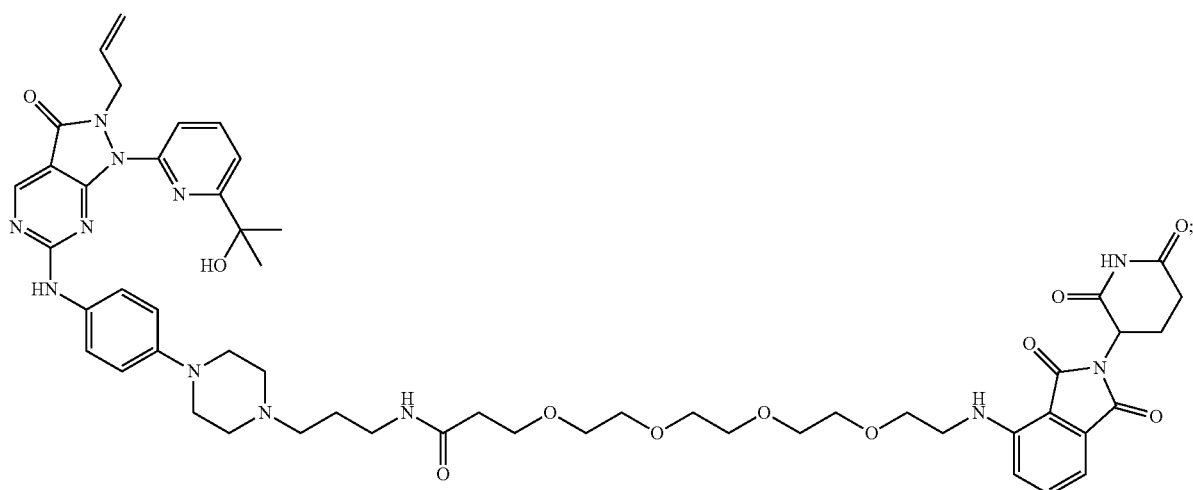
(8)

(9)
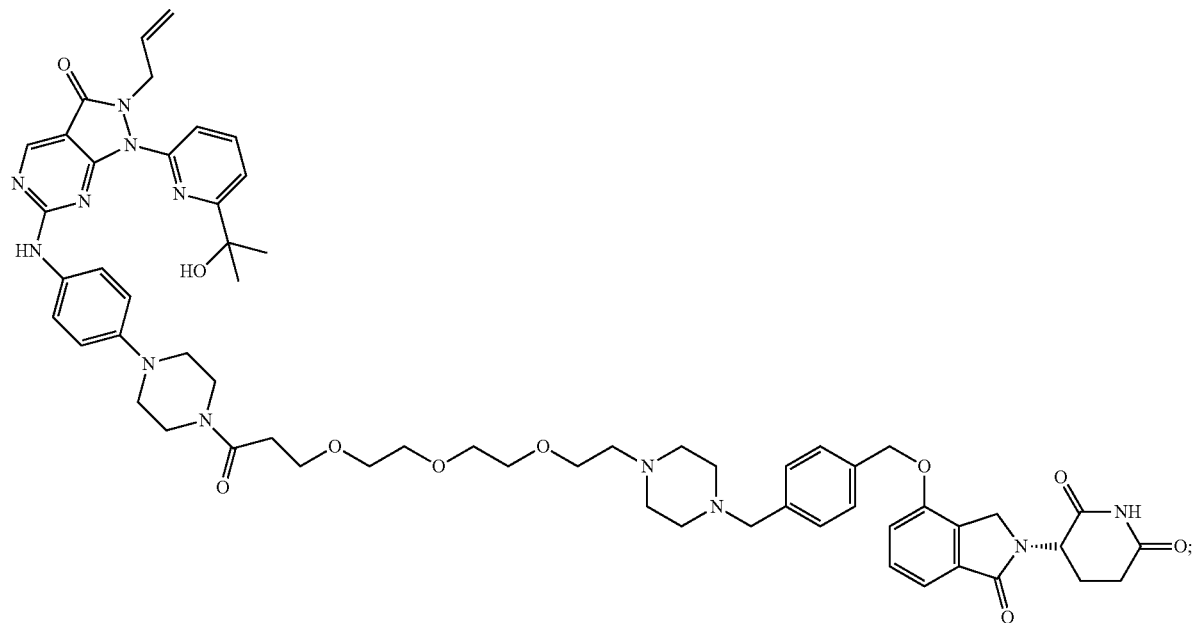
(10)
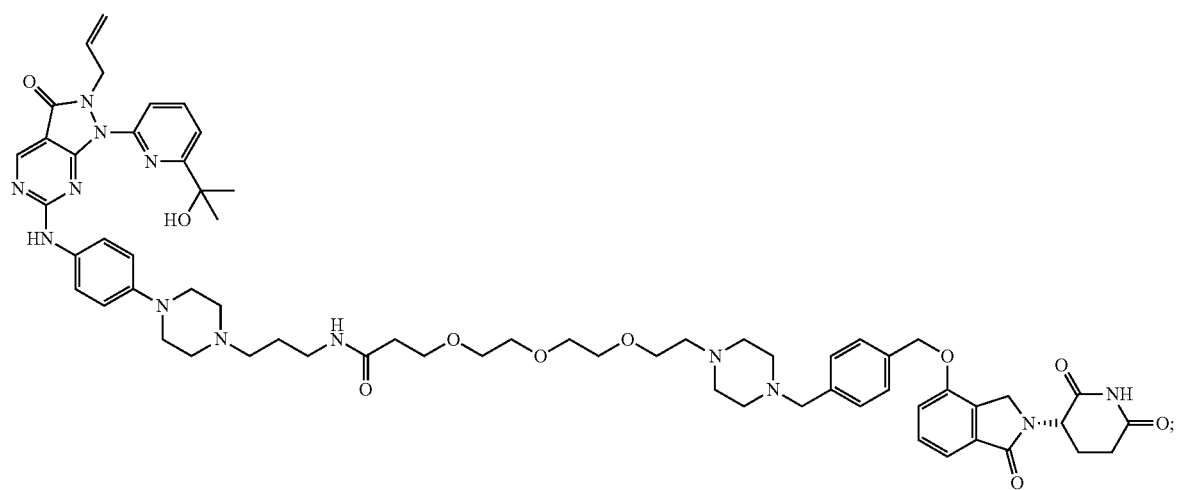
(11)
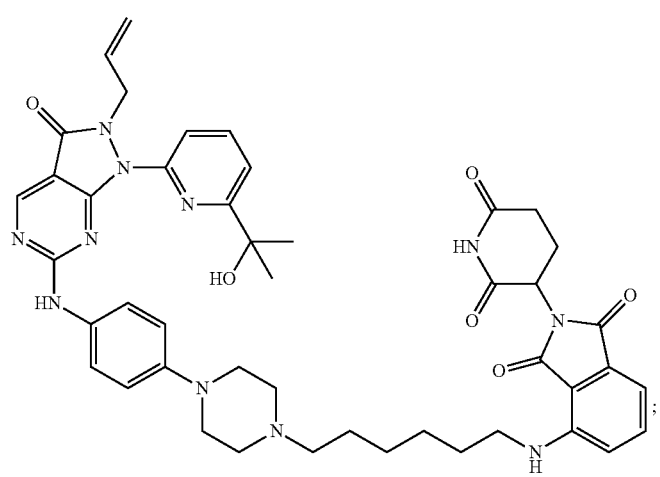

(12)
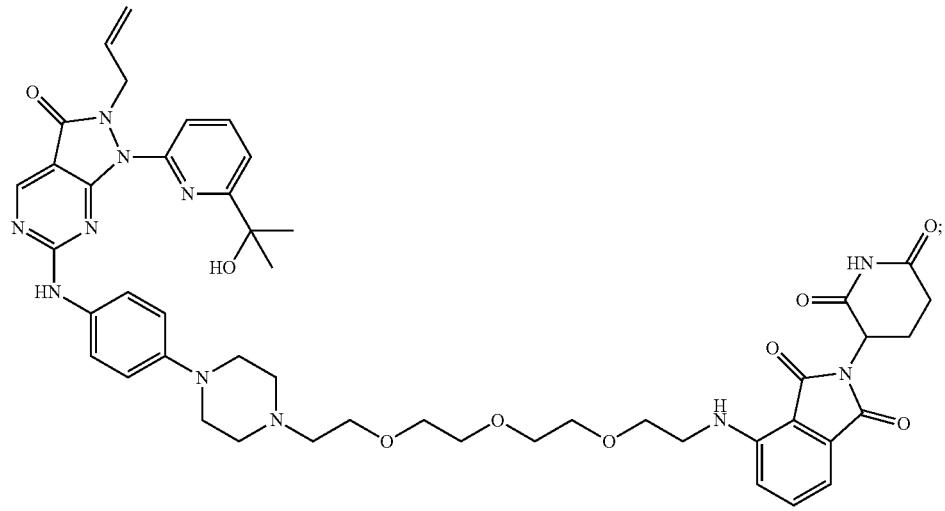
(13)
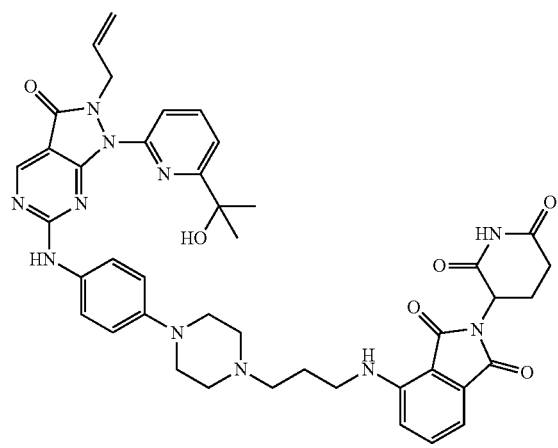
(14)
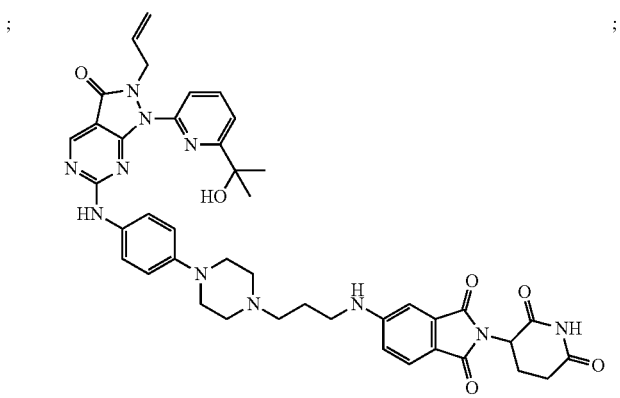
(15)
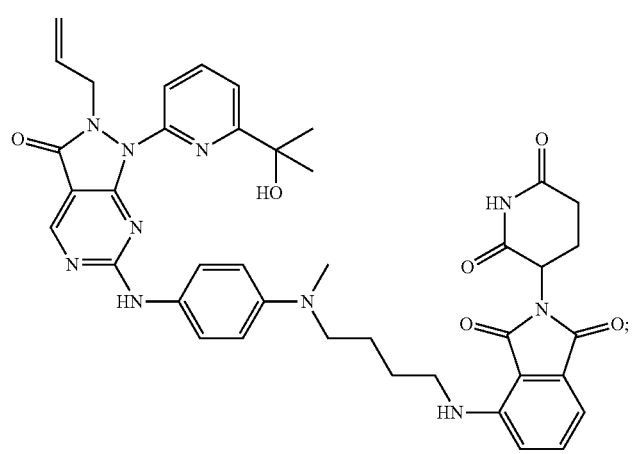

-continued
(16)
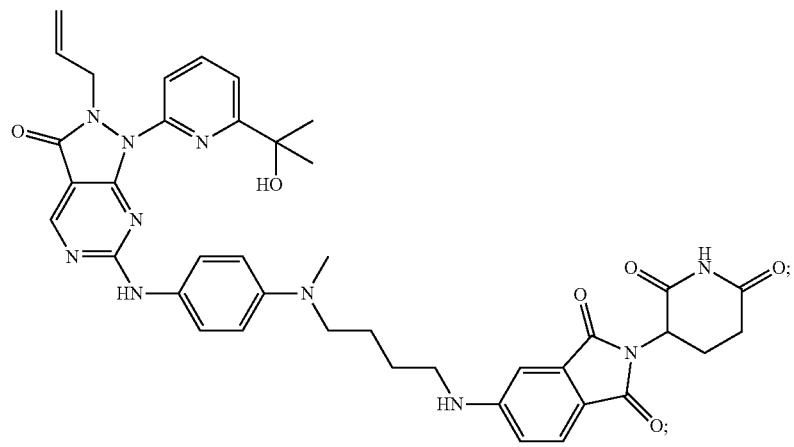
(17)
;
(18)
;
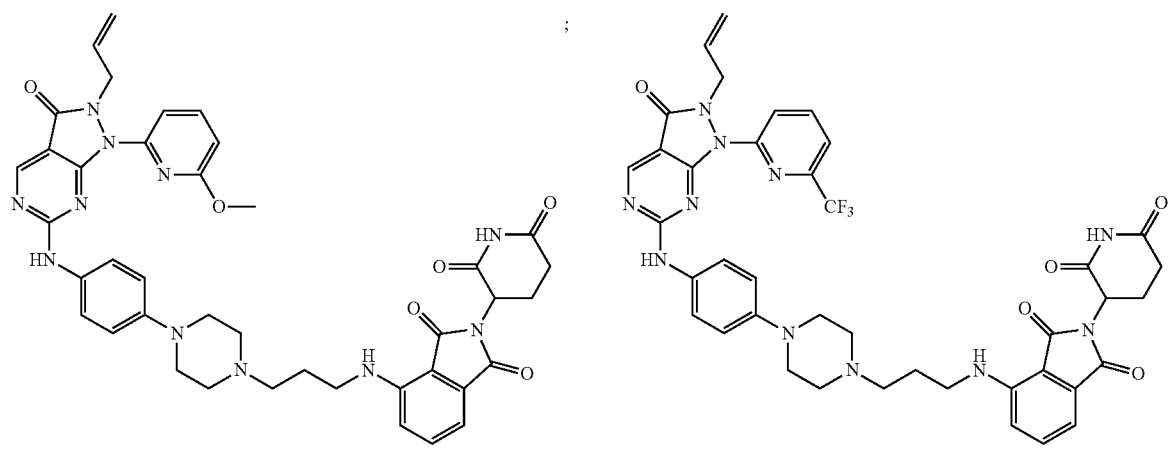
(19)
;
(21)
;
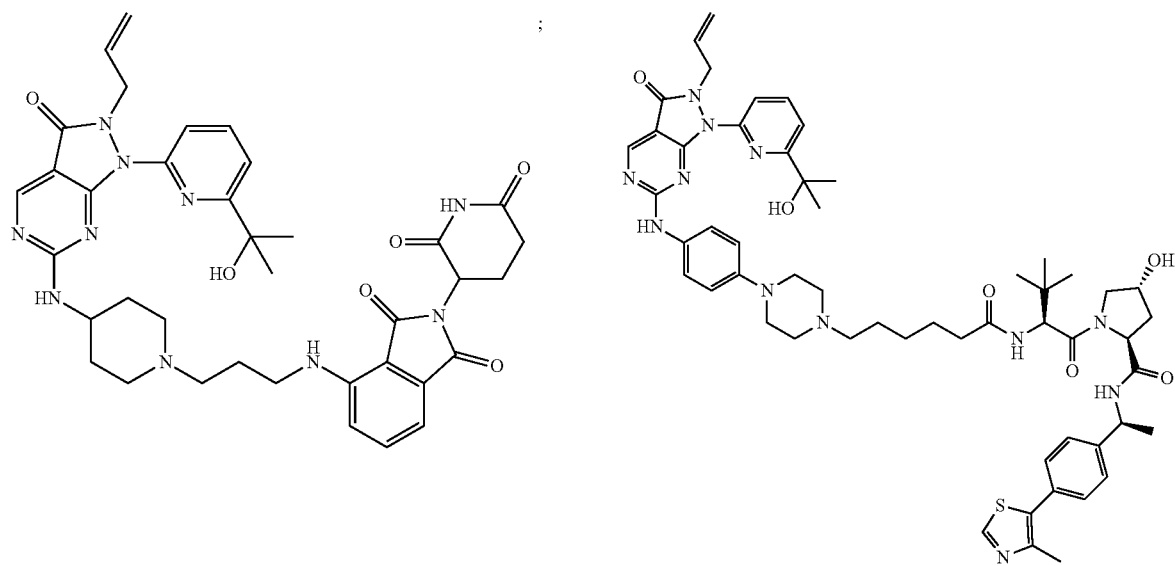

(22)
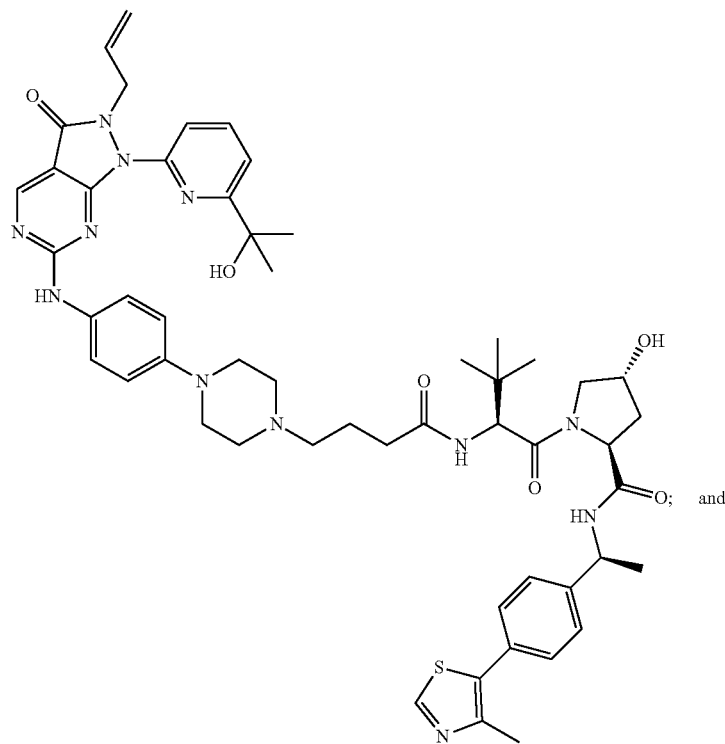
(23)
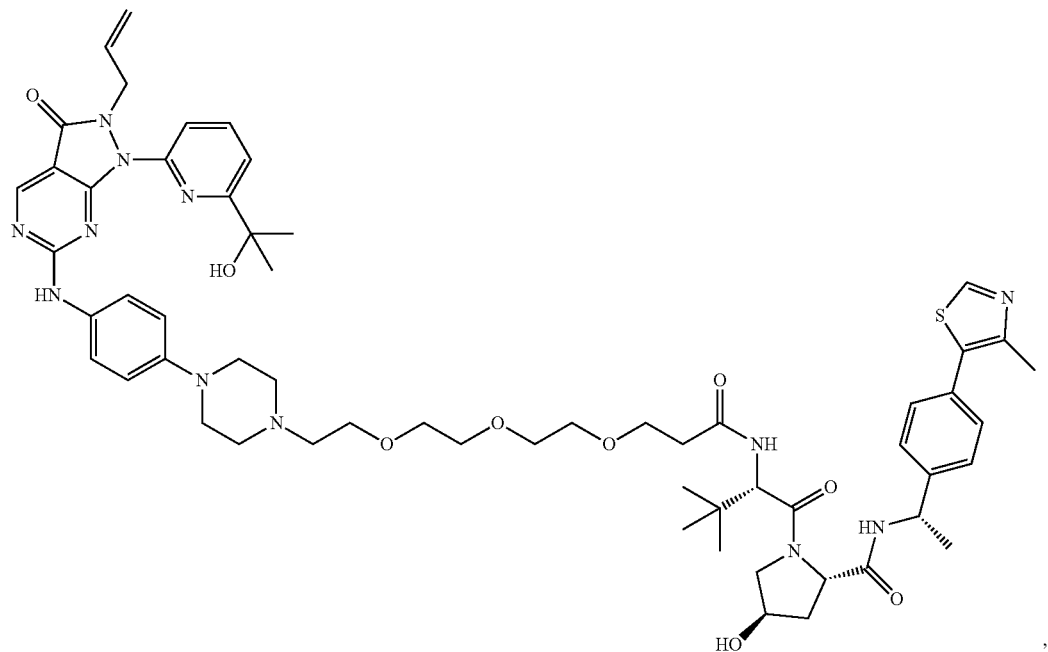
or pharmaceutically acceptable salts and stereoisomers thereof.

9. The compound of claim 1, which is:

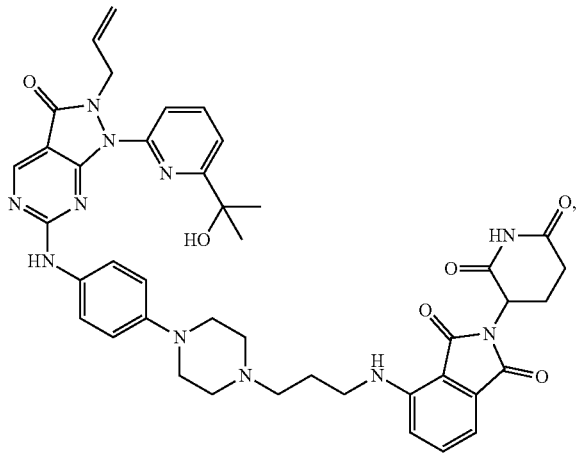

(13)

or pharmaceutically acceptable salts and stereoisomers thereof.

10. A pharmaceutical composition comprising a therapeutically effective amount of the compound of claim 9, or a pharmaceutically acceptable salt or stereoisomer thereof, and pharmaceutically acceptable carrier.

11. The compound of claim 1, wherein the linker is a $C_2$-$C_6$ alkylene group.

12. The compound of claim 11, wherein the linker is a $C_4$ alkylene group.

13. A pharmaceutical composition comprising a therapeutically effective amount of the compound of claim 1, or a pharmaceutically acceptable salt or stereoisomer thereof, and pharmaceutically acceptable carrier.

14. A method of treating a disease or disorder mediated by aberrant Wee1 kinase activity, comprising administrating a therapeutically effective amount of the compound of claim 1, or a pharmaceutically acceptable salt or stereoisomer thereof, to a subject in need thereof.

15. The method of claim 14, wherein the disease is a cancer.

16. The method of claim 15, wherein the cancer is ovarian cancer.

17. The method of claim 14, wherein the method further comprises administering the therapeutically effective amount of the compound of formula I or a pharmaceutically acceptable salt or stereoisomer thereof to the subject in combination with a therapeutically effective amount effective amount of an additional chemotherapeutic agent.

18. The method of claim 17, wherein the additional chemotherapeutic agent is a poly ADP ribose polymerase (PARP) inhibitor.

19. The method of claim 18, wherein the PARP inhibitor is Olaparib.

* * * * *